United States Patent
Yeung et al.

(10) Patent No.: US 12,024,559 B2
(45) Date of Patent: Jul. 2, 2024

(54) FUSIONS WITH CD8 ANTIGEN BINDING MOLECULES FOR MODULATING IMMUNE CELL FUNCTION

(71) Applicant: Asher Biotherapeutics, Inc., South San Francisco, CA (US)

(72) Inventors: Yik Andy Yeung, South San Francisco, CA (US); Ivana Djuretic, Pacifica, CA (US); Paul Bessette, San Francisco, CA (US); Wei Chen, Cupertino, CA (US); Sherman Michael Chin, Burlingame, CA (US); Kelly Dare Moynihan, San Francisco, CA (US); Henry C. Nguyen, San Francisco, CA (US); Irene Ni, Foster City, CA (US); Danielle C. Pappas, San Mateo, CA (US); Terrence Park, Hayward, CA (US)

(73) Assignee: Asher Biotherapeutics, Inc., South San Francisco, CA (US)

( * ) Notice: Subject to any disclaimer, the term of this patent is extended or adjusted under 35 U.S.C. 154(b) by 80 days.

(21) Appl. No.: 17/508,804

(22) Filed: Oct. 22, 2021

(65) Prior Publication Data

US 2022/0162314 A1 May 26, 2022

Related U.S. Application Data

(60) Provisional application No. 63/190,669, filed on May 19, 2021, provisional application No. 63/121,663, filed on Dec. 4, 2020, provisional application No. 63/105,162, filed on Oct. 23, 2020.

(51) Int. Cl.
| | |
|---|---|
| *C07K 16/28* | (2006.01) |
| *A61K 38/20* | (2006.01) |
| *A61K 47/65* | (2017.01) |
| *A61K 47/68* | (2017.01) |
| *A61P 31/12* | (2006.01) |
| *A61P 35/00* | (2006.01) |

(52) U.S. Cl.
CPC ...... *C07K 16/2815* (2013.01); *A61K 38/2013* (2013.01); *A61K 47/65* (2017.08); *A61K 47/6849* (2017.08); *A61P 31/12* (2018.01); *A61P 35/00* (2018.01)

(58) Field of Classification Search
CPC ........... C07K 16/2815; A61K 38/2013; A61K 47/65; A61K 47/6849; A61P 31/12; A61P 35/00
See application file for complete search history.

(56) References Cited

U.S. PATENT DOCUMENTS

| | | |
|---|---|---|
| 4,518,584 A | 5/1985 | Mark et al. |
| 5,206,344 A | 4/1993 | Katre et al. |
| 5,500,362 A | 3/1996 | Robinson et al. |
| 5,731,168 A | 3/1998 | Carter et al. |
| 5,821,333 A | 10/1998 | Carter et al. |
| 5,821,337 A | 10/1998 | Carter et al. |
| 6,410,319 B1 | 6/2002 | Raubitschek et al. |
| 6,451,995 B1 | 9/2002 | Cheung et al. |
| 6,940,003 B1 * | 9/2005 | Kinney ............. C12N 15/8243 435/235.1 |
| 7,070,995 B2 | 7/2006 | Jensen |
| 7,112,660 B1 | 9/2006 | Domingues et al. |
| 7,186,805 B2 | 3/2007 | Presnell et al. |
| 7,205,275 B2 | 4/2007 | Oliner et al. |
| 7,265,209 B2 | 9/2007 | Jensen |
| 7,276,478 B2 | 10/2007 | Sivakumar et al. |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,695,936 B2 | 4/2010 | Carter et al. |
| 8,034,326 B2 | 10/2011 | Hjorth et al. |
| 8,211,420 B2 | 7/2012 | Bondensgaard et al. |
| 8,324,353 B2 | 12/2012 | Jensen |
| 8,339,645 B2 | 12/2012 | Nakawaki |
| 8,383,367 B2 | 2/2013 | Hjorth et al. |
| 8,389,282 B2 | 3/2013 | Sadelain et al. |
| 8,398,282 B2 | 3/2013 | Kuhlman et al. |

(Continued)

FOREIGN PATENT DOCUMENTS

| | | |
|---|---|---|
| EP | 2288372 B1 | 2/2012 |
| EP | 1144454 B2 | 12/2012 |

(Continued)

OTHER PUBLICATIONS

Atwell et al., (1997). "Stable heterodimers from remodeling the domain interface of a homodimer using a phage display library," J Mol Biol, 270:26-35.

(Continued)

*Primary Examiner* — Jeffrey Stucker
*Assistant Examiner* — Brittney E Donoghue
(74) *Attorney, Agent, or Firm* — Morrison & Foerster LLP

(57) ABSTRACT

Provided herein are anti-CD8 antigen binding molecules and fusion polypeptides comprising the CD8 antigen binding molecules for selectively modulating the function of CD8+ T cells over other immune cells. In addition, the present disclosure also provides polynucleotides encoding the disclosed antigen binding molecules and fusion polypeptides, and vectors and host cells comprising such polynucleotides. The present disclosure further provides methods for producing the antigen binding molecules and fusion polypeptides, pharmaceutical compositions comprising the same, and uses thereof.

95 Claims, 41 Drawing Sheets

Specification includes a Sequence Listing.

(56) References Cited

U.S. PATENT DOCUMENTS

| | | | |
|---|---|---|---|
| 8,479,118 | B2 | 7/2013 | Lyndersay et al. |
| 8,822,653 | B2 * | 9/2014 | Sexton ............... C07K 16/40 530/389.3 |
| 9,447,159 | B2 | 9/2016 | Ast et al. |
| 9,732,134 | B2 | 8/2017 | Gavin et al. |
| 9,844,582 | B2 | 12/2017 | Wittrup et al. |
| 9,850,310 | B2 * | 12/2017 | Gaudet ............... A61P 35/00 |
| 10,150,802 | B2 | 12/2018 | Garcia et al. |
| 10,202,464 | B2 | 2/2019 | Ast et al. |
| 10,316,104 | B2 | 6/2019 | Ast et al. |
| 10,538,595 | B2 | 1/2020 | Zhang et al. |
| 10,562,949 | B2 | 2/2020 | Hosse et al. |
| 10,676,516 | B2 | 6/2020 | Viney et al. |
| 11,130,822 | B2 | 9/2021 | Ast et al. |
| 11,471,490 | B2 | 10/2022 | Andresen et al. |
| 11,518,808 | B2 | 12/2022 | Ali et al. |
| 11,541,103 | B2 | 1/2023 | Ali et al. |
| 2002/0131960 | A1 | 9/2002 | Sadelain et al. |
| 2003/0045474 | A1 | 3/2003 | Sailer et al. |
| 2008/0003294 | A1 | 1/2008 | Chen et al. |
| 2012/0107267 | A1 | 5/2012 | Kang et al. |
| 2012/0276125 | A1 | 11/2012 | Ast et al. |
| 2013/0149337 | A1 | 6/2013 | Cooper et al. |
| 2013/0287748 | A1 | 10/2013 | June et al. |
| 2013/0336982 | A1 | 12/2013 | Mader et al. |
| 2014/0294759 | A1 | 10/2014 | Chu et al. |
| 2015/0299324 | A1 | 10/2015 | Hofer et al. |
| 2018/0142027 | A1 | 5/2018 | Igawa et al. |
| 2018/0142040 | A1 | 5/2018 | Moore et al. |
| 2018/0200378 | A1 | 7/2018 | Bennett et al. |
| 2018/0326010 | A1 | 11/2018 | Deak et al. |
| 2019/0023790 | A1 | 1/2019 | Giurleo et al. |
| 2019/0046611 | A1 | 2/2019 | Ali et al. |
| 2019/0062448 | A1 | 2/2019 | Soros et al. |
| 2019/0085080 | A1 | 3/2019 | Kaplan et al. |
| 2019/0233517 | A1 | 8/2019 | Wu |
| 2019/0263877 | A1 | 8/2019 | Yeung et al. |
| 2019/0270817 | A1 | 9/2019 | Ali et al. |
| 2019/0315883 | A1 | 10/2019 | Ast et al. |
| 2019/0322763 | A1 | 10/2019 | Ast et al. |
| 2020/0078401 | A1 | 3/2020 | Vijayanand et al. |
| 2020/0317787 | A1 | 10/2020 | Li et al. |
| 2020/0330514 | A1 | 10/2020 | Andersen et al. |
| 2021/0017247 | A1 | 1/2021 | Jones et al. |
| 2021/0024631 | A1 | 1/2021 | Kley et al. |
| 2021/0163562 | A1 | 6/2021 | Lu et al. |
| 2022/0033455 | A1 | 2/2022 | Wong |
| 2022/0112288 | A1 | 4/2022 | Ganesan et al. |
| 2022/0251202 | A1 | 8/2022 | Djuretic et al. |
| 2023/0136331 | A1 | 5/2023 | Ban et al. |
| 2023/0340104 | A1 | 10/2023 | Yeung et al. |

FOREIGN PATENT DOCUMENTS

| | | | |
|---|---|---|---|
| EP | 2537416 | A1 | 12/2012 |
| EP | 2537416 | B1 | 11/2014 |
| EP | 2970486 | B1 | 5/2018 |
| EP | 3102595 | B1 | 11/2018 |
| EP | 3421495 | A2 | 1/2019 |
| EP | 3630163 | A2 | 4/2020 |
| EP | 3661954 | B1 | 2/2022 |
| TW | 202306988 | A | 2/2023 |
| WO | WO-1996013593 | A2 | 5/1996 |
| WO | WO-1996018105 | A1 | 6/1996 |
| WO | WO-1999018129 | A1 | 4/1999 |
| WO | WO-1999060120 | A2 | 11/1999 |
| WO | WO-2000014257 | A1 | 3/2000 |
| WO | WO-2003020763 | A2 | 3/2003 |
| WO | WO-2004033685 | A1 | 4/2004 |
| WO | WO-2004044004 | A2 | 5/2004 |
| WO | WO-2004044006 | A1 | 5/2004 |
| WO | WO-2004074322 | A1 | 9/2004 |
| WO | WO-2005113595 | A2 | 12/2005 |
| WO | WO-2005114215 | A2 | 12/2005 |
| WO | WO-2006000830 | A2 | 1/2006 |
| WO | WO-2006106905 | A1 | 10/2006 |
| WO | WO-2006111524 | A2 | 10/2006 |
| WO | WO-2006125962 | A2 | 11/2006 |
| WO | WO-2007110205 | A2 | 10/2007 |
| WO | WO-2008038002 | A2 | 4/2008 |
| WO | WO-2008039818 | A2 | 4/2008 |
| WO | WO-2010033140 | A2 | 3/2010 |
| WO | WO-2010066740 | A1 | 6/2010 |
| WO | WO-2010085495 | A1 | 7/2010 |
| WO | WO-2011044186 | A1 | 4/2011 |
| WO | WO-2011063770 | A2 | 6/2011 |
| WO | WO-2012062228 | A2 | 5/2012 |
| WO | WO-2012107416 | A2 | 8/2012 |
| WO | WO-2012129514 | A1 | 9/2012 |
| WO | WO-2012146628 | A1 | 11/2012 |
| WO | WO-2013071154 | A1 | 5/2013 |
| WO | WO-2013123061 | A1 | 8/2013 |
| WO | WO-2013126726 | A1 | 8/2013 |
| WO | WO-2013166321 | A1 | 11/2013 |
| WO | WO-2014023679 | A1 | 2/2014 |
| WO | WO-2014031687 | A1 | 2/2014 |
| WO | WO-2014055668 | A1 | 4/2014 |
| WO | WO-2014079000 | A1 | 5/2014 |
| WO | WO-2014145907 | A1 | 9/2014 |
| WO | WO-2015164815 | A1 | 10/2015 |
| WO | WO-2016014428 | A2 | 1/2016 |
| WO | WO-2016100375 | A2 | 6/2016 |
| WO | WO-2016164937 | A2 | 10/2016 |
| WO | WO-2017027422 | A1 | 2/2017 |
| WO | WO-2018089420 | A1 | 5/2018 |
| WO | WO-2018091003 | A1 | 5/2018 |
| WO | WO-2018119114 | A1 | 6/2018 |
| WO | WO-2018176505 | A1 | 10/2018 |
| WO | WO-2018184964 | A1 | 10/2018 |
| WO | WO-2018209115 | A1 | 11/2018 |
| WO | WO-2018217989 | A1 | 11/2018 |
| WO | WO-2018236010 | A1 | 12/2018 |
| WO | WO-2019010219 | A1 | 1/2019 |
| WO | WO-2019010224 | A1 | 1/2019 |
| WO | WO-2019148026 | A1 | 8/2019 |
| WO | WO-2019191519 | A1 | 10/2019 |
| WO | WO-2019196309 | A1 | 10/2019 |
| WO | WO-2019246392 | A1 | 12/2019 |
| WO | WO-2019246404 | A1 | 12/2019 |
| WO | WO-2020020783 | A1 | 1/2020 |
| WO | WO-2020056066 | A1 | 3/2020 |
| WO | WO-2020057645 | A1 | 3/2020 |
| WO | WO-2020057646 | A1 | 3/2020 |
| WO | WO-2020082057 | A1 | 4/2020 |
| WO | WO-2020088459 | A1 | 5/2020 |
| WO | WO-2020097325 | A1 | 5/2020 |
| WO | WO-2020117233 | A1 | 6/2020 |
| WO | WO-2020130300 | A1 | 6/2020 |
| WO | WO-2020146221 | A1 | 7/2020 |
| WO | WO-2020148554 | A1 | 7/2020 |
| WO | WO-2020247843 | A2 | 12/2020 |
| WO | WO-2021001289 | A1 | 1/2021 |
| WO | WO-2022006380 | A2 | 1/2022 |
| WO | WO-2022125711 | A1 | 6/2022 |
| WO | WO-2022135469 | A1 | 6/2022 |
| WO | WO-2022245500 | A1 | 11/2022 |
| WO | WO-2023048516 | A1 | 3/2023 |
| WO | WO-2023212056 | A2 | 11/2023 |

OTHER PUBLICATIONS

Blake et al., (2006). "Understanding the biological rationale for the diversity of cellulose- directed carbohydrate-binding modules in prokaryotic enzymes," J Biol Chem, 281:29321-29329.

Bosselut et al., (2000). "Role of CD8beta domains in CD8 coreceptor function: importance for Mhc I binding, signaling, and positive selection of CD8+ T cells in the thymus," Immunity, 12(4):409-18.

Brinkmann et al., (2017). "The making of bispecific antibodies," Mabs, 9(2):182-212.

Carter, (2001). "Bispecific human IgG by design," J Immunol Methods, 248:7-15.

(56) References Cited

OTHER PUBLICATIONS

Caudana et al., (2019). "IL2/Anti-IL2 Complex Combined with CTLA-4, But Not PD-1, Blockade Rescues Antitumor NK Cell Function by Regulatory T-cell Modulation," Cancer Immunol Res., 7(3):443-457.
Chinen et al., (2016). "An essential role for the IL-2 receptor in T cell function," Nat Immunol., 17(11):1322-1333, 28 pages.
Choi et al., (2013). "A heterodimeric Fc-based bispecific antibody simultaneously targeting VEGFR-2 and Met exhibits potent antitumor activity," Mol Cancer Ther, 12:2748-59.
Chothia et al., (1987). "Canonical structures for the hypervariable regions of immunoglobulins," J. Mol. Biol., 196:901-917.
Collison, (2019). "Low-dose IL-2 therapy for autoimmune diseases," Nat Rev Rheumatol., 15(1):2.
Davis et al., (2010). "SEEDbodies: fusion proteins based on strand-exchange engineered domain (Seed) CH3 heterodimers in an Fc analogue platform for asymmetric binders or immunofusions and bispecific antibodies," Protein Eng Des Sel, 23:195-202.
De Nardis et al., (2017). "A new approach for generating bispecific antibodies based on a common light chain format and the stable architecture of human immunoglobulin G1," J Biol Chem., 292(35):14706-14717.
Dimitrov, (2009). "Engineered CH2 domains (nanoantibodies)," MaBS., 1:26-8.
Egelston et al., (2018). "Human breast tumor-infiltrating CD8 + T cells retain polyfunctionality despite PD-1 expression," Nat Commun., 9(1):4297, 11 pages.
Fischer et al., (2015). "Exploiting light chains for the scalable generation and platform purification of native human bispecific IgG," Nature Communication, 6:6113, 12 pages.
Gebauer et al., (2009). "Engineered protein scaffolds as next-generation antibody therapeutics," Curr Opin Chem Biol., 13:245-55.
Geuijen et al., (2014). "Preclinical activity of MCLA-128, an ADCC enhanced bispecific IgG1 antibody targeting the HER2:HER3 heterodimer," Journal of Clinical Oncology, 32(1S):560, 3 pages.
Gros et al., (2014). "PD-1 identifies the patient-specific CD8+ tumor-reactive repertoire infiltrating human tumors," J Clin Invest., 4(5):2246-59.
Gunasekaran et al., (2010). "Enhancing antibody Fc heterodimer formation through electrostatic steering effects: applications to bispecific molecules and monovalent IgG," J Biol Chem, 285:19637-46.
Guo et al., (2015). "IL-15 Superagonist-Mediated Immunotoxicity: Role of NK Cells and Ifn-γ," J Immunol., 195(5):2353-64.
Heng et al., (2008). "Immunological Genome Project Consortium: networks of gene expression in immune cells," Nat Immunol., 9(10):1091-4.
Holliger et al., (1996). "Specific killing of lymphoma cells by cytotoxic T-cells mediated by a bispecific diabody," Protein Engineering, 9(3):299-305.
International Search Report and Written Opinion received for International Patent Application No. PCT/US2020/036454 mailed on Jan. 12, 2021, 12 pages.
International Search Report and Written Opinion received for International Patent Application No. PCT/US2021/56312 mailed on Mar. 17, 2022, 17 pages.
Jefferis et al., (2002). "Interaction sites on human IgG-Fc for FcgammaR: current models," Immunol Lett, 82:57-65.
Klein et al., (2017). "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunol., 6(3):e1277306, 15 pages.
Knight et al., (2000). "The collagen-binding A-domains of integrins alpha(1)beta(1) and alpha(2)beta(1) recognize the same specific amino acid sequence, GFOGER, in native (triple-helical) collagens," J Biol Chem., 275:35-40.
Kolmar et al., (2008). "Alternative binding proteins: biological activity and therapeutic potential of cysteine-knot miniproteins," FEBS J., 275:2684-2690.
Krieg et al., (2010). "Improved IL-2 immunotherapy by selective stimulation of IL-2 receptors on lymphocytes and endothelial cells," PNAS USA, 107(26):11906-11.
Labrijn et al., (2013). "Efficient generation of stable bispecific IgG1 by controlled Fab-arm exchange," PNAS USA, 110(13):5145-50.
Labrijn et al., (2019). "Bispecific antibodies: a mechanistic review of the pipeline," Nat Review Drug Discovery, 18:585-608.
Lopes et al., (2020). "ALKS 4230: a novel engineered IL-2 fusion protein with an improved cellular selectivity profile for cancer immunotherapy," J Immunother Cancer, 8(1):e000673, 13 pages.
Merchant et al., (1998). "An efficient route to human bispecific IgG," Nat Biotechnol, 16:677-681.
Milling et al., (2017). "Delivering safer immunotherapies for cancer," Adv Drug Deliv Rev., 114:79-101, 55 pages.
Moore et al., (2011). "A novel bispecific antibody format enables simultaneous bivalent and monovalent co-engagement of distinct target antigens," Mabs, 3:546-557.
Moore et al., (2019). "A robust heterodimeric Fc platform engineered for efficient development of bispecific antibodies of multiple formats," Methods, 154:38-50.
Moretti et al., (2013). "BEAT® the bispecific challenge: a novel and efficient platform for the expression of bispecific IgGs," BMC Proceedings, 7(Suppl6):O9, 3 pages.
Nygren et al., (2008). "Alternative binding proteins: Affibody binding proteins developed from a small three-helix bundle scaffold," FEBS Journal, 275(11):2668-76.
Ribas et al., (2018). "Cancer immunotherapy using checkpoint blockade," Science, 359(6382):1350-1355, 18 pages.
Ridgway et al., (1996). "Knobs-into-holes' engineering of antibody CH3 domains for heavy chain heterodimerization," Prot Eng, 9:617-621.
Rosenberg, (2014). "IL-2: the first effective immunotherapy for human cancer," J Immunol., 192(12):5451-8.
Ross et al., (2018). "Signaling and Function of Interleukin-2 in T Lymphocytes," Annu Rev Immunol., 36:411-433, 28 pages.
Rothschilds et al., (2019). "Order of administration of combination cytokine therapies can decouple toxicity from efficacy in syngeneic mouse tumor models," Oncoimmunology, 8(5):e1558678, 16 pages.
Sade-Feldman et al., (2018). "Defining T Cell States Associated with Response to Checkpoint Immunotherapy in Melanoma," Cell, 175(4):998-1013.
Schwartz et al., (2002). "Managing toxicities of high-dose interleukin-2," Oncology, 16(11 Suppl 13):11-20, 10 pages.
Silva et al., (2019). "De novo design of potent and selective mimics of IL-2 and IL-15," Nature, 565(7738):186-191.
Skegro et al., (2017). "Immunoglobulin domain interface exchange as a platform technology for the generation of Fc heterodimers and bispecific antibodies," J Biol Chem., 292(23):9745-9759.
Skerra, (2008). "Alternative binding proteins: Anticalins—harnessing the structural plasticity of the lipocalin ligand pocket to engineer novel binding activities," FEBS Journal, 275(11):2677-2683.
Stauber et al., (2006). "Crystal structure of the IL-2 signaling complex: paradigm for a heterotrimeric cytokine receptor," PNAS USA, 103(8):2788-93.
Strop et al., (2012). "Generating bispecific human IgG1 and IgG2 antibodies from any antibody pair," J Mol Biol, 420:204-19.
Stumpp et al., (2008). "DARPins: a new generation of protein therapeutics," Drug Discov Today, 13:695-701.
Thommen et al., (2018). "A transcriptionally and functionally distinct PD-1 + CD8 + T cell pool with predictive potential in non-small-cell lung cancer treated with PD-1 blockade," Nat Med., 24(7):994-1004, 28 pages.
Tustian et al., (2016). "Development of purification processes for fully human bispecific antibodies based upon modification of protein A binding avidity," Mabs, 8(4):828-38.
Von Kreudenstein et al., (2013). "Improving biophysical properties of a bispecific antibody scaffold to aid developability: quality by molecular design," Mabs, 5:646-54.

(56) References Cited

OTHER PUBLICATIONS

Wei et al., (2017). "Structural basis of a novel heterodimeric Fc for bispecific antibody production," Oncotarget, 8(31):51037-51049.
Wozniak-Knopp et al., (2010). "Introducing antigen-binding sites in structural loops of immunoglobulin constant domains: Fc fragments with engineered HER2/neu-binding sites and antibody properties," Protein Eng Des Sel., 23:289-97.
Zhu et al., (2015). "Synergistic innate and adaptive immune response to combination immunotherapy with anti-tumor antigen antibodies and extended serum half-life IL-2," Cancer Cell, 27(4):489-501.
Choi et al., (2015). "Crystal structures of immunoglobulin Fc heterodimers reveal the molecular basis for heterodimer formation," Mol Immunol, 65:377-83. Abstract Only.
Gao et al., (2019). "Optimization of the C-Terminus of an Autonomous Human IgG1 CH2 Domain for Stability and Aggregation Resistance," Mol Pharm., 16:3647-3656. Abstract Only.
Heeley et al., (2002). "Mutations flanking the polyglutamine repeat in the modulatory domain of rat glucocorticoid receptor lead to an increase in affinity for hormone," Endocr Res, 28(3):217-229. Abstract Only.
Labrijn et al., (2014). "Controlled Fab-arm exchange for the generation of stable bispecific IgG1," Nat Protoc, 9:2450-63. Abstract Only.
Tramontano et al., (1994). "The making of the minibody: an engineered beta-protein for the display of conformationally constrained peptides," J. Mol. Recognition, 7:9-24. Abstract Only.
Partial European Search Report received for European Patent Application No. 20819187.4 mailed on May 15, 2023, 7 pages.
Asher Biotherapeutics, (2022). "Asher Bio to Unveil Two New Immunotherapy Programs, a CD8+ T Cell Targeted IL-21 and a Cis-Targeted IL-2 for Cell Therapy Augmentation, at AACR Annual Meeting," available online at <https://asherbio.com/2022/04/08/asher-bio-to-unveil-two-new-immunotherapy-programs-a-cd8-t-cell-targeted-il-21-and-a-cis-targeted-il-2-for-cell-therapy-augmentation-at-aacr-annual-meeting/>, 5 pages.
Extended European Search Report and Written Opinion received for European Patent Application No. 20819187.4 mailed on Aug. 16, 2023, 19 pages.
International Search Report and Written Opinion received for International Patent Application No. PCT/US2023/019989 mailed on Oct. 11, 2023, 14 pages.
Bondensgaard et al., (2007). "The existence of multiple conformers of interleukin-21 directs engineering of a superpotent analogue," J Biol Chem., 282(32):23326-23336.
International Search Report and Written Opinion received for International Patent Application No. PCT/US2022/026584 mailed on Sep. 9, 2022, 19 pages.
Kang et al., (2010). "Rational design of interleukin-21 antagonist through selective elimination of the gammaC binding epitope," J Biol Chem., 285(16):12223-12231.
Shen et al., (2020). "Engineered IL-21 Cytokine Muteins Fused to Anti-PD-1 Antibodies Can Improve CD8+ T Cell Function and Anti-tumor Immunity," Front Immunol., 11:832, 14 pages.
Young et al., (2014). "Antibody-cytokine fusion proteins for treatment of cancer: engineering cytokines for improved efficacy and safety," Semin Oncol., 41(5):623-36, 19 pages.
Biopharma PEG, (2019). "Things about Polypeptide Antibiotic You Need Know," available online at <https://www.biochempeg.com/article/75.html>, 4 pages.
Bossi, ImmTAC-redirected Tumour Cell Killing Induces and Potentiates Antigen Cross-presentation by Dendritic Cells. Cancer immunology, Immunotherapy 63(5):437-448 (2014)., 12 pages.
Boulter, Stable, Soluble T-cell Receptor Molecules for Crystallization and Therapeutics. Protein Engineering 16(9):707-711 (2003).
Boulter, Stable, Soluble, High-affinity, Engineered T cell Receptors: Novel Antibody-like Proteins for Specific Targeting of Peptide Antigens. Clinical and Experimental Immunology 142(3):454-460 (2005).

Brentjens CD19-targeted T cells rapidly induce molecular remissions in adults with chemotherapy-refractory acute lymphoblastic leukemia. Sci Transl Med. Mar. 20, 2013;5(177):177ra38. 9 pages.
Chames Therapeutic antibodies: successes, limitations and hopes for the future. Br J Pharmacol 157(2):220-233 (2009).
Chan Therapeutic antibodies for autoimmunity and inflammation. Nat Rev Immunol 10(5):301-316 (2010).
Chervin, Adam S, Engineering Higher Affinity T Cell Receptors Using A T Cell Display System. Journal of Immunological Methods 339(2):175-184 (2008).
Chhabra TCR-Engineered, Customized, Antitumor T Cells for Cancer Immunotherapy: Advantages and Limitations. Scientific World Journal 11:121-129 (2011).
Chmielewski, Trucks: The Fourth Generation of CARs. Expert Opinion on Biological Therapy 15(8):1145-1154 (2015), 10 pages.
Cho, Human mammalian cell sorting using a highly integrated micro-fabricated fluorescence-activated cell sorter (microFACS). Lab Chip 10:1567-1573 (2010), 17 pages.
Chothia, The outline structure of the T-cell ab receptor. The EMBO Journal 7(12):3745-3755 (1988).
Collison. Low-dose IL-2 therapy for autoimmune diseases. Nat Rev Rheumatol. 15(1):2 (2019).
Davila, CD19 CAR-targeted T Cells Induce Long-term Remission and B Cell Aplasia in an Immunocompetent Mouse Model of B Cell Acute Lymphoblastic Leukemia. PLoS One 8(4):e61338 (2013), 14 pages.
Dunn, Directed Evolution of Human T cell Receptor CDR2 Residues by Phage Display Dramatically Enhances Affinity for Cognate Peptide-MHC Without Increasing Apparent Cross-reactivity. Protein Science 15(4):710-721 (2006).
Edelhoch, (1969). "Structural Studies on Polypeptide Hormones," The Journal of Biological Chemistry, 244(14):3876-3883.
Federov, PD-1-and CTLA-4-based Inhibitory Chimeric Antigen Receptors (iCARs) Divert off-target Immunotherapy Responses. Science Translational Medicine 5(215):215ra172 (2013).
Fenton, (2020). "Rheostat positions: A new classification of protein positions relevant to pharmacogenomics," Medicinal Chemistry Research, 29:1133-1146.
Godin, Microfluidics and photonics for Bio-System-on-a-Chip: A review of advancements in technology towards a microfluidic flow cytometry chip. Journal of Biophotonics 1(5):355-376 (2008), 43 pages.
Greenbaum, Chimeric Antigen Receptor T-Cells In B-Acute Lymphoblastic Leukemia: State of the Art and Future Directions. Frontiers in Oncology. 10(1594):1-7 (2020).
Gschweng, Hematopoietic Stem Cells for Cancer Immunotherapy. Immunological Reviews 257(1):237-249 (2014).
Guo, (2004). "Protein tolerance to random amino acid change," PNAS, 101(25):9205-9210.
Hamming, (2012). "Crystal Structure of Interleukin-21 Receptor (IL-21 R) Bound to IL-21 Reveals That Sugar Chain Interacting with WSXWS Motif Is Integral Part of IL-21 R," The Journal of Biological Chemistry, 287(12):9454-9460.
Hicklin, (2019). "Decoding the variety of human antibodies," available online at <https://www.nih.gov/news-events/nih-research-matters/decoding-variety-human-antibodies>, 2 pages.
Hinrichs, Exploiting the curative potential of adoptive T-cell therapy for cancer. Immunological reviews 257:56-71 (2014), 23 pages.
Holler, In Vitro Evolution Of A T Cell Receptor With High Affinity For Peptide/MHC. PNAS USA 97(10):5387-5392 (2000).
Holler, TCRs With high affinity for foreign pMHC Show self-reactivity. Nature Immunology 4:55-62 (2003).
Holliger, Engineered Antibody Fragments and the Rise of Single Domains. Nature Biotechnology 23(9):1126-1136 (2005).
Hoo Characterization of a single-chain T-cell receptor expressed in *Escherichia coli*. PNAS USA 89(104);4759-63 (1992).
International Search Report and Written Opinion received for International Patent Application No. PCT/US2021/062484 mailed on May 16, 2022, 16 pages.
Johnston, Tyrosine phosphorylation and activation of STAT5, STAT3, and Janus kinases by interleukins 2 and 15. PNAS USA 92:8705-8709 (1995).

(56) References Cited

OTHER PUBLICATIONS

Jores, Resolution of hypervariable regions in T-cell receptor Beta chains by a modified Wu-Kabat index of amino acid diversity. PNAS USA 87:9138-9142 (Dec. 1990).
Kabat Sequences of Proteins of Immunological Interest. 5th Ed. Public Health Service, National Institutes of Health, Bethesda, MD (1991), 2 pages.
Kochenderfer Treating B-cell cancer with T cells expressing anti-CD19 chimeric antigen receptors. Nat. Rev. Clin. Oncol. 10:267-276 (2013).
Kurucz, A Bacterially Expressed Single-chain Fv Construct From The 2b4 T-cell Receptor. Proceedings of the National Academy of Sciences of the United States of America 90(9):3830-3834 (1993).
Leavy. Therapeutic antibodies: past, present and future. Nat rev Immunol 10(5):297 (2010).
Lefranc IMGT unique numbering for immunoglobulin and T cell receptor variable domains and Ig superfamily V-like domains. Dev Comp Immunol 27(1):55-77 (2003).
Lefranc, IMGT®, the international ImMunoGeneTics information system® 25 years on. Nucleic Acids Research 43:D413-D422 (2014).
Li, Directed Evolution Of Human T-cell Receptors With Picomolar Affinities By Phage Display. Nature Biotechnology 23(3):349-354 (2005).
Liddy, Monoclonal TCR-redirected tumor cell killing. Nat Med. 18(6):980-987 (2012).
Liddy, Production of a Soluble Disulfide Bond-Linked TCR in the Cytoplasm of *Escherichia coli* trxB gor Mutants. Molecular Biotechnology 45(2):140-149 (2010).
Lipovsek. Adnectins: engineered target-binding protein therapeutics. Protein Eng Des Sel 24(1-2):3-9 (2011).
Marr, Immunology in the Clinic Review Series; Focus on Cancer: Double Trouble for Tumours: Bi-functional and Redirected T Cells as Effective Cancer Immunotherapies. Clinical and Experimental Immunology 167(2):216-225 (2012).
McCormack, Bi-specific TCR-anti CD3 Redirected T-cell Targeting of NY-ESO-1-and LAGE-1-Positive Tumors. Cancer Immunology, Immunotherapy 62(4):773-785 (2013).
Nie, Mechanisms Underlying Cd19-positive All Relapse After Anti-CD19 Car T Cell Therapy And Associated Strategies. Biomarker Research 8:18 (2020), 17 pages.
Oates, ImmTACs for Targeted Cancer Therapy: Why, What, How, and Which. Molecular Immunology 67(2 Pt A):67-74 (2015), 8 pages.
Oates, ImmTACs: Novel bi-specific agents for targeted cancer therapy. Oncoimmunology 2(2):e22891 (2013), 3 pages.
Peebles A new horizon in asthma: inhibiting ILC function. Sci Transl Med. 5(174):174FS7 (2013), 1 page.
Rentero Phage selection of bicyclic peptides. Methods 60(1):46-54 (2013).
Robinson-Mosher, Designing Cell-Targeted Therapeutic Proteins Reveals the Interplay between Domain Connectivity and Cell Binding. Biophysical Journal. 107:2456-2466 (2014).
Sadelain, The basic principles of chimeric antigen receptor (CAR) design. Cancer Discov. 3(4):388-398 (2013), 21 pages.
Saeidi, T-Cell Exhaustion in Chronic Infections: Reversing the State of Exhaustion and Reinvigorating Optimal Protective Immune Responses. Frontiers in Immunology. 9(2569):4 (2018).
Sami, Crystal Structures of High Affinity Human T-cell Receptors Bound to Peptide Major Histocompatibility Complex Reveal Native Diagonal Binding Geometry. Protein Engineering, Design & Selection 20(8):397-403 (2007).
Schlueter, Specificity and binding properties of a single-chain T cell receptor. Journal of Molecular Biology 256(5):859-869 (1996).
Schmitt, Enhanced-affinity murine T-cell receptors for tumor/self-antigens can be safe in gene therapy despite surpassing the threshold for thymic selection. Blood 122(3):348-356 (2013).
Shimamoto, Peptibodies: A flexible alternative format to antibodies. MAbs 4(5):586-591 (2012).
Stromnes, Re-adapting T Cells for Cancer Therapy: From Mouse Models to Clinical Trials. Immunological Reviews 257(1):145-164 (2014).
Terakura, Generation of CD19-chimeric antigen receptor modified CD8+ T cells derived from virus-specific central memory T cells. Blood 119:72-82 (2012).
Thaxton, To affinity and beyond: harnessing the T cell receptor for cancer immunotherapy. Human Vaccines & Immunotherapeutics 10(11):3313-3321 (2014), 34 pages.
Turtle, Engineered T Cells For Anti-cancer Therapy. Current Opinion in Immunology 24(5):633-639 (2012), 12 pages.
Walter, Crystal Structure Of Interleukin 10 Reveals An Interferon Gamma-like Fold. Biochemistry 34(38):12118-12125 (1995).
Wang, Phenotypic and Functional Attributes of Lentivirus-modified CD19-specific Human CD8+ Central Memory T Cells Manufactured at Clinical Scale. J. Immunother. 35(9):689-701 (2012).
Wu, Adoptive T-cell therapy using autologous tumor-infiltrating lymphocytes for metastatic melanoma: current status and future outlook. The Cancer Journal 18(2):160-175 (2012), 32 pages.
Wulfing, Correctly Folded T-cell Receptor Fragments In The Periplasm Of Escherichia Coli. Influence Of Folding Catalysts. Journal of Molecular Biology 242(5):655-669 (1994).
Zhang, Genetic engineering with T cell receptors. Advanced Drug Delivery Reviews 64(8):756-762 (2012).
Zoete, Structure-Based, Rational Design of T Cell Receptors. Frontiers in Immunology 4:268 (2013), 19 pages.

\* cited by examiner

| | # of amino acid liability | % similar to human germline ||||  |
| --- | --- | --- | --- | --- | --- | --- |
| | | VH | # of a.a. mismatch | VK | # of a.a. mismatch | Total # of a.a. mismatch |
| xhCD8v2 | 2 | 91% | 9 | 92% | 7 | 16 |
| xhCD8v3 | 1 | 91% | 9 | 92% | 7 | 16 |
| xhCD8v4 | 2 | 93% | 7 | 92% | 7 | 14 |
| xhCD8v5 | 3 | 91% | 9 | 92% | 7 | 16 |
| xhCD8v6 | 5 | 86% | 14 | 98% | 2 | 16 |
| xhCD8v9 | 0 | 97% | 3 | 92% | 7 | 10 |
| xhCD8v10 | 2 | 92% | 8 | 98% | 2 | 10 |
| xhCD8v11 | 2 | 92% | 8 | 98% | 2 | 10 |
| xhCD8v12 | 0 | 97% | 3 | 94% | 5 | 8 |
| xhCD8v13 | 0 | 97% | 3 | 92% | 7 | 10 |
| xhCD8v14 | 2 | 93% | 7 | 98% | 2 | 9 |
| xhCD8v15 | 2 | 93% | 7 | 98% | 2 | 9 |

FIG. 18A

```
xhCD8v1 VH        QVHLQQSGPELVKPGASVKMSCKTSGYTFTKYTMHWVKQGHEESLEWIGHFNPNNDETKY
VH1-69 germline   QVQLVQSGAEVKKPGSSVKVSCKASGGTFSSYAISWVRQAPGQGLEWMGGIIPIFGTANY
xhCD8v1.1 VH      QVQLVQSGAEVKKPGSSVKVSCKASGYTFTKYAISWVRQAPGQGLEWMGHFNPNNDETKY
                  *** :*.****:*:**.:**:* : * ***:.::**:*   . ::.* xhCD8v1 VH        NQKFTGKATLTVDKSSTTAYMELRSLTSDDSALYYCARDGLGLRLFADWGQGTLITVSA
VH1-69 germline   AQKFQGRVTITADESTSTAYMELSSLRSEDTAVYYCAR
xhCD8v1.1 VH      NQKFQGRVTITADESTSTAYMELSSLRSEDTAVYYCARDGLGLRLFADWGQGTLVTVSS
                  *** * :.*:*.:.**:*****.**.*:::* ****                  :***:

xhCD8v1 VK        DIQMTQSPASLSASVGETVTITCGASENIYGALNWYQRKQGKSPQLLIFGATNLADGVSS
VK1-39 germline   DIQMTQSPSSLSASVGDRVTITCRASQSISSYLNWYQQKPGKAPKLLIYAASSLQSGVPS
xhCD8v1.1 VK      DIQMTQSPSSLSASVGDRVTITCRASENIYGALNWYQQKPGKAPKLLIYGATNLADGVPS
                  ******:***:.** .  . :** .*.****:..:.*..**.* xhCD8v1 VK        RFSGSGSDRQYSLKISSLHPDDVATYYCQNILDTPWTFGGGTKLEIK
VK1-39 germline   RFSGSGSGTDFTLTISSLQPEDFATYYCQQSYSTP
xhCD8v1.1 VK      RFSGSGSGTDFTLTISSLQPEDFATYYCQNILDTPWTFGGGTKLEIK
                  *******. : :*.***:*:* *****: .  *
```

FIG. 18B

```
xhCD8v1.1   QVQLVQSGAEVKKPGSSVKVSCKASGYTFTKYAISWVRQAPGQGLEWMGHFNPNNDETKY
xhCD8v2     QVQLVQSGAEVKKPGSSVKVSCKASGYRFHNFAISWVRQAPGQGLEWMGGIIPGHAKANY
xhCD8v3     QVQLVQSGAEVKKPGSSVKVSCKASGSRFYKFAISWVRQAPGQGLEWMGGIIPGHAKANY
xhCD8v4     QVQLVQSGAEVKKPGSSVKVSCKASGYTFTKYAISWVRQAPGQGLEWMGGIIPGHAKANY
xhCD8v5     QVQLVQSGAEVKKPGSSVKVSCKASGSGFRGHAISWVRQAPGQGLEWMGGIIPGHAKANY
xhCD8v9     QVQLVQSGAEVKKPGSSVKVSCKASGGTFSSYAISWVRQAPGQGLEWMGGIIPGAATANY
xhCD8v12    QVQLVQSGAEVKKPGSSVKVSCKASGGTFSSYAISWVRQAPGQGLEWMGGIIPGYATANY
xhCD8v13    QVQLVQSGAEVKKPGSSVKVSCKASGGTFSSYAISWVRQAPGQGLEWMGGIIPGYATANY
            ************************ *    *********************  * xhCD8v1.1   NQKFQGRVTITADESTSTAYMELSSLRSEDTAVYYCARDGLGLRLFADWGQGTLVTVSS
xhCD8v2     AQKFQGRVTITADESTSTAYMELSSLRSEDTAVYYCARDGLGIRLFADWGQGTLVTVSS
xhCD8v3     AQKFQGRVTITADESTSTAYMELSSLRSEDTAVYYCARDGLGIRLFADWGQGTLVTVSS
xhCD8v4     AQKFQGRVTITADESTSTAYMELSSLRSEDTAVYYCARDGLGIRLFADWGQGTLVTVSS
xhCD8v5     AQKFQGRVTITADESTSTAYMELSSLRSEDTAVYYCARDGLGIRLFADWGQGTLVTVSS
xhCD8v9     AQKFQGRVTITADESTSTAYMELSSLRSEDTAVYYCARDAAGIRLFADWGQGTLVTVSS
xhCD8v12    AQKFQGRVTITADESTSTAYMELSSLRSEDTAVYYCARDAAGIRLFADWGQGTLVTVSS
xhCD8v13    AQKFQGRVTITADESTSTAYMELSSLRSEDTAVYYCARDAAGIRLFADWGQGTLVTVSS
            ********************************************  *************
```

FIG. 18C

```
xhCD8v1.1    DIQMTQSPSSLSASVGDRVTITCRASENIYGALNWYQQKPGKAPKLLIYGATNLADGVPS
xhCD8v2      DIQMTQSPSSLSASVGDRVTITCRASQEIYGALNWYQQKPGKAPKLLIYGATNLQSGVPS
xhCD8v3      DIQMTQSPSSLSASVGDRVTITCRASQEIYGALNWYQQKPGKAPKLLIYGATNLQSGVPS
xhCD8v4      DIQMTQSPSSLSASVGDRVTITCRASQKIYGALNWYQQKPGKAPKLLIYGATNLQSGVPS
xhCD8v5      DIQMTQSPSSLSASVGDRVTITCRASQEIYGALNWYQQKPGKAPKLLIYGATNLQSGVPS
xhCD8v9      DIQMTQSPSSLSASVGDRVTITCRASQEIYGALNWYQQKPGKAPKLLIYGATNLQSGVPS
xhCD8v12     DIQMTQSPSSLSASVGDRVTITCRASQSIYGALNWYQQKPGKAPKLLIYGASNLQSGVPS
xhCD8v13     DIQMTQSPSSLSASVGDRVTITCRASQEIYGALNWYQQKPGKAPKLLIYGATNLQSGVPS
             **********************:.:******************** ** xhCD8v1.1    RFSGSGSGTDFTLTISSLQPEDFATYYCQNILDTPWTFGGGTKLEIK
xhCD8v2      RFSGSGSGTDFTLTISSLQPEDFATYYCQDIYDAPWTFGGGTKVEIK
xhCD8v3      RFSGSGSGTDFTLTISSLQPEDFATYYCQDIYDAPWTFGGGTKVEIK
xhCD8v4      RFSGSGSGTDFTLTISSLQPEDFATYYCQNTYDTPWTFGGGTKVEIK
xhCD8v5      RFSGSGSGTDFTLTISSLQPEDFATYYCQNTYDTPWTFGGGTKVEIK
xhCD8v9      RFSGSGSGTDFTLTISSLQPEDFATYYCQNTYDTPWTFGGGTKVEIK
xhCD8v12     RFSGSGSGTDFTLTISSLQPEDFATYYCQSTYDAPWTFGGGTKVEIK
xhCD8v13     RFSGSGSGTDFTLTISSLQPEDFATYYCQSTYTAPWTFGGGTKVEIK
             ****************************.   :.********:***
```

FIG. 18D

SEQUENCE LISTING

```
<160> NUMBER OF SEQ ID NOS: 389

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Lys Tyr Thr Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

His Phe Asn Pro Asn Asn Asp Glu Thr Lys Tyr Asn Gln Lys Phe Thr
1               5                   10                  15
```

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asp Gly Leu Gly Leu Arg Leu Phe Ala Asp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Asn Ile Leu Asp Thr Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Lys Tyr Ala Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

His Phe Asn Pro Asn Asn Asp Glu Thr Lys Tyr Asn Gln Lys Phe Gln
1               5                   10                  15

```
Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Asp Gly Leu Gly Leu Arg Leu Phe Ala Asp
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Arg Ala Ser Glu Asn Ile Tyr Gly Ala Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Gly Ala Thr Asn Leu Ala Asp
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Asn Ile Leu Asp Thr Pro Trp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Asn Phe Ala Ile Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Gly Ile Ile Pro Gly His Ala Lys Ala Asn Tyr Ala Gln Lys Phe Gln
```

```
1               5                  10                 15
Gly

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Asp Gly Leu Gly Ile Arg Leu Phe Ala Asp
1               5                  10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Arg Ala Ser Gln Glu Ile Tyr Gly Ala Leu Asn
1               5                  10

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Gly Ala Thr Asn Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Gln Asp Ile Tyr Asp Ala Pro Trp Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Lys Phe Ala Ile Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20
```

```
Gly Ile Ile Pro Gly His Ala Lys Ala Asn Tyr Ala Gln Lys Phe Gln
1               5                   10                  15
Gly
```

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

```
Asp Gly Leu Gly Ile Arg Leu Phe Ala Asp
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

```
Arg Ala Ser Gln Glu Ile Tyr Gly Ala Leu Asn
1               5                   10
```

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

```
Gly Ala Thr Asn Leu Gln Ser
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

```
Gln Asp Ile Tyr Asp Ala Pro Trp Thr
1               5
```

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

```
Lys Tyr Ala Ile Ser
1               5
```

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Gly Ile Ile Pro Gly His Ala Lys Ala Asn Tyr Ala Gln Lys Phe Gln
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Asp Gly Leu Gly Ile Arg Leu Phe Ala Asp
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Arg Ala Ser Gln Lys Ile Tyr Gly Ala Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Gly Ala Thr Asn Leu Gln Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Gln Asn Thr Tyr Asp Thr Pro Trp Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Gly His Ala Ile Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct -continued

```
<400> SEQUENCE: 32

Gly Ile Ile Pro Gly His Ala Lys Ala Asn Tyr Ala Gln Lys Phe Gln
1               5                   10                  15
Gly

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Asp Gly Leu Gly Ile Arg Leu Phe Ala Asp
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Arg Ala Ser Gln Lys Ile Tyr Gly Ala Leu Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Gly Ala Thr Asn Leu Gln Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Gln Asn Thr Tyr Asp Thr Pro Trp Thr
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Asp Tyr Gly Met Ser
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct
```

-continued

```
<400> SEQUENCE: 38

Asp Ile Asn Trp Ser Gly Glu Ile Thr Ala Tyr Ala Asp Ser Val Lys
1               5                   10                  15

Gly

<210> SEQ ID NO 39
<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Ser Asn Ser Tyr Arg Trp Asp Asp Ala Leu Asp Ile
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Arg Ala Ser Gln Ser Val Ser Ser Asn Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Gly Ala Ser Ser Arg Ala Thr
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gln Gln Tyr Gly Ser Ser Pro Pro Val Thr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Asp Tyr Ala Met His
1               5

<210> SEQ ID NO 44
<211> LENGTH: 17
<212> TYPE: PRT
<213> ORGANISM: Artificial Sequence
<220> FEATURE:
```

```
<223> OTHER INFORMATION: Synthetic Construct

<400> SEQUENCE: 44

Val Ile Ser Tyr Asp Gly Ser Asn Lys Tyr Tyr Ala Asp Ser Val Lys
1               5                   10                  15

Gly

<210> SEQ ID NO 45
<211> LENGTH: 13
<212> TYPE: PRT
<213> ORGANISM: Artificial Sequence
<220> FEATURE:
<223> OTHER INFORMATION: Synthetic Construct

<400> SEQUENCE: 45

Asp Arg Ile Gly Trp Tyr Asp Tyr Asp Ala Phe Asp Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Arg Ala Ser His Ser Val Gly Ser Asn Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct

<400> SEQUENCE: 47

Asp Ala Ser Asn Arg Ala Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Gln Arg Ser Asn Trp Pro Pro Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Gly Tyr Thr Phe Thr Lys Tyr
1               5

<210> SEQ ID NO 50
<211> LENGTH: 6
<212> TYPE: PRT
<213> ORGANISM: Artificial Sequence
```

<220> FEATURE:
<223> OTHER INFORMATION: Synthetic Construct

<400> SEQUENCE: 50

Asn Pro Asn Asn Asp Glu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Gly Tyr Arg Phe His Asn Phe
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

Ile Pro Gly His Ala Lys
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Gly Ser Arg Phe Tyr Lys Phe
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Gly Ser Gly Phe Arg Gly His
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Gly Phe Thr Phe Asp Asp Tyr
1               5

<210> SEQ ID NO 56
<211> LENGTH: 6
<212> TYPE: PRT
<213> ORGANISM: Artificial Sequence
<220> FEATURE:

<223> OTHER INFORMATION: Synthetic Construct

<400> SEQUENCE: 56

Asn Trp Ser Gly Glu Ile
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Construct

<400> SEQUENCE: 57

Ser Tyr Asp Gly Ser Asn
1               5

<210> SEQ ID NO 58
<211> LENGTH: 119
<212> TYPE: PRT
<213> ORGANISM: Artificial Sequence
<220> FEATURE:
<223> OTHER INFORMATION: Synthetic Construct

<400> SEQUENCE: 58

Gln Val His Leu Gln Gln Ser Gly Pro Glu Leu Val Lys Pro Gly Ala
1               5                   10                  15

Ser Val Lys Met Ser Cys Lys Thr Ser Gly Tyr Thr Phe Thr Lys Tyr
            20                  25                  30

Thr Met His Trp Val Lys Gln Gly His Glu Glu Ser Leu Glu Trp Ile
        35                  40                  45

Gly His Phe Asn Pro Asn Asn Asp Glu Thr Lys Tyr Asn Gln Lys Phe
    50                  55                  60

Thr Gly Lys Ala Thr Leu Thr Val Asp Lys Ser Ser Thr Thr Ala Tyr
65                  70                  75                  80

Met Glu Leu Arg Ser Leu Thr Ser Asp Asp Ser Ala Leu Tyr Tyr Cys
                85                  90                  95

Ala Arg Asp Gly Leu Gly Leu Arg Leu Phe Ala Asp Trp Gly Gln Gly
            100                 105                 110

Thr Leu Ile Thr Val Ser Ala
        115

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Phe Gly Ala Thr Asn Leu Ala Asp Gly Val Ser Ser Arg Phe Ser Gly
    50                  55                  60

Ser Gly Ser Asp Arg Gln Tyr Ser Leu Lys Ile Ser Ser Leu His Pro
65                  70                  75                  80

Asp Asp Val Ala Thr Tyr Tyr Cys Gln Asn Ile Leu Asp Thr Pro Trp
                85                  90                  95

Thr Phe Gly Gly Gly Thr Lys Leu Glu Ile Lys
            100                 105

<210> SEQ ID NO 60
<211> LENGTH: 119
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Lys Tyr
                20                  25                  30

Ala Ile Ser Trp Val Arg Gln Ala Pro Gly Gln Gly Leu Glu Trp Met
            35                  40                  45

Gly His Phe Asn Pro Asn Asn Asp Glu Thr Lys Tyr Asn Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Leu Arg Leu Phe Ala Asp Trp Gly Gln Gly
                100                 105                 110

Thr Leu Val Thr Val Ser Ser
            115

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Ile Leu Asp Thr Pro Trp
                85                  90                  95

Thr Phe Gly Gly Gly Thr Lys Leu Glu Ile Lys
            100                 105

<210> SEQ ID NO 62
<211> LENGTH: 119
<212> TYPE: PRT
<213> ORGANISM: Artificial Sequence
<220> FEATURE:
<223> OTHER INFORMATION: Synthetic Construct -continued

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe His Asn Phe
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asp Ile Tyr Asp Ala Pro Trp
                85                  90                  95

Thr Phe Gly Gly Gly Thr Lys Val Glu Ile Lys
            100                 105

<210> SEQ ID NO 64
<211> LENGTH: 119
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Ser Arg Phe Tyr Lys Phe
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

-continued

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Leu Gly Ile Arg Leu Phe Ala Asp Trp Gly Gln Gly
            100                 105                 110

Thr Leu Val Thr Val Ser Ser
        115

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Tyr Gly Ala
             20                  25                  30

Leu Asn Trp Tyr Gln Gln Lys Pro Gly Lys Ala Pro Lys Leu Leu Ile
         35                  40                  45

Tyr Gly Ala Thr Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asp Ile Tyr Asp Ala Pro Trp
                 85                  90                  95

Thr Phe Gly Gly Gly Thr Lys Val Glu Ile Lys
            100                 105

<210> SEQ ID NO 66
<211> LENGTH: 119
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Lys Tyr
             20                  25                  30

Ala Ile Ser Trp Val Arg Gln Ala Pro Gly Gln Gly Leu Glu Trp Met
         35                  40                  45

Gly Gly Ile Ile Pro Gly His Ala Lys Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Leu Gly Ile Arg Leu Phe Ala Asp Trp Gly Gln Gly
            100                 105                 110

Thr Leu Val Thr Val Ser Ser
        115

<210> SEQ ID NO 67
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Tyr Asp Thr Pro Trp
                85                  90                  95

Thr Phe Gly Gly Gly Thr Lys Val Glu Ile Lys
            100                 105

<210> SEQ ID NO 68
<211> LENGTH: 119
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Ser Gly Phe Arg Gly His
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Gly Ala
            20                  25                  30
```

```
Leu Asn Trp Tyr Gln Gln Lys Pro Gly Lys Ala Pro Lys Leu Leu Ile
            35                  40                  45

Tyr Gly Ala Thr Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Thr Tyr Asp Thr Pro Trp
                 85                  90                  95

Thr Phe Gly Gly Gly Thr Lys Val Glu Ile Lys
            100                 105
```

<210> SEQ ID NO 70
<211> LENGTH: 121
<212> TYPE: PRT
<213> ORGANISM: Artificial Sequence
<220> FEATURE:
<223> OTHER INFORMATION: Synthetic Construct

<400> SEQUENCE: 70

```
Glu Val Gln Leu Val Glu Ser Gly Gly Gly Ala Val Arg Pro Gly Gly
 1               5                  10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
         35                  40                  45

Ser Asp Ile Asn Trp Ser Gly Glu Ile Thr Ala Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Asn Ser Tyr Arg Trp Asp Asp Ala Leu Asp Ile Trp Gly
            100                 105                 110

Gln Gly Thr Met Val Thr Val Ser Ser
         115                 120
```

<210> SEQ ID NO 71
<211> LENGTH: 108
<212> TYPE: PRT
<213> ORGANISM: Artificial Sequence
<220> FEATURE:
<223> OTHER INFORMATION: Synthetic Construct

<400> SEQUENCE: 71

```
Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Pro
                 85                  90                  95

Val Thr Phe Gly Gln Gly Thr Lys Val Glu Ile Lys
            100                 105
```

<210> SEQ ID NO 72
<211> LENGTH: 122
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Gly Trp Tyr Asp Tyr Asp Ala Phe Asp Ile Trp
            100                 105                 110

Gly Gln Gly Thr Met Val Thr Val Ser Ser
        115                 120

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Glu Ile Val Leu Thr Gln Ser Pro Ala Thr Leu Ser Val Thr Pro Gly
1               5                   10                  15

Glu Gly Ala Thr Leu Ser Cys Arg Ala Ser His Ser Val Gly Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Leu Ala Val Tyr Tyr Cys Gln Gln Arg Ser Asn Trp Pro Pro
                85                  90                  95

Thr Phe Gly Gln Gly Thr Arg Leu Glu Ile Lys
            100                 105

<210> SEQ ID NO 74
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of 1, 2, 3, 4, 5, 6,
      7, 8, 9, 10, 11, or 12
<220> FEATURE:

```
<221> NAME/KEY: VARIANT
<222> LOCATION: 5
<223> OTHER INFORMATION: Can be present in repeats of 0, 1, 2, or 3

<400> SEQUENCE: 74

Gly Gly Gly Ser Gly
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of 1, 2, 3, 4, 5, 6,
      7, 8, 9, 10, 11, or 12
<220> FEATURE:
<221> NAME/KEY: VARIANT
<222> LOCATION: 6
<223> OTHER INFORMATION: Can be present in repeats of 0, 1, 2, or 3

<400> SEQUENCE: 75

Gly Gly Gly Gly Ser Gly
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(6)
<223> OTHER INFORMATION: Can be present in repeats of 1, 2, 3, 4, 5, 6,
      7, 8, 9, 10, 11, or 12
<220> FEATURE:
<221> NAME/KEY: VARIANT
<222> LOCATION: 7
<223> OTHER INFORMATION: Can be present in repeats of 0, 1, 2, or 3

<400> SEQUENCE: 76

Gly Gly Gly Gly Gly Ser Gly
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of 2, 3, or 4
<220> FEATURE:
<221> NAME/KEY: VARIANT
<222> LOCATION: 6
<223> OTHER INFORMATION: Can be present in repeats of 0

<400> SEQUENCE: 77

Gly Gly Gly Gly Ser Gly
1               5

<210> SEQ ID NO 78
<211> LENGTH: 6
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of 3
<220> FEATURE:
<221> NAME/KEY: VARIANT
<222> LOCATION: 6
<223> OTHER INFORMATION: Can be present in repeats of 0

<400> SEQUENCE: 78

Gly Gly Gly Gly Ser Gly
1               5

<210> SEQ ID NO 79
<211> LENGTH: 15
<212> TYPE: PRT
<213> ORGANISM: Artificial Sequence
<220> FEATURE:
<223> OTHER INFORMATION: Synthetic Construct

<400> SEQUENCE: 79

Gly Gly Gly Gly Ser Gly Gly Gly Ser Gly Gly Gly Gly Ser
1               5                   10                  15

<210> SEQ ID NO 80
<211> LENGTH: 133
<212> TYPE: PRT
<213> ORGANISM: Artificial Sequence
<220> FEATURE:
<223> OTHER INFORMATION: Synthetic Construct

<400> SEQUENCE: 80

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
    115                 120                 125

Ile Ser Thr Leu Thr
    130

<210> SEQ ID NO 81
<211> LENGTH: 133
<212> TYPE: PRT
<213> ORGANISM: Artificial Sequence
<220> FEATURE:
<223> OTHER INFORMATION: Synthetic Construct

<400> SEQUENCE: 81

Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
                130

<210> SEQ ID NO 82
<211> LENGTH: 272
<212> TYPE: PRT
<213> ORGANISM: Artificial Sequence
<220> FEATURE:
<223> OTHER INFORMATION: Synthetic Construct

<400> SEQUENCE: 82

Met Asp Ser Tyr Leu Leu Met Trp Gly Leu Leu Thr Phe Ile Met Val
 1               5                  10                  15

Pro Gly Cys Gln Ala Glu Leu Cys Asp Asp Pro Pro Glu Ile Pro
                20                  25                  30

His Ala Thr Phe Lys Ala Met Ala Tyr Lys Glu Gly Thr Met Leu Asn
                 35                  40                  45

Cys Glu Cys Lys Arg Gly Phe Arg Arg Ile Lys Ser Gly Ser Leu Tyr
 50                  55                  60

Met Leu Cys Thr Gly Asn Ser Ser His Ser Ser Trp Asp Asn Gln Cys
 65                  70                  75                  80

Gln Cys Thr Ser Ser Ala Thr Arg Asn Thr Thr Lys Gln Val Thr Pro
                 85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
                115                 120                 125

Pro Pro Trp Glu Asn Glu Ala Thr Glu Arg Ile Tyr His Phe Val Val
 130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
                195                 200                 205

Ser Glu Thr Ser Cys Leu Val Thr Thr Thr Asp Phe Gln Ile Gln Thr
                210                 215                 220

Glu Met Ala Ala Thr Met Glu Thr Ser Ile Phe Thr Thr Glu Tyr Gln
225                 230                 235                 240
```

-continued

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Thr Ile
        260                 265                 270

<210> SEQ ID NO 83
<211> LENGTH: 551
<212> TYPE: PRT
<213> ORGANISM: Artificial Sequence
<220> FEATURE:
<223> OTHER INFORMATION: Synthetic Construct

<400> SEQUENCE: 83

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

```
Leu Leu Gln Gln Asp Lys Val Pro Glu Pro Ala Ser Leu Ser Ser Asn
                340                 345                 350

His Ser Leu Thr Ser Cys Phe Thr Asn Gln Gly Tyr Phe Phe Phe His
            355                 360                 365

Leu Pro Asp Ala Leu Glu Ile Glu Ala Cys Gln Val Tyr Phe Thr Tyr
        370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Pro Ser Thr Ala Pro Gly Gly Ser
        435                 440                 445

Gly Ala Gly Glu Glu Arg Met Pro Pro Ser Leu Gln Glu Arg Val Pro
        450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Glu Leu Val Leu Arg Glu Ala
            485                 490                 495

Gly Glu Glu Val Pro Asp Ala Gly Pro Arg Glu Gly Val Ser Phe Pro
                500                 505                 510

Trp Ser Arg Pro Pro Gly Gln Gly Glu Phe Arg Ala Leu Asn Ala Arg
            515                 520                 525

Leu Pro Leu Asn Thr Asp Ala Tyr Leu Ser Leu Gln Glu Leu Gln Gly
        530                 535                 540

Gln Asp Pro Thr His Leu Val
545                 550

<210> SEQ ID NO 84
<211> LENGTH: 369
<212> TYPE: PRT
<213> ORGANISM: Artificial Sequence
<220> FEATURE:
<223> OTHER INFORMATION: Synthetic Construct

<400> SEQUENCE: 84

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140
```

```
Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 85
<211> LENGTH: 133
<212> TYPE: PRT
<213> ORGANISM: Artificial Sequence
<220> FEATURE:
<223> OTHER INFORMATION: Synthetic Construct

<400> SEQUENCE: 85

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
```

```
<210> SEQ ID NO 86
<211> LENGTH: 133
<212> TYPE: PRT
<213> ORGANISM: Artificial Sequence
<220> FEATURE:
<223> OTHER INFORMATION: Synthetic Construct

<400> SEQUENCE: 86

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 87
<211> LENGTH: 133
<212> TYPE: PRT
<213> ORGANISM: Artificial Sequence
<220> FEATURE:
<223> OTHER INFORMATION: Synthetic Construct

<400> SEQUENCE: 87

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 88
<211> LENGTH: 133
```

<212> TYPE: PRT
<213> ORGANISM: Artificial Sequence
<220> FEATURE:
<223> OTHER INFORMATION: Synthetic Construct

<400> SEQUENCE: 88

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 89
<211> LENGTH: 133
<212> TYPE: PRT
<213> ORGANISM: Artificial Sequence
<220> FEATURE:
<223> OTHER INFORMATION: Synthetic Construct

<400> SEQUENCE: 89

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ser Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 90
<211> LENGTH: 133
<212> TYPE: PRT
<213> ORGANISM: Artificial Sequence
<220> FEATURE:
<223> OTHER INFORMATION: Synthetic Construct

<400> SEQUENCE: 90

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 91
<211> LENGTH: 133
<212> TYPE: PRT
<213> ORGANISM: Artificial Sequence
<220> FEATURE:
<223> OTHER INFORMATION: Synthetic Construct

<400> SEQUENCE: 91

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 92
<211> LENGTH: 133
<212> TYPE: PRT
<213> ORGANISM: Artificial Sequence
<220> FEATURE:
<223> OTHER INFORMATION: Synthetic Construct

<400> SEQUENCE: 92

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 93
<211> LENGTH: 133
<212> TYPE: PRT
<213> ORGANISM: Artificial Sequence
<220> FEATURE:
<223> OTHER INFORMATION: Synthetic Construct

<400> SEQUENCE: 93

Ala Pro Thr Ser Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 94
<211> LENGTH: 133
<212> TYPE: PRT
<213> ORGANISM: Artificial Sequence
<220> FEATURE:
<223> OTHER INFORMATION: Synthetic Construct

<400> SEQUENCE: 94

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

```
Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 95
<211> LENGTH: 133
<212> TYPE: PRT
<213> ORGANISM: Artificial Sequence
<220> FEATURE:
<223> OTHER INFORMATION: Synthetic Construct

<400> SEQUENCE: 95

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Glu Met Leu Thr Ala Lys Phe Tyr Met Pro Lys
             35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Ser Ser Ile
            115                 120                 125

Ile Ser Thr Leu Thr
            130

<210> SEQ ID NO 96
<211> LENGTH: 133
<212> TYPE: PRT
<213> ORGANISM: Artificial Sequence
<220> FEATURE:
<223> OTHER INFORMATION: Synthetic Construct

<400> SEQUENCE: 96

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Asp Met Leu Thr Ala Lys Phe Tyr Met Pro Lys
             35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
```

65                  70                  75                  80
Arg Pro Arg Asp Leu Ile Ser Ser Ile Asn Val Ile Val Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 97
<211> LENGTH: 133
<212> TYPE: PRT
<213> ORGANISM: Artificial Sequence
<220> FEATURE:
<223> OTHER INFORMATION: Synthetic Construct

<400> SEQUENCE: 97

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 98
<211> LENGTH: 133
<212> TYPE: PRT
<213> ORGANISM: Artificial Sequence
<220> FEATURE:
<223> OTHER INFORMATION: Synthetic Construct

<400> SEQUENCE: 98

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

```
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 99
<211> LENGTH: 133
<212> TYPE: PRT
<213> ORGANISM: Artificial Sequence
<220> FEATURE:
<223> OTHER INFORMATION: Synthetic Construct

<400> SEQUENCE: 99

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 100
<211> LENGTH: 133
<212> TYPE: PRT
<213> ORGANISM: Artificial Sequence
<220> FEATURE:
<223> OTHER INFORMATION: Synthetic Construct

<400> SEQUENCE: 100

Ala Pro Thr Ser Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125
```

Ile Ser Thr Leu Thr
    130

<210> SEQ ID NO 101
<211> LENGTH: 133
<212> TYPE: PRT
<213> ORGANISM: Artificial Sequence
<220> FEATURE:
<223> OTHER INFORMATION: Synthetic Construct

<400> SEQUENCE: 101

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 102
<211> LENGTH: 133
<212> TYPE: PRT
<213> ORGANISM: Artificial Sequence
<220> FEATURE:
<223> OTHER INFORMATION: Synthetic Construct

<400> SEQUENCE: 102

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ser Ser Ile
        115                 120                 125

Ile Ser Thr Leu Thr
    130

```
<210> SEQ ID NO 103
<211> LENGTH: 133
<212> TYPE: PRT
<213> ORGANISM: Artificial Sequence
<220> FEATURE:
<223> OTHER INFORMATION: Synthetic Construct

<400> SEQUENCE: 103

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ser Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 104
<211> LENGTH: 133
<212> TYPE: PRT
<213> ORGANISM: Artificial Sequence
<220> FEATURE:
<223> OTHER INFORMATION: Synthetic Construct

<400> SEQUENCE: 104

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 105
<211> LENGTH: 133
<212> TYPE: PRT
<213> ORGANISM: Artificial Sequence
<220> FEATURE:
```

<223> OTHER INFORMATION: Synthetic Construct

<400> SEQUENCE: 105

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 106
<211> LENGTH: 133
<212> TYPE: PRT
<213> ORGANISM: Artificial Sequence
<220> FEATURE:
<223> OTHER INFORMATION: Synthetic Construct

<400> SEQUENCE: 106

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 107
<211> LENGTH: 133
<212> TYPE: PRT
<213> ORGANISM: Artificial Sequence
<220> FEATURE:
<223> OTHER INFORMATION: Synthetic Construct

<400> SEQUENCE: 107

Ala Pro Thr Ser Ser Ser Thr Lys Lys Thr Gln Leu Gln Leu Glu Asp

```
                1               5                  10                 15
Leu Leu Leu Asp Leu Gln Met Ile Leu Asn Gly Ile Asn Asn Tyr Lys
                20                 25                 30

Asn Pro Lys Leu Thr Ala Met Leu Thr Lys Lys Phe Tyr Met Pro Lys
                35                 40                 45

Lys Ala Thr Glu Leu Lys His Leu Gln Cys Leu Glu Glu Leu Lys
                50                 55                 60

Pro Leu Glu Glu Val Leu Asn Leu Ala Gln Ser Lys Asn Phe His Leu
65                  70                 75                 80

Arg Pro Arg Asp Leu Ile Ser Asn Ile Asn Val Ile Val Leu Glu Leu
                85                 90                 95

Lys Gly Ser Glu Thr Thr Phe Met Cys Glu Tyr Ala Asp Glu Thr Ala
                100                105                110

Thr Ile Val Glu Phe Leu Asn Arg Trp Ile Thr Phe Cys Gln Ser Ile
                115                120                125

Ile Ser Thr Leu Thr
        130
```

<210> SEQ ID NO 108
<211> LENGTH: 133
<212> TYPE: PRT
<213> ORGANISM: Artificial Sequence
<220> FEATURE:
<223> OTHER INFORMATION: Synthetic Construct

<400> SEQUENCE: 108

```
Ala Pro Thr Ser Ser Ser Thr Lys Lys Thr Gln Leu Gln Leu Glu Glu
1               5                  10                 15

Leu Leu Leu Asp Leu Gln Met Ile Leu Asn Gly Ile Asn Asn Tyr Lys
                20                 25                 30

Asn Pro Lys Leu Thr Ala Met Leu Thr Lys Lys Phe Tyr Met Pro Lys
                35                 40                 45

Lys Ala Thr Glu Leu Lys His Leu Gln Cys Leu Glu Glu Leu Lys
                50                 55                 60

Pro Leu Glu Glu Val Leu Asn Leu Ala Gln Ser Lys Asn Phe His Leu
65                  70                 75                 80

Arg Pro Arg Asp Leu Ile Ser Asn Ile Asn Val Ile Val Leu Glu Leu
                85                 90                 95

Lys Gly Ser Glu Thr Thr Phe Met Cys Glu Tyr Ala Asp Glu Thr Ala
                100                105                110

Thr Ile Val Glu Phe Leu Asn Arg Trp Ile Thr Phe Cys Gln Ser Ile
                115                120                125

Ile Ser Thr Leu Thr
        130
```

<210> SEQ ID NO 109
<211> LENGTH: 133
<212> TYPE: PRT
<213> ORGANISM: Artificial Sequence
<220> FEATURE:
<223> OTHER INFORMATION: Synthetic Construct

<400> SEQUENCE: 109

```
Ala Pro Thr Ser Ser Ser Thr Lys Lys Thr Gln Leu Gln Leu Glu His
1               5                  10                 15

Leu Leu Leu Asp Leu Gln Met Ile Leu Asn Gly Ile Asn Asn Tyr Lys
                20                 25                 30
```

```
Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Ser Ser Ile
            115                 120                 125

Ile Ser Thr Leu Thr
        130

<210> SEQ ID NO 110
<211> LENGTH: 133
<212> TYPE: PRT
<213> ORGANISM: Artificial Sequence
<220> FEATURE:
<223> OTHER INFORMATION: Synthetic Construct

<400> SEQUENCE: 110

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ser Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 111
<211> LENGTH: 133
<212> TYPE: PRT
<213> ORGANISM: Artificial Sequence
<220> FEATURE:
<223> OTHER INFORMATION: Synthetic Construct

<400> SEQUENCE: 111

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
    50                  55                  60
```

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 112
<211> LENGTH: 133
<212> TYPE: PRT
<213> ORGANISM: Artificial Sequence
<220> FEATURE:
<223> OTHER INFORMATION: Synthetic Construct

<400> SEQUENCE: 112

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 113
<211> LENGTH: 133
<212> TYPE: PRT
<213> ORGANISM: Artificial Sequence
<220> FEATURE:
<223> OTHER INFORMATION: Synthetic Construct

<400> SEQUENCE: 113

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu

```
                    85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Cys Gln Ser Ile
                    115                 120                 125

Ile Ser Thr Leu Thr
            130

<210> SEQ ID NO 114
<211> LENGTH: 133
<212> TYPE: PRT
<213> ORGANISM: Artificial Sequence
<220> FEATURE:
<223> OTHER INFORMATION: Synthetic Construct

<400> SEQUENCE: 114

Ala Pro Thr Ser Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Cys Gln Ser Ile
                    115                 120                 125

Ile Ser Thr Leu Thr
            130

<210> SEQ ID NO 115
<211> LENGTH: 133
<212> TYPE: PRT
<213> ORGANISM: Artificial Sequence
<220> FEATURE:
<223> OTHER INFORMATION: Synthetic Construct

<400> SEQUENCE: 115

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110
```

Thr Ile Val Glu Phe Leu Asn Arg Trp Ile Thr Phe Cys Gln Ser Ile
            115                 120                 125

Ile Ser Thr Leu Thr
        130

<210> SEQ ID NO 116
<211> LENGTH: 133
<212> TYPE: PRT
<213> ORGANISM: Artificial Sequence
<220> FEATURE:
<223> OTHER INFORMATION: Synthetic Construct

<400> SEQUENCE: 116

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ser Ser Ile
            115                 120                 125

Ile Ser Thr Leu Thr
        130

<210> SEQ ID NO 117
<211> LENGTH: 133
<212> TYPE: PRT
<213> ORGANISM: Artificial Sequence
<220> FEATURE:
<223> OTHER INFORMATION: Synthetic Construct

<400> SEQUENCE: 117

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 118
<211> LENGTH: 133
<212> TYPE: PRT
<213> ORGANISM: Artificial Sequence
<220> FEATURE:
<223> OTHER INFORMATION: Synthetic Construct

<400> SEQUENCE: 118

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 119
<211> LENGTH: 133
<212> TYPE: PRT
<213> ORGANISM: Artificial Sequence
<220> FEATURE:
<223> OTHER INFORMATION: Synthetic Construct

<400> SEQUENCE: 119

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 120
<211> LENGTH: 133
<212> TYPE: PRT

<213> ORGANISM: Artificial Sequence
<220> FEATURE:
<223> OTHER INFORMATION: Synthetic Construct

<400> SEQUENCE: 120

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Ala Met Leu Thr Lys Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
    130
```

<210> SEQ ID NO 121
<211> LENGTH: 133
<212> TYPE: PRT
<213> ORGANISM: Artificial Sequence
<220> FEATURE:
<223> OTHER INFORMATION: Synthetic Construct

<400> SEQUENCE: 121

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Glu Met Leu Thr Ala Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Ser Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
    130
```

<210> SEQ ID NO 122
<211> LENGTH: 133
<212> TYPE: PRT
<213> ORGANISM: Artificial Sequence
<220> FEATURE:
<223> OTHER INFORMATION: Synthetic Construct

<400> SEQUENCE: 122

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 123
<211> LENGTH: 133
<212> TYPE: PRT
<213> ORGANISM: Artificial Sequence
<220> FEATURE:
<223> OTHER INFORMATION: Synthetic Construct

<400> SEQUENCE: 123

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 124
<211> LENGTH: 133
<212> TYPE: PRT
<213> ORGANISM: Artificial Sequence
<220> FEATURE:
<223> OTHER INFORMATION: Synthetic Construct

<400> SEQUENCE: 124

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys

```
            20                  25                  30
Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
            130

<210> SEQ ID NO 125
<211> LENGTH: 133
<212> TYPE: PRT
<213> ORGANISM: Artificial Sequence
<220> FEATURE:
<223> OTHER INFORMATION: Synthetic Construct

<400> SEQUENCE: 125

Ala Pro Thr Ser Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
            130

<210> SEQ ID NO 126
<211> LENGTH: 133
<212> TYPE: PRT
<213> ORGANISM: Artificial Sequence
<220> FEATURE:
<223> OTHER INFORMATION: Synthetic Construct

<400> SEQUENCE: 126

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45
```

```
Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
            130
```

<210> SEQ ID NO 127
<211> LENGTH: 133
<212> TYPE: PRT
<213> ORGANISM: Artificial Sequence
<220> FEATURE:
<223> OTHER INFORMATION: Synthetic Construct

<400> SEQUENCE: 127

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Glu Met Leu Thr Ala Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Ser Ser Ile
                115                 120                 125

Ile Ser Thr Leu Thr
            130
```

<210> SEQ ID NO 128
<211> LENGTH: 133
<212> TYPE: PRT
<213> ORGANISM: Artificial Sequence
<220> FEATURE:
<223> OTHER INFORMATION: Synthetic Construct

<400> SEQUENCE: 128

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Asp Met Leu Thr Ala Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80
```

Arg Pro Arg Asp Leu Ile Ser Ser Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 129
<211> LENGTH: 133
<212> TYPE: PRT
<213> ORGANISM: Artificial Sequence
<220> FEATURE:
<223> OTHER INFORMATION: Synthetic Construct

<400> SEQUENCE: 129

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 130
<211> LENGTH: 133
<212> TYPE: PRT
<213> ORGANISM: Artificial Sequence
<220> FEATURE:
<223> OTHER INFORMATION: Synthetic Construct

<400> SEQUENCE: 130

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala

```
            100                 105                 110
Thr Ile Val Glu Phe Leu Asn Arg Trp Ile Thr Phe Ala Gln Ser Ile
        115                 120                 125

Ile Ser Thr Leu Thr
        130

<210> SEQ ID NO 131
<211> LENGTH: 133
<212> TYPE: PRT
<213> ORGANISM: Artificial Sequence
<220> FEATURE:
<223> OTHER INFORMATION: Synthetic Construct

<400> SEQUENCE: 131

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 132
<211> LENGTH: 133
<212> TYPE: PRT
<213> ORGANISM: Artificial Sequence
<220> FEATURE:
<223> OTHER INFORMATION: Synthetic Construct

<400> SEQUENCE: 132

Ala Pro Thr Ser Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125
```

```
Ile Ser Thr Leu Thr
    130

<210> SEQ ID NO 133
<211> LENGTH: 133
<212> TYPE: PRT
<213> ORGANISM: Artificial Sequence
<220> FEATURE:
<223> OTHER INFORMATION: Synthetic Construct

<400> SEQUENCE: 133

Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 134
<211> LENGTH: 133
<212> TYPE: PRT
<213> ORGANISM: Artificial Sequence
<220> FEATURE:
<223> OTHER INFORMATION: Synthetic Construct

<400> SEQUENCE: 134

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Ser Ser Ile
        115                 120                 125

Ile Ser Thr Leu Thr
    130

<210> SEQ ID NO 135
```

<211> LENGTH: 133
<212> TYPE: PRT
<213> ORGANISM: Artificial Sequence
<220> FEATURE:
<223> OTHER INFORMATION: Synthetic Construct

<400> SEQUENCE: 135

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Ala Met Leu Thr Lys Lys Phe Tyr Met Pro Lys
        35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Ser Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
        130

<210> SEQ ID NO 136
<211> LENGTH: 133
<212> TYPE: PRT
<213> ORGANISM: Artificial Sequence
<220> FEATURE:
<223> OTHER INFORMATION: Synthetic Construct

<400> SEQUENCE: 136

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Ala Met Leu Thr Lys Lys Phe Tyr Met Pro Lys
        35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Ala Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
        130

<210> SEQ ID NO 137
<211> LENGTH: 133
<212> TYPE: PRT
<213> ORGANISM: Artificial Sequence
<220> FEATURE:
<223> OTHER INFORMATION: Synthetic Construct

<400> SEQUENCE: 137

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
    130

<210> SEQ ID NO 138
<211> LENGTH: 133
<212> TYPE: PRT
<213> ORGANISM: Artificial Sequence
<220> FEATURE:
<223> OTHER INFORMATION: Synthetic Construct

<400> SEQUENCE: 138

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
    130

<210> SEQ ID NO 139
<211> LENGTH: 133
<212> TYPE: PRT
<213> ORGANISM: Artificial Sequence
<220> FEATURE:
<223> OTHER INFORMATION: Synthetic Construct

<400> SEQUENCE: 139

Ala Pro Thr Ser Ser Ser Thr Lys Lys Thr Gln Leu Gln Leu Glu Asp
1               5                   10                  15

```
Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 140
<211> LENGTH: 133
<212> TYPE: PRT
<213> ORGANISM: Artificial Sequence
<220> FEATURE:
<223> OTHER INFORMATION: Synthetic Construct

<400> SEQUENCE: 140

Ala Pro Thr Ser Ser Ser Thr Lys Lys Thr Gln Leu Gln Leu Glu Glu
 1               5                  10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 141
<211> LENGTH: 133
<212> TYPE: PRT
<213> ORGANISM: Artificial Sequence
<220> FEATURE:
<223> OTHER INFORMATION: Synthetic Construct

<400> SEQUENCE: 141

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
```

```
                35                  40                  45
Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Ser Ser Ile
                115                 120                 125

Ile Ser Thr Leu Thr
                130

<210> SEQ ID NO 142
<211> LENGTH: 133
<212> TYPE: PRT
<213> ORGANISM: Artificial Sequence
<220> FEATURE:
<223> OTHER INFORMATION: Synthetic Construct

<400> SEQUENCE: 142

Ala Pro Thr Ser Ser Ser Thr Lys Lys Thr Gln Leu Gln Leu Glu His
 1                   5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
                 35                  40                  45

Lys Ala Thr Glu Leu Lys His Leu Gln Cys Leu Glu Glu Gln Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Ser Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
                130

<210> SEQ ID NO 143
<211> LENGTH: 133
<212> TYPE: PRT
<213> ORGANISM: Artificial Sequence
<220> FEATURE:
<223> OTHER INFORMATION: Synthetic Construct

<400> SEQUENCE: 143

Ala Pro Thr Ser Ser Ser Thr Lys Lys Thr Gln Leu Gln Leu Glu His
 1                   5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
                 35                  40                  45

Lys Ala Thr Glu Leu Lys His Leu Gln Cys Leu Glu Glu Gln Leu Lys
 50                  55                  60
```

Pro Leu Glu Glu Val Leu Asn Leu Ala Gln Ser Lys Asn Phe His Leu
 65                  70                  75                  80

Arg Pro Arg Asp Leu Ile Ser Ala Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 144
<211> LENGTH: 133
<212> TYPE: PRT
<213> ORGANISM: Artificial Sequence
<220> FEATURE:
<223> OTHER INFORMATION: Synthetic Construct

<400> SEQUENCE: 144

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
             35                  40                  45

Lys Ala Thr Glu Leu Lys His Leu Gln Cys Leu Glu Glu Gln Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Glu Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 145
<211> LENGTH: 133
<212> TYPE: PRT
<213> ORGANISM: Artificial Sequence
<220> FEATURE:
<223> OTHER INFORMATION: Synthetic Construct

<400> SEQUENCE: 145

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
             35                  40                  45

Lys Ala Thr Glu Leu Lys His Leu Gln Cys Leu Glu Glu Gln Leu Lys
         50                  55                  60

Pro Leu Glu Glu Val Leu Asn Leu Ala Gln Ser Lys Asn Phe His Leu
 65                  70                  75                  80

Arg Pro Arg His Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 146
<211> LENGTH: 133
<212> TYPE: PRT
<213> ORGANISM: Artificial Sequence
<220> FEATURE:
<223> OTHER INFORMATION: Synthetic Construct

<400> SEQUENCE: 146

Ala Pro Thr Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 147
<211> LENGTH: 133
<212> TYPE: PRT
<213> ORGANISM: Artificial Sequence
<220> FEATURE:
<223> OTHER INFORMATION: Synthetic Construct

<400> SEQUENCE: 147

Ala Pro Thr Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile

```
                    115                 120                 125

Ile Ser Thr Leu Thr
        130

<210> SEQ ID NO 148
<211> LENGTH: 133
<212> TYPE: PRT
<213> ORGANISM: Artificial Sequence
<220> FEATURE:
<223> OTHER INFORMATION: Synthetic Construct

<400> SEQUENCE: 148

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Ser Ser Ile
        115                 120                 125

Ile Ser Thr Leu Thr
        130

<210> SEQ ID NO 149
<211> LENGTH: 133
<212> TYPE: PRT
<213> ORGANISM: Artificial Sequence
<220> FEATURE:
<223> OTHER INFORMATION: Synthetic Construct

<400> SEQUENCE: 149

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ser Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130
```

<210> SEQ ID NO 150
<211> LENGTH: 133
<212> TYPE: PRT
<213> ORGANISM: Artificial Sequence
<220> FEATURE:
<223> OTHER INFORMATION: Synthetic Construct

<400> SEQUENCE: 150

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Ala Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130
```

<210> SEQ ID NO 151
<211> LENGTH: 133
<212> TYPE: PRT
<213> ORGANISM: Artificial Sequence
<220> FEATURE:
<223> OTHER INFORMATION: Synthetic Construct

<400> SEQUENCE: 151

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Glu Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130
```

<210> SEQ ID NO 152
<211> LENGTH: 133
<212> TYPE: PRT
<213> ORGANISM: Artificial Sequence
<220> FEATURE:
<223> OTHER INFORMATION: Synthetic Construct

<400> SEQUENCE: 152

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg His Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 153
<211> LENGTH: 133
<212> TYPE: PRT
<213> ORGANISM: Artificial Sequence
<220> FEATURE:
<223> OTHER INFORMATION: Synthetic Construct

<400> SEQUENCE: 153

Ala Pro Thr Ser Ser Thr Lys Lys Thr Gln Leu Gln Leu Glu Asp
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 154
<211> LENGTH: 133
<212> TYPE: PRT
<213> ORGANISM: Artificial Sequence
<220> FEATURE:
<223> OTHER INFORMATION: Synthetic Construct

<400> SEQUENCE: 154

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
                115                 120                 125

Ile Ser Thr Leu Thr
        130

<210> SEQ ID NO 155
<211> LENGTH: 133
<212> TYPE: PRT
<213> ORGANISM: Artificial Sequence
<220> FEATURE:
<223> OTHER INFORMATION: Synthetic Construct

<400> SEQUENCE: 155

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Ser Ser Ile
                115                 120                 125

Ile Ser Thr Leu Thr
        130

<210> SEQ ID NO 156
<211> LENGTH: 214
<212> TYPE: PRT
<213> ORGANISM: Artificial Sequence
<220> FEATURE:
<223> OTHER INFORMATION: Synthetic Construct

<400> SEQUENCE: 156

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

```
Leu Asn Trp Tyr Gln Arg Lys Gln Gly Lys Ser Pro Gln Leu Leu Ile
             35                  40                  45

Phe Gly Ala Thr Asn Leu Ala Asp Gly Val Ser Ser Arg Phe Ser Gly
         50                  55                  60

Ser Gly Ser Asp Arg Gln Tyr Ser Leu Lys Ile Ser Ser Leu His Pro
 65                  70                  75                  80

Asp Asp Val Ala Thr Tyr Tyr Cys Gln Asn Ile Leu Asp Thr Pro Trp
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 157
<211> LENGTH: 597
<212> TYPE: PRT
<213> ORGANISM: Artificial Sequence
<220> FEATURE:
<223> OTHER INFORMATION: Synthetic Construct

<400> SEQUENCE: 157

Gln Val His Leu Gln Gln Ser Gly Pro Glu Leu Val Lys Pro Gly Ala
1               5                  10                  15

Ser Val Lys Met Ser Cys Lys Thr Ser Gly Tyr Thr Phe Thr Lys Tyr
            20                  25                  30

Thr Met His Trp Val Lys Gln Gly His Glu Glu Ser Leu Glu Trp Ile
        35                  40                  45

Gly His Phe Asn Pro Asn Asn Asp Glu Thr Lys Tyr Asn Gln Lys Phe
    50                  55                  60

Thr Gly Lys Ala Thr Leu Thr Val Asp Lys Ser Ser Thr Thr Ala Tyr
65                  70                  75                  80

Met Glu Leu Arg Ser Leu Thr Ser Asp Asp Ser Ala Leu Tyr Tyr Cys
                85                  90                  95

Ala Arg Asp Gly Leu Gly Leu Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Ser Gly Gly Gly Gly Ser
    450                 455                 460

Ala Pro Thr Ser Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Leu Ala Gln Ser Lys Asn Phe His Leu
    530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590
```

Ile Ser Thr Leu Thr
        595

<210> SEQ ID NO 158
<211> LENGTH: 448
<212> TYPE: PRT
<213> ORGANISM: Artificial Sequence
<220> FEATURE:
<223> OTHER INFORMATION: Synthetic Construct

<400> SEQUENCE: 158

Gln Val His Leu Gln Gln Ser Gly Pro Glu Leu Val Lys Pro Gly Ala
1               5                   10                  15

Ser Val Lys Met Ser Cys Lys Thr Ser Gly Tyr Thr Phe Thr Lys Tyr
            20                  25                  30

Thr Met His Trp Val Lys Gln Gly His Glu Glu Ser Leu Glu Trp Ile
        35                  40                  45

Gly His Phe Asn Pro Asn Asn Asp Glu Thr Lys Tyr Asn Gln Lys Phe
    50                  55                  60

Thr Gly Lys Ala Thr Leu Thr Val Asp Lys Ser Ser Thr Thr Ala Tyr
65                  70                  75                  80

Met Glu Leu Arg Ser Leu Thr Ser Asp Asp Ser Ala Leu Tyr Tyr Cys
                85                  90                  95

Ala Arg Asp Gly Leu Gly Leu Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Val Cys Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 159
<211> LENGTH: 214
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asp Ile Tyr Asp Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 597
<212> TYPE: PRT
<213> ORGANISM: Artificial Sequence
<220> FEATURE:
<223> OTHER INFORMATION: Synthetic Construct

<400> SEQUENCE: 160

-continued

```
Gln Val Gln Leu Val Gln Ser Gly Ala Glu Lys Lys Pro Gly Ser
1               5                   10                  15

Ser Val Lys Val Ser Cys Lys Ala Ser Gly Tyr Arg Phe His Asn Phe
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Ser Gly Gly Gly Ser Gly Gly Gly Ser
    450                 455                 460

Ala Pro Thr Ser Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Leu Ala Gln Ser Lys Asn Phe His Leu
530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590

Ile Ser Thr Leu Thr
            595

<210> SEQ ID NO 161
<211> LENGTH: 448
<212> TYPE: PRT
<213> ORGANISM: Artificial Sequence
<220> FEATURE:
<223> OTHER INFORMATION: Synthetic Construct

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe His Asn Phe
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 162
<211> LENGTH: 214
<212> TYPE: PRT
<213> ORGANISM: Artificial Sequence
<220> FEATURE:
<223> OTHER INFORMATION: Synthetic Construct

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asp Ile Tyr Asp Ala Pro Trp
                85                  90                  95

```
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 163
<211> LENGTH: 597
<212> TYPE: PRT
<213> ORGANISM: Artificial Sequence
<220> FEATURE:
<223> OTHER INFORMATION: Synthetic Construct

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Ser Arg Phe Tyr Lys Phe
                20                  25                  30

Ala Ile Ser Trp Val Arg Gln Ala Pro Gly Gln Gly Leu Glu Trp Met
            35                  40                  45

Gly Gly Ile Ile Pro Gly His Ala Lys Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240
```

```
Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ser Gly Gly Gly Gly Ser Gly Gly Gly Gly Ser Gly Gly Gly Gly Ser
450                 455                 460

Ala Pro Thr Ser Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Leu Ala Gln Ser Lys Asn Phe His Leu
        530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
                580                 585                 590

Ile Ser Thr Leu Thr
            595

<210> SEQ ID NO 164
<211> LENGTH: 448
<212> TYPE: PRT
<213> ORGANISM: Artificial Sequence
<220> FEATURE:
<223> OTHER INFORMATION: Synthetic Construct

<400> SEQUENCE: 164
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Ser Arg Phe Tyr Lys Phe
            20                  25                  30

Ala Ile Ser Trp Val Arg Gln Ala Pro Gly Gln Gly Leu Glu Trp Met
        35                  40                  45

Gly Ile Ile Pro Gly His Ala Lys Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                         420                 425                 430

Ala Leu His Asn His Tyr Thr Gln Lys Ser Leu Ser Leu Ser Pro Gly
            435                 440                 445

<210> SEQ ID NO 165
<211> LENGTH: 214
<212> TYPE: PRT
<213> ORGANISM: Artificial Sequence
<220> FEATURE:
<223> OTHER INFORMATION: Synthetic Construct

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Tyr Asp Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 597
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Lys Tyr
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ser Gly Gly Gly Gly Ser Gly Gly Gly Ser Gly Gly Gly Gly Ser
            450                 455                 460

Ala Pro Thr Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys

```
                    485                 490                 495
Asn Pro Lys Leu Thr Glu Met Leu Thr Ala Lys Phe Tyr Met Pro Lys
            500                 505                 510
Lys Ala Thr Glu Leu Lys His Leu Gln Cys Leu Glu Glu Glu Leu Lys
            515                 520                 525
Pro Leu Glu Glu Val Leu Asn Leu Ala Gln Ser Lys Asn Phe His Leu
            530                 535                 540
Arg Pro Arg Asp Leu Ile Ser Ala Ile Asn Val Ile Val Leu Glu Leu
545                 550                 555                 560
Lys Gly Ser Glu Thr Thr Phe Met Cys Glu Tyr Ala Asp Glu Thr Ala
            565                 570                 575
Thr Ile Val Glu Phe Leu Asn Arg Trp Ile Thr Phe Ala Gln Ser Ile
            580                 585                 590
Ile Ser Thr Leu Thr
            595

<210> SEQ ID NO 167
<211> LENGTH: 448
<212> TYPE: PRT
<213> ORGANISM: Artificial Sequence
<220> FEATURE:
<223> OTHER INFORMATION: Synthetic Construct

<400> SEQUENCE: 167

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Lys Tyr
            20                  25                  30
Ala Ile Ser Trp Val Arg Gln Ala Pro Gly Gln Gly Leu Glu Trp Met
        35                  40                  45
Gly Gly Ile Ile Pro Gly His Ala Lys Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Gly Leu Gly Ile Arg Leu Phe Ala Asp Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
```

```
                    245                 250                 255

Arg Thr Pro Glu Val Thr Cys Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Glu Glu Met Thr Lys Asn Gln Val Ser Leu Trp
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 168
<211> LENGTH: 214
<212> TYPE: PRT
<213> ORGANISM: Artificial Sequence
<220> FEATURE:
<223> OTHER INFORMATION: Synthetic Construct

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Tyr Asp Thr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 169
<211> LENGTH: 597
<212> TYPE: PRT
<213> ORGANISM: Artificial Sequence
<220> FEATURE:
<223> OTHER INFORMATION: Synthetic Construct

<400> SEQUENCE: 169

```
Gln Val Gln Leu Val Gln Ser Gly Ala Glu Val Lys Lys Pro Gly Ser
1               5                   10                  15

Ser Val Lys Val Ser Cys Lys Ala Ser Gly Ser Gly Phe Arg Gly His
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

Tyr Lys Cys Lys Val Ser Asn Lys Ala Leu Pro Ala Pro Ile Glu Lys
              325                 330                 335

Thr Ile Ser Lys Ala Lys Gly Gln Pro Arg Glu Pro Gln Val Tyr Thr
              340                 345                 350

Leu Pro Pro Cys Arg Glu Glu Met Thr Lys Asn Gln Val Ser Leu Ser
              355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
              405                 410                 415

Ser Arg Trp Gln Gln Gly Asn Val Phe Ser Cys Ser Val Met His Glu
              420                 425                 430

Ala Leu His Asn His Tyr Thr Gln Lys Ser Leu Ser Leu Ser Pro Gly
              435                 440                 445

Ser Gly Gly Gly Gly Ser Gly Gly Gly Gly Ser Gly Gly Gly Gly Ser
450                 455                 460

Ala Pro Thr Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
              485                 490                 495

Asn Pro Lys Leu Thr Glu Met Leu Thr Ala Lys Phe Tyr Met Pro Lys
              500                 505                 510

Lys Ala Thr Glu Leu Lys His Leu Gln Cys Leu Glu Glu Glu Leu Lys
              515                 520                 525

Pro Leu Glu Glu Val Leu Asn Leu Ala Gln Ser Lys Asn Phe His Leu
              530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
              565                 570                 575

Thr Ile Val Glu Phe Leu Asn Arg Trp Ile Thr Phe Ala Gln Ser Ile
              580                 585                 590

Ile Ser Thr Leu Thr
              595

<210> SEQ ID NO 170
<211> LENGTH: 448
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Val Gln Ser Gly Ala Glu Val Lys Lys Pro Gly Ser
1               5                   10                  15

Ser Val Lys Val Ser Cys Lys Ala Ser Gly Ser Gly Phe Arg Gly His
              20                  25                  30

Ala Ile Ser Trp Val Arg Gln Ala Pro Gly Gln Gly Leu Glu Trp Met
              35                  40                  45

Gly Gly Ile Ile Pro Gly His Ala Lys Ala Asn Tyr Ala Gln Lys Phe
      50                  55                  60

Gln Gly Arg Val Thr Ile Thr Ala Asp Glu Ser Thr Ser Thr Ala Tyr

```
             65                  70                  75                  80
Met Glu Leu Ser Ser Leu Arg Ser Glu Asp Thr Ala Val Tyr Tyr Cys
                    85                  90                  95

Ala Arg Asp Gly Leu Gly Ile Arg Leu Phe Ala Asp Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 171
<211> LENGTH: 215
<212> TYPE: PRT
<213> ORGANISM: Artificial Sequence
<220> FEATURE:
<223> OTHER INFORMATION: Synthetic Construct

<400> SEQUENCE: 171

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 172
<211> LENGTH: 599
<212> TYPE: PRT
<213> ORGANISM: Artificial Sequence
<220> FEATURE:
<223> OTHER INFORMATION: Synthetic Construct

<400> SEQUENCE: 172

```
Glu Val Gln Leu Val Glu Ser Gly Gly Gly Ala Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Asn Trp Ser Gly Glu Ile Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ser Tyr Arg Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

-continued

```
                130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Cys Arg Glu Glu Met Thr Lys Asn Gln Val Ser
                355                 360                 365

Leu Ser Cys Ala Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Ser Gly Gly Gly Ser Gly Gly Gly Ser Gly Gly Gly
                450                 455                 460

Gly Ser Ala Pro Thr Ser Ser Thr Lys Lys Thr Gln Leu Gln Leu
465                 470                 475                 480

Glu His Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
                500                 505                 510

Pro Lys Lys Ala Thr Glu Leu Lys His Leu Gln Cys Leu Glu Glu Glu
                515                 520                 525

Leu Lys Pro Leu Glu Glu Val Leu Asn Leu Ala Gln Ser Lys Asn Phe
530                 535                 540

His Leu Arg Pro Arg Asp Leu Ile Ser Ala Ile Asn Val Ile Val Leu
545                 550                 555                 560
```

```
Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
        595

<210> SEQ ID NO 173
<211> LENGTH: 450
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Ala Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Asn Trp Ser Gly Glu Ile Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ser Tyr Arg Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 174
<211> LENGTH: 214
<212> TYPE: PRT
<213> ORGANISM: Artificial Sequence
<220> FEATURE:
<223> OTHER INFORMATION: Synthetic Construct

<400> SEQUENCE: 174

Glu Ile Val Leu Thr Gln Ser Pro Ala Thr Leu Ser Val Thr Pro Gly
1               5                   10                  15

Glu Gly Ala Thr Leu Ser Cys Arg Ala Ser His Ser Val Gly Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Leu Ala Val Tyr Tyr Cys Gln Gln Arg Ser Asn Trp Pro Pro
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 175
<211> LENGTH: 600
<212> TYPE: PRT
<213> ORGANISM: Artificial Sequence
<220> FEATURE:
<223> OTHER INFORMATION: Synthetic Construct

<400> SEQUENCE: 175
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Gly Trp Tyr Asp Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Glu Glu Met Thr Lys Asn Gln Val
        355                 360                 365

```
Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Ser Gly Gly Gly Ser Gly Gly Gly Ser Gly Gly
    450                 455                 460

Gly Gly Ser Ala Pro Thr Ser Ser Ser Thr Lys Lys Thr Gln Leu Gln
465                 470                 475                 480

Leu Glu His Leu Leu Leu Asp Leu Gln Met Ile Leu Asn Gly Ile Asn
                485                 490                 495

Asn Tyr Lys Asn Pro Lys Leu Thr Glu Met Leu Thr Ala Lys Phe Tyr
            500                 505                 510

Met Pro Lys Lys Ala Thr Glu Leu Lys His Leu Gln Cys Leu Glu Glu
        515                 520                 525

Glu Leu Lys Pro Leu Glu Glu Val Leu Asn Leu Ala Gln Ser Lys Asn
530                 535                 540

Phe His Leu Arg Pro Arg Asp Leu Ile Ser Ala Ile Asn Val Ile Val
545                 550                 555                 560

Leu Glu Leu Lys Gly Ser Glu Thr Thr Phe Met Cys Glu Tyr Ala Asp
                565                 570                 575

Glu Thr Ala Thr Ile Val Glu Phe Leu Asn Arg Trp Ile Thr Phe Ala
            580                 585                 590

Gln Ser Ile Ile Ser Thr Leu Thr
        595                 600

<210> SEQ ID NO 176
<211> LENGTH: 451
<212> TYPE: PRT
<213> ORGANISM: Artificial Sequence
<220> FEATURE:
<223> OTHER INFORMATION: Synthetic Construct

<400> SEQUENCE: 176

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Gly Trp Tyr Asp Tyr Asp Ala Phe Asp Ile Trp
            100                 105                 110

Gly Gln Gly Thr Met Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Ala Ala
225                 230                 235                 240
Gly Ala Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Cys Thr Leu Pro Pro Ser Arg Glu Glu Met Thr Lys Asn Gln Val
        355                 360                 365
Ser Leu Trp Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 177
<211> LENGTH: 5
<212> TYPE: PRT
<213> ORGANISM: Artificial Sequence
<220> FEATURE:
<223> OTHER INFORMATION: Synthetic Construct

<400> SEQUENCE: 177

Ser Tyr Trp Met Asn
1               5

<210> SEQ ID NO 178
```

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Gln Ile Tyr Pro Gly Asp Gly Asp Thr Asn Tyr Asn Gly Lys Phe Lys
1               5                   10                  15
Gly

<210> SEQ ID NO 179
<211> LENGTH: 13
<212> TYPE: PRT
<213> ORGANISM: Artificial Sequence
<220> FEATURE:
<223> OTHER INFORMATION: Synthetic Construct

<400> SEQUENCE: 179

Ser Gly Ala Ala Phe Ser Ser Tyr Tyr Ala Met Asp Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic Construct

<400> SEQUENCE: 180

Arg Ala Ser Glu Asn Ile Tyr Ser Asn Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Ala Ala Thr Asn Leu Ala Asp
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Gln His Phe Trp Gly Thr Pro Trp Thr
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct

<400> SEQUENCE: 183

Gly Tyr Ala Phe Ser Ser Tyr
1               5
```

```
<210> SEQ ID NO 184
<211> LENGTH: 6
<212> TYPE: PRT
<213> ORGANISM: Artificial Sequence
<220> FEATURE:
<223> OTHER INFORMATION: Synthetic Construct

<400> SEQUENCE: 184

Tyr Pro Gly Asp Gly Asp
1               5

<210> SEQ ID NO 185
<211> LENGTH: 122
<212> TYPE: PRT
<213> ORGANISM: Artificial Sequence
<220> FEATURE:
<223> OTHER INFORMATION: Synthetic Construct

<400> SEQUENCE: 185

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Ala Ala Phe Ser Ser Tyr Tyr Ala Met Asp Tyr Trp
            100                 105                 110

Gly Gln Gly Thr Ser Val Thr Val Ser Ser
        115                 120

<210> SEQ ID NO 186
<211> LENGTH: 107
<212> TYPE: PRT
<213> ORGANISM: Artificial Sequence
<220> FEATURE:
<223> OTHER INFORMATION: Synthetic Construct

<400> SEQUENCE: 186

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105

<210> SEQ ID NO 187
```

```
<211> LENGTH: 214
<212> TYPE: PRT
<213> ORGANISM: Artificial Sequence
<220> FEATURE:
<223> OTHER INFORMATION: Synthetic Construct

<400> SEQUENCE: 187

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 188
<211> LENGTH: 600
<212> TYPE: PRT
<213> ORGANISM: Artificial Sequence
<220> FEATURE:
<223> OTHER INFORMATION: Synthetic Construct

<400> SEQUENCE: 188

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Ala Ala Phe Ser Ser Tyr Tyr Ala Met Asp Tyr Trp
```

```
                100              105                110
Gly Gln Gly Thr Ser Val Thr Val Ser Ser Ala Ser Thr Lys Gly Pro
            115                 120                125

Ser Val Phe Pro Leu Ala Pro Ser Ser Lys Ser Thr Ser Gly Gly Thr
        130                 135                140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Glu Glu Met Thr Lys Asn Gln Val
        355                 360                 365

Ser Leu Ser Cys Ala Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Ser Gly Gly Gly Ser Gly Gly Gly Ser Gly Gly
450                 455                 460

Gly Gly Ser Ala Pro Thr Ser Ser Ser Thr Lys Lys Thr Gln Leu Gln
465                 470                 475                 480

Leu Glu His Leu Leu Leu Asp Leu Gln Met Ile Leu Asn Gly Ile Asn
                485                 490                 495

Asn Tyr Lys Asn Pro Lys Leu Thr Glu Met Leu Thr Ala Lys Phe Tyr
            500                 505                 510

Met Pro Lys Lys Ala Thr Glu Leu Lys His Leu Gln Cys Leu Glu Glu
        515                 520                 525
```

-continued

Glu Leu Lys Pro Leu Glu Val Leu Asn Leu Ala Gln Ser Lys Asn
            530                 535                 540

Phe His Leu Arg Pro Arg Asp Leu Ile Ser Ala Ile Asn Val Ile Val
545                 550                 555                 560

Leu Glu Leu Lys Gly Ser Glu Thr Thr Phe Met Cys Glu Tyr Ala Asp
                565                 570                 575

Glu Thr Ala Thr Ile Val Glu Phe Leu Asn Arg Trp Ile Thr Phe Ala
                580                 585                 590

Gln Ser Ile Ile Ser Thr Leu Thr
            595                 600

<210> SEQ ID NO 189
<211> LENGTH: 451
<212> TYPE: PRT
<213> ORGANISM: Artificial Sequence
<220> FEATURE:
<223> OTHER INFORMATION: Synthetic Construct

<400> SEQUENCE: 189

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Ala Ala Phe Ser Ser Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Glu Glu Met Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 190
<211> LENGTH: 133
<212> TYPE: PRT
<213> ORGANISM: Artificial Sequence
<220> FEATURE:
<223> OTHER INFORMATION: Synthetic Construct

<400> SEQUENCE: 190

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 191
<211> LENGTH: 133
<212> TYPE: PRT
<213> ORGANISM: Artificial Sequence
<220> FEATURE:
<223> OTHER INFORMATION: Synthetic Construct

<400> SEQUENCE: 191

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Lys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 192
<211> LENGTH: 133
<212> TYPE: PRT
<213> ORGANISM: Artificial Sequence
<220> FEATURE:
<223> OTHER INFORMATION: Synthetic Construct

<400> SEQUENCE: 192

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 193
<211> LENGTH: 133
<212> TYPE: PRT
<213> ORGANISM: Artificial Sequence
<220> FEATURE:
<223> OTHER INFORMATION: Synthetic Construct

<400> SEQUENCE: 193

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Gly Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
            130

<210> SEQ ID NO 194
<211> LENGTH: 133
<212> TYPE: PRT
<213> ORGANISM: Artificial Sequence
<220> FEATURE:
<223> OTHER INFORMATION: Synthetic Construct

<400> SEQUENCE: 194

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Lys Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
            130

<210> SEQ ID NO 195
<211> LENGTH: 133
<212> TYPE: PRT
<213> ORGANISM: Artificial Sequence
<220> FEATURE:
<223> OTHER INFORMATION: Synthetic Construct

<400> SEQUENCE: 195

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 196
<211> LENGTH: 133
<212> TYPE: PRT
<213> ORGANISM: Artificial Sequence
<220> FEATURE:
<223> OTHER INFORMATION: Synthetic Construct

<400> SEQUENCE: 196

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 197
<211> LENGTH: 133
<212> TYPE: PRT
<213> ORGANISM: Artificial Sequence
<220> FEATURE:
<223> OTHER INFORMATION: Synthetic Construct

<400> SEQUENCE: 197

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
```

65                  70                  75                  80
Arg Pro Arg Lys Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
        130

<210> SEQ ID NO 198
<211> LENGTH: 133
<212> TYPE: PRT
<213> ORGANISM: Artificial Sequence
<220> FEATURE:
<223> OTHER INFORMATION: Synthetic Construct

<400> SEQUENCE: 198

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Ala Met Leu Thr Lys Lys Phe Tyr Met Pro Lys
                35                  40                  45
Lys Ala Thr Glu Leu Lys His Leu Gln Cys Leu Glu Glu Leu Lys
            50                  55                  60
Pro Leu Glu Glu Val Leu Asn Leu Ala Gln Ser Lys Asn Phe His Leu
65                  70                  75                  80
Arg Pro Arg Arg Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
        130

<210> SEQ ID NO 199
<211> LENGTH: 133
<212> TYPE: PRT
<213> ORGANISM: Artificial Sequence
<220> FEATURE:
<223> OTHER INFORMATION: Synthetic Construct

<400> SEQUENCE: 199

Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Ala Lys Phe Tyr Met Pro Lys
                35                  40                  45
Lys Ala Thr Glu Leu Lys His Leu Gln Cys Leu Glu Glu Gln Leu Lys
            50                  55                  60
Pro Leu Glu Glu Val Leu Asn Leu Ala Gln Ser Lys Asn Phe His Leu
65                  70                  75                  80
Arg Pro Arg Asp Leu Ile Ser Gly Ile Asn Val Ile Val Leu Glu Leu
                    85                  90                  95

-continued

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 200
<211> LENGTH: 133
<212> TYPE: PRT
<213> ORGANISM: Artificial Sequence
<220> FEATURE:
<223> OTHER INFORMATION: Synthetic Construct

<400> SEQUENCE: 200

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Lys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 201
<211> LENGTH: 133
<212> TYPE: PRT
<213> ORGANISM: Artificial Sequence
<220> FEATURE:
<223> OTHER INFORMATION: Synthetic Construct

<400> SEQUENCE: 201

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

Ile Ser Thr Leu Thr
    130

<210> SEQ ID NO 202
<211> LENGTH: 133
<212> TYPE: PRT
<213> ORGANISM: Artificial Sequence
<220> FEATURE:
<223> OTHER INFORMATION: Synthetic Construct

<400> SEQUENCE: 202

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 203
<211> LENGTH: 133
<212> TYPE: PRT
<213> ORGANISM: Artificial Sequence
<220> FEATURE:
<223> OTHER INFORMATION: Synthetic Construct

<400> SEQUENCE: 203

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Lys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 204
<211> LENGTH: 133
<212> TYPE: PRT
<213> ORGANISM: Artificial Sequence
<220> FEATURE:
<223> OTHER INFORMATION: Synthetic Construct

<400> SEQUENCE: 204

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 205
<211> LENGTH: 133
<212> TYPE: PRT
<213> ORGANISM: Artificial Sequence
<220> FEATURE:
<223> OTHER INFORMATION: Synthetic Construct

<400> SEQUENCE: 205

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 206
<211> LENGTH: 133
<212> TYPE: PRT
<213> ORGANISM: Artificial Sequence
<220> FEATURE:

<223> OTHER INFORMATION: Synthetic Construct

<400> SEQUENCE: 206

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Asp Met Leu Thr Ala Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Lys Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
        130

<210> SEQ ID NO 207
<211> LENGTH: 133
<212> TYPE: PRT
<213> ORGANISM: Artificial Sequence
<220> FEATURE:
<223> OTHER INFORMATION: Synthetic Construct

<400> SEQUENCE: 207

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Asp Met Leu Thr Ala Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Arg Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ala Gln Ser Ile
        115                 120                 125
Ile Ser Thr Leu Thr
        130

<210> SEQ ID NO 208
<211> LENGTH: 133
<212> TYPE: PRT
<213> ORGANISM: Artificial Sequence
<220> FEATURE:
<223> OTHER INFORMATION: Synthetic Construct

<400> SEQUENCE: 208

Ala Pro Thr Ser Ser Ser Thr Lys Lys Thr Gln Leu Gln Leu Glu His

```
                1               5                   10                  15
Leu Leu Leu Asp Leu Gln Met Ile Leu Asn Gly Ile Asn Asn Tyr Lys
                20                  25                  30

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 209
<211> LENGTH: 133
<212> TYPE: PRT
<213> ORGANISM: Artificial Sequence
<220> FEATURE:
<223> OTHER INFORMATION: Synthetic Construct

<400> SEQUENCE: 209

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Lys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 210
<211> LENGTH: 133
<212> TYPE: PRT
<213> ORGANISM: Artificial Sequence
<220> FEATURE:
<223> OTHER INFORMATION: Synthetic Construct

<400> SEQUENCE: 210

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30
```

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Gln Leu Lys
 50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 211
<211> LENGTH: 133
<212> TYPE: PRT
<213> ORGANISM: Artificial Sequence
<220> FEATURE:
<223> OTHER INFORMATION: Synthetic Construct

<400> SEQUENCE: 211

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 212
<211> LENGTH: 133
<212> TYPE: PRT
<213> ORGANISM: Artificial Sequence
<220> FEATURE:
<223> OTHER INFORMATION: Synthetic Construct

<400> SEQUENCE: 212

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
 50                  55                  60

```
Pro Leu Glu Glu Val Leu Asn Leu Ala Gln Ser Lys Asn Phe His Leu
 65                  70                  75                  80

Arg Pro Arg Lys Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 213
<211> LENGTH: 133
<212> TYPE: PRT
<213> ORGANISM: Artificial Sequence
<220> FEATURE:
<223> OTHER INFORMATION: Synthetic Construct

<400> SEQUENCE: 213

Ala Pro Thr Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
             35                  40                  45

Lys Ala Thr Glu Leu Lys His Leu Gln Cys Leu Glu Glu Gln Leu Lys
         50                  55                  60

Pro Leu Glu Glu Val Leu Asn Leu Ala Gln Ser Lys Asn Phe His Leu
 65                  70                  75                  80

Arg Pro Arg Arg Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 214
<211> LENGTH: 133
<212> TYPE: PRT
<213> ORGANISM: Artificial Sequence
<220> FEATURE:
<223> OTHER INFORMATION: Synthetic Construct

<400> SEQUENCE: 214

Ala Pro Thr Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Ala Lys Phe Tyr Met Pro Lys
             35                  40                  45

Lys Ala Thr Glu Leu Lys His Leu Gln Cys Leu Glu Glu Gln Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Gly Ile Asn Val Ile Val Leu Glu Leu
```

```
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 215
<211> LENGTH: 133
<212> TYPE: PRT
<213> ORGANISM: Artificial Sequence
<220> FEATURE:
<223> OTHER INFORMATION: Synthetic Construct

<400> SEQUENCE: 215

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Lys Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 216
<211> LENGTH: 133
<212> TYPE: PRT
<213> ORGANISM: Artificial Sequence
<220> FEATURE:
<223> OTHER INFORMATION: Synthetic Construct

<400> SEQUENCE: 216

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Arg Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ala Gln Ser Ile
            115                 120                 125

Ile Ser Thr Leu Thr
        130

<210> SEQ ID NO 217
<211> LENGTH: 449
<212> TYPE: PRT
<213> ORGANISM: Artificial Sequence
<220> FEATURE:
<223> OTHER INFORMATION: Synthetic Construct

<400> SEQUENCE: 217

Gln Val His Leu Gln Gln Ser Gly Pro Glu Leu Val Lys Pro Gly Ala
1               5                   10                  15

Ser Val Lys Met Ser Cys Lys Thr Ser Gly Tyr Thr Phe Thr Lys Tyr
            20                  25                  30

Thr Met His Trp Val Lys Gln Gly His Glu Glu Ser Leu Glu Trp Ile
        35                  40                  45

Gly His Phe Asn Pro Asn Asn Asp Glu Thr Lys Tyr Asn Gln Lys Phe
    50                  55                  60

Thr Gly Lys Ala Thr Leu Thr Val Asp Lys Ser Ser Thr Thr Ala Tyr
65                  70                  75                  80

Met Glu Leu Arg Ser Leu Thr Ser Asp Asp Ser Ala Leu Tyr Tyr Cys
                85                  90                  95

Ala Arg Asp Gly Leu Gly Leu Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Cys Thr
                340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 218
<211> LENGTH: 449
<212> TYPE: PRT
<213> ORGANISM: Artificial Sequence
<220> FEATURE:
<223> OTHER INFORMATION: Synthetic Construct

<400> SEQUENCE: 218

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe His Asn Phe
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Glu Glu Met Thr Lys Asn Gln Val Ser Leu Trp
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 219
<211> LENGTH: 449
<212> TYPE: PRT
<213> ORGANISM: Artificial Sequence
<220> FEATURE:
<223> OTHER INFORMATION: Synthetic Construct

<400> SEQUENCE: 219

Gln Val Gln Leu Val Gln Ser Gly Ala Glu Val Lys Lys Pro Gly Ser
1               5                   10                  15

Ser Val Lys Val Ser Cys Lys Ala Ser Gly Ser Arg Phe Tyr Lys Phe
                20                  25                  30

Ala Ile Ser Trp Val Arg Gln Ala Pro Gly Gln Gly Leu Glu Trp Met
            35                  40                  45

Gly Gly Ile Ile Pro Gly His Ala Lys Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 220
<211> LENGTH: 449
<212> TYPE: PRT
<213> ORGANISM: Artificial Sequence
<220> FEATURE:
<223> OTHER INFORMATION: Synthetic Construct

<400> SEQUENCE: 220

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Lys Tyr
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 221
<211> LENGTH: 449
<212> TYPE: PRT
<213> ORGANISM: Artificial Sequence
<220> FEATURE:
<223> OTHER INFORMATION: Synthetic Construct

<400> SEQUENCE: 221

```
Gln Val Gln Leu Val Gln Ser Gly Ala Glu Val Lys Lys Pro Gly Ser
1               5                   10                  15

Ser Val Lys Val Ser Cys Lys Ala Ser Gly Ser Gly Phe Arg Gly His
            20                  25                  30

Ala Ile Ser Trp Val Arg Gln Ala Pro Gly Gln Gly Leu Glu Trp Met
        35                  40                  45

Gly Gly Ile Ile Pro Gly His Ala Lys Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Leu Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 222
<211> LENGTH: 451
<212> TYPE: PRT
<213> ORGANISM: Artificial Sequence
<220> FEATURE:
<223> OTHER INFORMATION: Synthetic Construct

<400> SEQUENCE: 222

Glu Val Gln Leu Val Glu Ser Gly Gly Gly Ala Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asp Ile Asn Trp Ser Gly Glu Ile Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ser Tyr Arg Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Glu Glu Met Thr Lys Asn Gln Val Ser
                355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 223
<211> LENGTH: 452
<212> TYPE: PRT
<213> ORGANISM: Artificial Sequence
<220> FEATURE:
<223> OTHER INFORMATION: Synthetic Construct

<400> SEQUENCE: 223

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Gly Trp Tyr Asp Tyr Asp Ala Phe Asp Ile Trp
                100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205
```

```
His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Glu Glu Met Thr Lys Asn Gln Val
        355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 224
<211> LENGTH: 452
<212> TYPE: PRT
<213> ORGANISM: Artificial Sequence
<220> FEATURE:
<223> OTHER INFORMATION: Synthetic Construct

<400> SEQUENCE: 224

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Ala Ala Phe Ser Tyr Tyr Ala Met Asp Tyr Trp
            100                 105                 110
```

```
Gly Gln Gly Thr Ser Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Ala Ala
225                 230                 235                 240
Gly Ala Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Cys Thr Leu Pro Pro Ser Arg Glu Glu Met Thr Lys Asn Gln Val
        355                 360                 365
Ser Leu Trp Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
450

<210> SEQ ID NO 225
<211> LENGTH: 5
<212> TYPE: PRT
<213> ORGANISM: Artificial Sequence
<220> FEATURE:
<223> OTHER INFORMATION: Synthetic Construct

<400> SEQUENCE: 225

Ser Tyr Ala Ile Ser
1               5
```

<210> SEQ ID NO 226
<211> LENGTH: 17
<212> TYPE: PRT
<213> ORGANISM: Artificial Sequence
<220> FEATURE:
<223> OTHER INFORMATION: Synthetic Construct

<400> SEQUENCE: 226

Gly Ile Ile Pro Gly Ala Ala Thr Ala Asn Tyr Ala Gln Lys Phe Gln
1               5                   10                  15

Gly

<210> SEQ ID NO 227
<211> LENGTH: 10
<212> TYPE: PRT
<213> ORGANISM: Artificial Sequence
<220> FEATURE:
<223> OTHER INFORMATION: Synthetic Construct

<400> SEQUENCE: 227

Asp Ala Ala Gly Ile Arg Leu Phe Ala Asp
1               5                   10

<210> SEQ ID NO 228
<211> LENGTH: 9
<212> TYPE: PRT
<213> ORGANISM: Artificial Sequence
<220> FEATURE:
<223> OTHER INFORMATION: Synthetic Construct

<400> SEQUENCE: 228

Gln Ser Thr Tyr Asp Ala Pro Trp Thr
1               5

<210> SEQ ID NO 229
<211> LENGTH: 5
<212> TYPE: PRT
<213> ORGANISM: Artificial Sequence
<220> FEATURE:
<223> OTHER INFORMATION: Synthetic Construct

<400> SEQUENCE: 229

Ser Tyr Ala Met Ser
1               5

<210> SEQ ID NO 230
<211> LENGTH: 17
<212> TYPE: PRT
<213> ORGANISM: Artificial Sequence
<220> FEATURE:
<223> OTHER INFORMATION: Synthetic Construct

<400> SEQUENCE: 230

Asp Ile Thr Tyr Ala Gly Gly Ser Thr Ala Tyr Ala Asp Ser Val Lys
1               5                   10                  15

Gly

<210> SEQ ID NO 231
<211> LENGTH: 12
<212> TYPE: PRT
<213> ORGANISM: Artificial Sequence
<220> FEATURE:
<223> OTHER INFORMATION: Synthetic Construct

<400> SEQUENCE: 231

```
Ser Asn Ala Tyr Ala Trp Asp Asp Ala Leu Asp Ile
1               5                   10
```

<210> SEQ ID NO 232
<211> LENGTH: 17
<212> TYPE: PRT
<213> ORGANISM: Artificial Sequence
<220> FEATURE:
<223> OTHER INFORMATION: Synthetic Construct

<400> SEQUENCE: 232

```
Gly Ile Ile Pro Gly Tyr Ala Thr Ala Asn Tyr Ala Gln Lys Phe Gln
1               5                   10                  15

Gly
```

<210> SEQ ID NO 233
<211> LENGTH: 10
<212> TYPE: PRT
<213> ORGANISM: Artificial Sequence
<220> FEATURE:
<223> OTHER INFORMATION: Synthetic Construct

<400> SEQUENCE: 233

```
Asp Ala Ala Gly Ile Arg Leu Phe Ala Asp
1               5                   10
```

<210> SEQ ID NO 234
<211> LENGTH: 11
<212> TYPE: PRT
<213> ORGANISM: Artificial Sequence
<220> FEATURE:
<223> OTHER INFORMATION: Synthetic Construct

<400> SEQUENCE: 234

```
Arg Ala Ser Gln Ser Ile Tyr Gly Ala Leu Asn
1               5                   10
```

<210> SEQ ID NO 235
<211> LENGTH: 7
<212> TYPE: PRT
<213> ORGANISM: Artificial Sequence
<220> FEATURE:
<223> OTHER INFORMATION: Synthetic Construct

<400> SEQUENCE: 235

```
Gly Ala Ser Asn Leu Gln Ser
1               5
```

<210> SEQ ID NO 236
<211> LENGTH: 9
<212> TYPE: PRT
<213> ORGANISM: Artificial Sequence
<220> FEATURE:
<223> OTHER INFORMATION: Synthetic Construct

<400> SEQUENCE: 236

```
Gln Ser Thr Tyr Thr Ala Pro Trp Thr
1               5
```

<210> SEQ ID NO 237
<211> LENGTH: 17
<212> TYPE: PRT
<213> ORGANISM: Artificial Sequence
<220> FEATURE:
<223> OTHER INFORMATION: Synthetic Construct

<400> SEQUENCE: 237

```
Asp Ile Ser Tyr Ala Gly Gly Ser Thr Ala Tyr Ala Asp Ser Val Lys
1               5                   10                  15
Gly

<210> SEQ ID NO 238
<211> LENGTH: 7
<212> TYPE: PRT
<213> ORGANISM: Artificial Sequence
<220> FEATURE:
<223> OTHER INFORMATION: Synthetic Construct

<400> SEQUENCE: 238

Gly Gly Thr Phe Ser Ser Tyr
1               5

<210> SEQ ID NO 239
<211> LENGTH: 6
<212> TYPE: PRT
<213> ORGANISM: Artificial Sequence
<220> FEATURE:
<223> OTHER INFORMATION: Synthetic Construct

<400> SEQUENCE: 239

Ile Pro Gly Ala Ala Thr
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic Construct

<400> SEQUENCE: 240

Gly Phe Thr Phe Ser Ser Tyr
1               5

<210> SEQ ID NO 241
<211> LENGTH: 6
<212> TYPE: PRT
<213> ORGANISM: Artificial Sequence
<220> FEATURE:
<223> OTHER INFORMATION: Synthetic Construct

<400> SEQUENCE: 241

Thr Tyr Ala Gly Gly Ser
1               5

<210> SEQ ID NO 242
<211> LENGTH: 12
<212> TYPE: PRT
<213> ORGANISM: Artificial Sequence
<220> FEATURE:
<223> OTHER INFORMATION: Synthetic Construct

<400> SEQUENCE: 242

Ser Asn Ala Tyr Ala Trp Asp Asp Ala Leu Asp Ile
1               5                   10

<210> SEQ ID NO 243
<211> LENGTH: 6
<212> TYPE: PRT
<213> ORGANISM: Artificial Sequence
<220> FEATURE:
<223> OTHER INFORMATION: Synthetic Construct
```

-continued

```
<400> SEQUENCE: 243

Ile Pro Gly Tyr Ala Thr
1               5

<210> SEQ ID NO 244
<211> LENGTH: 6
<212> TYPE: PRT
<213> ORGANISM: Artificial Sequence
<220> FEATURE:
<223> OTHER INFORMATION: Synthetic Construct

<400> SEQUENCE: 244

Ser Tyr Ala Gly Gly Ser
1               5

<210> SEQ ID NO 245
<211> LENGTH: 119
<212> TYPE: PRT
<213> ORGANISM: Artificial Sequence
<220> FEATURE:
<223> OTHER INFORMATION: Synthetic Construct

<400> SEQUENCE: 245

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Ala Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser
        115

<210> SEQ ID NO 246
<211> LENGTH: 107
<212> TYPE: PRT
<213> ORGANISM: Artificial Sequence
<220> FEATURE:
<223> OTHER INFORMATION: Synthetic Construct

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Asp Ala Pro Trp
                85                  90                  95
```

```
Thr Phe Gly Gly Gly Thr Lys Val Glu Ile Lys
            100                 105

<210> SEQ ID NO 247
<211> LENGTH: 121
<212> TYPE: PRT
<213> ORGANISM: Artificial Sequence
<220> FEATURE:
<223> OTHER INFORMATION: Synthetic Construct

<400> SEQUENCE: 247

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser
        115                 120

<210> SEQ ID NO 248
<211> LENGTH: 108
<212> TYPE: PRT
<213> ORGANISM: Artificial Sequence
<220> FEATURE:
<223> OTHER INFORMATION: Synthetic Construct

<400> SEQUENCE: 248

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys
            100                 105

<210> SEQ ID NO 249
<211> LENGTH: 121
<212> TYPE: PRT
<213> ORGANISM: Artificial Sequence
<220> FEATURE:
<223> OTHER INFORMATION: Synthetic Construct

<400> SEQUENCE: 249
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser
            115                 120
```

<210> SEQ ID NO 250
<211> LENGTH: 108
<212> TYPE: PRT
<213> ORGANISM: Artificial Sequence
<220> FEATURE:
<223> OTHER INFORMATION: Synthetic Construct

<400> SEQUENCE: 250

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys
            100                 105
```

<210> SEQ ID NO 251
<211> LENGTH: 119
<212> TYPE: PRT
<213> ORGANISM: Artificial Sequence
<220> FEATURE:
<223> OTHER INFORMATION: Synthetic Construct

<400> SEQUENCE: 251

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser
        115

<210> SEQ ID NO 252
<211> LENGTH: 107
<212> TYPE: PRT
<213> ORGANISM: Artificial Sequence
<220> FEATURE:
<223> OTHER INFORMATION: Synthetic Construct

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Thr Ala Pro Trp
                85                  90                  95

Thr Phe Gly Gly Gly Thr Lys Val Glu Ile Lys
            100                 105

<210> SEQ ID NO 253
<211> LENGTH: 119
<212> TYPE: PRT
<213> ORGANISM: Artificial Sequence
<220> FEATURE:
<223> OTHER INFORMATION: Synthetic Construct

<400> SEQUENCE: 253

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser
        115

<210> SEQ ID NO 254
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 254

Asp Ile Gln Met Thr Gln Ser Pro Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Asp Ala Pro Trp
                85                  90                  95

Thr Phe Gly Gly Gly Thr Lys Val Glu Ile Lys
            100                 105

<210> SEQ ID NO 255
<211> LENGTH: 121
<212> TYPE: PRT
<213> ORGANISM: Artificial Sequence
<220> FEATURE:
<223> OTHER INFORMATION: Synthetic Construct

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser
        115                 120

<210> SEQ ID NO 256
<211> LENGTH: 108
<212> TYPE: PRT
<213> ORGANISM: Artificial Sequence
<220> FEATURE:
<223> OTHER INFORMATION: Synthetic Construct

<400> SEQUENCE: 256

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

Tyr Gly Ala Ser Ser Arg Ala Thr Gly Ile Pro Asp Arg Phe Ser Gly
            50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys
            100                 105

<210> SEQ ID NO 257
<211> LENGTH: 121
<212> TYPE: PRT
<213> ORGANISM: Artificial Sequence
<220> FEATURE:
<223> OTHER INFORMATION: Synthetic Construct

<400> SEQUENCE: 257

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser
        115                 120

<210> SEQ ID NO 258
<211> LENGTH: 108
<212> TYPE: PRT
<213> ORGANISM: Artificial Sequence
<220> FEATURE:
<223> OTHER INFORMATION: Synthetic Construct

<400> SEQUENCE: 258

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys
            100                 105

-continued

<210> SEQ ID NO 259
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S, K, G, N, R, D, T, or G
<220> FEATURE:
<221> NAME/KEY: VARIANT
<222> LOCATION: 2
<223> OTHER INFORMATION: Xaa = Y, L, H, or F

<400> SEQUENCE: 259

Xaa Xaa Ala Ile Ser
1               5

<210> SEQ ID NO 260
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G or H
<220> FEATURE:
<221> NAME/KEY: VARIANT
<222> LOCATION: 2
<223> OTHER INFORMATION: Xaa = I or F
<220> FEATURE:
<221> NAME/KEY: VARIANT
<222> LOCATION: 3
<223> OTHER INFORMATION: Xaa = I, N, or M
<220> FEATURE:
<221> NAME/KEY: VARIANT
<222> LOCATION: 5
<223> OTHER INFORMATION: Xaa = G, N, H, S, R, I, or A
<220> FEATURE:
<221> NAME/KEY: VARIANT
<222> LOCATION: 6
<223> OTHER INFORMATION: Xaa = A, N, H, S, T, F, or Y
<220> FEATURE:
<221> NAME/KEY: VARIANT
<222> LOCATION: 7
<223> OTHER INFORMATION: Xaa = A, D, or G
<220> FEATURE:
<221> NAME/KEY: VARIANT
<222> LOCATION: 8
<223> OTHER INFORMATION: Xaa = T, E, K, V, Q, or A
<220> FEATURE:
<221> NAME/KEY: VARIANT
<222> LOCATION: 9
<223> OTHER INFORMATION: Xaa = A or T
<220> FEATURE:
<221> NAME/KEY: VARIANT
<222> LOCATION: 10
<223> OTHER INFORMATION: Xaa = N or K
<220> FEATURE:
<221> NAME/KEY: VARIANT
<222> LOCATION: 12
<223> OTHER INFORMATION: Xaa = A or N
<220> FEATURE:
<221> NAME/KEY: VARIANT
<222> LOCATION: 16
<223> OTHER INFORMATION: Xaa = Q or T

<400> SEQUENCE: 260

Xaa Xaa Xaa Pro Xaa Xaa Xaa Xaa Xaa Tyr Xaa Gln Lys Phe Xaa
1               5                   10                  15

Gly

```
<210> SEQ ID NO 261
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = D or A
<220> FEATURE:
<221> NAME/KEY: VARIANT
<222> LOCATION: 2
<223> OTHER INFORMATION: Xaa = A, G, E, R, Y, K, N, Q, L, or F
<220> FEATURE:
<221> NAME/KEY: VARIANT
<222> LOCATION: 3
<223> OTHER INFORMATION: Xaa = A, L, P, or Y
<220> FEATURE:
<221> NAME/KEY: VARIANT
<222> LOCATION: 5
<223> OTHER INFORMATION: Xaa = I or L
<220> FEATURE:
<221> NAME/KEY: VARIANT
<222> LOCATION: 6
<223> OTHER INFORMATION: Xaa = R, A, Q, or S
<220> FEATURE:
<221> NAME/KEY: VARIANT
<222> LOCATION: 9
<223> OTHER INFORMATION: Xaa = A or D
<220> FEATURE:
<221> NAME/KEY: VARIANT
<222> LOCATION: 10
<223> OTHER INFORMATION: Xaa = D, E, A, or S

<400> SEQUENCE: 261

Xaa Xaa Xaa Gly Xaa Xaa Leu Phe Xaa Xaa
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = R or G
<220> FEATURE:
<221> NAME/KEY: VARIANT
<222> LOCATION: 2
<223> OTHER INFORMATION: Xaa = A or T
<220> FEATURE:
<221> NAME/KEY: VARIANT
<222> LOCATION: 4
<223> OTHER INFORMATION: Xaa = Q or E
<220> FEATURE:
<221> NAME/KEY: VARIANT
<222> LOCATION: 5
<223> OTHER INFORMATION: Xaa = E, N, T, S, A, K, D, G, R, or Q
<220> FEATURE:
<221> NAME/KEY: VARIANT
<222> LOCATION: 7
<223> OTHER INFORMATION: Xaa = Y or S
<220> FEATURE:
<221> NAME/KEY: VARIANT
<222> LOCATION: 9
<223> OTHER INFORMATION: Xaa = A or V

<400> SEQUENCE: 262

Xaa Xaa Ser Xaa Xaa Ile Xaa Gly Xaa Leu Asn
1               5                   10
```

```
<210> SEQ ID NO 263
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = A or S
<220> FEATURE:
<221> NAME/KEY: VARIANT
<222> LOCATION: 3
<223> OTHER INFORMATION: Xaa = T, S, E, Q, or D
<220> FEATURE:
<221> NAME/KEY: VARIANT
<222> LOCATION: 4
<223> OTHER INFORMATION: Xaa = N, R, A, E, or H
<220> FEATURE:
<221> NAME/KEY: VARIANT
<222> LOCATION: 6
<223> OTHER INFORMATION: Xaa = Q or A
<220> FEATURE:
<221> NAME/KEY: VARIANT
<222> LOCATION: 7
<223> OTHER INFORMATION: Xaa = S or D

<400> SEQUENCE: 263

Gly Xaa Xaa Xaa Leu Xaa Xaa
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = S, N, D, Q, A, or E
<220> FEATURE:
<221> NAME/KEY: VARIANT
<222> LOCATION: 3
<223> OTHER INFORMATION: Xaa = T, I, or S
<220> FEATURE:
<221> NAME/KEY: VARIANT
<222> LOCATION: 4
<223> OTHER INFORMATION: Xaa = Y, L, or F
<220> FEATURE:
<221> NAME/KEY: VARIANT
<222> LOCATION: 5
<223> OTHER INFORMATION: Xaa = D, G, T, E, Q, A, or Y
<220> FEATURE:
<221> NAME/KEY: VARIANT
<222> LOCATION: 6
<223> OTHER INFORMATION: Xaa = A, T, R, S, K, or Y

<400> SEQUENCE: 264

Gln Xaa Xaa Xaa Xaa Xaa Pro Trp Thr
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = G, Y, S, or A
<220> FEATURE:
<221> NAME/KEY: VARIANT
<222> LOCATION: 3
```

```
<223> OTHER INFORMATION: Xaa = T, S, G, R, N, or H
<220> FEATURE:
<221> NAME/KEY: VARIANT
<222> LOCATION: 5
<223> OTHER INFORMATION: Xaa = S, T, R, H, Y, G, or P
<220> FEATURE:
<221> NAME/KEY: VARIANT
<222> LOCATION: 6
<223> OTHER INFORMATION: Xaa = S, K, G, N, R, D, T, or G
<220> FEATURE:
<221> NAME/KEY: VARIANT
<222> LOCATION: 7
<223> OTHER INFORMATION: Xaa = Y, L, H, or F

<400> SEQUENCE: 265

Gly Xaa Xaa Phe Xaa Xaa Xaa
1               5

<210> SEQ ID NO 266
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = I, N, or M
<220> FEATURE:
<221> NAME/KEY: VARIANT
<222> LOCATION: 3
<223> OTHER INFORMATION: Xaa = G, N, H, S, R, I, or A
<220> FEATURE:
<221> NAME/KEY: VARIANT
<222> LOCATION: 4
<223> OTHER INFORMATION: Xaa = A, N, H, S, T, F, or Y
<220> FEATURE:
<221> NAME/KEY: VARIANT
<222> LOCATION: 5
<223> OTHER INFORMATION: Xaa = A, D, or G
<220> FEATURE:
<221> NAME/KEY: VARIANT
<222> LOCATION: 6
<223> OTHER INFORMATION: Xaa = T, E, K, V, Q, or A

<400> SEQUENCE: 266

Xaa Pro Xaa Xaa Xaa Xaa
1               5

<210> SEQ ID NO 267
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = D or A
<220> FEATURE:
<221> NAME/KEY: VARIANT
<222> LOCATION: 2
<223> OTHER INFORMATION: Xaa = A, G, E, R, Y, K, N, Q, L, or F
<220> FEATURE:
<221> NAME/KEY: VARIANT
<222> LOCATION: 3
<223> OTHER INFORMATION: Xaa = A, L, P, or Y
<220> FEATURE:
<221> NAME/KEY: VARIANT
<222> LOCATION: 5
<223> OTHER INFORMATION: Xaa = I or L
<220> FEATURE:
<221> NAME/KEY: VARIANT
<222> LOCATION: 6
<223> OTHER INFORMATION: Xaa = R, A, Q, or S
```

```
<220> FEATURE:
<221> NAME/KEY: VARIANT
<222> LOCATION: 9
<223> OTHER INFORMATION: Xaa = A or D
<220> FEATURE:
<221> NAME/KEY: VARIANT
<222> LOCATION: 10
<223> OTHER INFORMATION: Xaa = D, E, A, or S

<400> SEQUENCE: 267

Xaa Xaa Xaa Gly Xaa Xaa Leu Phe Xaa Xaa
1               5                   10

<210> SEQ ID NO 268
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S, D, E, A, or Q
<220> FEATURE:
<221> NAME/KEY: VARIANT
<222> LOCATION: 3
<223> OTHER INFORMATION: Xaa = A, G, or T

<400> SEQUENCE: 268

Xaa Tyr Xaa Met Ser
1               5

<210> SEQ ID NO 269
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = T, N, S, Q, E, H, R, or A
<220> FEATURE:
<221> NAME/KEY: VARIANT
<222> LOCATION: 4
<223> OTHER INFORMATION: Xaa = Y, W, F, or H
<220> FEATURE:
<221> NAME/KEY: VARIANT
<222> LOCATION: 5
<223> OTHER INFORMATION: Xaa = A, S, Q, E, or T
<220> FEATURE:
<221> NAME/KEY: VARIANT
<222> LOCATION: 7
<223> OTHER INFORMATION: Xaa = G or E
<220> FEATURE:
<221> NAME/KEY: VARIANT
<222> LOCATION: 8
<223> OTHER INFORMATION: Xaa = S or I
<220> FEATURE:
<221> NAME/KEY: VARIANT
<222> LOCATION: 10
<223> OTHER INFORMATION: Xaa = A or G

<400> SEQUENCE: 269

Asp Ile Xaa Xaa Xaa Gly Xaa Xaa Thr Xaa Tyr Ala Asp Ser Val Lys
1               5                   10                  15

Gly

<210> SEQ ID NO 270
<211> LENGTH: 12
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S or A
<220> FEATURE:
<221> NAME/KEY: VARIANT
<222> LOCATION: 2
<223> OTHER INFORMATION: Xaa = N, H, A, D, L, Q, Y, or R
<220> FEATURE:
<221> NAME/KEY: VARIANT
<222> LOCATION: 3
<223> OTHER INFORMATION: Xaa = A, N, S, or G
<220> FEATURE:
<221> NAME/KEY: VARIANT
<222> LOCATION: 5
<223> OTHER INFORMATION: Xaa = A, V, R, E, or S
<220> FEATURE:
<221> NAME/KEY: VARIANT
<222> LOCATION: 7
<223> OTHER INFORMATION: Xaa = D or S
<220> FEATURE:
<221> NAME/KEY: VARIANT
<222> LOCATION: 8
<223> OTHER INFORMATION: Xaa = D, N, Q, E, S, T, or L
<220> FEATURE:
<221> NAME/KEY: VARIANT
<222> LOCATION: 10
<223> OTHER INFORMATION: Xaa = L, F, or M
<220> FEATURE:
<221> NAME/KEY: VARIANT
<222> LOCATION: 12
<223> OTHER INFORMATION: Xaa = I, Y, or V

<400> SEQUENCE: 270

Xaa Xaa Xaa Tyr Xaa Trp Xaa Xaa Ala Xaa Asp Xaa
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = S, D, E, Q, S, or A
<220> FEATURE:
<221> NAME/KEY: VARIANT
<222> LOCATION: 6
<223> OTHER INFORMATION: Xaa = S, D, E, A, or Q

<400> SEQUENCE: 271

Gly Phe Thr Phe Xaa Xaa Tyr
1               5

<210> SEQ ID NO 272
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = T, N, S, Q, E, H, R or A
<220> FEATURE:
<221> NAME/KEY: VARIANT
<222> LOCATION: 2
<223> OTHER INFORMATION: Xaa = Y, W, F, or H
<220> FEATURE:
<221> NAME/KEY: VARIANT
<222> LOCATION: 3
```

```
<223> OTHER INFORMATION: Xaa = A, S, Q, E, or T
<220> FEATURE:
<221> NAME/KEY: VARIANT
<222> LOCATION: 5
<223> OTHER INFORMATION: Xaa = G or E
<220> FEATURE:
<221> NAME/KEY: VARIANT
<222> LOCATION: 6
<223> OTHER INFORMATION: Xaa = S or I

<400> SEQUENCE: 272

Xaa Xaa Xaa Gly Xaa Xaa
1               5

<210> SEQ ID NO 273
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S or A
<220> FEATURE:
<221> NAME/KEY: VARIANT
<222> LOCATION: 2
<223> OTHER INFORMATION: Xaa = N, H, A, D, L, Q, Y, or R
<220> FEATURE:
<221> NAME/KEY: VARIANT
<222> LOCATION: 3
<223> OTHER INFORMATION: Xaa = A, N, S, or G
<220> FEATURE:
<221> NAME/KEY: VARIANT
<222> LOCATION: 5
<223> OTHER INFORMATION: Xaa = A, V, R, E, or S
<220> FEATURE:
<221> NAME/KEY: VARIANT
<222> LOCATION: 7
<223> OTHER INFORMATION: Xaa = D or S
<220> FEATURE:
<221> NAME/KEY: VARIANT
<222> LOCATION: 8
<223> OTHER INFORMATION: Xaa = D, N, Q, E, S, T, or L
<220> FEATURE:
<221> NAME/KEY: VARIANT
<222> LOCATION: 10
<223> OTHER INFORMATION: Xaa = L, F, or M
<220> FEATURE:
<221> NAME/KEY: VARIANT
<222> LOCATION: 12
<223> OTHER INFORMATION: Xaa = I, Y, or V

<400> SEQUENCE: 273

Xaa Xaa Xaa Tyr Xaa Trp Xaa Xaa Ala Xaa Asp Xaa
1               5                   10

<210> SEQ ID NO 274
<211> LENGTH: 30
<212> TYPE: PRT
<213> ORGANISM: Artificial Sequence
<220> FEATURE:
<223> OTHER INFORMATION: Synthetic Construct

<400> SEQUENCE: 274

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 275
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 275

Trp Val Arg Gln Ala Pro Gly Gln Gly Leu Glu Trp Met Gly
1               5                   10

<210> SEQ ID NO 276
<211> LENGTH: 32
<212> TYPE: PRT
<213> ORGANISM: Artificial Sequence
<220> FEATURE:
<223> OTHER INFORMATION: Synthetic Construct

<400> SEQUENCE: 276

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 277
<211> LENGTH: 11
<212> TYPE: PRT
<213> ORGANISM: Artificial Sequence
<220> FEATURE:
<223> OTHER INFORMATION: Synthetic Construct

<400> SEQUENCE: 277

Trp Gly Gln Gly Thr Leu Val Thr Val Ser Ser
1               5                   10

<210> SEQ ID NO 278
<211> LENGTH: 25
<212> TYPE: PRT
<213> ORGANISM: Artificial Sequence
<220> FEATURE:
<223> OTHER INFORMATION: Synthetic Construct

<400> SEQUENCE: 278

Gln Val Gln Leu Val Gln Ser Gly Ala Glu Val Lys Lys Pro Gly Ser
1               5                   10                  15

Ser Val Lys Val Ser Cys Lys Ala Ser
                20                  25

<210> SEQ ID NO 279
<211> LENGTH: 19
<212> TYPE: PRT
<213> ORGANISM: Artificial Sequence
<220> FEATURE:
<223> OTHER INFORMATION: Synthetic Construct

<400> SEQUENCE: 279

Ala Ile Ser Trp Val Arg Gln Ala Pro Gly Gln Gly Leu Glu Trp Met
1               5                   10                  15

Gly Gly Ile

<210> SEQ ID NO 280
<211> LENGTH: 41
<212> TYPE: PRT
<213> ORGANISM: Artificial Sequence
<220> FEATURE:
<223> OTHER INFORMATION: Synthetic Construct

<400> SEQUENCE: 280
```

Ala Asn Tyr Ala Gln Lys Phe Gln Gly Arg Val Thr Ile Thr Ala Asp
1               5                   10                  15

Glu Ser Thr Ser Thr Ala Tyr Met Glu Leu Ser Ser Leu Arg Ser Glu
                20                  25                  30

Asp Thr Ala Val Tyr Tyr Cys Ala Arg
        35                  40

<210> SEQ ID NO 281
<211> LENGTH: 30
<212> TYPE: PRT
<213> ORGANISM: Artificial Sequence
<220> FEATURE:
<223> OTHER INFORMATION: Synthetic Construct

<400> SEQUENCE: 281

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 282
<211> LENGTH: 14
<212> TYPE: PRT
<213> ORGANISM: Artificial Sequence
<220> FEATURE:
<223> OTHER INFORMATION: Synthetic Construct

<400> SEQUENCE: 282

Trp Val Arg Gln Ala Pro Gly Lys Gly Leu Glu Trp Val Ser
1               5                   10

<210> SEQ ID NO 283
<211> LENGTH: 32
<212> TYPE: PRT
<213> ORGANISM: Artificial Sequence
<220> FEATURE:
<223> OTHER INFORMATION: Synthetic Construct

<400> SEQUENCE: 283

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 284
<211> LENGTH: 11
<212> TYPE: PRT
<213> ORGANISM: Artificial Sequence
<220> FEATURE:
<223> OTHER INFORMATION: Synthetic Construct

<400> SEQUENCE: 284

Trp Gly Gln Gly Thr Met Val Thr Val Ser Ser
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Synthetic Construct

<400> SEQUENCE: 285

Trp Gly Gln Gly Thr Leu Val Thr Val Ser Ser

```
<210> SEQ ID NO 286
<211> LENGTH: 25
<212> TYPE: PRT
<213> ORGANISM: Artificial Sequence
<220> FEATURE:
<223> OTHER INFORMATION: Synthetic Construct

<400> SEQUENCE: 286

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 287
<211> LENGTH: 19
<212> TYPE: PRT
<213> ORGANISM: Artificial Sequence
<220> FEATURE:
<223> OTHER INFORMATION: Synthetic Construct

<400> SEQUENCE: 287

Ala Met Ser Trp Val Arg Gln Ala Pro Gly Lys Gly Leu Glu Trp Val
1               5                   10                  15

Ser Asp Ile

<210> SEQ ID NO 288
<211> LENGTH: 41
<212> TYPE: PRT
<213> ORGANISM: Artificial Sequence
<220> FEATURE:
<223> OTHER INFORMATION: Synthetic Construct

<400> SEQUENCE: 288

Thr Ala Tyr Ala Asp Ser Val Lys Gly Arg Phe Thr Ile Ser Arg Asp
1               5                   10                  15

Asn Ala Lys Asn Ser Leu Tyr Leu Gln Met Asn Ser Leu Arg Ala Glu
            20                  25                  30

Asp Thr Ala Val Tyr Tyr Cys Ala Arg
            35                  40

<210> SEQ ID NO 289
<211> LENGTH: 23
<212> TYPE: PRT
<213> ORGANISM: Artificial Sequence
<220> FEATURE:
<223> OTHER INFORMATION: Synthetic Construct

<400> SEQUENCE: 289

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 290
<211> LENGTH: 15
<212> TYPE: PRT
<213> ORGANISM: Artificial Sequence
<220> FEATURE:
<223> OTHER INFORMATION: Synthetic Construct

<400> SEQUENCE: 290

Trp Tyr Gln Gln Lys Pro Gly Lys Ala Pro Lys Leu Leu Ile Tyr
```

<210> SEQ ID NO 291
<211> LENGTH: 32
<212> TYPE: PRT
<213> ORGANISM: Artificial Sequence
<220> FEATURE:
<223> OTHER INFORMATION: Synthetic Construct

<400> SEQUENCE: 291

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 292
<211> LENGTH: 10
<212> TYPE: PRT
<213> ORGANISM: Artificial Sequence
<220> FEATURE:
<223> OTHER INFORMATION: Synthetic Construct

<400> SEQUENCE: 292

Phe Gly Gly Gly Thr Lys Val Glu Ile Lys
1               5                   10

<210> SEQ ID NO 293
<211> LENGTH: 23
<212> TYPE: PRT
<213> ORGANISM: Artificial Sequence
<220> FEATURE:
<223> OTHER INFORMATION: Synthetic Construct

<400> SEQUENCE: 293

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 294
<211> LENGTH: 15
<212> TYPE: PRT
<213> ORGANISM: Artificial Sequence
<220> FEATURE:
<223> OTHER INFORMATION: Synthetic Construct

<400> SEQUENCE: 294

Trp Tyr Gln Gln Lys Pro Gly Gln Ala Pro Arg Leu Leu Ile Tyr
1               5                   10                  15

<210> SEQ ID NO 295
<211> LENGTH: 32
<212> TYPE: PRT
<213> ORGANISM: Artificial Sequence
<220> FEATURE:
<223> OTHER INFORMATION: Synthetic Construct

<400> SEQUENCE: 295

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 296
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 296

Phe Gly Gln Gly Thr Lys Val Glu Ile Lys
1               5                   10

<210> SEQ ID NO 297
<211> LENGTH: 133
<212> TYPE: PRT
<213> ORGANISM: Artificial Sequence
<220> FEATURE:
<223> OTHER INFORMATION: Synthetic Construct

<400> SEQUENCE: 297

Ala Pro Thr Ser Ser Ser Thr Lys Lys Thr Gln Leu Gln Leu Glu Glu
1               5                   10                  15

Leu Leu Leu Asp Leu Gln Met Ile Leu Asn Gly Ile Asn Asn Tyr Lys
                20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 298
<211> LENGTH: 214
<212> TYPE: PRT
<213> ORGANISM: Artificial Sequence
<220> FEATURE:
<223> OTHER INFORMATION: Synthetic Construct

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Asp Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
              115                 120                 125
Thr Ala Ser Val Val Cys Leu Leu Asn Asn Phe Tyr Pro Arg Glu Ala
          130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 299
<211> LENGTH: 597
<212> TYPE: PRT
<213> ORGANISM: Artificial Sequence
<220> FEATURE:
<223> OTHER INFORMATION: Synthetic Construct

<400> SEQUENCE: 299

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Gly Ala Ala Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Ala Ala Gly Ile Arg Leu Phe Ala Asp Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
```

```
              260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
        340                 345                 350
Leu Pro Pro Cys Arg Glu Glu Met Thr Lys Asn Gln Val Ser Leu Ser
        355                 360                 365
Cys Ala Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
        435                 440                 445
Ser Gly Gly Gly Gly Ser Gly Gly Gly Ser Gly Gly Gly Gly Ser
450                 455                 460
Ala Pro Thr Ser Ser Thr Lys Lys Thr Gln Leu Gln Leu Glu His
465                 470                 475                 480
Leu Leu Leu Asp Leu Gln Met Ile Leu Asn Gly Ile Asn Asn Tyr Lys
                485                 490                 495
Asn Pro Lys Leu Thr Glu Met Leu Thr Ala Lys Phe Tyr Met Pro Lys
            500                 505                 510
Lys Ala Thr Glu Leu Lys His Leu Gln Cys Leu Glu Glu Glu Leu Lys
        515                 520                 525
Pro Leu Glu Glu Val Leu Asn Leu Ala Gln Ser Lys Asn Phe His Leu
        530                 535                 540
Arg Pro Arg Asp Leu Ile Ser Ala Ile Asn Val Ile Val Leu Glu Leu
545                 550                 555                 560
Lys Gly Ser Glu Thr Thr Phe Met Cys Glu Tyr Ala Asp Glu Thr Ala
                565                 570                 575
Thr Ile Val Glu Phe Leu Asn Arg Trp Ile Thr Phe Ala Gln Ser Ile
            580                 585                 590
Ile Ser Thr Leu Thr
        595

<210> SEQ ID NO 300
<211> LENGTH: 448
<212> TYPE: PRT
<213> ORGANISM: Artificial Sequence
<220> FEATURE:
<223> OTHER INFORMATION: Synthetic Construct

<400> SEQUENCE: 300

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

-continued

```
             20                  25                  30
Ala Ile Ser Trp Val Arg Gln Ala Pro Gly Gln Gly Leu Glu Trp Met
             35                  40                  45
Gly Gly Ile Ile Pro Gly Ala Ala Thr Ala Asn Tyr Ala Gln Lys Phe
         50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ala Ala Gly Ile Arg Leu Phe Ala Asp Trp Gly Gln Gly
             100                 105                 110
Thr Leu Val Thr Val Ser Ser Ala Ser Thr Lys Gly Pro Ser Val Phe
             115                 120                 125
Pro Leu Ala Pro Ser Ser Lys Ser Thr Ser Gly Gly Thr Ala Ala Leu
             130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                 165                 170                 175
Gln Ser Ser Gly Leu Tyr Ser Leu Ser Ser Val Val Thr Val Pro Ser
             180                 185                 190
Ser Ser Leu Gly Thr Gln Thr Tyr Ile Cys Asn Val Asn His Lys Pro
             195                 200                 205
Ser Asn Thr Lys Val Asp Lys Lys Val Glu Pro Lys Ser Cys Asp Lys
         210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser His Glu Asp
             260                 265                 270
Pro Glu Val Lys Phe Asn Trp Tyr Val Asp Gly Val Glu Val His Asn
             275                 280                 285
Ala Lys Thr Lys Pro Arg Glu Glu Gln Tyr Asn Ser Thr Tyr Arg Val
         290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                 325                 330                 335
Thr Ile Ser Lys Ala Lys Gly Gln Pro Arg Glu Pro Gln Val Cys Thr
             340                 345                 350
Leu Pro Pro Ser Arg Glu Glu Met Thr Lys Asn Gln Val Ser Leu Trp
             355                 360                 365
Cys Leu Val Lys Gly Phe Tyr Pro Ser Asp Ile Ala Val Glu Trp Glu
         370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                 405                 410                 415
Ser Arg Trp Gln Gln Gly Asn Val Phe Ser Cys Ser Val Met His Glu
             420                 425                 430
Ala Leu His Asn His Tyr Thr Gln Lys Ser Leu Ser Leu Ser Pro Gly
             435                 440                 445
```

```
<210> SEQ ID NO 301
<211> LENGTH: 449
<212> TYPE: PRT
<213> ORGANISM: Artificial Sequence
<220> FEATURE:
<223> OTHER INFORMATION: Synthetic Construct

<400> SEQUENCE: 301

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Gly Ala Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
    355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 302
<211> LENGTH: 215
<212> TYPE: PRT
<213> ORGANISM: Artificial Sequence
<220> FEATURE:
<223> OTHER INFORMATION: Synthetic Construct

<400> SEQUENCE: 302

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 303
<211> LENGTH: 599
<212> TYPE: PRT
<213> ORGANISM: Artificial Sequence
<220> FEATURE:
<223> OTHER INFORMATION: Synthetic Construct

<400> SEQUENCE: 303
```

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ser Asn Ala Tyr Ala Trp Asp Asp Ala Leu Asp Ile Trp Gly
        100                 105                 110

Gln Gly Thr Met Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Ser Gly Gly Gly Ser Gly Gly Gly Ser Gly Gly Gly
450                 455                 460

Gly Ser Ala Pro Thr Ser Ser Thr Lys Lys Thr Gln Leu Gln Leu
465                 470                 475                 480

Glu His Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
            500                 505                 510

Pro Lys Lys Ala Thr Glu Leu Lys His Leu Gln Cys Leu Glu Glu Glu
            515                 520                 525

Leu Lys Pro Leu Glu Glu Val Leu Asn Leu Ala Gln Ser Lys Asn Phe
530                 535                 540

His Leu Arg Pro Arg Asp Leu Ile Ser Ala Ile Asn Val Ile Val Leu
545                 550                 555                 560

Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
            595

<210> SEQ ID NO 304
<211> LENGTH: 450
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 305
<211> LENGTH: 451
<212> TYPE: PRT
<213> ORGANISM: Artificial Sequence
<220> FEATURE:
<223> OTHER INFORMATION: Synthetic Construct

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                 85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 306
<211> LENGTH: 215
<212> TYPE: PRT
<213> ORGANISM: Artificial Sequence
<220> FEATURE:
<223> OTHER INFORMATION: Synthetic Construct
```

<400> SEQUENCE: 306

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 307
<211> LENGTH: 599
<212> TYPE: PRT
<213> ORGANISM: Artificial Sequence
<220> FEATURE:
<223> OTHER INFORMATION: Synthetic Construct

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
            355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Ser Gly Gly Gly Gly Ser Gly Gly Gly Gly Ser Gly Gly Gly
    450                 455                 460

Gly Ser Ala Pro Thr Ser Ser Thr Lys Lys Thr Gln Leu Gln Leu
465                 470                 475                 480

Glu His Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
                500                 505                 510

Pro Lys Lys Ala Thr Glu Leu Lys His Leu Gln Cys Leu Glu Glu Glu
            515                 520                 525

Leu Lys Pro Leu Glu Glu Val Leu Asn Leu Ala Gln Ser Lys Asn Phe
530                 535                 540

His Leu Arg Pro Arg Asp Leu Ile Ser Ala Ile Asn Val Ile Val Leu
```

-continued

```
545                 550                 555                 560
Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
            595

<210> SEQ ID NO 308
<211> LENGTH: 450
<212> TYPE: PRT
<213> ORGANISM: Artificial Sequence
<220> FEATURE:
<223> OTHER INFORMATION: Synthetic Construct

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 309
<211> LENGTH: 451
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
                210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Cys Thr Leu Pro Pro Ser Arg Glu Glu Met Thr Lys Asn Gln Val Ser
                355                 360                 365

Leu Trp Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 310
<211> LENGTH: 214
<212> TYPE: PRT
<213> ORGANISM: Artificial Sequence
<220> FEATURE:
<223> OTHER INFORMATION: Synthetic Construct

<400> SEQUENCE: 310

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Gly Ala
                20                  25                  30

Leu Asn Trp Tyr Gln Gln Lys Pro Gly Lys Ala Pro Lys Leu Leu Ile
                35                  40                  45

Tyr Gly Ala Ser Asn Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Thr Ala Pro Trp
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
        180                 185                 190
Ala Cys Glu Val Thr His Gln Gly Leu Ser Ser Pro Val Thr Lys Ser
                195                 200                 205
Phe Asn Arg Gly Glu Cys
            210

<210> SEQ ID NO 311
<211> LENGTH: 597
<212> TYPE: PRT
<213> ORGANISM: Artificial Sequence
<220> FEATURE:
<223> OTHER INFORMATION: Synthetic Construct

<400> SEQUENCE: 311

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
        35                  40                  45
Gly Gly Ile Ile Pro Gly Tyr Ala Thr Ala Asn Tyr Ala Gln Lys Phe
    50                  55                  60
Gln Gly Arg Val Thr Ile Thr Ala Asp Glu Ser Ser Thr Ala Tyr
65              70                  75                  80
Met Glu Leu Ser Ser Leu Arg Ser Glu Asp Thr Ala Val Tyr Tyr Cys
                85                  90                  95
Ala Arg Asp Ala Ala Gly Ile Arg Leu Phe Ala Asp Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
```

```
                 260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Ser Gly Gly Gly Gly Ser
    450                 455                 460

Ala Pro Thr Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Leu Ala Gln Ser Lys Asn Phe His Leu
    530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590

Ile Ser Thr Leu Thr
        595

<210> SEQ ID NO 312
<211> LENGTH: 448
<212> TYPE: PRT
<213> ORGANISM: Artificial Sequence
<220> FEATURE:
<223> OTHER INFORMATION: Synthetic Construct

<400> SEQUENCE: 312

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

-continued

```
             20                  25                  30
Ala Ile Ser Trp Val Arg Gln Ala Pro Gly Gln Gly Leu Glu Trp Met
         35                  40                  45
Gly Gly Ile Ile Pro Gly Tyr Ala Thr Ala Asn Tyr Ala Gln Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ala Ala Gly Ile Arg Leu Phe Ala Asp Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Cys Thr
            340                 345                 350
Leu Pro Pro Ser Arg Glu Glu Met Thr Lys Asn Gln Val Ser Leu Trp
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

<210> SEQ ID NO 313
<211> LENGTH: 449
<212> TYPE: PRT
<213> ORGANISM: Artificial Sequence
<220> FEATURE:
<223> OTHER INFORMATION: Synthetic Construct

<400> SEQUENCE: 313

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365
```

-continued

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 314
<211> LENGTH: 214
<212> TYPE: PRT
<213> ORGANISM: Artificial Sequence
<220> FEATURE:
<223> OTHER INFORMATION: Synthetic Construct

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Asp Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 315
<211> LENGTH: 597
<212> TYPE: PRT
<213> ORGANISM: Artificial Sequence
<220> FEATURE:
<223> OTHER INFORMATION: Synthetic Construct

<400> SEQUENCE: 315

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Gly Gly Gly Gly Ser
    450                 455                 460

Ala Pro Thr Ser Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Leu Ala Gln Ser Lys Asn Phe His Leu
530                 535                 540

Arg Pro Arg Asp Leu Ile Ser Ala Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590

Ile Ser Thr Leu Thr
            595

<210> SEQ ID NO 316
<211> LENGTH: 448
<212> TYPE: PRT
<213> ORGANISM: Artificial Sequence
<220> FEATURE:
<223> OTHER INFORMATION: Synthetic Construct

<400> SEQUENCE: 316

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
                385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
435                 440                 445

<210> SEQ ID NO 317
<211> LENGTH: 449
<212> TYPE: PRT
<213> ORGANISM: Artificial Sequence
<220> FEATURE:
<223> OTHER INFORMATION: Synthetic Construct

<400> SEQUENCE: 317

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 318
<211> LENGTH: 215
<212> TYPE: PRT
<213> ORGANISM: Artificial Sequence
<220> FEATURE:
<223> OTHER INFORMATION: Synthetic Construct

<400> SEQUENCE: 318

Glu Ile Val Leu Thr Gln Ser Pro Gly Thr Leu Ser Leu Ser Pro Gly

-continued

```
                1               5                  10                   15
            Glu Arg Ala Thr Leu Ser Cys Arg Ala Ser Gln Ser Val Ser Ser Asn
                               20                  25                  30

Leu Ala Trp Tyr Gln Gln Lys Pro Gly Gln Ala Pro Arg Leu Leu Ile
                           35                  40                  45

Tyr Gly Ala Ser Ser Arg Ala Thr Gly Ile Pro Asp Arg Phe Ser Gly
                       50                  55                  60

Ser Gly Ser Gly Thr Asp Phe Thr Leu Thr Ile Ser Arg Leu Glu Pro
            65                  70                  75                  80

Glu Asp Phe Ala Val Tyr Tyr Cys Gln Gln Tyr Gly Ser Ser Pro Pro
                               85                  90                  95

Val Thr Phe Gly Gln Gly Thr Lys Val Glu Ile Lys Arg Thr Val Ala
                           100                 105                 110

Ala Pro Ser Val Phe Ile Phe Pro Pro Ser Asp Glu Gln Leu Lys Ser
                       115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
            145                 150                 155                 160

Gln Glu Ser Val Thr Glu Gln Asp Ser Lys Asp Ser Thr Tyr Ser Leu
                               165                 170                 175

Ser Ser Thr Leu Thr Leu Ser Lys Ala Asp Tyr Glu Lys His Lys Val
                           180                 185                 190

Tyr Ala Cys Glu Val Thr His Gln Gly Leu Ser Ser Pro Val Thr Lys
                       195                 200                 205

Ser Phe Asn Arg Gly Glu Cys
            210                 215

<210> SEQ ID NO 319
<211> LENGTH: 599
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Glu Ser Gly Gly Gly Leu Val Gln Pro Gly Gly
            1               5                   10                  15

Ser Leu Arg Leu Ser Cys Ala Ala Ser Gly Phe Thr Phe Ser Ser Tyr
                               20                  25                  30

Ala Met Ser Trp Val Arg Gln Ala Pro Gly Lys Gly Leu Glu Trp Val
                           35                  40                  45

Ser Asp Ile Ser Tyr Ala Gly Gly Ser Thr Ala Tyr Ala Asp Ser Val
                       50                  55                  60

Lys Gly Arg Phe Thr Ile Ser Arg Asp Asn Ala Lys Asn Ser Leu Tyr
            65                  70                  75                  80

Leu Gln Met Asn Ser Leu Arg Ala Glu Asp Thr Ala Val Tyr Tyr Cys
                               85                  90                  95

Ala Arg Ser Asn Ala Tyr Ala Trp Asp Asp Ala Leu Asp Ile Trp Gly
                           100                 105                 110

Gln Gly Thr Met Val Thr Val Ser Ser Ala Ser Thr Lys Gly Pro Ser
                       115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
```

-continued

|     |     |     |     |     |     |     |     |     |     |     |     |
|-----|-----|-----|-----|-----|-----|-----|-----|-----|-----|-----|-----|
| 145 |     |     |     | 150 |     |     |     | 155 |     |     | 160 |
| Ser | Trp | Asn | Ser | Gly | Ala | Leu | Thr | Ser | Gly | Val | His |
|     |     |     | 165 |     |     |     | 170 |     |     |     | 175 |
| Thr | Phe | Pro | Ala | Val | Leu | Gln | Ser | Ser | Gly | Leu | Tyr |
|     |     |     | 180 |     |     |     | 185 |     |     |     | 190 |
| Ser | Leu | Ser | Ser | Val | Val | Thr | Val | Pro | Ser | Ser | Leu |
|     |     |     | 195 |     |     |     | 200 |     |     |     | 205 |
| Gly | Thr | Gln | Thr | Tyr | Ile | Cys | Asn | Val | Asn | His | Lys |
|     |     |     | 210 |     |     |     | 215 |     |     |     | 220 |
| Pro | Ser | Asn | Thr | Lys | Val | Asp | Lys | Val | Glu | Pro | Lys |
|     |     |     | 225 |     |     |     | 230 |     |     |     |     |
| Ser | Cys | Asp | Lys | Thr | His | Thr | Cys | Pro | Pro | Cys | Pro |
|     |     |     |     | 235 |     |     |     | 240 |     |     |     |
| Ala | Pro | Glu | Ala | Ala | Gly | Ala | Pro | Ser | Val | Phe | Leu |
|     |     |     |     | 245 |     |     |     | 250 |     |     |     |
| Phe | Pro | Pro | Lys | Pro | Lys | Asp | Thr | Leu | Met | Ile | Ser |
|     |     |     |     | 255 |     |     |     | 260 |     |     |     |
| Arg | Thr | Pro | Glu | Val | Thr | Cys | Val | Val | Val | Asp | Val |
|     |     |     |     | 265 |     |     |     | 270 |     |     |     |
| Ser | His | Glu | Asp | Pro | Glu | Val | Lys | Phe | Asn | Trp | Tyr |
|     |     |     |     | 275 |     |     |     | 280 |     |     |     |
| Val | Asp | Gly | Val | Glu | Val | His | Asn | Ala | Lys | Thr | Lys |
|     |     |     |     | 285 |     |     |     | 290 |     |     |     |
| Pro | Arg | Glu | Glu | Gln | Tyr | Asn | Ser | Thr | Tyr | Arg | Val |
|     |     |     |     | 295 |     |     |     | 300 |     |     |     |
| Val | Ser | Val | Leu | Thr | Val | Leu | His | Gln | Asp | Trp | Leu |
|     | 305 |     |     |     | 310 |     |     |     | 315 |     |     |
| Asn | Gly | Lys | Glu | Tyr | Lys | Cys | Lys | Val | Ser | Asn | Lys |
|     | 320 |     |     |     | 325 |     |     |     | 330 |     |     |
| Ala | Leu | Pro | Ala | Pro | Ile | Glu | Lys | Thr | Ile | Ser | Lys |
|     |     |     | 335 |     |     |     | 340 |     |     |     |     |
| Ala | Lys | Gly | Gln | Pro | Arg | Glu | Pro | Gln | Val | Tyr | Thr |
|     |     |     |     | 345 |     |     |     | 350 |     |     |     |
| Leu | Pro | Pro | Cys | Arg | Glu | Glu | Met | Thr | Lys | Asn | Gln |
|     |     |     |     | 355 |     |     |     | 360 |     |     |     |
| Val | Ser | Leu | Ser | Cys | Ala | Val | Lys | Gly | Phe | Tyr | Pro |
|     |     |     |     | 365 |     |     |     | 370 |     |     |     |
| Ser | Asp | Ile | Ala | Val | Glu | Trp | Glu | Ser | Asn | Gly | Gln |
|     |     |     |     | 375 |     |     |     | 380 |     |     |     |
| Pro | Glu | Asn | Asn | Tyr | Lys | Thr | Thr | Pro | Pro | Val | Leu |
|     | 385 |     |     |     | 390 |     |     |     | 395 |     | 400 |
| Asp | Ser | Asp | Gly | Ser | Phe | Phe | Leu | Val | Ser | Lys | Leu |
|     |     |     | 405 |     |     |     | 410 |     |     |     | 415 |
| Thr | Val | Asp | Lys | Ser | Arg | Trp | Gln | Gln | Gly | Asn | Val |
|     |     |     |     |     | 420 |     |     |     | 425 |     |     |
| Phe | Ser | Cys | Ser | Val | Met | His | Glu | Ala | Leu | His | Asn |
|     |     |     | 430 |     |     |     | 435 |     |     |     |     |
| His | Tyr | Thr | Gln | Lys | Ser | Leu | Ser | Leu | Ser | Pro | Gly |
|     |     |     | 440 |     |     |     | 445 |     |     |     | 450 |
| Ser | Gly | Gly | Gly | Gly | Ser | Gly | Gly | Gly | Gly | Ser | Gly |
|     |     |     | 455 |     |     |     | 460 |     |     |     |     |
| Gly | Gly | Gly | Ser | Ala | Pro | Thr | Ser | Ser | Ser | Thr | Lys |
|     | 465 |     |     |     | 470 |     |     |     | 475 |     |     |
| Lys | Thr | Gln | Leu | Gln | Leu | Glu | His | Leu | Leu | Leu | Asp |
|     |     |     |     | 480 |     |     |     | 485 |     |     |     |
| Leu | Gln | Met | Ile | Leu | Asn | Gly | Ile | Asn | Asn | Tyr | Lys |
|     |     |     |     | 490 |     |     |     | 495 |     |     |     |
| Asn | Pro | Lys | Leu | Thr | Glu | Met | Leu | Thr | Ala | Lys | Phe |
|     |     | 500 |     |     |     | 505 |     |     |     | 510 |     |
| Tyr | Met | Pro | Lys | Lys | Ala | Thr | Glu | Leu | Lys | His | Leu |
|     |     |     |     | 515 |     |     |     | 520 |     |     |     |
| Gln | Cys | Leu | Glu | Glu | Glu | Leu | Lys | Pro | Leu | Glu | Glu |
|     |     |     | 525 |     |     |     | 530 |     |     |     |     |
| Val | Leu | Asn | Leu | Ala | Gln | Ser | Lys | Asn | Phe | His | Leu |
|     |     |     |     | 535 |     |     |     | 540 |     |     |     |
| Arg | Pro | Arg | Asp | Leu | Ile | Ser | Ala | Ile | Asn | Val | Ile |
|     | 545 |     |     |     | 550 |     |     |     | 555 |     |     |
| Val | Leu | Glu | Leu | Lys | Gly | Ser | Glu | Thr | Thr | Phe | Met |
|     | 560 |     |     |     | 565 |     |     |     | 570 |     |     |
| Cys | Glu | Tyr | Ala | Asp | Glu |     |     |     |     |     |     |
|     | 575 |     |     |     |     |     |     |     |     |     |     |

```
Thr Ala Thr Ile Val Glu Phe Leu Asn Arg Trp Ile Thr Phe Ala Gln
            580                 585                 590

Ser Ile Ile Ser Thr Leu Thr
            595

<210> SEQ ID NO 320
<211> LENGTH: 450
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 321
<211> LENGTH: 451
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 322
<211> LENGTH: 215
<212> TYPE: PRT
<213> ORGANISM: Artificial Sequence
<220> FEATURE:
<223> OTHER INFORMATION: Synthetic Construct

<400> SEQUENCE: 322

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 323
<211> LENGTH: 599
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ser Gly Gly Gly Gly Ser Gly Gly Gly Ser Gly Gly Gly
    450                 455                 460

Gly Ser Ala Pro Thr Ser Ser Ser Thr Lys Lys Thr Gln Leu Gln Leu
465                 470                 475                 480

Glu His Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
            500                 505                 510

Pro Lys Lys Ala Thr Glu Leu Lys His Leu Gln Cys Leu Glu Glu Glu
        515                 520                 525

Leu Lys Pro Leu Glu Glu Val Leu Asn Leu Ala Gln Ser Lys Asn Phe
    530                 535                 540

His Leu Arg Pro Arg Asp Leu Ile Ser Ala Ile Asn Val Ile Val Leu
545                 550                 555                 560

Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
        595

<210> SEQ ID NO 324
<211> LENGTH: 450
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Asp Ile Ser Tyr Ala Gly Gly Ser Thr Ala Tyr Ala Asp Ser Val
    50              55                  60

Lys Gly Arg Phe Thr Ile Ser Arg Asp Asn Ala Lys Asn Ser Leu Tyr
 65              70                  75                  80

Leu Gln Met Asn Ser Leu Arg Ala Glu Asp Thr Ala Val Tyr Tyr Cys
                 85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
450
```

```
<210> SEQ ID NO 325
<211> LENGTH: 451
<212> TYPE: PRT
<213> ORGANISM: Artificial Sequence
<220> FEATURE:
<223> OTHER INFORMATION: Synthetic Construct

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365
```

```
Leu Trp Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 326
<211> LENGTH: 214
<212> TYPE: PRT
<213> ORGANISM: Artificial Sequence
<220> FEATURE:
<223> OTHER INFORMATION: Synthetic Construct

<400> SEQUENCE: 326

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Glu Ile Tyr Gly Ala
            20                  25                  30
Leu Asn Trp Tyr Gln Gln Lys Pro Gly Lys Ala Pro Lys Leu Leu Ile
        35                  40                  45
Tyr Gly Ala Thr Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Ser Tyr Asp Ala Pro Trp
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 327
<211> LENGTH: 597
<212> TYPE: PRT
<213> ORGANISM: Artificial Sequence
<220> FEATURE:
<223> OTHER INFORMATION: Synthetic Construct

<400> SEQUENCE: 327
```

```
Gln Val Gln Leu Val Gln Ser Gly Ala Glu Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Gly Ala Ala Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ala Ala Gly Ile Arg Leu Phe Ala Asp Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ser Gly Gly Gly Gly Ser Gly Gly Gly Ser Gly Gly Gly Gly Ser
450                 455                 460

Ala Pro Thr Ser Ser Ser Thr Lys Lys Thr Gln Leu Gln Leu Glu Glu
465                 470                 475                 480

Leu Leu Leu Asp Leu Gln Met Ile Leu Asn Gly Ile Asn Asn Tyr Lys
            485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
            515                 520                 525

Pro Leu Glu Glu Val Leu Asn Leu Ala Gln Ser Lys Asn Phe His Leu
            530                 535                 540

Arg Pro Arg Asp Leu Ile Ser Asn Ile Asn Val Ile Val Leu Glu Leu
545                 550                 555                 560

Lys Gly Ser Glu Thr Thr Phe Met Cys Glu Tyr Ala Asp Glu Thr Ala
            565                 570                 575

Thr Ile Val Glu Phe Leu Asn Arg Trp Ile Thr Phe Ala Gln Ser Ile
            580                 585                 590

Ile Ser Thr Leu Thr
            595

<210> SEQ ID NO 328
<211> LENGTH: 448
<212> TYPE: PRT
<213> ORGANISM: Artificial Sequence
<220> FEATURE:
<223> OTHER INFORMATION: Synthetic Construct

<400> SEQUENCE: 328

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Gly Ala Ala Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 329
<211> LENGTH: 449
<212> TYPE: PRT
<213> ORGANISM: Artificial Sequence
<220> FEATURE:
<223> OTHER INFORMATION: Synthetic Construct

<400> SEQUENCE: 329

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Gly Ala Ala Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95
```

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 330
<211> LENGTH: 215
<212> TYPE: PRT
<213> ORGANISM: Artificial Sequence
<220> FEATURE:
<223> OTHER INFORMATION: Synthetic Construct

<400> SEQUENCE: 330

Glu Ile Val Leu Thr Gln Ser Pro Gly Thr Leu Ser Leu Ser Pro Gly

```
1               5                   10                  15
Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 331
<211> LENGTH: 599
<212> TYPE: PRT
<213> ORGANISM: Artificial Sequence
<220> FEATURE:
<223> OTHER INFORMATION: Synthetic Construct

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Asp Ile Thr Tyr Ala Gly Gly Ser Thr Ala Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
```

Ser Trp Asn Ser Gly Ala Leu Thr Ser Gly Val His Thr Phe Pro Ala
145                 150                 155                 160

Val Leu Gln Ser Ser Gly Leu Tyr Ser Leu Ser Ser Val Val Thr Val
            165                 170                 175

Pro Ser Ser Ser Leu Gly Thr Gln Thr Tyr Ile Cys Asn Val Asn His
        180                 185                 190

Lys Pro Ser Asn Thr Lys Val Asp Lys Lys Val Glu Pro Lys Ser Cys
    195                 200                 205

Asp Lys Thr His Thr Cys Pro Pro Cys Pro Ala Pro Glu Ala Ala Gly
210                 215                 220

Ala Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
            245                 250                 255

Glu Asp Pro Glu Val Lys Phe Asn Trp Tyr Val Asp Gly Val Glu Val
        260                 265                 270

His Asn Ala Lys Thr Lys Pro Arg Glu Glu Gln Tyr Asn Ser Thr Tyr
    275                 280                 285

Arg Val Val Ser Val Leu Thr Val Leu His Gln Asp Trp Leu Asn Gly
290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
            325                 330                 335

Tyr Thr Leu Pro Pro Cys Arg Glu Glu Met Thr Lys Asn Gln Val Ser
        340                 345                 350

Leu Ser Cys Ala Val Lys Gly Phe Tyr Pro Ser Asp Ile Ala Val Glu
    355                 360                 365

Trp Glu Ser Asn Gly Gln Pro Glu Asn Asn Tyr Lys Thr Thr Pro Pro
370                 375                 380

Val Leu Asp Ser Asp Gly Ser Phe Phe Leu Val Ser Lys Leu Thr Val
385                 390                 395                 400

Asp Lys Ser Arg Trp Gln Gln Gly Asn Val Phe Ser Cys Ser Val Met
            405                 410                 415

His Glu Ala Leu His Asn His Tyr Thr Gln Lys Ser Leu Ser Leu Ser
        420                 425                 430

Pro Gly Ser Gly Gly Gly Gly Ser Gly Gly Gly Gly Ser Gly Gly Gly
    435                 440                 445

Gly Ser Ala Pro Thr Ser Ser Ser Thr Lys Lys Thr Gln Leu Gln Leu
450                 455                 460

Glu Glu Leu Leu Leu Asp Leu Gln Met Ile Leu Asn Gly Ile Asn Asn
465                 470                 475                 480

Tyr Lys Asn Pro Lys Leu Thr Glu Met Leu Thr Ala Lys Phe Tyr Met
            485                 490                 495

Pro Lys Lys Ala Thr Glu Leu Lys His Leu Gln Cys Leu Glu Glu Glu
        500                 505                 510

Leu Lys Pro Leu Glu Glu Val Leu Asn Leu Ala Gln Ser Lys Asn Phe
    515                 520                 525

His Leu Arg Pro Arg Asp Leu Ile Ser Asn Ile Asn Val Ile Val Leu
530                 535                 540

Glu Leu Lys Gly Ser Glu Thr Thr Phe Met Cys Glu Tyr Ala Asp Glu
545                 550                 555                 560

```
Thr Ala Thr Ile Val Glu Phe Leu Asn Arg Trp Ile Thr Phe Ala Gln
            580                 585                 590

Ser Ile Ile Ser Thr Leu Thr
            595

<210> SEQ ID NO 332
<211> LENGTH: 450
<212> TYPE: PRT
<213> ORGANISM: Artificial Sequence
<220> FEATURE:
<223> OTHER INFORMATION: Synthetic Construct

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 333
<211> LENGTH: 451
<212> TYPE: PRT
<213> ORGANISM: Artificial Sequence
<220> FEATURE:
<223> OTHER INFORMATION: Synthetic Construct

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240
```

Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
            355                 360                 365

Leu Trp Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 334
<211> LENGTH: 215
<212> TYPE: PRT
<213> ORGANISM: Artificial Sequence
<220> FEATURE:
<223> OTHER INFORMATION: Synthetic Construct

<400> SEQUENCE: 334

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 335
<211> LENGTH: 599
<212> TYPE: PRT
<213> ORGANISM: Artificial Sequence
<220> FEATURE:
<223> OTHER INFORMATION: Synthetic Construct

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ser Gly Gly Gly Gly Ser Gly Gly Gly Ser Gly Gly Gly
    450                 455                 460

Gly Ser Ala Pro Thr Ser Ser Ser Thr Lys Lys Thr Gln Leu Gln Leu
465                 470                 475                 480

Glu Glu Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
            500                 505                 510

Pro Lys Lys Ala Thr Glu Leu Lys His Leu Gln Cys Leu Glu Glu Glu
        515                 520                 525

Leu Lys Pro Leu Glu Glu Val Leu Asn Leu Ala Gln Ser Lys Asn Phe
    530                 535                 540

His Leu Arg Pro Arg Asp Leu Ile Ser Asn Ile Asn Val Ile Val Leu
545                 550                 555                 560

Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
            580                 585                 590

Ser Ile Ile Ser Thr Leu Thr
        595

<210> SEQ ID NO 336
<211> LENGTH: 450
<212> TYPE: PRT
<213> ORGANISM: Artificial Sequence
<220> FEATURE:
<223> OTHER INFORMATION: Synthetic Construct

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

-continued

```
Ser Asp Ile Thr Tyr Ala Gly Gly Ser Thr Ala Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Ser Asn Ala Tyr Ala Trp Asp Asp Ala Leu Asp Ile Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Glu Glu Met Thr Lys Asn Gln Val Ser
        355                 360                 365
Leu Trp Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
450
```

-continued

```
<210> SEQ ID NO 337
<211> LENGTH: 451
<212> TYPE: PRT
<213> ORGANISM: Artificial Sequence
<220> FEATURE:
<223> OTHER INFORMATION: Synthetic Construct

<400> SEQUENCE: 337

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Thr Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365
```

```
Leu Trp Cys Leu Val Lys Gly Phe Tyr Pro Ser Asp Ile Ala Val Glu
370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 338
<211> LENGTH: 214
<212> TYPE: PRT
<213> ORGANISM: Artificial Sequence
<220> FEATURE:
<223> OTHER INFORMATION: Synthetic Construct

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Thr Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 339
<211> LENGTH: 597
<212> TYPE: PRT
<213> ORGANISM: Artificial Sequence
<220> FEATURE:
<223> OTHER INFORMATION: Synthetic Construct

<400> SEQUENCE: 339
```

```
Gln Val Gln Leu Val Gln Ser Gly Ala Glu Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Cys Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Gly Gly Gly Gly Ser
    450                 455                 460

Ala Pro Thr Ser Ser Ser Thr Lys Lys Thr Gln Leu Gln Leu Glu Glu
465                 470                 475                 480

Leu Leu Leu Asp Leu Gln Met Ile Leu Asn Gly Ile Asn Asn Tyr Lys
                485                 490                 495

Asn Pro Lys Leu Thr Glu Met Leu Thr Ala Lys Phe Tyr Met Pro Lys
            500                 505                 510

Lys Ala Thr Glu Leu Lys His Leu Gln Cys Leu Glu Glu Glu Leu Lys
            515                 520                 525

Pro Leu Glu Glu Val Leu Asn Leu Ala Gln Ser Lys Asn Phe His Leu
        530                 535                 540

Arg Pro Arg Asp Leu Ile Ser Asn Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590

Ile Ser Thr Leu Thr
            595

<210> SEQ ID NO 340
<211> LENGTH: 448
<212> TYPE: PRT
<213> ORGANISM: Artificial Sequence
<220> FEATURE:
<223> OTHER INFORMATION: Synthetic Construct

<400> SEQUENCE: 340

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 341
<211> LENGTH: 449
<212> TYPE: PRT
<213> ORGANISM: Artificial Sequence
<220> FEATURE:
<223> OTHER INFORMATION: Synthetic Construct

<400> SEQUENCE: 341

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 342
<211> LENGTH: 214
<212> TYPE: PRT
<213> ORGANISM: Artificial Sequence
<220> FEATURE:
<223> OTHER INFORMATION: Synthetic Construct

<400> SEQUENCE: 342

Asp Ile Gln Met Thr Gln Ser Pro Ser Ser Leu Ser Ala Ser Val Gly

```
            1               5                  10                 15
         Asp Arg Val Thr Ile Thr Cys Arg Ala Ser Gln Glu Ile Tyr Gly Ala
                         20                 25                 30
         Leu Asn Trp Tyr Gln Gln Lys Pro Gly Lys Ala Pro Lys Leu Leu Ile
                         35                 40                 45
         Tyr Gly Ala Thr Asn Leu Gln Ser Gly Val Pro Ser Arg Phe Ser Gly
                         50                 55                 60
         Ser Gly Ser Gly Thr Asp Phe Thr Leu Thr Ile Ser Ser Leu Gln Pro
         65                  70                 75                 80
         Glu Asp Phe Ala Thr Tyr Tyr Cys Gln Ser Thr Tyr Asp Ala Pro Trp
                         85                 90                 95
         Thr Phe Gly Gly Gly Thr Lys Val Glu Ile Lys Arg Thr Val Ala Ala
                         100                105                110
         Pro Ser Val Phe Ile Phe Pro Pro Ser Asp Glu Gln Leu Lys Ser Gly
                         115                120                125
         Thr Ala Ser Val Val Cys Leu Leu Asn Asn Phe Tyr Pro Arg Glu Ala
                         130                135                140
         Lys Val Gln Trp Lys Val Asp Asn Ala Leu Gln Ser Gly Asn Ser Gln
         145                 150                155                160
         Glu Ser Val Thr Glu Gln Asp Ser Lys Asp Ser Thr Tyr Ser Leu Ser
                         165                170                175
         Ser Thr Leu Thr Leu Ser Lys Ala Asp Tyr Glu Lys His Lys Val Tyr
                         180                185                190
         Ala Cys Glu Val Thr His Gln Gly Leu Ser Ser Pro Val Thr Lys Ser
                         195                200                205
         Phe Asn Arg Gly Glu Cys
                         210

<210> SEQ ID NO 343
<211> LENGTH: 597
<212> TYPE: PRT
<213> ORGANISM: Artificial Sequence
<220> FEATURE:
<223> OTHER INFORMATION: Synthetic Construct

<400> SEQUENCE: 343

Gln Val Gln Leu Val Gln Ser Gly Ala Glu Val Lys Lys Pro Gly Ser
         1               5                  10                 15
         Ser Val Lys Val Ser Cys Lys Ala Ser Gly Gly Thr Phe Ser Ser Tyr
                         20                 25                 30
         Ala Ile Ser Trp Val Arg Gln Ala Pro Gly Gln Gly Leu Glu Trp Met
                         35                 40                 45
         Gly Gly Ile Ile Pro Gly Tyr Ala Thr Ala Asn Tyr Ala Gln Lys Phe
                         50                 55                 60
         Gln Gly Arg Val Thr Ile Thr Ala Asp Glu Ser Thr Ser Thr Ala Tyr
         65                  70                 75                 80
         Met Glu Leu Ser Ser Leu Arg Ser Glu Asp Thr Ala Val Tyr Tyr Cys
                         85                 90                 95
         Ala Arg Asp Ala Ala Gly Ile Arg Leu Phe Ala Asp Trp Gly Gln Gly
                         100                105                110
         Thr Leu Val Thr Val Ser Ser Ala Ser Thr Lys Gly Pro Ser Val Phe
                         115                120                125
         Pro Leu Ala Pro Ser Ser Lys Ser Thr Ser Gly Gly Thr Ala Ala Leu
                         130                135                140
         Gly Cys Leu Val Lys Asp Tyr Phe Pro Glu Pro Val Thr Val Ser Trp
```

```
             145                 150                 155                 160
Asn Ser Gly Ala Leu Thr Ser Gly Val His Thr Phe Pro Ala Val Leu
                 165                 170                 175
Gln Ser Ser Gly Leu Tyr Ser Leu Ser Ser Val Val Thr Val Pro Ser
                 180                 185                 190
Ser Ser Leu Gly Thr Gln Thr Tyr Ile Cys Asn Val Asn His Lys Pro
                 195                 200                 205
Ser Asn Thr Lys Val Asp Lys Lys Val Glu Pro Lys Ser Cys Asp Lys
                 210                 215                 220
Thr His Thr Cys Pro Pro Cys Pro Ala Pro Glu Ala Ala Gly Ala Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser His Glu Asp
                 260                 265                 270
Pro Glu Val Lys Phe Asn Trp Tyr Val Asp Gly Val Glu Val His Asn
                 275                 280                 285
Ala Lys Thr Lys Pro Arg Glu Glu Gln Tyr Asn Ser Thr Tyr Arg Val
                 290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                 325                 330                 335
Thr Ile Ser Lys Ala Lys Gly Gln Pro Arg Glu Pro Gln Val Tyr Thr
                 340                 345                 350
Leu Pro Pro Cys Arg Glu Glu Met Thr Lys Asn Gln Val Ser Leu Ser
                 355                 360                 365
Cys Ala Val Lys Gly Phe Tyr Pro Ser Asp Ile Ala Val Glu Trp Glu
                 370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                 405                 410                 415
Ser Arg Trp Gln Gln Gly Asn Val Phe Ser Cys Ser Val Met His Glu
                 420                 425                 430
Ala Leu His Asn His Tyr Thr Gln Lys Ser Leu Ser Leu Ser Pro Gly
                 435                 440                 445
Ser Gly Gly Gly Gly Ser Gly Gly Gly Gly Ser Gly Gly Gly Gly Ser
                 450                 455                 460
Ala Pro Thr Ser Ser Ser Thr Lys Lys Thr Gln Leu Gln Leu Glu Glu
465                 470                 475                 480
Leu Leu Leu Asp Leu Gln Met Ile Leu Asn Gly Ile Asn Asn Tyr Lys
                 485                 490                 495
Asn Pro Lys Leu Thr Glu Met Leu Thr Ala Lys Phe Tyr Met Pro Lys
                 500                 505                 510
Lys Ala Thr Glu Leu Lys His Leu Gln Cys Leu Glu Glu Glu Leu Lys
                 515                 520                 525
Pro Leu Glu Glu Val Leu Asn Leu Ala Gln Ser Lys Asn Phe His Leu
                 530                 535                 540
Arg Pro Arg Asp Leu Ile Ser Asn Ile Asn Val Ile Val Leu Glu Leu
545                 550                 555                 560
Lys Gly Ser Glu Thr Thr Phe Met Cys Glu Tyr Ala Asp Glu Thr Ala
                 565                 570                 575
```

```
Thr Ile Val Glu Phe Leu Asn Arg Trp Ile Thr Phe Ala Gln Ser Ile
            580                 585                 590

Ile Ser Thr Leu Thr
        595

<210> SEQ ID NO 344
<211> LENGTH: 448
<212> TYPE: PRT
<213> ORGANISM: Artificial Sequence
<220> FEATURE:
<223> OTHER INFORMATION: Synthetic Construct

<400> SEQUENCE: 344

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 345
<211> LENGTH: 449
<212> TYPE: PRT
<213> ORGANISM: Artificial Sequence
<220> FEATURE:
<223> OTHER INFORMATION: Synthetic Construct

<400> SEQUENCE: 345

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Tyr Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Gly Ile Arg Leu Phe Ala Asp Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 346
<211> LENGTH: 215
<212> TYPE: PRT
<213> ORGANISM: Artificial Sequence
<220> FEATURE:
<223> OTHER INFORMATION: Synthetic Construct

<400> SEQUENCE: 346

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

-continued

```
Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 347
<211> LENGTH: 599
<212> TYPE: PRT
<213> ORGANISM: Artificial Sequence
<220> FEATURE:
<223> OTHER INFORMATION: Synthetic Construct

<400> SEQUENCE: 347

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Ser Gly Gly Gly Ser Gly Gly Gly Ser Gly Gly Gly
450                 455                 460

Gly Ser Ala Pro Thr Ser Ser Thr Lys Lys Thr Gln Leu Gln Leu
465                 470                 475                 480

Glu Glu Leu Leu Leu Asp Leu Gln Met Ile Leu Asn Gly Ile Asn Asn
                485                 490                 495

Tyr Lys Asn Pro Lys Leu Thr Glu Met Leu Thr Ala Lys Phe Tyr Met
            500                 505                 510

Pro Lys Lys Ala Thr Glu Leu Lys His Leu Gln Cys Leu Glu Glu Glu
        515                 520                 525

Leu Lys Pro Leu Glu Glu Val Leu Asn Leu Ala Gln Ser Lys Asn Phe
    530                 535                 540

His Leu Arg Pro Arg Asp Leu Ile Ser Asn Ile Asn Val Ile Val Leu
545                 550                 555                 560

Glu Leu Lys Gly Ser Glu Thr Thr Phe Met Cys Glu Tyr Ala Asp Glu
                565                 570                 575

Thr Ala Thr Ile Val Glu Phe Leu Asn Arg Trp Ile Thr Phe Ala Gln
                580                 585                 590

Ser Ile Ile Ser Thr Leu Thr
            595

<210> SEQ ID NO 348
<211> LENGTH: 450
<212> TYPE: PRT
<213> ORGANISM: Artificial Sequence
<220> FEATURE:
<223> OTHER INFORMATION: Synthetic Construct

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Ser Asn Ala Tyr Ala Trp Asp Asp Ala Leu Asp Ile Trp Gly
        100                 105                 110

Gln Gly Thr Met Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 349
<211> LENGTH: 451
<212> TYPE: PRT
```

<213> ORGANISM: Artificial Sequence
<220> FEATURE:
<223> OTHER INFORMATION: Synthetic Construct

<400> SEQUENCE: 349

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Asp | Ile | Ser | Tyr | Ala | Gly | Gly | Ser | Thr | Ala | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ser | Asn | Ala | Tyr | Ala | Trp | Asp | Asp | Ala | Leu | Asp | Ile | Trp | Gly |
| | | | 100 | | | | | 105 | | | | | 110 | | |
| Gln | Gly | Thr | Met | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Lys | Lys | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Ala | Ala | Gly |
| 225 | | | | | 230 | | | | | 235 | | | | | 240 |
| Ala | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | 275 | | | | | 280 | | | | | 285 | | | | |
| His | Asn | Ala | Lys | Thr | Lys | Pro | Arg | Glu | Glu | Gln | Tyr | Asn | Ser | Thr | Tyr |
| 290 | | | | | 295 | | | | | 300 | | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Cys | Thr | Leu | Pro | Pro | Ser | Arg | Glu | Glu | Met | Thr | Lys | Asn | Gln | Val | Ser |
| | | 355 | | | | | 360 | | | | | 365 | | | |
| Leu | Trp | Cys | Leu | Val | Lys | Gly | Phe | Tyr | Pro | Ser | Asp | Ile | Ala | Val | Glu |
| | 370 | | | | | 375 | | | | | 380 | | | | |
| Trp | Glu | Ser | Asn | Gly | Gln | Pro | Glu | Asn | Asn | Tyr | Lys | Thr | Thr | Pro | Pro |

```
                            385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 350
<211> LENGTH: 215
<212> TYPE: PRT
<213> ORGANISM: Artificial Sequence
<220> FEATURE:
<223> OTHER INFORMATION: Synthetic Construct

<400> SEQUENCE: 350

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 351
<211> LENGTH: 599
<212> TYPE: PRT
<213> ORGANISM: Artificial Sequence
<220> FEATURE:
<223> OTHER INFORMATION: Synthetic Construct

<400> SEQUENCE: 351

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Asp Ile Ser Tyr Ala Gly Gly Ser Thr Ala Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Asn Ala Tyr Ala Trp Asp Asp Ala Leu Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

435                 440                 445
Pro Gly Ser Gly Gly Gly Ser Gly Gly Gly Ser Gly Gly
            450                 455                 460
Gly Ser Ala Pro Thr Ser Ser Thr Lys Lys Thr Gln Leu Gln Leu
465                 470                 475                 480
Glu Glu Leu Leu Leu Asp Leu Gln Met Ile Leu Asn Gly Ile Asn Asn
                        485                 490                 495
Tyr Lys Asn Pro Lys Leu Thr Glu Met Leu Thr Ala Lys Phe Tyr Met
                500                 505                 510
Pro Lys Lys Ala Thr Glu Leu Lys His Leu Gln Cys Leu Glu Glu Glu
            515                 520                 525
Leu Lys Pro Leu Glu Glu Val Leu Asn Leu Ala Gln Ser Lys Asn Phe
530                 535                 540
His Leu Arg Pro Arg Asp Leu Ile Ser Asn Ile Asn Val Ile Val Leu
545                 550                 555                 560
Glu Leu Lys Gly Ser Glu Thr Thr Phe Met Cys Glu Tyr Ala Asp Glu
                565                 570                 575
Thr Ala Thr Ile Val Glu Phe Leu Asn Arg Trp Ile Thr Phe Ala Gln
                580                 585                 590
Ser Ile Ile Ser Thr Leu Thr
            595

<210> SEQ ID NO 352
<211> LENGTH: 450
<212> TYPE: PRT
<213> ORGANISM: Artificial Sequence
<220> FEATURE:
<223> OTHER INFORMATION: Synthetic Construct

<400> SEQUENCE: 352

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Asp Ile Ser Tyr Ala Gly Gly Ser Thr Ala Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Ser Asn Ala Tyr Ala Trp Asp Asp Ala Leu Asp Ile Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His

-continued

```
                195                 200                 205
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 353
<211> LENGTH: 451
<212> TYPE: PRT
<213> ORGANISM: Artificial Sequence
<220> FEATURE:
<223> OTHER INFORMATION: Synthetic Construct

<400> SEQUENCE: 353

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Tyr Ala Gly Gly Ser Thr Ala Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Asn Ala Tyr Ala Trp Asp Asp Ala Leu Asp Ile Trp Gly
```

```
            100                 105                 110
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 354
<211> LENGTH: 133
<212> TYPE: PRT
<213> ORGANISM: Artificial Sequence
<220> FEATURE:
<223> OTHER INFORMATION: Synthetic Construct

<400> SEQUENCE: 354

Ala Pro Thr Ser Ser Ser Thr Lys Lys Thr Gln Leu Gln Leu Glu His
```

```
1               5                   10                  15
Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
            130
```

<210> SEQ ID NO 355
<211> LENGTH: 133
<212> TYPE: PRT
<213> ORGANISM: Artificial Sequence
<220> FEATURE:
<223> OTHER INFORMATION: Synthetic Construct

<400> SEQUENCE: 355

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
            130
```

<210> SEQ ID NO 356
<211> LENGTH: 133
<212> TYPE: PRT
<213> ORGANISM: Artificial Sequence
<220> FEATURE:
<223> OTHER INFORMATION: Synthetic Construct

<400> SEQUENCE: 356

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 357
<211> LENGTH: 133
<212> TYPE: PRT
<213> ORGANISM: Artificial Sequence
<220> FEATURE:
<223> OTHER INFORMATION: Synthetic Construct

<400> SEQUENCE: 357

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 358
<211> LENGTH: 133
<212> TYPE: PRT
<213> ORGANISM: Artificial Sequence
<220> FEATURE:
<223> OTHER INFORMATION: Synthetic Construct

<400> SEQUENCE: 358

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 359
<211> LENGTH: 133
<212> TYPE: PRT
<213> ORGANISM: Artificial Sequence
<220> FEATURE:
<223> OTHER INFORMATION: Synthetic Construct

<400> SEQUENCE: 359

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Glu Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 360
<211> LENGTH: 133
<212> TYPE: PRT
<213> ORGANISM: Artificial Sequence
<220> FEATURE:
<223> OTHER INFORMATION: Synthetic Construct

<400> SEQUENCE: 360

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 361
<211> LENGTH: 133
<212> TYPE: PRT
<213> ORGANISM: Artificial Sequence
<220> FEATURE:
<223> OTHER INFORMATION: Synthetic Construct

<400> SEQUENCE: 361

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 362
<211> LENGTH: 133
<212> TYPE: PRT
<213> ORGANISM: Artificial Sequence
<220> FEATURE:
<223> OTHER INFORMATION: Synthetic Construct

<400> SEQUENCE: 362

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asp Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 363
<211> LENGTH: 133
<212> TYPE: PRT
<213> ORGANISM: Artificial Sequence
<220> FEATURE:
<223> OTHER INFORMATION: Synthetic Construct

<400> SEQUENCE: 363

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 364
<211> LENGTH: 133
<212> TYPE: PRT
<213> ORGANISM: Artificial Sequence
<220> FEATURE:
<223> OTHER INFORMATION: Synthetic Construct

<400> SEQUENCE: 364

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 365
<211> LENGTH: 133
<212> TYPE: PRT
<213> ORGANISM: Artificial Sequence
<220> FEATURE:
<223> OTHER INFORMATION: Synthetic Construct

<400> SEQUENCE: 365

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 366
<211> LENGTH: 133
<212> TYPE: PRT
<213> ORGANISM: Artificial Sequence
<220> FEATURE:
<223> OTHER INFORMATION: Synthetic Construct

<400> SEQUENCE: 366

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 367
<211> LENGTH: 133
<212> TYPE: PRT

```
<213> ORGANISM: Artificial Sequence
<220> FEATURE:
<223> OTHER INFORMATION: Synthetic Construct

<400> SEQUENCE: 367

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 368
<211> LENGTH: 133
<212> TYPE: PRT
<213> ORGANISM: Artificial Sequence
<220> FEATURE:
<223> OTHER INFORMATION: Synthetic Construct

<400> SEQUENCE: 368

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Gln Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 369
<211> LENGTH: 133
<212> TYPE: PRT
<213> ORGANISM: Artificial Sequence
<220> FEATURE:
<223> OTHER INFORMATION: Synthetic Construct

<400> SEQUENCE: 369
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 370
<211> LENGTH: 133
<212> TYPE: PRT
<213> ORGANISM: Artificial Sequence
<220> FEATURE:
<223> OTHER INFORMATION: Synthetic Construct

<400> SEQUENCE: 370

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Glu Met Leu Thr Ala Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 371
<211> LENGTH: 133
<212> TYPE: PRT
<213> ORGANISM: Artificial Sequence
<220> FEATURE:
<223> OTHER INFORMATION: Synthetic Construct

<400> SEQUENCE: 371

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys

```
                20                  25                  30

Asn Pro Lys Leu Thr Glu Met Leu Thr Ala Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 372
<211> LENGTH: 133
<212> TYPE: PRT
<213> ORGANISM: Artificial Sequence
<220> FEATURE:
<223> OTHER INFORMATION: Synthetic Construct

<400> SEQUENCE: 372

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Asp Met Leu Thr Ala Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 373
<211> LENGTH: 133
<212> TYPE: PRT
<213> ORGANISM: Artificial Sequence
<220> FEATURE:
<223> OTHER INFORMATION: Synthetic Construct

<400> SEQUENCE: 373

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Asp Met Leu Thr Ala Lys Phe Tyr Met Pro Lys
             35                  40                  45
```

```
Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Thr Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
            130

<210> SEQ ID NO 374
<211> LENGTH: 133
<212> TYPE: PRT
<213> ORGANISM: Artificial Sequence
<220> FEATURE:
<223> OTHER INFORMATION: Synthetic Construct

<400> SEQUENCE: 374

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Asp Met Leu Thr Ala Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
            130

<210> SEQ ID NO 375
<211> LENGTH: 133
<212> TYPE: PRT
<213> ORGANISM: Artificial Sequence
<220> FEATURE:
<223> OTHER INFORMATION: Synthetic Construct

<400> SEQUENCE: 375

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Ala Met Leu Thr Lys Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80
```

```
Arg Pro Arg Asp Leu Ile Ser Arg Ile Asn Val Ile Val Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 376
<211> LENGTH: 133
<212> TYPE: PRT
<213> ORGANISM: Artificial Sequence
<220> FEATURE:
<223> OTHER INFORMATION: Synthetic Construct

<400> SEQUENCE: 376

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
            130

<210> SEQ ID NO 377
<211> LENGTH: 133
<212> TYPE: PRT
<213> ORGANISM: Artificial Sequence
<220> FEATURE:
<223> OTHER INFORMATION: Synthetic Construct

<400> SEQUENCE: 377

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
```

```
                    100                 105                 110
Thr Ile Val Glu Phe Leu Asn Arg Trp Ile Thr Phe Ala Gln Ser Ile
            115                 120                 125

Ile Ser Thr Leu Thr
        130

<210> SEQ ID NO 378
<211> LENGTH: 133
<212> TYPE: PRT
<213> ORGANISM: Artificial Sequence
<220> FEATURE:
<223> OTHER INFORMATION: Synthetic Construct

<400> SEQUENCE: 378

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 379
<211> LENGTH: 133
<212> TYPE: PRT
<213> ORGANISM: Artificial Sequence
<220> FEATURE:
<223> OTHER INFORMATION: Synthetic Construct

<400> SEQUENCE: 379

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Gln Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125
```

Ile Ser Thr Leu Thr
    130

<210> SEQ ID NO 380
<211> LENGTH: 133
<212> TYPE: PRT
<213> ORGANISM: Artificial Sequence
<220> FEATURE:
<223> OTHER INFORMATION: Synthetic Construct

<400> SEQUENCE: 380

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
    130

<210> SEQ ID NO 381
<211> LENGTH: 133
<212> TYPE: PRT
<213> ORGANISM: Artificial Sequence
<220> FEATURE:
<223> OTHER INFORMATION: Synthetic Construct

<400> SEQUENCE: 381

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
            115                 120                 125

Ile Ser Thr Leu Thr
    130

<210> SEQ ID NO 382

<211> LENGTH: 133
<212> TYPE: PRT
<213> ORGANISM: Artificial Sequence
<220> FEATURE:
<223> OTHER INFORMATION: Synthetic Construct

<400> SEQUENCE: 382

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Thr Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 383
<211> LENGTH: 133
<212> TYPE: PRT
<213> ORGANISM: Artificial Sequence
<220> FEATURE:
<223> OTHER INFORMATION: Synthetic Construct

<400> SEQUENCE: 383

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130

<210> SEQ ID NO 384
<211> LENGTH: 98
<212> TYPE: PRT
<213> ORGANISM: Artificial Sequence
<220> FEATURE:
<223> OTHER INFORMATION: Synthetic Construct

<400> SEQUENCE: 384

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 385
<211> LENGTH: 95
<212> TYPE: PRT
<213> ORGANISM: Artificial Sequence
<220> FEATURE:
<223> OTHER INFORMATION: Synthetic Construct

<400> SEQUENCE: 385

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 386
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(5)
<223> OTHER INFORMATION: Can be present in repeats of 1, 2, 3, 4, 5, 6,
      7, 8, 9, 10, 11, or 12
<220> FEATURE:
<221> NAME/KEY: VARIANT
<222> LOCATION: 6
<223> OTHER INFORMATION: Can be present in repeats of 0, 1, 2, or 3

<400> SEQUENCE: 386

Ser Gly Gly Gly Ser Gly
1               5

<210> SEQ ID NO 387
<211> LENGTH: 7
<212> TYPE: PRT
<213> ORGANISM: Artificial Sequence
<220> FEATURE:

```
<223> OTHER INFORMATION: Synthetic Construct
<220> FEATURE:
<221> NAME/KEY: VARIANT
<222> LOCATION: (2)..(6)
<223> OTHER INFORMATION: Can be present in repeats of 1, 2, 3, 4, 5, 6,
      7, 8, 9, 10, 11, or 12
<220> FEATURE:
<221> NAME/KEY: VARIANT
<222> LOCATION: 7
<223> OTHER INFORMATION: Can be present in repeats of 0, 1, 2, or 3

<400> SEQUENCE: 387

Ser Gly Gly Gly Gly Ser Gly
1               5

<210> SEQ ID NO 388
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(7)
<223> OTHER INFORMATION: Can be present in repeats of 1, 2, 3, 4, 5, 6,
      7, 8, 9, 10, 11, or 12
<220> FEATURE:
<221> NAME/KEY: VARIANT
<222> LOCATION: 8
<223> OTHER INFORMATION: Can be present in repeats of 0, 1, 2, or 3

<400> SEQUENCE: 388

Ser Gly Gly Gly Gly Gly Ser Gly
1               5

<210> SEQ ID NO 389
<211> LENGTH: 16
<212> TYPE: PRT
<213> ORGANISM: Artificial Sequence
<220> FEATURE:
<223> OTHER INFORMATION: Synthetic Construct

<400> SEQUENCE: 389

Ser Gly Gly Gly Gly Ser Gly Gly Gly Ser Gly Gly Gly Gly Ser
1               5                   10                  15
```

FUSIONS WITH CD8 ANTIGEN BINDING MOLECULES FOR MODULATING IMMUNE CELL FUNCTION

CROSS-REFERENCE TO RELATED APPLICATIONS

This application claims the priority benefit of U.S. Provisional Application Nos. 63/105,162, filed Oct. 23, 2020; 63/121,663, filed Dec. 4, 2020; and 63/190,669, filed May 19, 2021; each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 182842000400SEQLIST.TXT, date recorded: Oct. 21, 2021, size: 557,283 bytes).

FIELD

The present disclosure discloses CD8 antigen binding molecules and fusion polypeptides comprising the CD8 antigen binding molecules for selectively modulating the function of CD8+ T cells over other immune cells. In addition, the present disclosure also provides polynucleotides encoding the disclosed antigen binding molecules and fusion polypeptides, and vectors and host cells comprising such polynucleotides. The present disclosure further provides methods for producing the antigen binding molecules and fusion polypeptides, pharmaceutical compositions comprising the same, and uses thereof.

BACKGROUND

CD8+ T cells expressing alpha beta T cell receptors are a large subset of major histocompatibility (MHC) class I-restricted T cells that mediate adaptive immunity to various pathogens and cancers. In addition, they can also be pathogenic and cause disease in certain autoimmune and inflammatory conditions. Modulating the function of CD8+ T cells, either by activating their function in the context of infection and cancer, or by inhibiting their function in the context of certain autoimmune diseases, can have therapeutic benefits.

CD8+ T cell activation and differentiation is in large part controlled by soluble immunomodulatory proteins such as cytokines. Biological activity of cytokines is mediated by binding to their respective cytokine receptors on the cell surface, typically with very high affinity, resulting in their ability to potently stimulate signal transduction downstream of their receptors triggering various cellular processes that regulate immune cell phenotype and function. Cytokines typically have pleiotropic effects, causing multiple downstream cellular events such as activation, proliferation, survival, apoptosis, and secretion of other immunomodulatory proteins. In addition, because their receptors are expressed on multiple immune cell subsets, cytokines act not only on CD8+ T cells but also on other immune and non-immune cells that express their receptors.

For example, interleukin-2 (IL-2) is a cytokine that regulates many lymphocyte subsets, including alpha beta CD4+ and CD8 T+ cells, and various innate and innate-like lymphocytes such as NK cells, NK T cells, gamma delta T cells (Tγδ) cells, and innate lymphoid cells (ILC1, ILC2, and ILC3 cells).

IL-2 can signal by binding with an intermediate affinity to a receptor complex consisting of IL-2Rβ and IL-2Rγ subunits (IL-2Rβγ, intermediate affinity receptor), both of which are required and sufficient to trigger downstream signaling in immune cells. In addition, IL-2 binds with high affinity to a receptor complex consisting of IL-2Rα, IL-2Rβ, and IL-2Rγ subunits (IL-2Rαβγ, high affinity receptor) (Stauber et al, Proc Natl Acad Sci USA. 2006 Feb. 21; 103(8):2788-93). IL-2Rα expression is restricted to CD4+ Treg cells, activated T lymphocytes, and ILC2 and ILC3 cells, making these subsets the most sensitive to IL-2 signaling. IL-2Rβ and IL-2Rγ subunits are shared with another related cytokine, IL-15, and IL-2Rγ subunit is shared among other common gamma chain cytokines (IL-4, IL-7, IL-9, and IL-21). Most innate and innate-like lymphocytes including NK cells, NK T cells, Tγδ cells, and ILC1, ILC2, and ILC3 cells express high levels of IL-2Rβ (ImmGen consortium; Heng T S et al, Immunological Genome Project Consortium. Nat Immunol. 2008 October; 9(10): 1091-4), which also makes them sensitive to both IL-2 and IL-15 cytokines.

Binding of IL-2 to its receptor induces the phosphorylation of receptor-associated Janus kinases, JAK3 and JAK1, which promote the phosphorylation of STAT5 transcription factor (pSTAT5) that regulates transcription of many genes in lymphocytes. IL-2 signaling in lymphocytes promotes cell survival, proliferation, and increased effector function, including pro-inflammatory cytokine secretion and cytotoxic function, and in some cases, activation-induced cell death (reviewed in Ross & Cantrell, Annu Rev Immunol. 2018 Apr. 26; 36:411-433).

CD8+ T cells express CD8, which is a type I transmembrane glycoprotein found on the cell surface as a CD8 alpha (CD8α, CD8a) homodimer and CD8 alpha-CD8 beta (CD8ϐ, CD8b) heterodimer. CD8 dimers interact with the MHC class I molecules on target cells and this interaction keeps the TCR closely engaged with MHC during CD8+ T cell activation. The cytoplasmic tail of CD8α contains binding sites for a T cell kinase (Lck) that initiates signal transduction downstream of the TCR during T cell activation, while the role of CD8ϐ is thought to be in increasing the avidity of CD8 binding to MHC class I and influencing specificity of the CD8/MHC/TCR interaction (Bosselut et al, Immunity. 2000 April; 12(4):409-18). TCR alpha beta-expressing CD8+ T cells typically express both CD8ab and CD8aa dimers, however high levels of CD8aa but not CD8ab dimers can be found on some innate lymphocytes such as NK cells, mucosal-associated invariant T (MAIT) cells, and gamma delta T cells.

Accordingly, there is a need for antibodies that selectively bind to CD8ab heterodimers over CD8aa homodimers. These antibodies can be used, e.g., for targeting certain immunomodulatory polypeptides, such as IL-2, to CD8ab+ T cells, and limiting their activity on CD8− immune cells and CD8aa+ immune cells such as NK cells.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

The present disclosure describes, inter alia, human or humanized antibodies, antigen binding fragments, and fusion proteins that bind human CD8b. In some embodiments, the human or humanized antibodies, antigen binding fragments, and fusion proteins bind human CD8b or a human CD8ab heterodimer preferentially over binding to a human CD8aa homodimer In some embodiments, the human or humanized antibodies, antigen binding fragments, and fusion proteins bind CD8b, CD8ab, or both.

Certain aspects of the present disclosure relate to human or humanized antibodies or antigen binding fragments thereof. In some embodiments, the antibody or fragment specifically binds human CD8b and/or human CD8ab with at least 10-fold higher affinity than its binding to human CD8a and/or human CD8aa. In some embodiments, the antibody or fragment specifically binds the extracellular domain(s) of human CD8b and/or human CD8ab with at least 10-fold higher affinity than its binding to the extracellular domain(s) of human CD8a and/or human CD8aa. In some embodiments, the antibody or fragment binds to a cell expressing a human CD8ab heterodimer on its surface with an EC50 that is less than 1000 nM. In some embodiments, the antibody or fragment binds human CD8+ T cells. In some embodiments, the antibody or fragment specifically binds human CD8b and/or human CD8ab with at least 10-fold higher affinity than its binding to human CD8a and/or human CD8aa expressed on the surface of an natural killer (NK) cell. In some embodiments, the antibody or fragment specifically binds a cell expressing human CD8b and/or human CD8ab on its surface (e.g., a T cell) with at least 10-fold higher affinity than its binding to a cell expressing human CD8a and/or human CD8aa on its surface (e.g., an NK cell).

In some embodiments, the antibody or fragment comprises a heavy chain variable (VH) domain and a light chain variable (VL) domain; wherein the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the antibody or fragment comprises a heavy chain variable (VH) domain and a light chain variable (VL) domain; wherein the VH domain comprises a CDR-H1 comprising the amino acid sequence of SEQ ID NO:51, a CDR-H2 comprising the amino acid sequence of SEQ ID NO:52, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the VH domain comprises an amino acid sequence that is at least 90%, at least 95%, at least 99%, or 100% identical to the sequence of SEQ ID NO:62, and wherein the VL domain comprises an amino acid sequence that is at least 90%, at least 95%, at least 99%, or 100% identical to the sequence of SEQ ID NO:63. In some embodiments, the antibody or fragment comprises a heavy chain variable (VH) domain and a light chain variable (VL) domain; wherein the VH domain comprises a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21; and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24. In some embodiments, the antibody or fragment comprises a heavy chain variable (VH) domain and a light chain variable (VL) domain; wherein the VH domain comprises a CDR-H1 comprising the amino acid sequence of SEQ ID NO:53, a CDR-H2 comprising the amino acid sequence of SEQ ID NO:52, and a CDR-H3 comprising the amino acid sequence of SEQ ID NO:21; and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24. In some embodiments, the VH domain comprises an amino acid sequence that is at least 90%, at least 95%, at least 99%, or 100% identical to the sequence of SEQ ID NO:64, and wherein the VL domain comprises an amino acid sequence that is at least 90%, at least 95%, at least 99%, or 100% identical to the sequence of SEQ ID NO:65. In some embodiments, the antibody or fragment comprises a heavy chain variable (VH) domain and a light chain variable (VL) domain; wherein the VH domain comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30. In some embodiments, the antibody or fragment comprises a heavy chain variable (VH) domain and a light chain variable (VL) domain; wherein the VH domain comprises a CDR-H1 comprising the amino acid sequence of SEQ ID NO:49, a CDR-H2 comprising the amino acid sequence of SEQ ID NO:52, and a CDR-H3 comprising the amino acid sequence of SEQ ID NO:27; and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30. In some embodiments, the VH domain comprises an amino acid sequence that is at least 90%, at least 95%, at least 99%, or 100% identical to the sequence of SEQ ID NO:66, and wherein the VL domain comprises an amino acid sequence that is at least 90%, at least 95%, at least 99%, or 100% identical to the sequence of SEQ ID NO:67. In some embodiments, the antibody or fragment comprises a heavy chain variable (VH) domain and a light chain variable (VL) domain; wherein the VH domain comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36. In some embodiments, the antibody or fragment comprises a heavy chain variable (VH) domain and a light chain variable (VL) domain; wherein the VH domain comprises a CDR-H1 comprising the amino acid sequence of SEQ ID NO:54, a CDR-H2 comprising the amino acid sequence of SEQ ID NO:52, and a CDR-H3 comprising the amino acid sequence of SEQ ID NO:33; and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36. In some embodiments, the VH domain comprises an amino acid sequence that is at least 90%, at least 95%, at least 99%, or 100% identical to the sequence of SEQ ID NO:68, and wherein the VL domain comprises an amino acid sequence that is at least 90%, at least 95%, at least 99%, or 100% identical to the sequence of SEQ ID NO:69. In some embodiments, the antibody or fragment comprises a heavy chain variable (VH) domain and a light chain variable (VL) domain; wherein the VH domain comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the antibody or fragment comprises a heavy chain variable (VH) domain and a light chain variable (VL) domain; wherein the VH domain comprises a CDR-H1 comprising the amino acid sequence of SEQ ID NO:55, a CDR-H2 comprising the amino acid sequence of SEQ ID NO:56, and a CDR-H3 comprising the amino acid sequence of SEQ ID NO:39; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:70, and wherein the VL domain comprises an amino acid sequence that is at least 90%, at least 95%, at least 99%, or 100% identical to the sequence of SEQ ID NO:71. In some embodiments, the antibody or fragment comprises a heavy chain variable (VH) domain and a light chain variable (VL) domain; wherein the VH domain comprises a CDR-H1 comprising the amino acid sequence of SEQ ID NO:43, a CDR-H2 comprising the amino acid sequence of SEQ ID NO:44, and a CDR-H3 comprising the amino acid sequence of SEQ ID NO:45; and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48. In some embodiments, the antibody or fragment comprises a heavy chain variable (VH) domain and a light chain variable (VL) domain; wherein the VH domain comprises a CDR-H1 comprising the amino acid sequence of SEQ ID NO:55, a CDR-H2 comprising the amino acid sequence of SEQ ID NO:57, and a CDR-H3 comprising the amino acid sequence of SEQ ID NO:45; and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48. In some embodiments, the VH domain comprises an amino acid sequence that is at least 90%, at least 95%, at least 99%, or 100% identical to the sequence of SEQ ID NO:72, and wherein the VL domain comprises an amino acid sequence that is at least 90%, at least 95%, at least 99%, or 100% identical to the sequence of SEQ ID NO:73. In some embodiments, the antibody or fragment comprises a heavy chain variable (VH) domain and a light chain variable (VL) domain; wherein the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the antibody or fragment comprises a heavy chain variable (VH) domain and a light chain variable (VL) domain; wherein the VH domain comprises a CDR-H1 comprising the amino acid sequence of SEQ ID NO:49, a CDR-H2 comprising the amino acid sequence of SEQ ID NO:50, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the antibody or fragment comprises a heavy chain variable (VH) domain and a light chain variable (VL) domain; wherein the VH domain comprises a CDR-H1 comprising the amino acid sequence of SEQ ID NO:177, a CDR-H2 comprising the amino acid sequence of SEQ ID NO:178, and a CDR-H3 comprising the amino acid sequence of SEQ ID NO:179; and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182. In some embodiments, the antibody or fragment comprises a heavy chain variable (VH) domain and a light chain variable (VL) domain; wherein the VH domain comprises a CDR-H1 comprising the amino acid sequence of SEQ ID NO:183, a CDR-H2 comprising the amino acid sequence of SEQ ID NO:184, and a CDR-H3 comprising the amino acid sequence of SEQ ID NO:179; and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182. In some embodiments, the VH domain comprises an amino acid sequence that is at least 90%, at least 95%, at least 99%, or 100% identical to the sequence of SEQ ID NO:185, and wherein the VL domain comprises an amino acid sequence that is at least 90%, at least 95%, at least 99%, or 100% identical to the sequence of SEQ ID NO:186.

In some embodiments, the antibody or fragment comprises a heavy chain variable (VH) domain and a light chain variable (VL) domain; wherein the VH domain comprises a CDR-H1 comprising the amino acid sequence of $X_1X_2AIS$, wherein $X_1$ is S, K, G, N, R, D, T, or G, and wherein $X_2$ is Y, L, H, or F (SEQ ID NO:259), a CDR-H2 comprising the amino acid sequence of $X_1X_2X_3PX_4X_5X_6X_7X_8X_9YX_{10}QKFX_{11}G$, wherein $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, and $X_{11}$ is Q or T (SEQ ID NO:260), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:261); and wherein the VL domain comprises a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:262), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:263), and a CDR-L3 comprising the amino acid sequence of QX₁X₂X₃X₄X₅PWT, wherein X₁ is S, N, D, Q, A, or E, X₂ is T, I, or S, X₃ is Y, L, or F, X₄ is D, G, T, E, Q, A, or Y, and X₅ is A, T, R, S, K, or Y (SEQ ID NO:264). In some embodiments, the antibody or fragment comprises a heavy chain variable (VH) domain and a light chain variable (VL) domain; wherein the VH domain comprises a CDR-H1 comprising the amino acid sequence of SEQ ID NO:225, a CDR-H2 comprising the amino acid sequence of SEQ ID NO:226, and a CDR-H3 comprising the amino acid sequence of SEQ ID NO:227; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:245, and wherein the VL domain comprises an amino acid sequence that is at least 90%, at least 95%, at least 99%, or 100% identical to the sequence of SEQ ID NO:246. In some embodiments, the antibody or fragment comprises a heavy chain variable (VH) domain and a light chain variable (VL) domain; wherein the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233; and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236. In some embodiments, the VH domain comprises an amino acid sequence that is at least 90%, at least 95%, at least 99%, or 100% identical to the sequence of SEQ ID NO:251, and wherein the VL domain comprises an amino acid sequence that is at least 90%, at least 95%, at least 99%, or 100% identical to the sequence of SEQ ID NO:252. In some embodiments, the VH domain comprises the amino acid sequence of SEQ ID NO:251; and the VL domain comprises the amino acid sequence of SEQ ID NO:252. In some embodiments, the antibody or fragment comprises a heavy chain variable (VH) domain and a light chain variable (VL) domain; wherein the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:253, and wherein the VL domain comprises an amino acid sequence that is at least 90%, at least 95%, at least 99%, or 100% identical to the sequence of SEQ ID NO:254. In some embodiments, the VH domain further comprises a FW-1 comprising the sequence QVQLVQSGAEVKKPGSSVKVSCKASGGTFS (SEQ ID NO:274), a FW-2 comprising the sequence WVRQAPGQGLEWMG (SEQ ID NO:275), a FW-3 comprising the sequence RVTITADESTSTAYMELSSLRSEDTAVYYCAR (SEQ ID NO:276), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, the antibody or fragment comprises a heavy chain variable (VH) domain and a light chain variable (VL) domain; wherein the VH domain comprises a CDR-H1 comprising the amino acid sequence of GX₁X₂FX₃X₄X₅, wherein X₁ is G, Y, S, or A, X₂ is T, S, G, R, N, or H, X₃ is S, T, R, H, Y, G, or P, X₄ is S, K, G, N, R, D, T, or G, and X₅ is Y, L, H, or F (SEQ ID NO:265), a CDR-H2 comprising the amino acid sequence of X₁PX₂X₃X₄X₅, wherein X₁ is I, N, or M, X₂ is G, N, H, S, R, I, or A, X₃ is A, N, H, S, T, F, or Y, X₄ is A, D, or G, and X₅ is T, E, K, V, Q, or A (SEQ ID NO:266), and a CDR-H3 comprising the amino acid sequence of X₁X₂X₃GX₄X₅LFX₆X₇, wherein X₁ is D or A, X₂ is A, G, E, R, Y, K, N, Q, L, or F, X₃ is A, L, P, or Y, X₄ is I or L, X₅ is R, A, Q, or S, X₆ is A or D, and X₇ is D, E, A, or S (SEQ ID NO:267); and wherein the VL domain comprises a CDR-L1 comprising the amino acid sequence of X₁X₂SX₃X₄IX₅GX₆LN, wherein X₁ is R or G, X₂ is A or T, X₃ is Q or E, X₄ is E, N, T, S, A, K, D, G, R, or Q, X₅ is Y or S, and X₆ is A or V (SEQ ID NO:262), a CDR-L2 comprising the amino acid sequence of GX₁X₂X₃LX₄X₅, wherein X₁ is A or S, X₂ is T, S, E, Q, or D, X₃ is N, R, A, E, or H, X₄ is Q or A, and X₅ is S or D (SEQ ID NO:263), and a CDR-L3 comprising the amino acid sequence of QX₁X₂X₃X₄X₅PWT, wherein X₁ is S, N, D, Q, A, or E, X₂ is T, I, or S, X₃ is Y, L, or F, X₄ is D, G, T, E, Q, A, or Y, and X₅ is A, T, R, S, K, or Y (SEQ ID NO:264). In some embodiments, the VH domain comprises a CDR-H1 comprising the amino acid sequence of SEQ ID NO:238, a CDR-H2 comprising the amino acid sequence of SEQ ID NO:239, and a CDR-H3 comprising the amino acid sequence of SEQ ID NO:233; and the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:245; and wherein the VL domain comprises an amino acid sequence that is at least 90%, at least 95%, at least 99%, or 100% identical to the sequence of SEQ ID NO:246. In some embodiments, the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233; and the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236. In some embodiments, the VH domain comprises an amino acid sequence that is at least 90%, at least 95%, at least 99%, or 100% identical to the sequence of SEQ ID NO:251; and wherein the VL domain comprises an amino acid sequence that is at least 90%, at least 95%, at least 99%, or 100% identical to the sequence of SEQ ID NO:252. In some embodiments, the VH domain comprises the amino acid sequence of SEQ ID NO:251; and the VL domain comprises the amino acid sequence of SEQ ID NO:252. In some embodiments, the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233; and the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:253; and wherein the VL domain comprises an amino acid sequence that is at least 90%, at least 95%, at least 99%, or 100% identical to the sequence of SEQ ID NO:254. In some embodiments, the VH domain further comprises a FW-1 comprising the sequence QVQLVQSGAEVKKPGSSVKVSCKAS (SEQ ID NO:278), a FW-2 comprising the sequence AISWVRQAPGQGLEWMGGI (SEQ ID NO:279), a FW-3 comprising the sequence ANYAQKFQGRVTITADEST-STAYMELSSLRSEDTAVYYCAR (SEQ ID NO:280), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, the antibody or fragment comprises a heavy chain variable (VH) domain and a light chain variable (VL) domain; wherein the VH domain comprises a CDR-H1 comprising the amino acid sequence of $X_1YX_2MS$, wherein $X_1$ is S, D, E, A, or Q and $X_2$ is A, G, or T (SEQ ID NO:268), a CDR-H2 comprising the amino acid sequence of $DIX_1X_2X_3GX_4X_5TX_6YADSVKG$, wherein $X_1$ is T, N, S, Q, E, H, R, or A, $X_2$ is Y, W, F, or H, $X_3$ is A, S, Q, E, or T, $X_4$ is G or E, $X_5$ is S or I, and $X_6$ is A or G (SEQ ID NO:269), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:270) and a VL domain comprising a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42). In some embodiments, the antibody or fragment comprises a heavy chain variable (VH) domain and a light chain variable (VL) domain; wherein the VH domain comprises a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:247, and wherein the VL domain comprises an amino acid sequence that is at least 90%, at least 95%, at least 99%, or 100% identical to the sequence of SEQ ID NO:248. In some embodiments, the VH domain comprises an amino acid sequence that is at least 90%, at least 95%, at least 99%, or 100% identical to the sequence of SEQ ID NO:249, and wherein the VL domain comprises an amino acid sequence that is at least 90%, at least 95%, at least 99%, or 100% identical to the sequence of SEQ ID NO:250. In some embodiments, the VH domain comprises the amino acid sequence of SEQ ID NO:249, and wherein the VL domain comprises the amino acid sequence of SEQ ID NO:250. In some embodiments, the antibody or fragment comprises a heavy chain variable (VH) domain and a light chain variable (VL) domain; wherein the VH domain comprises a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:255, and wherein the VL domain comprises an amino acid sequence that is at least 90%, at least 95%, at least 99%, or 100% identical to the sequence of SEQ ID NO:256. In some embodiments, the VH domain comprises an amino acid sequence that is at least 90%, at least 95%, at least 99%, or 100% identical to the sequence of SEQ ID NO:257, and wherein the VL domain comprises an amino acid sequence that is at least 90%, at least 95%, at least 99%, or 100% identical to the sequence of SEQ ID NO:258. In some embodiments, the VH domain further comprises a FW-1 comprising the sequence EVQLVESGGGLVQPGGSLRLSCAASGFTFS (SEQ ID NO:281), a FW-2 comprising the sequence WVRQAPGK-GLEWVS (SEQ ID NO:282), a FW-3 comprising the sequence RFTISRDNAKNSLYLQMNSLRAEDTAVYY-CAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISR-LEPEDFAVYYC (SEQ ID NO:295), and/or a FW-4 comprising the sequence FGQGTKVEIK (SEQ ID NO:296).

In some embodiments, the antibody or fragment comprises a heavy chain variable (VH) domain and a light chain variable (VL) domain; wherein the VH domain comprises a CDR-H1 comprising the amino acid sequence of $GFTFX_1X_2Y$, wherein $X_1$ is S, D, E, Q, S, or A and $X_2$ is S, D, E, A, or Q (SEQ ID NO:271), a CDR-H2 comprising the amino acid sequence of $X_1X_2X_3GX_4X_5$, wherein $X_1$ is T, N, S, Q, E, H, R or A, $X_2$ is Y, W, F, or H, $X_3$ is A, S, Q, E, or T, $X_4$ is G or E, and $X_5$ is S or I (SEQ ID NO:272), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:273); and wherein the VL domain comprises a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42). In some embodiments, the VH domain comprises a CDR-H1 comprising the amino acid sequence of SEQ ID NO:240, a CDR-H2 comprising the amino acid sequence of SEQ ID NO:241, and a CDR-H3 comprising the amino acid sequence of SEQ ID NO:242; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:247; and wherein the VL domain comprises an amino acid sequence that is at least 90%, at least 95%, at least 99%, or 100% identical to the sequence of SEQ ID NO:248. In some embodiments, the VH domain comprises an amino acid sequence that is at least 90%, at least 95%, at least 99%, or 100% identical to the sequence of SEQ ID NO:249; and wherein the VL domain comprises an amino acid sequence that is at least 90%, at least 95%, at least 99%, or 100% identical to the sequence of SEQ ID NO:250. In some embodiments, the VH domain comprises the amino acid sequence of SEQ ID NO:249, and wherein the VL domain comprises the amino acid sequence of SEQ ID NO:250. In some embodiments, the VH domain comprises a CDR-H1 comprising the amino acid sequence of SEQ ID NO:240, a CDR-H2 comprising the amino acid sequence of SEQ ID NO:244, and a CDR-H3 comprising the amino acid sequence of SEQ ID NO:242; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:255; and wherein the VL domain comprises an amino acid sequence that is at least 90%, at least 95%, at least 99%, or 100% identical to the sequence of SEQ ID NO:256. In some embodiments, the VH domain comprises an amino acid sequence that is at least 90%, at least 95%, at least 99%, or 100% identical to the sequence of SEQ ID NO:257; and wherein the VL domain comprises an amino acid sequence that is at least 90%, at least 95%, at least 99%, or 100% identical to the sequence of SEQ ID NO:258. In some embodiments, the VH domain further comprises a FW-1 comprising the sequence EVQLVESGGGLVQPGGSLRLS-CAAS (SEQ ID NO:286), a FW-2 comprising the sequence AMSWVRQAPGKGLEWVSDI (SEQ ID NO:287), a FW-3 comprising the sequence TAYADSVKGRFTISRDNAKNS-LYLQMNSLRAEDTAVYYCAR (SEQ ID NO:288), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGER-ATLSC (SEQ ID NO:293), a FW-2 comprising the sequence WYQQKPGQAPRLLIY (SEQ ID NO:294), a FW-3 comprising the sequence GIPDRFSGSGSGTDFTLTISR-LEPEDFAVYYC (SEQ ID NO:295), and a FW-4 comprising the sequence FGQGTKVEIK (SEQ ID NO:296).

In some embodiments according to any of the embodiments described herein, the antibody is a multispecific antibody (e.g., a bispecific antibody).

Further provided herein are fusion proteins comprising a first moiety comprising the antibody or fragment of any one of the above embodiments and a second moiety comprising a cytokine, chemokine, or growth factor. In some embodiments, the first moiety is fused to the second moiety directly or via a linker. In some embodiments, the first moiety comprises a human or humanized antibody or antigen-binding fragment thereof that specifically binds CD8b and/or CD8ab, wherein the antibody or fragment comprises a heavy chain variable (VH) domain and a light chain variable (VL) domain, wherein: the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain comprises a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21; and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:43, a CDR-H2 comprising the amino acid sequence of SEQ ID NO:44, and a CDR-H3 comprising the amino acid sequence of SEQ ID NO:45; and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain comprises a CDR-H1 comprising the amino acid sequence of SEQ ID NO:177, a CDR-H2 comprising the amino acid sequence of SEQ ID NO:178, and a CDR-H3 comprising the amino acid sequence of SEQ ID NO:179; and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain comprises a CDR-H1 comprising the amino acid sequence of SEQ ID NO:225, a CDR-H2 comprising the amino acid sequence of SEQ ID NO:226, and a CDR-H3 comprising the amino acid sequence of SEQ ID NO:227; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain comprises a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231; and wherein the VL domain comprises a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42); the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233; and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain comprises a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231, and wherein the VL domain comprises a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42). In some embodiments, the first moiety comprises a human or humanized antibody or antigen-binding fragment thereof that specifically binds CD8b and/or CD8ab, wherein the antibody or fragment comprises a heavy chain variable (VH) domain and a light chain variable (VL) domain, wherein: the VH domain comprises a CDR-H1 comprising the amino acid sequence of SEQ ID NO:51, a CDR-H2 comprising the amino acid sequence of SEQ ID NO:52, and a CDR-H3 comprising the amino acid sequence of SEQ ID NO:15, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain comprises a CDR-H1 comprising the amino acid sequence of SEQ ID NO:53, a CDR-H2 comprising the amino acid sequence of SEQ ID NO:52, and a CDR-H3 comprising the amino acid sequence of SEQ ID NO:21, and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain comprises a CDR-H1 comprising the amino acid sequence of SEQ ID NO:49, a CDR-H2 comprising the amino acid sequence of SEQ ID NO:52, and a CDR-H3 comprising the amino acid sequence of SEQ ID NO:27, and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain comprises a CDR-H1 comprising the amino acid sequence of SEQ ID NO:54, a CDR-H2 comprising the amino acid sequence of SEQ ID NO:52, and a CDR-H3 comprising the amino acid sequence of SEQ ID NO:33, and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain comprises a CDR-H1 comprising the amino acid sequence of SEQ ID NO:55, a CDR-H2 comprising the amino acid sequence of SEQ ID NO:56, and a CDR-H3 comprising the amino acid sequence of SEQ ID NO:39, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:55, a CDR-H2 comprising the amino acid sequence of SEQ ID NO:57, and a CDR-H3 comprising the amino acid sequence of SEQ ID NO:45, and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain comprises a CDR-H1 comprising the amino acid sequence of SEQ ID NO:49, a CDR-H2 comprising the amino acid sequence of SEQ ID NO:50, and a CDR-H3 comprising the amino acid sequence of SEQ ID NO:3, and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain comprises a CDR-H1 comprising the amino acid sequence of SEQ ID NO:183, a CDR-H2 comprising the amino acid sequence of SEQ ID NO:184, and a CDR-H3 comprising the amino acid sequence of SEQ ID NO:179, and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain comprises a CDR-H1 comprising the amino acid sequence of SEQ ID NO:238, a CDR-H2 comprising the amino acid sequence of SEQ ID NO:239, and a CDR-H3 comprising the amino acid sequence of SEQ ID NO:233, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain comprises a CDR-H1 comprising the amino acid sequence of SEQ ID NO:240, a CDR-H2 comprising the amino acid sequence of SEQ ID NO:241, and a CDR-H3 comprising the amino acid sequence of SEQ ID NO:242, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain comprises a CDR-H1 comprising the amino acid sequence of SEQ ID NO:240, a CDR-H2 comprising the amino acid sequence of SEQ ID NO:244, and a CDR-H3 comprising the amino acid sequence of SEQ ID NO:242, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42.

In some embodiments according to any of the embodiments described herein (e.g., a fusion protein of the present disclosure), the second moiety induces activation of CD8+ T cells. In some embodiments, the fusion protein induces activation of cells expressing a human CD8ab heterodimer with at least 10-fold higher potency than activation of cells expressing a human CD8aa homodimer. In some embodiments, the fusion protein induces activation of CD8+ T cells with at least 10-fold higher potency than activation of NK cells. In some embodiments, potency of activation is measured by EC50, as assessed by cell proliferation. In some embodiments, the first moiety comprises two antibody heavy chain polypeptides comprising a structure according to formula [I], from N-terminus to C-terminus:

VH-CH1-hinge-CH2-CH3 [I]

and two antibody light chain polypeptides comprising a structure according to formula [II], from N-terminus to C-terminus:

VL-CL [II]

wherein VH is an antibody heavy chain variable (VH) domain, wherein CH1 is an antibody CH1 domain, wherein hinge is an antibody hinge domain, wherein CH2-CH3 is an antibody Fc domain, wherein VL is an antibody light chain variable (VL) domain, and wherein CL is an antibody constant light chain domain; and wherein the N-terminus of the second moiety is fused to the C-terminus of one of the two CH3 domains (e.g., via a linker of the present disclosure). In some embodiments, the first moiety comprises a first antibody heavy chain polypeptide comprising a structure according to formula [I], from N-terminus to C-terminus:

VH-CH1-hinge-CH2-CH3 [I], an antibody light chain polypeptide comprising a structure according to formula [II], from N-terminus to C-terminus:

VL-CL [II], and a second antibody heavy chain polypeptide comprising a structure according to formula [III], from N-terminus to C-terminus:

hinge-CH2-CH3 [III], wherein VH is an antibody heavy chain variable (VH) domain, wherein CH1 is an antibody CH1 domain, wherein hinge is an antibody hinge domain, wherein CH2-CH3 is an antibody Fc domain, wherein VL is an antibody light chain variable (VL) domain, and wherein CL is an antibody constant light chain domain; and wherein the N-terminus of the second moiety is fused to the C-terminus of the CH3 domain of the second antibody heavy chain polypeptide (e.g., via a linker of the present disclosure). In some embodiments, the N-terminus of the second moiety is fused to the C-terminus of the CH3 domain of the first antibody heavy chain polypeptide (e.g., via a linker of the present disclosure). In some embodiments, the first moiety comprises a first antibody heavy chain polypeptide comprising a structure according to formula [I], from N-terminus to C-terminus:

VH-CH1-hinge-CH2-CH3 [I], an antibody light chain polypeptide comprising a structure according to formula [II], from N-terminus to C-terminus:

VL-CL [II], and a second antibody heavy chain polypeptide comprising a structure according to formula [III], from N-terminus to C-terminus:

hinge-CH2-CH3 [III], wherein VH is an antibody heavy chain variable (VH) domain, wherein CH1 is an antibody CH1 domain, wherein hinge is an antibody hinge domain, wherein CH2-CH3 is an antibody Fc domain, wherein VL is an antibody light chain variable (VL) domain, and wherein CL is an antibody constant light chain domain; and wherein the C-terminus of the second moiety is fused to the N-terminus of the hinge domain of the second antibody heavy chain polypeptide (e.g., via a linker of the present disclosure). In some embodiments, the first moiety comprises one or two antibody heavy chain polypeptides and one or two antibody light chain polypeptides. In some embodiments, the first moiety comprises a single chain antibody or single chain variable fragment (scFv). In some embodiments, the first moiety comprises a VHH antibody. In some embodiments according to any of the embodiments described herein (e.g., the fusion proteins described above), VH and VL form an antigen binding site (e.g., that specifically binds CD8b and/or CD8ab). In some embodiments, the first moiety comprises a first antibody heavy chain polypeptide comprising a structure according to formula [I], from N-terminus to C-terminus:

VH-CH1-hinge-CH2-CH3 [I], an antibody light chain polypeptide comprising a structure according to formula [II], from N-terminus to C-terminus:

VL-CL [II], and a second antibody heavy chain polypeptide comprising a structure according to formula [III], from N-terminus to C-terminus:

hinge-CH2-CH3 [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain; and wherein the N-terminus of the second moiety is fused to the C-terminus of the CH3 domain of the first antibody heavy chain polypeptide. In some embodiments, the VH domain of both antibody heavy chain polypeptides comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain of both antibody heavy chain polypeptides comprises a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21, and wherein the VL domain of both antibody light chain polypeptides comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain of both antibody heavy chain polypeptides comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27, and wherein the VL domain of both antibody light chain polypeptides comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain of both antibody heavy chain polypeptides comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33, and wherein the VL domain of both antibody light chain polypeptides comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain of both antibody heavy chain polypeptides comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain of both antibody heavy chain polypeptides comprises a CDR-H1 comprising the amino acid sequence of SEQ ID NO:43, a CDR-H2 comprising the amino acid sequence of SEQ ID NO:44, and a CDR-H3 comprising the amino acid sequence of SEQ ID NO:45, and wherein the VL domain of both antibody light chain polypeptides comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain of both antibody heavy chain polypeptides comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3, and wherein the VL domain of both antibody light chain polypeptides comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain of both antibody heavy chain polypeptides comprises a CDR-H1 comprising the amino acid sequence of SEQ ID NO:177, a CDR-H2 comprising the amino acid sequence of SEQ ID NO:178, and a CDR-H3 comprising the amino acid sequence of SEQ ID NO:179, and wherein the VL domain of both antibody light chain polypeptides comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain of both antibody heavy chain polypeptides comprises a CDR-H1 comprising the amino acid sequence of SEQ ID NO:225, a CDR-H2 comprising the amino acid sequence of SEQ ID NO:226, and a CDR-H3 comprising the amino acid sequence of SEQ ID NO:227, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain of both antibody heavy chain polypeptides comprises a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain of both antibody heavy chain polypeptides comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233, and wherein the VL domain of both antibody light chain polypeptides comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain of both antibody heavy chain polypeptides comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain of both antibody heavy chain polypeptides comprises a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain of both antibody heavy chain polypeptides comprises a CDR-H1 comprising the amino acid sequence of SEQ ID NO:51, a CDR-H2 comprising the amino acid sequence of SEQ ID NO:52, and a CDR-H3 comprising the amino acid sequence of SEQ ID NO:15, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain of both antibody heavy chain polypeptides comprises a CDR-H1 comprising the amino acid sequence of SEQ ID NO:53, a CDR-H2 comprising the amino acid sequence of SEQ ID NO:52, and a CDR-H3 comprising the amino acid sequence of SEQ ID NO:21, and wherein the VL domain of both antibody light chain polypeptides comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain of both antibody heavy chain polypeptides comprises a CDR-H1 comprising the amino acid sequence of SEQ ID NO:49, a CDR-H2 comprising the amino acid sequence of SEQ ID NO:52, and a CDR-H3 comprising the amino acid sequence of SEQ ID NO:27, and wherein the VL domain of both antibody light chain polypeptides comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain of both antibody heavy chain polypeptides comprises a CDR-H1 comprising the amino acid sequence of SEQ ID NO:54, a CDR-H2 comprising the amino acid sequence of SEQ ID NO:52, and a CDR-H3 comprising the amino acid sequence of SEQ ID NO:33, and wherein the VL domain of both antibody light chain polypeptides comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain of both antibody heavy chain polypeptides comprises a CDR-H1 comprising the amino acid sequence of SEQ ID NO:55, a CDR-H2 comprising the amino acid sequence of SEQ ID NO:56, and a CDR-H3 comprising the amino acid sequence of SEQ ID NO:39, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain of both antibody heavy chain polypeptides comprises a CDR-H1 comprising the amino acid sequence of SEQ ID NO:55, a CDR-H2 comprising the amino acid sequence of SEQ ID NO:57, and a CDR-H3 comprising the amino acid sequence of SEQ ID NO:45, and wherein the VL domain of both antibody light chain polypeptides comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain of both antibody heavy chain polypeptides comprises a CDR-H1 comprising the amino acid sequence of SEQ ID NO:49, a CDR-H2 comprising the amino acid sequence of SEQ ID NO:50, and a CDR-H3 comprising the amino acid sequence of SEQ ID NO:3, and wherein the VL domain of both antibody light chain polypeptides comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain of both antibody heavy chain polypeptides comprises a CDR-H1 comprising the amino acid sequence of SEQ ID NO:183, a CDR-H2 comprising the amino acid sequence of SEQ ID NO:184, and a CDR-H3 comprising the amino acid sequence of SEQ ID NO:179, and wherein the VL domain of both antibody light chain polypeptides comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain of both antibody heavy chain polypeptides comprises a CDR-H1 comprising the amino acid sequence of SEQ ID NO:238, a CDR-H2 comprising the amino acid sequence of SEQ ID NO:239, and a CDR-H3 comprising the amino acid sequence of SEQ ID NO:233, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain of both antibody heavy chain polypeptides comprises a CDR-H1 comprising the amino acid sequence of SEQ ID NO:240, a CDR-H2 comprising the amino acid sequence of SEQ ID NO:241, and a CDR-H3 comprising the amino acid sequence of SEQ ID NO:242, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain of both antibody heavy chain polypeptides comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain of both antibody light chain polypeptides comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain of both antibody heavy chain polypeptides comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain of both antibody light chain polypeptides comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain of both antibody heavy chain polypeptides comprises a CDR-H1 comprising the amino acid sequence of SEQ ID NO:240, a CDR-H2 comprising the amino acid sequence of SEQ ID NO:244, and a CDR-H3 comprising the amino acid sequence of SEQ ID NO:242, and wherein the VL domain of both antibody light chain polypeptides comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain comprises a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21, and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27, and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33, and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:43, a CDR-H2 comprising the amino acid sequence of SEQ ID NO:44, and a CDR-H3 comprising the amino acid sequence of SEQ ID NO:45, and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3, and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain comprises a CDR-H1 comprising the amino acid sequence of SEQ ID NO:177, a CDR-H2 comprising the amino acid sequence of SEQ ID NO:178, and a CDR-H3 comprising the amino acid sequence of SEQ ID NO:179, and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain comprises a CDR-H1 comprising the amino acid sequence of SEQ ID NO:225, a CDR-H2 comprising the amino acid sequence of SEQ ID NO:226, and a CDR-H3 comprising the amino acid sequence of SEQ ID NO:227, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain comprises a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233, and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain comprises a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises a CDR-H1 comprising the amino acid sequence of SEQ ID NO:51, a CDR-H2 comprising the amino acid sequence of SEQ ID NO:52, and a CDR-H3 comprising the amino acid sequence of SEQ ID NO:15, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18; the VH domain comprises a CDR-H1 comprising the amino acid sequence of SEQ ID NO:53, a CDR-H2 comprising the amino acid sequence of SEQ ID NO:52, and a CDR-H3 comprising the amino acid sequence of SEQ ID NO:21, and wherein the VL domain comprises a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24; the VH domain comprises a CDR-H1 comprising the amino acid sequence of SEQ ID NO:49, a CDR-H2 comprising the amino acid sequence of SEQ ID NO:52, and a CDR-H3 comprising the amino acid sequence of SEQ ID NO:27, and wherein the VL domain comprises a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30; the VH domain comprises a CDR-H1 comprising the amino acid sequence of SEQ ID NO:54, a CDR-H2 comprising the amino acid sequence of SEQ ID NO:52, and a CDR-H3 comprising the amino acid sequence of SEQ ID NO:33, and wherein the VL domain comprises a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36; the VH domain comprises a CDR-H1 comprising the amino acid sequence of SEQ ID NO:55, a CDR-H2 comprising the amino acid sequence of SEQ ID NO:56, and a CDR-H3 comprising the amino acid sequence of SEQ ID NO:39, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:55, a CDR-H2 comprising the amino acid sequence of SEQ ID NO:57, and a CDR-H3 comprising the amino acid sequence of SEQ ID NO:45, and wherein the VL domain comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; the VH domain comprises a CDR-H1 comprising the amino acid sequence of SEQ ID NO:49, a CDR-H2 comprising the amino acid sequence of SEQ ID NO:50, and a CDR-H3 comprising the amino acid sequence of SEQ ID NO:3, and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6; the VH domain comprises a CDR-H1 comprising the amino acid sequence of SEQ ID NO:183, a CDR-H2 comprising the amino acid sequence of SEQ ID NO:184, and a CDR-H3 comprising the amino acid sequence of SEQ ID NO:179, and wherein the VL domain comprises a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182; the VH domain comprises a CDR-H1 comprising the amino acid sequence of SEQ ID NO:238, a CDR-H2 comprising the amino acid sequence of SEQ ID NO:239, and a CDR-H3 comprising the amino acid sequence of SEQ ID NO:233, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; the VH domain comprises a CDR-H1 comprising the amino acid sequence of SEQ ID NO:240, a CDR-H2 comprising the amino acid sequence of SEQ ID NO:241, and a CDR-H3 comprising the amino acid sequence of SEQ ID NO:242, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42; the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228; or the VH domain comprises a CDR-H1 comprising the amino acid sequence of SEQ ID NO:240, a CDR-H2 comprising the amino acid sequence of SEQ ID NO:244, and a CDR-H3 comprising the amino acid sequence of SEQ ID NO:242, and wherein the VL domain comprises a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain of both antibody heavy chain polypeptides comprises an amino acid sequence that is at least 90%, at least 95%, at least 99%, or 100% identical to the sequence of SEQ ID NO:62, and wherein the VL domain of both antibody light chain polypeptides comprises an amino acid sequence that is at least 90%, at least 95%, at least 99%, or 100% identical to the sequence of SEQ ID NO:63; the VH domain of both antibody heavy chain polypeptides comprises an amino acid sequence that is at least 90%, at least 95%, at least 99%, or 100% identical to the sequence of SEQ ID NO:64, and wherein the VL domain of both antibody light chain polypeptides comprises an amino acid sequence that is at least 90%, at least 95%, at least 99%, or 100% identical to the sequence of SEQ ID NO:65; the VH domain of both antibody heavy chain polypeptides comprises an amino acid sequence that is at least 90%, at least 95%, at least 99%, or 100% identical to the sequence of SEQ ID NO:66, and wherein the VL domain of both antibody light chain polypeptides comprises an amino acid sequence that is at least 90%, at least 95%, at least 99%, or 100% identical to the sequence of SEQ ID NO:67; the VH domain of both antibody heavy chain polypeptides comprises an amino acid sequence that is at least 90%, at least 95%, at least 99%, or 100% identical to the sequence of SEQ ID NO:68, and wherein the VL domain of both antibody light chain polypeptides comprises an amino acid sequence that is at least 90%, at least 95%, at least 99%, or 100% identical to the sequence of SEQ ID NO:69; the VH domain of both antibody heavy chain polypeptides comprises an amino acid sequence that is at least 90%, at least 95%, at least 99%, or 100% identical to the sequence of SEQ ID NO:70, and wherein the VL domain of both antibody light chain polypeptides comprises an amino acid sequence that is at least 90%, at least 95%, at least 99%, or 100% identical to the sequence of SEQ ID NO:71; the VH domain of both antibody heavy chain polypeptides comprises an amino acid sequence that is at least 90%, at least 95%, at least 99%, or 100% identical to the sequence of SEQ ID NO:72, and wherein the VL domain of both antibody light chain polypeptides comprises an amino acid sequence that is at least 90%, at least 95%, at least 99%, or 100% identical to the sequence of SEQ ID NO:73; the VH domain of both antibody heavy chain polypeptides comprises an amino acid sequence that is at least 90%, at least 95%, at least 99%, or 100% identical to the sequence of SEQ ID NO:185, and wherein the VL domain of both antibody light chain polypeptides comprises an amino acid sequence that is at least 90%, at least 95%, at least 99%, or 100% identical to the sequence of SEQ ID NO:186; the VH domain of both antibody heavy chain polypeptides comprises an amino acid sequence that is at least 90%, at least 95%, at least 99%, or 100% identical to the sequence of SEQ ID NO:245, and wherein the VL domain of both antibody light chain polypeptides comprises an amino acid sequence that is at least 90%, at least 95%, at least 99%, or 100% identical to the sequence of SEQ ID NO:246; the VH domain of both antibody heavy chain polypeptides comprises an amino acid sequence that is at least 90%, at least 95%, at least 99%, or 100% identical to the sequence of SEQ ID NO:251, and wherein the VL domain of both antibody light chain polypeptides comprises an amino acid sequence that is at least 90%, at least 95%, at least 99%, or 100% identical to the sequence of SEQ ID NO:252; the VH domain comprises the amino acid sequence of SEQ ID NO:251, and wherein the VL domain comprises the amino acid sequence of SEQ ID NO:252; the VH domain of both antibody heavy chain polypeptides comprises an amino acid sequence that is at least 90%, at least 95%, at least 99%, or 100% identical to the sequence of SEQ ID NO:253, and wherein the VL domain of both antibody light chain polypeptides comprises an amino acid sequence that is at least 90%, at least 95%, at least 99%, or 100% identical to the sequence of SEQ ID NO:254; the VH domain of both antibody heavy chain polypeptides comprises an amino acid sequence that is at least 90%, at least 95%, at least 99%, or 100% identical to the sequence of SEQ ID NO:247, and wherein the VL domain of both antibody light chain polypeptides comprises an amino acid sequence that is at least 90%, at least 95%, at least 99%, or 100% identical to the sequence of SEQ ID NO:248; the VH domain of both antibody heavy chain polypeptides comprises an amino acid sequence that is at least 90%, at least 95%, at least 99%, or 100% identical to the sequence of SEQ ID NO:249, and wherein the VL domain of both antibody light chain polypeptides comprises an amino acid sequence that is at least 90%, at least 95%, at least 99%, or 100% identical to the sequence of SEQ ID NO:250; the VH domain comprises the amino acid sequence of SEQ ID NO:249, and wherein the VL domain comprises the amino acid sequence of SEQ ID NO:250; the VH domain of both antibody heavy chain polypeptides comprises an amino acid sequence that is at least 90%, at least 95%, at least 99%, or 100% identical to the sequence of SEQ ID NO:255, and wherein the VL domain of both antibody light chain polypeptides comprises an amino acid sequence that is at least 90%, at least 95%, at least 99%, or 100% identical to the sequence of SEQ ID NO:256; or the VH domain of both antibody heavy chain polypeptides comprises an amino acid sequence that is at least 90%, at least 95%, at least 99%, or 100% identical to the sequence of SEQ ID NO:257, and wherein the VL domain of both antibody light chain polypeptides comprises an amino acid sequence that is at least 90%, at least 95%, at least 99%, or 100% identical to the sequence of SEQ ID NO:258. In some embodiments, the VH domain comprises an amino acid sequence that is at least 90%, at least 95%, at least 99%, or 100% identical to the sequence of SEQ ID NO:62, and wherein the VL domain comprises an amino acid sequence that is at least 90%, at least 95%, at least 99%, or 100% identical to the sequence of SEQ ID NO:63; the VH domain comprises an amino acid sequence that is at least 90%, at least 95%, at least 99%, or 100% identical to the sequence of SEQ ID NO:64, and wherein the VL domain comprises an amino acid sequence that is at least 90%, at least 95%, at least 99%, or 100% identical to the sequence of SEQ ID NO:65; the VH domain comprises an amino acid sequence that is at least 90%, at least 95%, at least 99%, or 100% identical to the sequence of SEQ ID NO:66, and wherein the VL domain comprises an amino acid sequence that is at least 90%, at least 95%, at least 99%, or 100% identical to the sequence of SEQ ID NO:67; the VH domain comprises an amino acid sequence that is at least 90%, at least 95%, at least 99%, or 100% identical to the sequence of SEQ ID NO:68, and wherein the VL domain comprises an amino acid sequence that is at least 90%, at least 95%, at least 99%, or 100% identical to the sequence of SEQ ID NO:69; the VH domain comprises an amino acid sequence that is at least 90%, at least 95%, at least 99%, or 100% identical to the sequence of SEQ ID NO:70, and wherein the VL domain comprises an amino acid sequence that is at least 90%, at least 95%, at least 99%, or 100% identical to the sequence of SEQ ID NO:71; the VH domain comprises an amino acid sequence that is at least 90%, at least 95%, at least 99%, or 100% identical to the sequence of SEQ ID NO:72, and wherein the VL domain comprises an amino acid sequence that is at least 90%, at least 95%, at least 99%, or 100% identical to the sequence of SEQ ID NO:73; the VH domain comprises an amino acid sequence that is at least 90%, at least 95%, at least 99%, or 100% identical to the sequence of SEQ ID NO:185, and wherein the VL domain comprises an amino acid sequence that is at least 90%, at least 95%, at least 99%, or 100% identical to the sequence of SEQ ID NO:186; the VH domain comprises an amino acid sequence that is at least 90%, at least 95%, at least 99%, or 100% identical to the sequence of SEQ ID NO:245, and wherein the VL domain comprises an amino acid sequence that is at least 90%, at least 95%, at least 99%, or 100% identical to the sequence of SEQ ID NO:246; the VH domain comprises an amino acid sequence that is at least 90%, at least 95%, at least 99%, or 100% identical to the sequence of SEQ ID NO:251, and wherein the VL domain comprises an amino acid sequence that is at least 90%, at least 95%, at least 99%, or 100% identical to the sequence of SEQ ID NO:252; the VH domain comprises the amino acid sequence of SEQ ID NO:251, and wherein the VL domain comprises the amino acid sequence of SEQ ID NO:252; the VH domain comprises an amino acid sequence that is at least 90%, at least 95%, at least 99%, or 100% identical to the sequence of SEQ ID NO:253, and wherein the VL domain comprises an amino acid sequence that is at least 90%, at least 95%, at least 99%, or 100% identical to the sequence of SEQ ID NO:254; the VH domain comprises an amino acid sequence that is at least 90%, at least 95%, at least 99%, or 100% identical to the sequence of SEQ ID NO:247, and wherein the VL domain comprises an amino acid sequence that is at least 90%, at least 95%, at least 99%, or 100% identical to the sequence of SEQ ID NO:248; the VH domain comprises an amino acid sequence that is at least 90%, at least 95%, at least 99%, or 100% identical to the sequence of SEQ ID NO:249, and wherein the VL domain comprises an amino acid sequence that is at least 90%, at least 95%, at least 99%, or 100% identical to the sequence of SEQ ID NO:250; the VH domain comprises the amino acid sequence of SEQ ID NO:249, and wherein the VL domain comprises the amino acid sequence of SEQ ID NO:250; the VH domain comprises an amino acid sequence that is at least 90%, at least 95%, at least 99%, or 100% identical to the sequence of SEQ ID NO:255, and wherein the VL domain comprises an amino acid sequence that is at least 90%, at least 95%, at least 99%, or 100% identical to the sequence of SEQ ID NO:256; or the VH domain comprises an amino acid sequence that is at least 90%, at least 95%, at least 99%, or 100% identical to the sequence of SEQ ID NO:257, and wherein the VL domain comprises an amino acid sequence that is at least 90%, at least 95%, at least 99%, or 100% identical to the sequence of SEQ ID NO:258. In some embodiments, one or both of the antibody heavy chain polypeptides comprise(s) the following amino acid substitutions: L234A, L235A, and G237A, numbering according to EU index. In some embodiments, a first of the antibody heavy chain polypeptides comprises amino acid substitutions Y349C and T366W, and a second of the antibody heavy chain polypeptides comprises amino acid substitutions S354C, T366S, L368A and Y407V, numbering according to EU index.

In some embodiments according to any of the embodiments described herein, the second moiety comprises an IL-2 polypeptide. In some embodiments, the IL-2 polypeptide is a mutant IL-2 polypeptide comprising one or more mutations relative to a human IL-2 polypeptide comprising the sequence of APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLNRWITFCQSIISTLT (SEQ ID NO:81). In some embodiments, the mutant IL-2 polypeptide has a binding affinity to IL-2Rα that is reduced by 50% or more, compared to binding affinity of a wild-type IL-2 polypeptide comprising the sequence of SEQ ID: 81 for IL-2Rα. In some embodiments, the mutant IL-2 polypeptide has a binding affinity to IL-2Rβ that is reduced by 50% or more, compared to binding affinity of a wild-type IL-2 polypeptide comprising the sequence of SEQ ID: 81 for IL-2Rβ; and/or the mutant IL-2 polypeptide has a binding affinity to IL-2Rγ that is reduced by 50% or more, compared to binding affinity of a wild-type IL-2 polypeptide comprising the sequence of SEQ ID: 81 for IL-2Rγ. In some embodiments, the IL-2 polypeptide comprises the sequence of SEQ ID NO:81 with one, two, three, four, or five amino acid substitutions relative to SEQ ID NO:81, and wherein the one, two, three, four, or five substitution(s) comprise substitution(s) at positions of SEQ ID NO:81 selected from the group consisting of: Q11, H16, L18, L19, D20, Q22, R38, F42, K43, Y45, E62, P65, E68, V69, L72, D84, S87, N88, V91, I92, T123, Q126, S127, I129, and S130. In some embodiments, the IL-2 polypeptide comprises the sequence of SEQ ID NO:81 with one of the following sets of amino acid substitutions (relative to the sequence of SEQ ID NO:81): R38E and F42A; R38D and F42A; F42A and E62Q; R38A and F42K; R38E, F42A, and N88S; R38E, F42A, and N88A; R38E, F42A, and N88G; R38E, F42A, and N88R; R38E, F42A, and N88T; R38E, F42A, and N88D; R38E, F42A, and V91E; R38E, F42A, and D84H; R38E, F42A, and D84K; R38E, F42A, and D84R; H16D, R38E and F42A; H16E, R38E and F42A; R38E, F42A and Q126S; R38D, F42A and N88S; R38D, F42A and N88A; R38D, F42A and N88G; R38D, F42A and N88R; R38D, F42A and N88T; R38D, F42A and N88D; R38D, F42A and V91E; R38D, F42A, and D84H; R38D, F42A, and D84K; R38D, F42A, and D84R; H16D, R38D and F42A; H16E, R38D and F42A; R38D, F42A and Q126S; R38A, F42K, and N88S; R38A, F42K, and N88A; R38A, F42K, and N88G; R38A, F42K, and N88R; R38A, F42K, and N88T; R38A, F42K, and N88D; R38A, F42K, and V91E; R38A, F42K, and D84H; R38A, F42K, and D84K; R38A, F42K, and D84R; H16D, R38A, and F42K; H16E, R38A, and F42K; R38A, F42K, and Q126S; F42A, E62Q, and N88S; F42A, E62Q, and N88A; F42A, E62Q, and N88G; F42A, E62Q, and N88R; F42A, E62Q, and N88T; F42A, E62Q, and N88D; F42A, E62Q, and V91E; F42A, E62Q, and D84H; F42A, E62Q, and D84K; F42A, E62Q, and D84R; H16D, F42A, and E62Q; H16E, F42A, and E62Q; F42A, E62Q, and Q126S. In some embodiments, the IL-2 polypeptide comprises the sequence of SEQ ID NO:81 with a further amino acid substitution relative to SEQ ID NO:81 at position C125. In some embodiments, the IL-2 polypeptide comprises the sequence of SEQ ID NO:81 with one of the following sets of amino acid substitutions (relative to the sequence of SEQ ID NO:81): R38E, F42A, and C125A; R38D, F42A, and C125A; F42A, E62Q, and C125A; R38A, F42K, and C125A; R38E, F42A, N88S, and C125A; R38E, F42A, N88A, and C125A; R38E, F42A, N88G, and C125A; R38E, F42A, N88R, and C125A; R38E, F42A, N88T, and C125A; R38E, F42A, N88D, and C125A; R38E, F42A, V91E, and C125A; R38E, F42A, D84H, and C125A; R38E, F42A, D84K, and C125A; R38E, F42A, D84R, and C125A; H16D, R38E, F42A, and C125A; H16E, R38E, F42A, and C125A; R38E, F42A, C125A and Q126S; R38D, F42A, N88S, and C125A; R38D, F42A, N88A, and C125A; R38D, F42A, N88G, and C125A; R38D, F42A, N88R, and C125A; R38D, F42A, N88T, and C125A; R38D, F42A, N88D, and C125A; R38D, F42A, V91E, and C125A; R38D, F42A, D84H, and C125A; R38D, F42A, D84K, and C125A; R38D, F42A, D84R, and C125A; H16D, R38D, F42A, and C125A; H16E, R38D, F42A, and C125A; R38D, F42A, C125A and Q126S; R38A, F42K, N88S, and C125A; R38A, F42K, N88A, and C125A; R38A, F42K, N88G, and C125A; R38A, F42K, N88R, and C125A; R38A, F42K, N88T, and C125A; R38A, F42K, N88D, and C125A; R38A, F42K, N88A, and C125A; R38A, F42K, V91E, and C125A; R38A, F42K, D84H, and C125A; R38A, F42K, D84K, and C125A; R38A, F42K, D84R, and C125A; H16D, R38A, F42K, and C125A; H16E, R38A, F42K, and C125A; R38A, F42K, C125A and Q126S; F42A, E62Q, N88S, and C125A; F42A, E62Q, N88A, and C125A; F42A, E62Q, N88G, and C125A; F42A, E62Q, N88R, and C125A; F42A, E62Q, N88T, and C125A; F42A, E62Q, N88D, and C125A; F42A, E62Q, V91E, and C125A; F42A, E62Q, and D84H, and C125A; F42A, E62Q, and D84K, and C125A; F42A, E62Q, and D84R, and C125A; H16D, F42A, and E62Q, and C125A; H16E, F42A, E62Q, and C125A; F42A, E62Q, C125A and Q126S; F42A, N88S, and C125A; F42A, N88A, and C125A; F42A, N88G, and C125A; F42A, N88R, and C125A; F42A, N88T, and C125A; F42A, N88D, and C125A; F42A, V91E, and C125A; F42A, D84H, and C125A; F42A, D84K, and C125A; F42A, D84R, and C125A; H16D, F42A, and C125A; H16E, F42A, and C125A; and F42A, C125A and Q126S. In some embodiments, the IL-2 polypeptide comprises the sequence APTSSSTKKTQLQLEHLLLD-LQMILNGINNYKNPKLTEMLTAKFYMPK-KATELKHLQCL EEELKPLEEVLNLAQSKNFHLRPRDLISAIN-VIVLELKGSETTFMCEYADETATIVEFLNR WITFAQSIISTLT (SEQ ID NO:80). In some embodiments, the IL-2 polypeptide comprises the sequence APTSSSTKKTQLQLEELLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFAQSIISTLT (SEQ ID NO:297). In some embodiments, the IL-2 polypeptide comprises a sequence selected from the group consisting of SEQ ID Nos: 85-155 and 190-216. In some embodiments, the IL-2 polypeptide comprises a sequence selected from the group consisting of SEQ ID Nos: 80, 85-155, 190-216, 297, and 354-383. In some embodiments, the second moiety comprises a polypeptide that induces signaling via IL2Rβγ. In some embodiments, the second moiety comprises an IL-21 polypeptide.

In some embodiments according to any of the embodiments described herein (e.g., a fusion protein of the present disclosure), one or both of the antibody Fc domains comprise(s) human IgG1 Fc domains with the following amino acid substitutions: L234A, L235A, G237A, and K322A, numbering according to EU index. In some embodiments, one or both of the antibody Fc domains do not have a C-terminal lysine. In some embodiments, one or both of the antibody Fc domains comprise(s) human IgG1 Fc domains with the following amino acid substitutions: L234A, L235A, and G237A, numbering according to EU index. In some embodiments, one or both of the antibody Fc domains do not have a C-terminal lysine. In some embodiments, a first of the two Fc domains comprises a human IgG1 Fc domain with amino acid substitutions Y349C and T366W, and a second of the two Fc domain comprises a human IgG1 Fc domain with amino acid substitutions S354C, T366S, L368A and Y407V, numbering according to EU index. In some embodiments, one or both of the antibody Fc domains do not have a C-terminal lysine. In some embodiments (e.g., a fusion protein of the present disclosure), the linker comprises the sequence (GGGS)xGn (SEQ ID NO:74), (GGGGS)xGn (SEQ ID NO:75), or (GGGGGS)xGn (SEQ ID NO:76), S(GGGS)xGn (SEQ ID NO:386), S(GGGGS)xGn (SEQ ID NO:387), or S(GGGGGS)xGn (SEQ ID NO:388), wherein x=1, 2, 3, 4, 5, 6, 7, 8, 9, 10, 11, or 12, and wherein n=0, 1, 2 or 3. In some embodiments, the linker comprises the sequence GGGGSGGGGSGGGGS (SEQ ID NO:79) or SGGGGSGGGGSGGGGS (SEQ ID NO:389). In some embodiments (e.g., in a fusion protein of the present disclosure), the linker connects a first moiety of the present disclosure (e.g., a human or humanized antibody or antigen-binding fragment thereof that specifically binds CD8b and/or CD8ab) and a second moiety of the present disclosure (e.g., an IL-2 polypeptide of the present disclosure, IL-21 polypeptide of the present disclosure, or a polypeptide that induces signaling via IL2Rβγ of the present disclosure).

In some embodiments, a fusion protein of the present disclosure comprises one or two light chains comprising the amino acid sequence of SEQ ID NO:156, a heavy chain comprising the amino acid sequence of SEQ ID NO:157, and a heavy chain comprising the amino acid sequence of SEQ ID NO:158. In some embodiments, a fusion protein of the present disclosure comprises one or two light chains comprising the amino acid sequence of SEQ ID NO:156, a heavy chain comprising the amino acid sequence of SEQ ID NO:157, and a heavy chain comprising the amino acid sequence of SEQ ID NO:217. In some embodiments, a fusion protein of the present disclosure comprises one or two light chains comprising the amino acid sequence of SEQ ID NO:159, a heavy chain comprising the amino acid sequence of SEQ ID NO:160, and a heavy chain comprising the amino acid sequence of SEQ ID NO:161. In some embodiments, a fusion protein of the present disclosure comprises one or two light chains comprising the amino acid sequence of SEQ ID NO:159, a heavy chain comprising the amino acid sequence of SEQ ID NO:160, and a heavy chain comprising the amino acid sequence of SEQ ID NO:218. In some embodiments, a fusion protein of the present disclosure comprises one or two light chains comprising the amino acid sequence of SEQ ID NO:162, a heavy chain comprising the amino acid sequence of SEQ ID NO:163, and a heavy chain comprising the amino acid sequence of SEQ ID NO:164. In some embodiments, a fusion protein of the present disclosure comprises one or two light chains comprising the amino acid sequence of SEQ ID NO:162, a heavy chain comprising the amino acid sequence of SEQ ID NO:163, and a heavy chain comprising the amino acid sequence of SEQ ID NO:219. In some embodiments, a fusion protein of the present disclosure comprises one or two light chains comprising the amino acid sequence of SEQ ID NO:165, a heavy chain comprising the amino acid sequence of SEQ ID NO:166, and a heavy chain comprising the amino acid sequence of SEQ ID NO:167. In some embodiments, a fusion protein of the present disclosure comprises one or two light chains comprising the amino acid sequence of SEQ ID NO:165, a heavy chain comprising the amino acid sequence of SEQ ID NO:166, and a heavy chain comprising the amino acid sequence of SEQ ID NO:220. In some embodiments, a fusion protein of the present disclosure comprises one or two light chains comprising the amino acid sequence of SEQ ID NO:168, a heavy chain comprising the amino acid sequence of SEQ ID NO:169, and a heavy chain comprising the amino acid sequence of SEQ ID NO:170. In some embodiments, a fusion protein of the present disclosure comprises one or two light chains comprising the amino acid sequence of SEQ ID NO:168, a heavy chain comprising the amino acid sequence of SEQ ID NO:169, and a heavy chain comprising the amino acid sequence of SEQ ID NO:221. In some embodiments, a fusion protein of the present disclosure comprises one or two light chains comprising the amino acid sequence of SEQ ID NO:171, a heavy chain comprising the amino acid sequence of SEQ ID NO:172, and a heavy chain comprising the amino acid sequence of SEQ ID NO:173. In some embodiments, a fusion protein of the present disclosure comprises one or two light chains comprising the amino acid sequence of SEQ ID NO:171, a heavy chain comprising the amino acid sequence of SEQ ID NO:172, and a heavy chain comprising the amino acid sequence of SEQ ID NO:222. In some embodiments, a fusion protein of the present disclosure comprises one or two light chains comprising the amino acid sequence of SEQ ID NO:174, a heavy chain comprising the amino acid sequence of SEQ ID NO:175, and a heavy chain comprising the amino acid sequence of SEQ ID NO:176. In some embodiments, a fusion protein of the present disclosure comprises one or two light chains comprising the amino acid sequence of SEQ ID NO:174, a heavy chain comprising the amino acid sequence of SEQ ID NO:175, and a heavy chain comprising the amino acid sequence of SEQ ID NO:223. In some embodiments, a fusion protein of the present disclosure comprises one or two light chains comprising the amino acid sequence of SEQ ID NO:187, a heavy chain comprising the amino acid sequence of SEQ ID NO:188, and a heavy chain comprising the amino acid sequence of SEQ ID NO:189. In some embodiments, a fusion protein of the present disclosure comprises one or two light chains comprising the amino acid sequence of SEQ ID NO:187, a heavy chain comprising the amino acid sequence of SEQ ID NO:188, and a heavy chain comprising the amino acid sequence of SEQ ID NO:224. In some embodiments, a fusion protein of the present disclosure comprises one or two light chains comprising the amino acid sequence of SEQ ID NO:298, a heavy chain comprising the amino acid sequence of SEQ ID NO:299, and a heavy chain comprising the amino acid sequence of SEQ ID NO:300. In some embodiments, a fusion protein of the present disclosure comprises one or two light chains comprising the amino acid sequence of SEQ ID NO:298, a heavy chain comprising the amino acid sequence of SEQ ID NO:299, and a heavy chain comprising the amino acid sequence of SEQ ID NO:301. In some embodiments, a fusion protein of the present disclosure comprises one or two light chains comprising the amino acid sequence of SEQ ID NO:302, a heavy chain comprising the amino acid sequence of SEQ ID NO:303, and a heavy chain comprising the amino acid sequence of SEQ ID NO:304. In some embodiments, a fusion protein of the present disclosure comprises one or two light chains comprising the amino acid sequence of SEQ ID NO:302, a heavy chain comprising the amino acid sequence of SEQ ID NO:303, and a heavy chain comprising the amino acid sequence of SEQ ID NO:305. In some embodiments, a fusion protein of the present disclosure comprises one or two light chains comprising the amino acid sequence of SEQ ID NO:306, a heavy chain comprising the amino acid sequence of SEQ ID NO:307, and a heavy chain comprising the amino acid sequence of SEQ ID NO:308. In some embodiments, a fusion protein of the present disclosure comprises one or two light chains comprising the amino acid sequence of SEQ ID NO:306, a heavy chain comprising the amino acid sequence of SEQ ID NO:307, and a heavy chain comprising the amino acid sequence of SEQ ID NO:309. In some embodiments, a fusion protein of the present disclosure comprises one or two light chains comprising the amino acid sequence of SEQ ID NO:310, a heavy chain comprising the amino acid sequence of SEQ ID NO:311, and a heavy chain comprising the amino acid sequence of SEQ ID NO:312. In some embodiments, a fusion protein of the present disclosure comprises one or two light chains comprising the amino acid sequence of SEQ ID NO:310, a heavy chain comprising the amino acid sequence of SEQ ID NO:311, and a heavy chain comprising the amino acid sequence of SEQ ID NO:313. In some embodiments, a fusion protein of the present disclosure comprises one or two light chains comprising the amino acid sequence of SEQ ID NO:314, a heavy chain comprising the amino acid sequence of SEQ ID NO:315, and a heavy chain comprising the amino acid sequence of SEQ ID NO:316. In some embodiments, a fusion protein of the present disclosure comprises one or two light chains comprising the amino acid sequence of SEQ ID NO:314, a heavy chain comprising the amino acid sequence of SEQ ID NO:315, and a heavy chain comprising the amino acid sequence of SEQ ID NO:317. In some embodiments, a fusion protein of the present disclosure comprises one or two light chains comprising the amino acid sequence of SEQ ID NO:318, a heavy chain comprising the amino acid sequence of SEQ ID NO:319, and a heavy chain comprising the amino acid sequence of SEQ ID NO:320. In some embodiments, a fusion protein of the present disclosure comprises one or two light chains comprising the amino acid sequence of SEQ ID NO:318, a heavy chain comprising the amino acid sequence of SEQ ID NO:319, and a heavy chain comprising the amino acid sequence of SEQ ID NO:321. In some embodiments, a fusion protein of the present disclosure comprises one or two light chains comprising the amino acid sequence of SEQ ID NO:322, a heavy chain comprising the amino acid sequence of SEQ ID NO:323, and a heavy chain comprising the amino acid sequence of SEQ ID NO:324. In some embodiments, a fusion protein of the present disclosure comprises one or two light chains comprising the amino acid sequence of SEQ ID NO:322, a heavy chain comprising the amino acid sequence of SEQ ID NO:323, and a heavy chain comprising the amino acid sequence of SEQ ID NO:325. In some embodiments, a fusion protein of the present disclosure comprises one or two light chains comprising the amino acid sequence of SEQ ID NO:326, a heavy chain comprising the amino acid sequence of SEQ ID NO:327, and a heavy chain comprising the amino acid sequence of SEQ ID NO:328. In some embodiments, a fusion protein of the present disclosure comprises one or two light chains comprising the amino acid sequence of SEQ ID NO:326, a heavy chain comprising the amino acid sequence of SEQ ID NO:327, and a heavy chain comprising the amino acid sequence of SEQ ID NO:329. In some embodiments, a fusion protein of the present disclosure comprises one or two light chains comprising the amino acid sequence of SEQ ID NO:330, a heavy chain comprising the amino acid sequence of SEQ ID NO:331, and a heavy chain comprising the amino acid sequence of SEQ ID NO:332. In some embodiments, a fusion protein of the present disclosure comprises one or two light chains comprising the amino acid sequence of SEQ ID NO:330, a heavy chain comprising the amino acid sequence of SEQ ID NO:331, and a heavy chain comprising the amino acid sequence of SEQ ID NO:333. In some embodiments, a fusion protein of the present disclosure comprises one or two light chains comprising the amino acid sequence of SEQ ID NO:334, a heavy chain comprising the amino acid sequence of SEQ ID NO:335, and a heavy chain comprising the amino acid sequence of SEQ ID NO:336. In some embodiments, a fusion protein of the present disclosure comprises one or two light chains comprising the amino acid sequence of SEQ ID NO:334, a heavy chain comprising the amino acid sequence of SEQ ID NO:335, and a heavy chain comprising the amino acid sequence of SEQ ID NO:337. In some embodiments, a fusion protein of the present disclosure comprises one or two light chains comprising the amino acid sequence of SEQ ID NO:338, a heavy chain comprising the amino acid sequence of SEQ ID NO:339, and a heavy chain comprising the amino acid sequence of SEQ ID NO:340. In some embodiments, a fusion protein of the present disclosure comprises one or two light chains comprising the amino acid sequence of SEQ ID NO:338, a heavy chain comprising the amino acid sequence of SEQ ID NO:339, and a heavy chain comprising the amino acid sequence of SEQ ID NO:341. In some embodiments, a fusion protein of the present disclosure comprises one or two light chains comprising the amino acid sequence of SEQ ID NO:342, a heavy chain comprising the amino acid sequence of SEQ ID NO:343, and a heavy chain comprising the amino acid sequence of SEQ ID NO:344. In some embodiments, a fusion protein of the present disclosure comprises one or two light chains comprising the amino acid sequence of SEQ ID NO:342, a heavy chain comprising the amino acid sequence of SEQ ID NO:343, and a heavy chain comprising the amino acid sequence of SEQ ID NO:345. In some embodiments, a fusion protein of the present disclosure comprises one or two light chains comprising the amino acid sequence of SEQ ID NO:346, a heavy chain comprising the amino acid sequence of SEQ ID NO:347, and a heavy chain comprising the amino acid sequence of SEQ ID NO:348. In some embodiments, a fusion protein of the present disclosure comprises one or two light chains comprising the amino acid sequence of SEQ ID NO:346, a heavy chain comprising the amino acid sequence of SEQ ID NO:347, and a heavy chain comprising the amino acid sequence of SEQ ID NO:349. In some embodiments, a fusion protein of the present disclosure comprises one or two light chains comprising the amino acid sequence of SEQ ID NO:350, a heavy chain comprising the amino acid sequence of SEQ ID NO:351, and a heavy chain comprising the amino acid sequence of SEQ ID NO:352. In some embodiments, a fusion protein of the present disclosure comprises one or two light chains one or two light chains comprising the amino acid sequence of SEQ ID NO:156, a heavy chain comprising the amino acid sequence of SEQ ID NO:157, and a heavy chain comprising the amino acid sequence of SEQ ID NO:217. In some embodiments, a fusion protein of the present disclosure comprises one or two light chains one or two light chains comprising the amino acid sequence of SEQ ID NO:159, a heavy chain comprising the amino acid sequence of SEQ ID NO:160, and a heavy chain comprising the amino acid sequence of SEQ ID NO:218. In some embodiments, a fusion protein of the present disclosure comprises one or two light chains one or two light chains comprising the amino acid sequence of SEQ ID NO:162, a heavy chain comprising the amino acid sequence of SEQ ID NO:163, and a heavy chain comprising the amino acid sequence of SEQ ID NO:219. In some embodiments, a fusion protein of the present disclosure comprises one or two light chains one or two light chains comprising the amino acid sequence of SEQ ID NO:165, a heavy chain comprising the amino acid sequence of SEQ ID NO:166, and a heavy chain comprising the amino acid sequence of SEQ ID NO:220. In some embodiments, a fusion protein of the present disclosure comprises one or two light chains one or two light chains comprising the amino acid sequence of SEQ ID NO:168, a heavy chain comprising the amino acid sequence of SEQ ID NO:169, and a heavy chain comprising the amino acid sequence of SEQ ID NO:221. In some embodiments, a fusion protein of the present disclosure comprises one or two light chains one or two light chains comprising the amino acid sequence of SEQ ID NO:171, a heavy chain comprising the amino acid sequence of SEQ ID NO:172, and a heavy chain comprising the amino acid sequence of SEQ ID NO:222. In some embodiments, a fusion protein of the present disclosure comprises one or two light chains one or two light chains comprising the amino acid sequence of SEQ ID NO:174, a heavy chain comprising the amino acid sequence of SEQ ID NO:175, and a heavy chain comprising the amino acid sequence of SEQ ID NO:223. In some embodiments, a fusion protein of the present disclosure comprises one or two light chains one or two light chains comprising the amino acid sequence of SEQ ID NO:187, a heavy chain comprising the amino acid sequence of SEQ ID NO:188, and a heavy chain comprising the amino acid sequence of SEQ ID NO:224. In some embodiments, a fusion protein of the present disclosure comprises one or two light chains one or two light chains comprising the amino acid sequence of SEQ ID NO:298, a heavy chain comprising the amino acid sequence of SEQ ID NO:299, and a heavy chain comprising the amino acid sequence of SEQ ID NO:301. In some embodiments, a fusion protein of the present disclosure comprises one or two light chains one or two light chains comprising the amino acid sequence of SEQ ID NO:302, a heavy chain comprising the amino acid sequence of SEQ ID NO:303, and a heavy chain comprising the amino acid sequence of SEQ ID NO:305. In some embodiments, a fusion protein of the present disclosure comprises one or two light chains one or two light chains comprising the amino acid sequence of SEQ ID NO:306, a heavy chain comprising the amino acid sequence of SEQ ID NO:307, and a heavy chain comprising the amino acid sequence of SEQ ID NO:309. In some embodiments, a fusion protein of the present disclosure comprises one or two light chains one or two light chains comprising the amino acid sequence of SEQ ID NO:310, a heavy chain comprising the amino acid sequence of SEQ ID NO:311, and a heavy chain comprising the amino acid sequence of SEQ ID NO:313. In some embodiments, a fusion protein of the present disclosure comprises one or two light chains one or two light chains comprising the amino acid sequence of SEQ ID NO:314, a heavy chain comprising the amino acid sequence of SEQ ID NO:315, and a heavy chain comprising the amino acid sequence of SEQ ID NO:317. In some embodiments, a fusion protein of the present disclosure comprises one or two light chains one or two light chains comprising the amino acid sequence of SEQ ID NO:318, a heavy chain comprising the amino acid sequence of SEQ ID NO:319, and a heavy chain comprising the amino acid sequence of SEQ ID NO:321. In some embodiments, a fusion protein of the present disclosure comprises one or two light chains one or two light chains comprising the amino acid sequence of SEQ ID NO:322, a heavy chain comprising the amino acid sequence of SEQ ID NO:323, and a heavy chain comprising the amino acid sequence of SEQ ID NO:325. In some embodiments, a fusion protein of the present disclosure comprises one or two light chains one or two light chains comprising the amino acid sequence of SEQ ID NO:326, a heavy chain comprising the amino acid sequence of SEQ ID NO:327, and a heavy chain comprising the amino acid sequence of SEQ ID NO:329. In some embodiments, a fusion protein of the present disclosure comprises one or two light chains one or two light chains comprising the amino acid sequence of SEQ ID NO:330, a heavy chain comprising the amino acid sequence of SEQ ID NO:331, and a heavy chain comprising the amino acid sequence of SEQ ID NO:333. In some embodiments, a fusion protein of the present disclosure comprises one or two light chains one or two light chains comprising the amino acid sequence of SEQ ID NO:334, a heavy chain comprising the amino acid sequence of SEQ ID NO:335, and a heavy chain comprising the amino acid sequence of SEQ ID NO:337. In some embodiments, a fusion protein of the present disclosure comprises one or two light chains one or two light chains comprising the amino acid sequence of SEQ ID NO:338, a heavy chain comprising the amino acid sequence of SEQ ID NO:339, and a heavy chain comprising the amino acid sequence of SEQ ID NO:341. In some embodiments, a fusion protein of the present disclosure comprises one or two light chains one or two light chains comprising the amino acid sequence of SEQ ID NO:342, a heavy chain comprising the amino acid sequence of SEQ ID NO:343, and a heavy chain comprising the amino acid sequence of SEQ ID NO:345. In some embodiments, a fusion protein of the present disclosure comprises one or two light chains one or two light chains comprising the amino acid sequence of SEQ ID NO:346, a heavy chain comprising the amino acid sequence of SEQ ID NO:347, and a heavy chain comprising the amino acid sequence of SEQ ID NO:349. In some embodiments, a fusion protein of the present disclosure comprises one or two light chains one or two light chains comprising the amino acid sequence of SEQ ID NO:350, a heavy chain comprising the amino acid sequence of SEQ ID NO:351, and a heavy chain comprising the amino acid sequence of SEQ ID NO:353. In some embodiments, the fusion protein comprises one or two antigen binding sites, each antigen binding site comprising a VL domain from one of the light chain(s) and a VH domain from one of the heavy chains (e.g., the fusion protein comprises two antigen binding sites: one comprising a VL domain from one of the two light chains and a VH domain from one of the heavy chains, and another comprising a VL domain from the other light chain and a VH domain from the other heavy chain).

In some embodiments, a fusion protein of the present disclosure comprises one or two polypeptides comprising the amino acid sequence of SEQ ID NO:156, a polypeptide comprising the amino acid sequence of SEQ ID NO:157, and a polypeptide comprising the amino acid sequence of SEQ ID NO:158. In some embodiments, a fusion protein of the present disclosure comprises one or two polypeptides comprising the amino acid sequence of SEQ ID NO:156, a polypeptide comprising the amino acid sequence of SEQ ID NO:157, and a polypeptide comprising the amino acid sequence of SEQ ID NO:217. In some embodiments, a fusion protein of the present disclosure comprises one or two polypeptides comprising the amino acid sequence of SEQ ID NO:159, a polypeptide comprising the amino acid sequence of SEQ ID NO:160, and a polypeptide comprising the amino acid sequence of SEQ ID NO:161. In some embodiments, a fusion protein of the present disclosure comprises one or two polypeptides comprising the amino acid sequence of SEQ ID NO:159, a polypeptide comprising the amino acid sequence of SEQ ID NO:160, and a polypeptide comprising the amino acid sequence of SEQ ID NO:218. In some embodiments, a fusion protein of the present disclosure comprises one or two polypeptides comprising the amino acid sequence of SEQ ID NO:162, a polypeptide comprising the amino acid sequence of SEQ ID NO:163, and a polypeptide comprising the amino acid sequence of SEQ ID NO:164. In some embodiments, a fusion protein of the present disclosure comprises one or two polypeptides comprising the amino acid sequence of SEQ ID NO:162, a polypeptide comprising the amino acid sequence of SEQ ID NO:163, and a polypeptide comprising the amino acid sequence of SEQ ID NO:219. In some embodiments, a fusion protein of the present disclosure comprises one or two polypeptides comprising the amino acid sequence of SEQ ID NO:165, a polypeptide comprising the amino acid sequence of SEQ ID NO:166, and a polypeptide comprising the amino acid sequence of SEQ ID NO:167. In some embodiments, a fusion protein of the present disclosure comprises one or two polypeptides comprising the amino acid sequence of SEQ ID NO:165, a polypeptide comprising the amino acid sequence of SEQ ID NO:166, and a polypeptide comprising the amino acid sequence of SEQ ID NO:220. In some embodiments, a fusion protein of the present disclosure comprises one or two polypeptides comprising the amino acid sequence of SEQ ID NO:168, a polypeptide comprising the amino acid sequence of SEQ ID NO:169, and a polypeptide comprising the amino acid sequence of SEQ ID NO:170. In some embodiments, a fusion protein of the present disclosure comprises one or two polypeptides comprising the amino acid sequence of SEQ ID NO:168, a polypeptide comprising the amino acid sequence of SEQ ID NO:169, and a polypeptide comprising the amino acid sequence of SEQ ID NO:221. In some embodiments, a fusion protein of the present disclosure comprises one or two polypeptides comprising the amino acid sequence of SEQ ID NO:171, a polypeptide comprising the amino acid sequence of SEQ ID NO:172, and a polypeptide comprising the amino acid sequence of SEQ ID NO:173. In some embodiments, a fusion protein of the present disclosure comprises one or two polypeptides comprising the amino acid sequence of SEQ ID NO:171, a polypeptide comprising the amino acid sequence of SEQ ID NO:172, and a polypeptide comprising the amino acid sequence of SEQ ID NO:222. In some embodiments, a fusion protein of the present disclosure comprises one or two polypeptides comprising the amino acid sequence of SEQ ID NO:174, a polypeptide comprising the amino acid sequence of SEQ ID NO:175, and a polypeptide comprising the amino acid sequence of SEQ ID NO:176. In some embodiments, a fusion protein of the present disclosure comprises one or two polypeptides comprising the amino acid sequence of SEQ ID NO:174, a polypeptide comprising the amino acid sequence of SEQ ID NO:175, and a polypeptide comprising the amino acid sequence of SEQ ID NO:223. In some embodiments, a fusion protein of the present disclosure comprises one or two polypeptides comprising the amino acid sequence of SEQ ID NO:187, a polypeptide comprising the amino acid sequence of SEQ ID NO:188, and a polypeptide comprising the amino acid sequence of SEQ ID NO:189. In some embodiments, a fusion protein of the present disclosure comprises one or two polypeptides comprising the amino acid sequence of SEQ ID NO:187, a polypeptide comprising the amino acid sequence of SEQ ID NO:188, and a polypeptide comprising the amino acid sequence of SEQ ID NO:224. In some embodiments, a fusion protein of the present disclosure comprises one or two polypeptides comprising the amino acid sequence of SEQ ID NO:298, a polypeptide comprising the amino acid sequence of SEQ ID NO:299, and a polypeptide comprising the amino acid sequence of SEQ ID NO:300. In some embodiments, a fusion protein of the present disclosure comprises one or two polypeptides comprising the amino acid sequence of SEQ ID NO:298, a polypeptide comprising the amino acid sequence of SEQ ID NO:299, and a polypeptide comprising the amino acid sequence of SEQ ID NO:301. In some embodiments, a fusion protein of the present disclosure comprises one or two polypeptides comprising the amino acid sequence of SEQ ID NO:302, a polypeptide comprising the amino acid sequence of SEQ ID NO:303, and a polypeptide comprising the amino acid sequence of SEQ ID NO:304. In some embodiments, a fusion protein of the present disclosure comprises one or two polypeptides comprising the amino acid sequence of SEQ ID NO:302, a polypeptide comprising the amino acid sequence of SEQ ID NO:303, and a polypeptide comprising the amino acid sequence of SEQ ID NO:305. In some embodiments, a fusion protein of the present disclosure comprises one or two polypeptides comprising the amino acid sequence of SEQ ID NO:306, a polypeptide comprising the amino acid sequence of SEQ ID NO:307, and a polypeptide comprising the amino acid sequence of SEQ ID NO:308. In some embodiments, a fusion protein of the present disclosure comprises one or two polypeptides comprising the amino acid sequence of SEQ ID NO:306, a polypeptide comprising the amino acid sequence of SEQ ID NO:307, and a polypeptide comprising the amino acid sequence of SEQ ID NO:309. In some embodiments, a fusion protein of the present disclosure comprises one or two polypeptides comprising the amino acid sequence of SEQ ID NO:310, a polypeptide comprising the amino acid sequence of SEQ ID NO:311, and a polypeptide comprising the amino acid sequence of SEQ ID NO:312. In some embodiments, a fusion protein of the present disclosure comprises one or two polypeptides comprising the amino acid sequence of SEQ ID NO:310, a polypeptide comprising the amino acid sequence of SEQ ID NO:311, and a polypeptide comprising the amino acid sequence of SEQ ID NO:313. In some embodiments, a fusion protein of the present disclosure comprises one or two polypeptides comprising the amino acid sequence of SEQ ID NO:314, a polypeptide comprising the amino acid sequence of SEQ ID NO:315, and a polypeptide comprising the amino acid sequence of SEQ ID NO:316. In some embodiments, a fusion protein of the present disclosure comprises one or two polypeptides comprising the amino acid sequence of SEQ ID NO:314, a polypeptide comprising the amino acid sequence of SEQ ID NO:315, and a polypeptide comprising the amino acid sequence of SEQ ID NO:317. In some embodiments, a fusion protein of the present disclosure comprises one or two polypeptides comprising the amino acid sequence of SEQ ID NO:318, a polypeptide comprising the amino acid sequence of SEQ ID NO:319, and a polypeptide comprising the amino acid sequence of SEQ ID NO:320. In some embodiments, a fusion protein of the present disclosure comprises one or two polypeptides comprising the amino acid sequence of SEQ ID NO:318, a polypeptide comprising the amino acid sequence of SEQ ID NO:319, and a polypeptide comprising the amino acid sequence of SEQ ID NO:321. In some embodiments, a fusion protein of the present disclosure comprises one or two polypeptides comprising the amino acid sequence of SEQ ID NO:322, a polypeptide comprising the amino acid sequence of SEQ ID NO:323, and a polypeptide comprising the amino acid sequence of SEQ ID NO:324. In some embodiments, a fusion protein of the present disclosure comprises one or two polypeptides comprising the amino acid sequence of SEQ ID NO:322, a polypeptide comprising the amino acid sequence of SEQ ID NO:323, and a polypeptide comprising the amino acid sequence of SEQ ID NO:325. In some embodiments, a fusion protein of the present disclosure comprises one or two polypeptides comprising the amino acid sequence of SEQ ID NO:326, a polypeptide comprising the amino acid sequence of SEQ ID NO:327, and a polypeptide comprising the amino acid sequence of SEQ ID NO:328. In some embodiments, a fusion protein of the present disclosure comprises one or two polypeptides comprising the amino acid sequence of SEQ ID NO:326, a polypeptide comprising the amino acid sequence of SEQ ID NO:327, and a polypeptide comprising the amino acid sequence of SEQ ID NO:329. In some embodiments, a fusion protein of the present disclosure comprises one or two polypeptides comprising the amino acid sequence of SEQ ID NO:330, a polypeptide comprising the amino acid sequence of SEQ ID NO:331, and a polypeptide comprising the amino acid sequence of SEQ ID NO:332. In some embodiments, a fusion protein of the present disclosure comprises one or two polypeptides comprising the amino acid sequence of SEQ ID NO:330, a polypeptide comprising the amino acid sequence of SEQ ID NO:331, and a polypeptide comprising the amino acid sequence of SEQ ID NO:333. In some embodiments, a fusion protein of the present disclosure comprises one or two polypeptides comprising the amino acid sequence of SEQ ID NO:334, a polypeptide comprising the amino acid sequence of SEQ ID NO:335, and a polypeptide comprising the amino acid sequence of SEQ ID NO:336. In some embodiments, a fusion protein of the present disclosure comprises one or two polypeptides comprising the amino acid sequence of SEQ ID NO:334, a polypeptide comprising the amino acid sequence of SEQ ID NO:335, and a polypeptide comprising the amino acid sequence of SEQ ID NO:337. In some embodiments, a fusion protein of the present disclosure comprises one or two polypeptides comprising the amino acid sequence of SEQ ID NO:338, a polypeptide comprising the amino acid sequence of SEQ ID NO:339, and a polypeptide comprising the amino acid sequence of SEQ ID NO:340. In some embodiments, a fusion protein of the present disclosure comprises one or two polypeptides comprising the amino acid sequence of SEQ ID NO:338, a polypeptide comprising the amino acid sequence of SEQ ID NO:339, and a polypeptide comprising the amino acid sequence of SEQ ID NO:341. In some embodiments, a fusion protein of the present disclosure comprises one or two polypeptides comprising the amino acid sequence of SEQ ID NO:342, a polypeptide comprising the amino acid sequence of SEQ ID NO:343, and a polypeptide comprising the amino acid sequence of SEQ ID NO:344. In some embodiments, a fusion protein of the present disclosure comprises one or two polypeptides comprising the amino acid sequence of SEQ ID NO:342, a polypeptide comprising the amino acid sequence of SEQ ID NO:343, and a polypeptide comprising the amino acid sequence of SEQ ID NO:345. In some embodiments, a fusion protein of the present disclosure comprises one or two polypeptides comprising the amino acid sequence of SEQ ID NO:346, a polypeptide comprising the amino acid sequence of SEQ ID NO:347, and a polypeptide comprising the amino acid sequence of SEQ ID NO:348. In some embodiments, a fusion protein of the present disclosure comprises one or two polypeptides comprising the amino acid sequence of SEQ ID NO:346, a polypeptide comprising the amino acid sequence of SEQ ID NO:347, and a polypeptide comprising the amino acid sequence of SEQ ID NO:349. In some embodiments, a fusion protein of the present disclosure comprises one or two polypeptides comprising the amino acid sequence of SEQ ID NO:350, a polypeptide comprising the amino acid sequence of SEQ ID NO:351, and a polypeptide comprising the amino acid sequence of SEQ ID NO:352. In some embodiments, a fusion protein of the present disclosure comprises one or two polypeptides comprising the amino acid sequence of SEQ ID NO:350, a polypeptide comprising the amino acid sequence of SEQ ID NO:351, and a polypeptide comprising the amino acid sequence of SEQ ID NO:353.

Further provided herein are fusion proteins, comprising a first moiety that binds to a human CD8b and a second moiety comprising an IL2 polypeptide, wherein the fusion protein comprises four polypeptide chains, wherein: (1) the first polypeptide chain comprises the amino acid sequence of SEQ ID NO:334, the second polypeptide chain comprises the amino acid sequence of SEQ ID NO:335, the third polypeptide chain comprises the amino acid sequence of SEQ ID NO:336, and the fourth polypeptide chain comprises the amino acid sequence of SEQ ID NO:334; (2) the first polypeptide chain comprises the amino acid sequence of SEQ ID NO:334, the second polypeptide chain comprises the amino acid sequence of SEQ ID NO:335, the third polypeptide chain comprises the amino acid sequence of SEQ ID NO:337, and the fourth polypeptide chain comprises the amino acid sequence of SEQ ID NO:334; (3) the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:340, and the fourth polypeptide chain comprises the amino acid sequence of SEQ ID NO:338; or (4) the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:341, and the fourth polypeptide chain comprises the amino acid sequence of SEQ ID NO:338.

Further provided herein are polynucleotides (e.g., isolated polynucleotides) encoding the antibody or fusion protein according to any one of the above embodiments. Further provided herein are vectors (e.g., expression vectors) comprising the polynucleotide(s) according to any one of the above embodiments. Further provided herein are host cells (e.g., isolated host cells or cell lines) comprising the polynucleotide(s) or vector(s) according to any one of the above embodiments. Further provided herein are methods of producing an antibody or fusion protein, comprising culturing the host cell according to any one of the above embodiments under conditions suitable for production of the antibody or fusion protein. In some embodiments, the methods further comprise recovering the antibody or fusion protein from the host cell.

Further provided herein are pharmaceutical compositions comprising the antibody or fusion protein according to any one of the above embodiments and a pharmaceutically acceptable carrier.

Further provided herein is the use of the antibody, fusion protein, or composition according to any one of the above embodiments as a medicament. Further provided herein is the use of the antibody, fusion protein, or composition according to any one of the above embodiments in a method for treating cancer or infection (e.g., chronic infection). Further provided herein is the use of the antibody, fusion protein, or composition according to any one of the above embodiments for the manufacture of a medicament for treating cancer or infection (e.g., chronic infection). Further provided herein are methods of treating cancer comprising administering to an individual with cancer an effective amount of the antibody, fusion protein, or composition according to any one of the above embodiments. In some embodiments, the methods further comprise administering to the individual a T cell therapy, cancer vaccine, chemotherapeutic agent, or immune checkpoint inhibitor (ICI). Further provided herein are methods of treating infection (e.g., chronic infection) comprising administering to an individual with infection an effective amount of the antibody, fusion protein, or composition according to any one of the above embodiments. Further provided herein are methods of expanding T cells (e.g., ex vivo) comprising contacting one or more T cells (e.g., tumor infiltrating lymphocytes) ex vivo (e.g., ex vivo) with an effective amount of the antibody, fusion protein, or composition according to any one of the above embodiments.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

In FIG. 13A, all fusion proteins contained the CD8ab antibody of the present disclosure, xhCD8v1, and various mutant IL-2 polypeptides of the present disclosure, IL2m1, IL2m2, and IL2m6 to IL2m10, and were of format A. In FIG. 13B, fusion proteins contained the CD8ab antibodies of the present disclosure, xhCD8v11 and xhCD8v12, and various mutant IL-2 polypeptides of the present disclosure, IL2m11, IL2m12, and IL2m13, and were of format A. NK cells were identified as CD3-Perforin+.

FIG. 18A shows numbers of amino acid liabilities (e.g., putative N-linked glycosylation, deamination, or acid cleavage sites) and amino acid mismatches as compared to human germline of the indicated anti-CD8ab antibodies.

FIG. 18B shows alignments illustrating how CDRs (italics) from xhCD8v1 VH (top) and VK (bottom) were grafted onto VH1-69 and VK1-39 human germline frameworks, respectively. VH domain sequences (top) correspond to SEQ ID Nos: 58, 384, and 60, respectively (top to bottom). VL domain sequences (bottom) correspond to SEQ ID Nos: 59, 385, and 61, respectively (top to bottom). Underlined residues depict framework residues of human germline.

FIGS. 18C & 18D show alignments of VH (FIG. 18C) and VL (FIG. 18D) domains of the indicated anti-CD8ab antibodies of the present disclosure. VH domain sequences (FIG. 18C) correspond to SEQ ID Nos: 60, 62, 64, 66, 68, 245, 251, and 253, respectively (top to bottom). VL domain sequences (FIG. 18D) correspond to SEQ ID Nos: 61, 63, 65, 67, 69, 246, 252, and 254, respectively (top to bottom).

DETAILED DESCRIPTION

Definitions

Figures 1A, 1B, 1C:
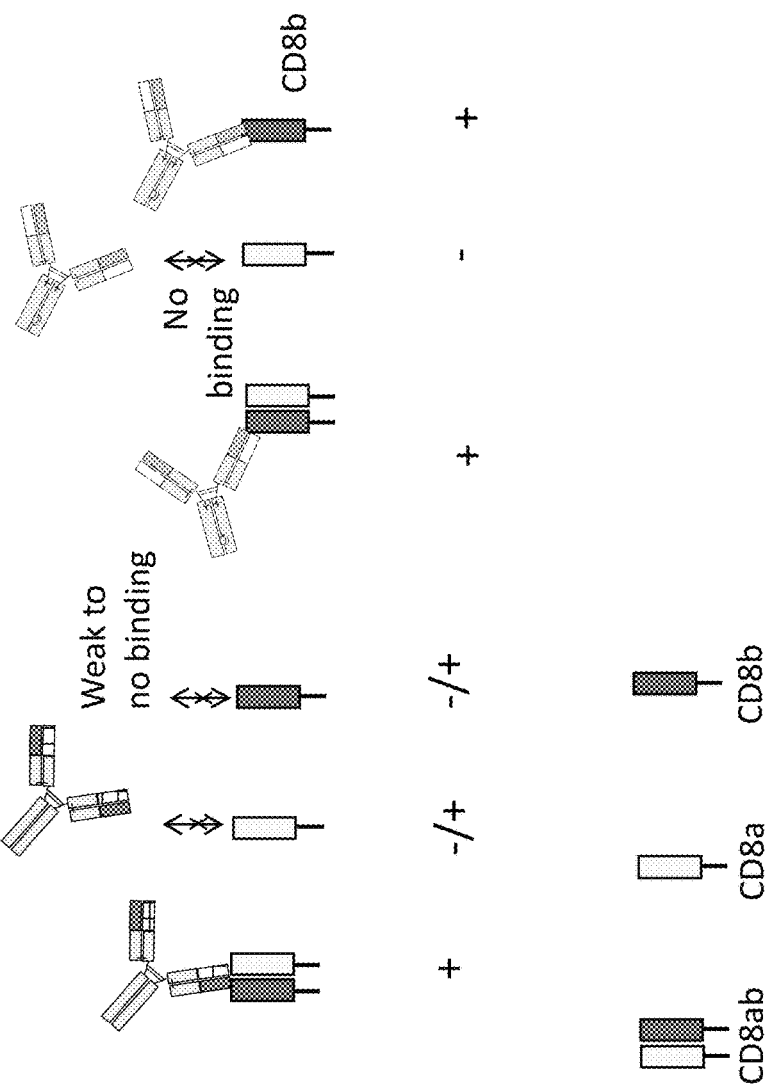
FIGS. 1A-1C depict the three types of CD8ab antibodies that could be identified according to their binding preference for CD8a, CD8b and CD8ab heterodimer. Antibodies binding CD8a epitopes are shown in FIG. 1A, antibodies binding epitopes that span both CD8a and CD8b are shown in FIG. 1B, and antibodies binding to CD8b epitopes are shown in FIG. 1C. Binding preference for CD8a, CD8b and CD8ab heterodimer by each antibody type is also depicted.

As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that aspects and embodiments of the present disclosure include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

"Immune cells" as used here are cells of the immune system that react to organisms or other entities that are deemed foreign to the immune system of the host. They protect the host against foreign pathogens, organisms and diseases. Immune cells, also called leukocytes, are involved in both innate and adaptive and immune responses to fight pathogens. Innate immune responses occur immediately upon exposure to pathogens without additional priming or learning processes. Adaptive immune processes require initial priming, and subsequently create memory, which in turn leads to enhanced responsiveness during subsequent encounters with the same pathogen. Innate immune cells include, but are not limited to, monocytes, macrophages, dendritic cells, innate lymphoid cells (ILCs) including natural killer (NK) cells, neutrophils, megakaryocytes, eosinophils and basophils. Adaptive immune cells include B and T lymphocytes/cells. T cells subsets include, but are not limited to, alpha beta CD4+ T (naïve CD4+, memory CD4+, effector memory CD4+, effector CD4+, regulatory CD4+), and alpha beta CD8+ T (naïve CD8+, memory CD8+, effector memory CD8+, effector CD8+). B cell subsets include, but is not limited to, naïve B, memory B, and plasma cells. NK T cells and T gamma delta (Tγδ) cells exhibit properties of both innate and adaptive lymphocytes.

"T cells" or "T lymphocytes" are immune cells that play a key role in the orchestration of immune responses in health and disease. Two major T cell subsets exist that have unique functions and properties: T cells that express the CD8 antigen (CD8$^+$ T cells) are cytotoxic or killer T cells that can lyse target cells using the cytotoxic proteins such as granzymes and perforin; and T cells that express the CD4 antigen (CD4$^+$ T cells) are helper T cells that are capable of regulating the function of many other immune cell types including that of CD8$^+$ T cells, B cells, macrophages etc. Furthermore, CD4$^+$ T cells are further subdivided into several subsets such as: T regulatory (Treg) cells that are capable of suppressing the immune response, and T helper 1 (Th1), T helper 2 (Th2), and T helper 17 (Th17) cells that regulate different types of immune responses by secreting immunomodulatory proteins such as cytokines. T cells recognize their targets via alpha beta T cell receptors that bind to unique antigen-specific motifs and this recognition mechanism is generally required in order to trigger their cytotoxic and cytokine-secreting functions. "Innate lymphocytes" can also exhibit properties of CD8+ and CD4$^+$ T cells, such as the cytotoxic activity or the secretion of Th1, Th2, and Th17 cytokines. Some of these innate lymphocyte subsets include NK cells and ILC1, ILC2, and ILC3 cells; and innate-like T cells such as Tγδ cells; and NK T cells. Typically, these cells can rapidly respond to inflammatory stimuli from infected or injured tissues, such as immunomodulatory cytokines, but unlike alpha beta T cells, they can respond without the need to recognize antigen-specific patterns.

"Cytokine" is a form of immunomodulatory polypeptide that mediates cross-talk between initiating/primary cells and target/effector cells. It can function as a soluble form or cell-surface associated to bind the "cytokine receptor" on target immune cells to activate signaling. "Cytokine receptor" as used here is the polypeptide on the cell surface that activates intracellular signaling upon binding the cytokine on the extracellular cell surface. Cytokines includes, but are not limited to, chemokines, interferons, interleukins, lymphokines, and tumor necrosis factors. Cytokines are produced by a wide range of cells, including immune cells, endothelial cells, fibroblasts, and stromal cells. A given cytokine may be produced by more than one cell type. Cytokine are pleiotropic; since the receptors are expressed on multiple immune cell subsets, one cytokine can activate the signaling pathway in multiple cells. However, depending on the cell type, the signaling events for a cytokine can result in different downstream cellular events such as activation, proliferation, survival, apoptosis, effector function and secretion of other immunomodulatory proteins.

"Amino acid" as used here refers to naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

"Polypeptide" or "protein" as used here refers to a molecule where monomers (amino acids) are linearly linked to one another by peptide bonds (also known as amide bonds). The term "polypeptide" refers to any chain of two or more amino acids and does not refer to a specific length of the product. Thus, peptides, dipeptides, tripeptides, oligopeptides, "protein", "amino acid chain", or any other term used to refer to a chain of two or more amino acids, are included within the definition of "polypeptide", and the term "polypeptide" may be used instead of, or interchangeably with any of these terms. The term "polypeptide" is also intended to refer to the products of A polypeptide may be derived from a natural biological source or produced by recombinant technology but is not necessarily translated from a designated nucleic acid sequence. It may be generated in any manner, including by chemical synthesis. Polypeptides normally have a defined three-dimensional structure, but they do not necessarily have such structure. A polypeptide of the present disclosure may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides with a defined three-dimensional structure are referred to as folded, and polypeptides which do not possess a defined three-dimensional structure, but rather can adopt many different conformations and are referred to as unfolded. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. The terms "polypeptide" and "protein" also refer to modified polypeptides/proteins wherein the post-expression modification is affected including without limitation glycosylation, acetylation, phosphorylation, amidation, derivatization by known protecting/blocking groups, proteolytic cleavage, or modification by non-naturally occurring amino acids.

"Residue" as used herein is meant a position in a protein and its associated amino acid identity. For example, Leu 234 (also referred to as Leu234 or L234) is a residue at position 234 in the human antibody IgG1.

"Wild-type" herein means an amino acid sequence or a nucleotide sequence that is found in nature, including allelic variations. A wild-type protein has an amino acid sequence or a nucleotide sequence that has not been intentionally modified.

"Substitution" or "mutation" refers to a change to the polypeptide backbone wherein an amino acid occurring naturally in the wild-type sequence of a polypeptide is substituted to another amino acid not naturally occurring at the same position in the said polypeptide. Preferably, a mutation or mutations are introduced to modify polypeptide's affinity to its receptor thereby altering its activity such that it becomes different from the affinity and activity of the wild-type cognate polypeptide. Mutations can also improve polypeptide's biophysical properties. Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

"CD8" as used here refers to any native human CD8. Unless otherwise indicated expressly or by context, references to "CD8" refer to CD8aa and/or CD8ab. The amino acid sequence of an exemplary human CD8b, the beta chain of human CD8, is described under UniProt P10966 (CD8B_HUMAN). "CD8a" refers to the alpha chain of human CD8 (e.g., as is described under UniProt P01732 (CD8A_HUMAN)). "CD8aa" refers to a homodimer of CD8a. "CD8ab" refers to a heterodimer of CD8a and CD8b. "CD8," "CD8a," "CD8b," "CD8aa," and "CD8ab" encompass unprocessed forms as well as mature forms that result from processing in the cell. "CD8," "CD8a," "CD8b," "CD8aa," and "CD8ab" also include but are not limited to naturally occurring variants, e.g. allelic or splice variants or variants.

"Interleukin-2" or "IL-2" as used here refers to any native human IL-2, unless otherwise indicated. "IL-2" encompasses unprocessed IL-2 as well as "mature IL-2" which is a form of IL-2 that results from processing in the cell. The sequence of "mature IL-2" is depicted in FIG. 1A. One exemplary form of unprocessed human IL-2 comprises of an additional N-terminal amino acid signal peptide attached to mature IL-2. "IL-2" also includes but is not limited to naturally occurring variants of IL-2, e.g. allelic or splice variants or variants. The amino acid sequence of an exemplary human IL-2 is described under UniProt P60568 (IL2_HUMAN).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity can generally be represented by the dissociation constant ($K_D$), which is the ratio of dissociation and association rate constants (koff and kon, respectively). Thus, equivalent affinities may comprise different rate constants, as long as the ratio of the rate constants remains the same. Affinity can be measured by common methods known in the art, such as enzyme-linked immunosorbent assay (ELISA), surface plasmon resonance (SPR) technologies (e.g. BIAcore), Bio- Layer Interferometry (BLI) technologies (e.g. Octet) and other traditional binding assays (Heeley, Endocr Res 28, 217-229 (2002).

"Binding" or "specific binding" as used here, refers the ability of a polypeptide or an antigen binding molecule to selectively interact with the receptor for the polypeptide or target antigen, respectively, and this specific interaction can be distinguished from non-targeted or undesired or non-specific interactions. Examples of specific binding include but are not limited to IL-2 cytokine binding to its specific receptors (e.g. IL-2Rα, IL-2Rβ and IL-2Rγ) and an antigen binding molecule binding to a specific antigen (e.g. CD8 or PD-1).

"Mutant IL-2 polypeptide" refers to IL-2 polypeptide that has reduced affinity to its receptor wherein such decreased affinity will result in reduced biological activity of the mutant. Reduction in affinity and thereby activity can be obtained by introducing a small number of amino acid mutations or substitutions. The mutant IL-2 polypeptides can also have other modifications to the peptide backbone, including but not limited to amino acid deletion, permutation, cyclization, disulfide bonds, or the post-translational modifications (e.g. glycosylation or altered carbohydrate) of a polypeptide, chemical or enzymatic modifications to the polypeptide (e.g. attaching PEG to the polypeptide backbone), addition of peptide tags or labels, or fusion to proteins or protein domains to generate a final construct with desired characteristics, such as reduced affinity to IL-2Rβγ. Desired activity may also include improved biophysical properties compared to the wild-type IL-2 polypeptide. Multiple modifications may be combined to achieve desired activity modification, such as reduction in affinity or improved biophysical properties. As a non-limiting example, amino acid sequences for consensus N-link glycosylation may be incorporated into the polypeptide to allow for glycosylation. Another non-limiting example is that a lysine may be incorporated onto the polypeptide to enable pegylation. Preferably, a mutation or mutations are introduced to the polypeptide to modify its activity.

The terms "antibody" and "immunoglobulin" are used interchangeably and herein are used in the broadest sense and encompasses various antibody structures, including but not limited to monoclonal antibodies (e.g., full length or intact monoclonal antibodies), polyclonal antibodies, multispecific antibodies (e.g. bispecific antibodies), antibody fragments and single domain antibody (as described in greater detail herein), so long as they exhibit the desired antigen binding activity.

Antibodies (immunoglobulins) refer to a protein having a structure substantially similar to a native antibody structure. "Native antibodies" refer to naturally occurring immunoglobulin molecules with varying structures. For example, native immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The subunit structures and three-dimensional configurations of the different classes of immunoglobulins are well known and described generally, for example, in Abbas et al., 2000, Cellular and Mol, and Kindt et al., Kuby Immunology, 6th ed., W.H. Freeman and Co., page 91 (2007). Antibodies (immunoglobulins) are assigned to different classes, depending on the amino acid sequences of the heavy chain constant domains. There are five major classes of antibodies: α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

"Fc" or "Fc region" or "Fc domain" as used herein refers to the C-terminal region of an antibody heavy chain that contains at least a portion of the constant region. The term includes native sequence Fc regions and variant Fc regions. An Fc can refer to the last two constant region immunoglobulin domains (e.g., CH2 and CH3) of IgA, IgD, and IgG, the last three constant region immunoglobulin domains of IgE and IgM, and optionally, all or a portion of the flexible hinge N-terminal to these domains. For IgA and IgM, Fc may include the J chain. An IgG Fc region comprises an IgG CH2 and an IgG CH3 domain and in some cases, inclusive of the hinge. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The "hinge" region usually extends from amino acid residue at about position 216 to amino acid residue at about position 230. The hinge region herein may be a native hinge domain or variant hinge domain. The "CH2 domain" of a human IgG Fc region usually extends from an amino acid residue at about position 231 to an amino acid residue at about position 340. The CH2 domain herein may be a native sequence CH2 domain or variant CH2 domain. The "CH3 domain" comprises the stretch of residues C-terminal to a CH2 domain in an Fc region, from an amino acid residue at about position 341 to an amino acid residue at about position 447 of an IgG. The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Thus, the definition of "Fc domain" includes both amino acids 231-447 (CH2-CH3) or 216-447 (hinge-CH2-CH3), or fragments thereof. An "Fc fragment" in this context may contain fewer amino acids from either or both of the N- and C-termini but still retains the ability to form a dimer with another Fc domain or Fc fragment as can be detected using standard methods, generally based on size (e.g. non-denaturing chromatography, size exclusion chromatography, etc.). Human IgG Fc domains are of particular use in the present disclosure, and can be the Fc domain from human IgG1, IgG2 or IgG4.

A "variant Fc domain" or "Fc variant" or "variant Fc" contains amino acid modifications (e.g. substitution, addition, and deletion) as compared to a parental Fc domain. The term also includes naturally occurring allelic variants of the Fc region of an immunoglobulin. In general, variant Fc domains have at least about 80, 85, 90, 95, 97, 98 or 99 percent identity to the corresponding parental human IgG Fc domain (using the identity algorithms discussed below, with one embodiment utilizing the BLAST algorithm as is known in the art, using default parameters). Alternatively, the variant Fc domains can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. For example, one or more amino acids can be deleted from the N-terminus or C-terminus of the Fc region of an immunoglobulin without substantial loss of biological function. Additionally, as discussed herein, the variant Fc domains herein still retain the ability to form a dimer with another Fc domain as measured using known techniques as described herein, such as non-denaturing gel electrophoresis.

"Fc gamma receptor", "FcγR" or "Fc gamma R" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "effector function" as used herein is meant a biochemical event that results from the interaction of an antibody Fc region with an Fc receptor or ligand, which vary with the antibody isotype. Effector functions include but are not limited to antibody-dependent cell-mediated cytotoxicity (ADCC), antibody-dependent cell-mediated phagocytosis (ADCP), complement-dependent cytotoxicity (CDC), cytokine secretion, immune complex-mediated antigen uptake by antigen presenting cells, down regulation of cell surface receptors (e.g. B cell receptor), and B cell activation. "Antibody-dependent cell-mediated cytotoxicity" or "ADCC" refer to a cell-mediated reaction in which nonspecific cytotoxic cells that express FcRs (such as Natural Killer (NK) cells, neutrophils, and macrophages) recognize bound antibody on a target cell and subsequently cause lysis of the target cell. ADCC is correlated with binding to FcγRIIIa; increased binding to FcγRIIIa leads to an increase in ADCC activity. To assess ADCC activity of a molecule of interest, an in vitro ADCC assay such as that described in U.S. Pat. No. 5,500,362 or 5,821,337 may be performed. "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

"Fc null" and "Fc null variant" are used interchangeably and used herein to describe a modified Fc which have reduced or abolished effector functions. Such Fc null or Fc null variant have reduced or abolished to FcγRs and/or complement receptors. Preferably, such Fc null or Fc null variant has abolished effector functions. Exemplary methods for the modification include but not limited to chemical alteration, amino acid residue substitution, insertion and deletions. Exemplary amino acid positions on Fc molecules where one or more modifications were introduced to decrease effector function of the resulting variant (numbering based on the EU numbering scheme) at position i) IgG1: C220, C226, C229, E233, L234, L235, G237, P238, S239 D265, S267, N297, L328, P331, K322, A327 and P329, ii) IgG2: V234, G237, D265, H268, N297, V309, A330, A331, K322 and iii) IgG4: L235, G237, D265 and E318. Exemplary Fc molecules having decreased effector function include those having one or more of the following substitutions: i) IgG1: N297A, N297Q, N297G, D265A/N297A, D265A/N297Q, C220S/C226S/C229S/P238S, S267E/L328F, C226S/C229S/E233P/L234V/L235A, L234F/L235E/P331S, L234A/L235A, L234A/L235A/G237A, L234A/L235A/G237A/K322A, L234A/L235A/G237A/A330S/A331S, L234A/L235A/P329G, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, L234A/L235A/G237deleted; ii) IgG2: A330S/A331S, V234A/G237A, V234A/G237A/D265A, D265A/A330S/A331S, V234A/G237A/D265A/A330S/A331S, and H268Q/V309L/A330S/A331S; iii) IgG4: L235A/G237A/E318A, D265A, L235A/G237A/D265A and L235A/G237A/D265A/E318A.

"Epitope" as used herein refers to a determinant capable of specific binding to the variable region of an antibody molecule known as a paratope. Epitopes are groupings of molecules such as amino acids or sugar side chains and usually have specific structural characteristics, as well as specific charge characteristics. A single antigen may have more than one epitope. The epitope may comprise amino acid residues directly involved in the binding and other amino acid residues, which are not directly involved in the binding, such as amino acid residues which are effectively blocked by the antigen binding peptide (in other words, the amino acid residue is within the footprint of the antigen binding peptide). Epitopes may be either conformational or linear. An epitope typically includes at least 3, and more usually, at least 5 or 8-10 amino acids. Antibodies that recognize the same epitope can be verified in a simple immunoassay showing the ability of one antibody to block the binding of another antibody to a target antigen, for example "binning".

"Linker" as used herein refers to a molecule that connect two polypeptide chains. Linker can be a polypeptide linker or a synthetic chemical linker (for example, see disclosed in Protein Engineering, 9(3), 299-305, 1996). The length and sequence of the polypeptide linkers is not particularly limited and can be selected according to the purpose by those skilled in the art. Polypeptide linker comprises one or more amino acids. In some embodiments, the polypeptide linker is a peptide with a length of at least 5 amino acids, preferably with a length of 5 to 100, more preferably of 10 to 50 amino acids. In one embodiment, said peptide linker is G, S, GS, SG, SGG, GGS, and GSG (with G=glycine and S=serine). In another embodiment, said peptide linker is (GGGS)xGn (SEQ ID NO:74) or (GGGGS)xGn (SEQ ID NO:75) or (GGGGGS)xGn (SEQ ID NO:76) or S(GGGS)xGn (SEQ ID NO:386) or S(GGGGS)xGn (SEQ ID NO:387) or S(GGGGGS)xGn (SEQ ID NO:388), with x=1, 2, 3, 4, 5, 6, 7, 8, 9, 10, 11, or 12 and n=0, 1, 2 or 3. Preferably, the said linker is (GGGGS)xGn with x=2, 3, or 4 and n=0 (SEQ ID NO:77); more preferably the said linker is (GGGGS)xGn with x=3 and n=0 (SEQ ID NO:78). In some embodiments, the linker comprises the sequence GGGGSGGGGSGGGGS (SEQ ID NO:79) or or SGGGGSGGGGSGGGGS (SEQ ID NO:389). Synthetic chemical linkers include crosslinking agents that are routinely used to crosslink peptides, for example, N-hydroxy succinimide (NHS), disuccinimidyl suberate (DSS), bis(succinimidyl) suberate (BS3), dithiobis (succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis[2-(succinimidoxycarbonyloxy)ethyl] sulfone (sulfo-BSOCOES).

The term "polynucleotide" refers to an isolated nucleic acid molecule or construct, e.g. messenger RNA (mRNA), virally-derived RNA, or plasmid DNA (pDNA) encoding the polypeptides of the present disclosure. A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide. In some aspects, one or more vectors (particularly expression vectors) comprising such nucleic acids are provided. In one aspect, a method for making a polypeptide of the present disclosure is provided, wherein the methods comprises culturing a host cell comprising a nucleic acid encoding the polypeptide under conditions suitable for expression of the polypeptide and recovering the polypeptide from the host cell. "Recombinant" means the proteins are generated using recombinant nucleic acid techniques in exogeneous host cells. Recombinantly produced proteins expressed in host cells are considered isolated for the purpose of the present disclosure, as are native or recombinant proteins which have been separated, fractionated, or partially or substantially purified by any suitable technique.

"Isolated," when used to describe the various polypeptides disclosed herein, means a polypeptide that has been identified and separated and/or recovered from a cell or cell culture from which it was expressed. Typically, an isolated polypeptide will be purified by at least one purification step. There is no required level of purity; "purification" or "purified" refers to increase of the target protein concentration relative to the concentration of contaminants in a composition as compared to the starting material. An "isolated protein," as used herein refers to a target protein which is substantially free of other proteins having different binding specificities.

The terms "cancer" refers the physiological condition in mammals that is typically characterized by unregulated and abnormal cell growth with the potential to invade or spread to other parts of the body. Examples of cancer include but are not limited to, carcinoma, lymphoma, blastoma, sarcoma, and leukemia. More particular examples of such cancers include lung cancer, small-cell lung cancer, non-small cell lung (NSCL) cancer, bronchioloalviolar cell lung cancer, squamous cell cancer, adenocarcinoma of the lung, squamous carcinoma of the lung, cancer of the peritoneum, head and neck cancer, bone cancer, pancreatic cancer, skin cancer, cancer of the head or neck, cutaneous or intraocular melanoma, thyroid cancer, uterine cancer, gastrointestinal cancer, ovarian cancer, rectal cancer, cancer of the anal region, stomach cancer, gastric cancer, colon cancer, breast cancer, endometrial carcinoma, uterine cancer, carcinoma of the fallopian tubes, carcinoma of the cervix, carcinoma of the vagina, vulval cancer, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, bladder cancer, liver cancer, hepatoma, hepatocellular cancer, cervical cancer, salivary gland carcinoma, biliay cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Antibodies and Antigen Binding Domains

Certain aspects of the present disclosure relate to antibodies, antibody fragments, and antigen binding domains that specifically bind human CD8b and/or human CD8ab. Any of the anti-CD8 antibodies of the present disclosure (e.g., that specifically bind human CD8b and/or human CD8ab) may find use in the fusion proteins, methods, and uses disclosed herein.

In some embodiments, the anti-CD8 antibody of the present disclosure specifically binds human CD8b and/or human CD8ab with at least 10-fold, at least 20-fold, at least 30-fold, at least 40-fold, at least 50-fold, at least 60-fold, at least 70-fold, at least 80-fold, at least 90-fold, at least 100-fold, or at least 200-fold higher affinity than its binding to human CD8a and/or human CD8aa, e.g., as expressed on natural killer (NK) cells (e.g., human NK cells). In some embodiments, the anti-CD8 antibody of the present disclosure specifically binds human CD8b and/or human CD8ab with at least 10-fold higher affinity than its binding to human CD8a and/or human CD8aa, e.g., as expressed on natural killer (NK) cells. In some embodiments, the human CD8b and/or human CD8ab are expressed on the surface of a human cell, e.g., a human T cell.

In some embodiments, the anti-CD8 antibody of the present disclosure specifically binds to a cell expressing a human CD8ab heterodimer on its surface (e.g., a human T cell) with an EC50 that is less than 1000 nM. In some embodiments, the anti-CD8 antibody of the present disclosure specifically binds to human CD8+ T cells.

In some embodiments, the anti-CD8 antibody of the present disclosure is a human antibody or antibody fragment. In some embodiments, a human antibody or antibody fragment comprises human-derived CDRs and framework sequences in the variable domain, e.g., as isolated from a human or generated using a library with human antibody sequences (e.g., CDR sequences). In some embodiments, the anti-CD8 antibody of the present disclosure is a humanized antibody or antibody fragment. In some embodiments, a humanized antibody or antibody fragment comprises non-human-derived CDRs (e.g., from a mouse, rabbit, goat, etc.) and human-derived framework sequences in the variable domain. In some embodiments, a human or humanized antibody further comprises a human Fc region. In some embodiments, the human Fc region further comprises one or more Fc mutations, e.g., as disclosed herein. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

Multiple definitions for the CDR sequences of antibody variable domains are known in the art. Unless otherwise specified, CDR sequences are described herein according to the definition of Kabat (see, e.g., Kabat et al., *Sequences of Proteins of Immunological Interest*, Fifth Edition, NIH Publication 91-3242, Bethesda MD (1991), vols. 1-3). However, other definitions are known and contemplated for use. For example, in some embodiments, CDR sequences can be described by the definition of Chothia (see, e.g., Chothia and Lesk, *J. Mol. Biol.* 196:901-917 (1987). Depending upon the specific CDR definition used, the precise framework sequences can also vary, but, as is known in the art, the first framework sequence (FW-1) refers to the sequence from the N-terminus of the VH or VL domain to the beginning of CDR-H1/-L1, the second framework sequence (FW-2) refers to the sequence from end of CDR-H1/-L1 to the beginning of CDR-H2/-L2, the third framework sequence (FW-3) refers to the sequence from end of CDR-H2/-L2 to the beginning of CDR-H3/-L3, and the fourth framework sequence (FW-4) refers to the sequence from end of CDR-H3/-L3 to the C-terminal boundary of the VH or VL domain.

In some embodiments, an anti-CD8 antibody of the present disclosure comprises a VH domain comprising a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3 and a VL domain comprising a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, an anti-CD8 antibody of the present disclosure comprises 1, 2, or 3 heavy chain CDRs of antibody xhCD8v1 (e.g., as shown in Tables 1-3) and/or 1, 2, or 3 light chain CDRs of antibody xhCD8v1 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:58 and a VL domain comprising a CDR-L1, CDR-L2, and CDR-L3 from the sequence of SEQ ID NO:59.

In some embodiments, an anti-CD8 antibody of the present disclosure comprises a VH domain comprising a CDR-H1 comprising the amino acid sequence of SEQ ID NO:177, a CDR-H2 comprising the amino acid sequence of SEQ ID NO:178, and a CDR-H3 comprising the amino acid sequence of SEQ ID NO:179 and a VL domain comprising a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182. In some embodiments, an anti-CD8 antibody of the present disclosure comprises 1, 2, or 3 heavy chain CDRs of antibody xhCD8v8 (e.g., as shown in Tables 1-3) and/or 1, 2, or 3 light chain CDRs of antibody xhCD8v8 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:185 and a VL domain comprising a CDR-L1, CDR-L2, and CDR-L3 from the sequence of SEQ ID NO:186.

In some embodiments, an anti-CD8 antibody of the present disclosure comprises a VH domain comprising a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the VH domain comprises an amino acid sequence that is at least 90%, at least 95%, at least 99%, or 100% identical to the sequence of SEQ ID NO:62 and/or the VL domain comprises an amino acid sequence that is at least 90%, at least 95%, at least 99%, or 100% identical to the sequence of SEQ ID NO:63. In some embodiments, an anti-CD8 antibody of the present disclosure comprises 1, 2, or 3 heavy chain CDRs of antibody xhCD8v2 (e.g., as shown in Tables 1-3) and/or 1, 2, or 3 light chain CDRs of antibody xhCD8v2 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:62 and a VL domain comprising a CDR-L1, CDR-L2, and CDR-L3 from the sequence of SEQ ID NO:63.

In some embodiments, an anti-CD8 antibody of the present disclosure comprises a VH domain comprising a CDR-H1 comprising the amino acid sequence of SEQ ID NO:19, a CDR-H2 comprising the amino acid sequence of SEQ ID NO:20, and a CDR-H3 comprising the amino acid sequence of SEQ ID NO:21 and a VL domain comprising a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24. In some embodiments, the VH domain comprises an amino acid sequence that is at least 90%, at least 95%, at least 99%, or 100% identical to the sequence of SEQ ID NO:64 and/or the VL domain comprises an amino acid sequence that is at least 90%, at least 95%, at least 99%, or 100% identical to the sequence of SEQ ID NO:65. In some embodiments, an anti-CD8 antibody of the present disclosure comprises 1, 2, or 3 heavy chain CDRs of antibody xhCD8v3 (e.g., as shown in Tables 1-3) and/or 1, 2, or 3 light chain CDRs of antibody xhCD8v3 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:64 and a VL domain comprising a CDR-L1, CDR-L2, and CDR-L3 from the sequence of SEQ ID NO:65.

In some embodiments, an anti-CD8 antibody of the present disclosure comprises a VH domain comprising a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27 and a VL domain comprising a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30. In some embodiments, the VH domain comprises an amino acid sequence that is at least 90%, at least 95%, at least 99%, or 100% identical to the sequence of SEQ ID NO:66 and/or the VL domain comprises an amino acid sequence that is at least 90%, at least 95%, at least 99%, or 100% identical to the sequence of SEQ ID NO:67. In some embodiments, an anti-CD8 antibody of the present disclosure comprises 1, 2, or 3 heavy chain CDRs of antibody xhCD8v4 (e.g., as shown in Tables 1-3) and/or 1, 2, or 3 light chain CDRs of antibody xhCD8v4 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:66 and a VL domain comprising a CDR-L1, CDR-L2, and CDR-L3 from the sequence of SEQ ID NO:67.

In some embodiments, an anti-CD8 antibody of the present disclosure comprises a VH domain comprising a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33 and a VL domain comprising a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36. In some embodiments, the VH domain comprises an amino acid sequence that is at least 90%, at least 95%, at least 99%, or 100% identical to the sequence of SEQ ID NO:68 and/or the VL domain comprises an amino acid sequence that is at least 90%, at least 95%, at least 99%, or 100% identical to the sequence of SEQ ID NO:69. In some embodiments, an anti-CD8 antibody of the present disclosure comprises 1, 2, or 3 heavy chain CDRs of antibody xhCD8v5 (e.g., as shown in Tables 1-3) and/or 1, 2, or 3 light chain CDRs of antibody xhCD8v5 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:68 and a VL domain comprising a CDR-L1, CDR-L2, and CDR-L3 from the sequence of SEQ ID NO:69.

In some embodiments, an anti-CD8 antibody of the present disclosure comprises a VH domain comprising a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:70 and/or the VL domain comprises an amino acid sequence that is at least 90%, at least 95%, at least 99%, or 100% identical to the sequence of SEQ ID NO:71. In some embodiments, an anti-CD8 antibody of the present disclosure comprises 1, 2, or 3 heavy chain CDRs of antibody xhCD8v6 (e.g., as shown in Tables 1-3) and/or 1, 2, or 3 light chain CDRs of antibody xhCD8v6 (e.g., as shown in Tables 1-3). In some embodiments, the antibody is human. In some embodiments, an anti-CD8 antibody of the present disclosure comprises a VH domain comprising a CDR-H1, CDR-H2, and CDR-H3 from the sequence of SEQ ID NO:70 and a VL domain comprising a CDR-L1, CDR-L2, and CDR-L3 from the sequence of SEQ ID NO:71.

In some embodiments, an anti-CD8 antibody of the present disclosure comprises a VH domain comprising a CDR-H1 comprising the amino acid sequence of SEQ ID NO:43, a CDR-H2 comprising the amino acid sequence of SEQ ID NO:44, and a CDR-H3 comprising the amino acid sequence of SEQ ID NO:45 and a VL domain comprising a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48. In some embodiments, the VH domain comprises an amino acid sequence that is at least 90%, at least 95%, at least 99%, or 100% identical to the sequence of SEQ ID NO:72 and/or the VL domain comprises an amino acid sequence that is at least 90%, at least 95%, at least 99%, or 100% identical to the sequence of SEQ ID NO:73. In some embodiments, an anti-CD8 antibody of the present disclosure comprises 1, 2, or 3 heavy chain CDRs of antibody xhCD8v7 (e.g., as shown in Tables 1-3) and/or 1, 2, or 3 light chain CDRs of antibody xhCD8v7 (e.g., as shown in Tables 1-3). In some embodiments, the antibody is human. In some embodiments, an anti-CD8 antibody of the present disclosure comprises a VH domain comprising a CDR-H1, CDR-H2, and CDR-H3 from the sequence of SEQ ID NO:72 and a VL domain comprising a CDR-L1, CDR-L2, and CDR-L3 from the sequence of SEQ ID NO:73.

In some embodiments, an anti-CD8 antibody of the present disclosure comprises a VH domain comprising a CDR-H1 comprising the amino acid sequence of $X_1X_2AIS$, wherein $X_1$ is S, K, G, N, R, D, T, or G, and wherein $X_2$ is Y, L, H, or F (SEQ ID NO:259), a CDR-H2 comprising the amino acid sequence of $X_1X_2X_3PX_4X_5X_6X_7X_8X_9YX_{10}QKFX_{11}G$, wherein $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, and $X_1$ is Q or T (SEQ ID NO:260), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:261) and a VL domain comprising a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:262), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:263), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:264). In some embodiments, the VH domain further comprises a FW-1 comprising the sequence QVQLVQS-GAEVKKPGSSVKVSCKASGGTFS (SEQ ID NO:274), a FW-2 comprising the sequence WVRQAPGQGLEWMG (SEQ ID NO:275), a FW-3 comprising the sequence RVTI-TADESTSTAYMELSSLRSEDTAVYYCAR (SEQ ID NO:276), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:225, a CDR-H2 comprising the amino acid sequence of SEQ ID NO:226, and a CDR-H3 comprising the amino acid sequence of SEQ ID NO:227 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:245 and/or the VL domain comprises an amino acid sequence that is at least 90%, at least 95%, at least 99%, or 100% identical to the sequence of SEQ ID NO:246. In some embodiments, an anti-CD8 antibody of the present disclosure comprises 1, 2, or 3 heavy chain CDRs of antibody xhCD8v9 (e.g., as shown in Tables 1-3) and/or 1, 2, or 3 light chain CDRs of antibody xhCD8v9

(e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:245 and a VL domain comprising a CDR-L1, CDR-L2, and CDR-L3 from the sequence of SEQ ID NO:246. In some embodiments, the VH domain further comprises a FW-1 comprising the sequence QVQLVQSGAEVKKPGSSVKVSCKASGGTFS (SEQ ID NO:274), a FW-2 comprising the sequence WVRQAPGQGLEWMG (SEQ ID NO:275), a FW-3 comprising the sequence RVTITADESTSTAYMELSSLRSEDTAVYYCAR (SEQ ID NO:276), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233 and a VL domain comprising a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236. In some embodiments, the VH domain comprises an amino acid sequence that is at least 90%, at least 95%, at least 99%, or 100% identical to the sequence of SEQ ID NO:251 and/or the VL domain comprises an amino acid sequence that is at least 90%, at least 95%, at least 99%, or 100% identical to the sequence of SEQ ID NO:252. In some embodiments, the VH domain comprises the amino acid sequence of SEQ ID NO:251; and the VL domain comprises the amino acid sequence of SEQ ID NO:252. In some embodiments, an anti-CD8 antibody of the present disclosure comprises 1, 2, or 3 heavy chain CDRs of antibody xhCD8v12 (e.g., as shown in Tables 1-3) and/or 1, 2, or 3 light chain CDRs of antibody xhCD8v12 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:251 and a VL domain comprising a CDR-L1, CDR-L2, and CDR-L3 from the sequence of SEQ ID NO:252. In some embodiments, the VH domain further comprises a FW-1 comprising the sequence QVQLVQSGAEVKKPGSSVKVSCKASGGTFS (SEQ ID NO:274), a FW-2 comprising the sequence WVRQAPGQGLEWMG (SEQ ID NO:275), a FW-3 comprising the sequence RVTITADESTSTAYMELSSLRSEDTAVYYCAR (SEQ ID NO:276), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain comprises an amino acid sequence that is at least 90%, at least 95%, at least 99%, or 100% identical to the sequence of SEQ ID NO:253 and/or the VL domain comprises an amino acid sequence that is at least 90%, at least 95%, at least 99%, or 100% identical to the sequence of SEQ ID NO:254. In some embodiments, an anti-CD8 antibody of the present disclosure comprises 1, 2, or 3 heavy chain CDRs of antibody xhCD8v13 (e.g., as shown in Tables 1-3) and/or 1, 2, or 3 light chain CDRs of antibody xhCD8v13 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:253 and a VL domain comprising a CDR-L1, CDR-L2, and CDR-L3 from the sequence of SEQ ID NO:254. In some embodiments, the VH domain further comprises a FW-1 comprising the sequence QVQLVQSGAEVKKPGSSVKVSCKASGGTFS (SEQ ID NO:274), a FW-2 comprising the sequence WVRQAPGQGLEWMG (SEQ ID NO:275), a FW-3 comprising the sequence RVTITADESTSTAYMELSSLRSEDTAVYYCAR (SEQ ID NO:276), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of $X_1YX_2MS$, wherein $X_1$ is S, D, E, A, or Q and $X_2$ is A, G, or T (SEQ ID NO:268), a CDR-H2 comprising the amino acid sequence of $DIX_1X_2X_3GX_4X_5TX_6YADSVKG$, wherein $X_1$ is T, N, S, Q, E, H, R, or A, $X_2$ is Y, W, F, or H, $X_3$ is A, S, Q, E, or T, $X_4$ is G or E, $X_5$ is S or I, and $X_6$ is A or G (SEQ ID NO:269), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:270) and a VL domain comprising a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42). In some embodiments, the VH domain further comprises a FW-1 comprising the sequence EVQLVESGGGLVQPGGSLRLSCAASGFTFS (SEQ ID NO:281), a FW-2 comprising the sequence WVRQAPGKGLEWVS (SEQ ID NO:282), a FW-3 comprising the sequence RFTISRDNAKNSLYLQMNSLRAEDTAVYYCAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:247 and/or the VL domain comprises an amino acid sequence that is at least 90%, at least 95%, at least 99%, or 100% identical to the sequence of SEQ ID NO:248. In some embodiments, an anti-CD8 antibody of the present disclosure comprises 1, 2, or 3 heavy chain CDRs of antibody xhCD8v10 (e.g., as shown in Tables 1-3) and/or 1, 2, or 3 light chain CDRs of antibody xhCD8v10 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:247 and a VL domain comprising a CDR-L1, CDR-L2, and CDR-L3 from the sequence of SEQ ID NO:248. In some embodiments, the VH domain further comprises a FW-1 comprising the sequence EVQLVESGGGLVQPGGSLRLSCAASGFTFS (SEQ ID NO:281), a FW-2 comprising the sequence WVRQAPGKGLEWVS (SEQ ID NO:282), a FW-3 comprising the sequence RFTISRDNAKNSLYLQMNSLRAEDTAVYYCAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:229, a CDR-H2 comprising the amino acid sequence of SEQ ID NO:230, and a CDR-H3 comprising the amino acid sequence of SEQ ID NO:231 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:249 and/or the VL domain comprises an amino acid sequence that is at least 90%, at least 95%, at least 99%, or 100% identical to the sequence of SEQ ID NO:250. In some embodiments, the VH domain comprises the amino acid sequence of SEQ ID NO:249; and the VL domain comprises the amino acid sequence of SEQ ID NO:250. In some embodiments, an anti-CD8 antibody of the present disclosure comprises 1, 2, or 3 heavy chain CDRs of antibody xhCD8v11 (e.g., as shown in Tables 1-3) and/or 1, 2, or 3 light chain CDRs of antibody xhCD8v11 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:249 and a VL domain comprising a CDR-L1, CDR-L2, and CDR-L3 from the sequence of SEQ ID NO:250. In some embodiments, the VH domain further comprises a FW-1 comprising the sequence EVQLVESGGGLVQPGGSLRLSCAASGFTFS (SEQ ID NO:281), a FW-2 comprising the sequence WVRQAPGKGLEWVS (SEQ ID NO:282), a FW-3 comprising the sequence RFTISRDNAKNSLYLQMNSLRAEDTAVYYCAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:255 and/or the VL domain comprises an amino acid sequence that is at least 90%, at least 95%, at least 99%, or 100% identical to the sequence of SEQ ID NO:256. In some embodiments, an anti-CD8 antibody of the present disclosure comprises 1, 2, or 3 heavy chain CDRs of antibody xhCD8v14 (e.g., as shown in Tables 1-3) and/or 1, 2, or 3 light chain CDRs of antibody xhCD8v14 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:255 and a VL domain comprising a CDR-L1, CDR-L2, and CDR-L3 from the sequence of SEQ ID NO:256. In some embodiments, the VH domain further comprises a FW-1 comprising the sequence EVQLVESGGGLVQPGGSLRLSCAASGFTFS (SEQ ID NO:281), a FW-2 comprising the sequence WVRQAPGKGLEWVS (SEQ ID NO:282), a FW-3 comprising the sequence RFTISRDNAKNSLYLQMNSLRAEDTAVYYCAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:229, a CDR-H2 comprising the amino acid sequence of SEQ ID NO:237, and a CDR-H3 comprising the amino acid sequence of SEQ ID NO:231 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain comprises an amino acid sequence that is at least 90%, at least 95%, at least 99%, or 100% identical to the sequence of SEQ ID NO:257 and/or the VL domain comprises an amino acid sequence that is at least 90%, at least 95%, at least 99%, or 100% identical to the sequence of SEQ ID NO:258. In some embodiments, an anti-CD8 antibody of the present disclosure comprises 1, 2, or 3 heavy chain CDRs of antibody xhCD8v15 (e.g., as shown in Tables 1-3) and/or 1, 2, or 3 light chain CDRs of antibody xhCD8v15 (e.g., as shown in Tables 1-3). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:257 and a VL domain comprising a CDR-L1, CDR-L2, and CDR-L3 from the sequence of SEQ ID NO:258. In some embodiments, the VH domain further comprises a FW-1 comprising the sequence EVQLVESGGGLVQPGGSLRLSCAASGFTFS (SEQ ID NO:281), a FW-2 comprising the sequence WVRQAPGKGLEWVS (SEQ ID NO:282), a FW-3 comprising the sequence RFTISRDNAKNSLYLQMNSLRAEDTAVYYCAR (SEQ ID NO:283), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:49, a CDR-H2 comprising the amino acid sequence of SEQ ID NO:50, and a CDR-H3 comprising the amino acid sequence of SEQ ID NO:3 and a VL domain comprising a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, an anti-CD8 antibody of the present disclosure comprises a VH domain comprising a CDR-H1 comprising the amino acid sequence of SEQ ID NO:51, a CDR-H2 comprising the amino acid sequence of SEQ ID NO:52, and a CDR-H3 comprising the amino acid sequence of SEQ ID NO:15 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, an anti-CD8 antibody of the present disclosure comprises a VH domain comprising a CDR-H1 comprising the amino acid sequence of SEQ ID NO:53, a CDR-H2 comprising the amino acid sequence of SEQ ID NO:52, and a CDR-H3 comprising the amino acid sequence of SEQ ID NO:21 and a VL domain comprising a CDR-L1 comprising the amino acid sequence of SEQ ID NO:22, a CDR-L2 comprising the amino acid sequence of SEQ ID NO:23, and a CDR-L3 comprising the amino acid sequence of SEQ ID NO:24. In some embodiments, an anti-CD8 antibody of the present disclosure comprises a VH domain comprising a CDR-H1 comprising the amino acid sequence of SEQ ID NO:49, a CDR-H2 comprising the amino acid sequence of SEQ ID NO:52, and a CDR-H3 comprising the amino acid sequence of SEQ ID NO:27 and a VL domain comprising a CDR-L1 comprising the amino acid sequence of SEQ ID NO:28, a CDR-L2 comprising the amino acid sequence of SEQ ID NO:29, and a CDR-L3 comprising the amino acid sequence of SEQ ID NO:30. In some embodiments, an anti-CD8 antibody of the present disclosure comprises a VH domain comprising a CDR-H1 comprising the amino acid sequence of SEQ ID NO:54, a CDR-H2 comprising the amino acid sequence of SEQ ID NO:52, and a CDR-H3 comprising the amino acid sequence of SEQ ID NO:33 and a VL domain comprising a CDR-L1 comprising the amino acid sequence of SEQ ID NO:34, a CDR-L2 comprising the amino acid sequence of SEQ ID NO:35, and a CDR-L3 comprising the amino acid sequence of SEQ ID NO:36. In some embodiments, an anti-CD8 antibody of the present disclosure comprises a VH domain comprising a CDR-H1 comprising the amino acid sequence of SEQ ID NO:55, a CDR-H2 comprising the amino acid sequence of SEQ ID NO:56, and a CDR-H3 comprising the amino acid sequence of SEQ ID NO:39 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, an anti-CD8 antibody of the present disclosure comprises a VH domain comprising a CDR-H1 comprising the amino acid sequence of SEQ ID NO:55, a CDR-H2 comprising the amino acid sequence of SEQ ID NO:57, and a CDR-H3 comprising the amino acid sequence of SEQ ID NO:45 and a VL domain comprising a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48. In some embodiments, an anti-CD8 antibody of the present disclosure comprises a VH domain comprising a CDR-H1 comprising the amino acid sequence of SEQ ID NO:183, a CDR-H2 comprising the amino acid sequence of SEQ ID NO:184, and a CDR-H3 comprising the amino acid sequence of SEQ ID NO:179 and a VL domain comprising a CDR-L1 comprising the amino acid sequence of SEQ ID NO:180, a CDR-L2 comprising the amino acid sequence of SEQ ID NO:181, and a CDR-L3 comprising the amino acid sequence of SEQ ID NO:182.

In some embodiments, an anti-CD8 antibody of the present disclosure comprises a VH domain comprising a CDR-H1 comprising the amino acid sequence of $GX_1X_2FX_3X_4X_5$, wherein $X_1$ is G, Y, S, or A, $X_2$ is T, S, G, R, N, or H, $X_3$ is S, T, R, H, Y, G, or P, $X_4$ is S, K, G, N, R, D, T, or G, and $X_5$ is Y, L, H, or F (SEQ ID NO:265), a CDR-H2 comprising the amino acid sequence of $X_1PX_2X_3X_4X_5$, wherein $X_1$ is I, N, or M, $X_2$ is G, N, H, S, R, I, or A, $X_3$ is A, N, H, S, T, F, or Y, $X_4$ is A, D, or G, and $X_5$ is T, E, K, V, Q, or A (SEQ ID NO:266), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:267) and a VL domain comprising a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:262), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:263), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:264). In some embodiments, the VH domain further comprises a FW-1 comprising the sequence QVQLVQSGAEVKKPGSSVKVSCKAS (SEQ ID NO:278), a FW-2 comprising the sequence AISWVRQAPGQGLEWMGGI (SEQ ID NO:279), a FW-3 comprising the sequence ANYAQKFQGRVTITADESTSTAYMELSSLRSEDTAVYYCAR (SEQ ID NO:280), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:238, a CDR-H2 comprising the amino acid sequence of SEQ ID NO:239, and a CDR-H3 comprising the amino acid sequence of SEQ ID NO:233 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain further comprises a FW-1 comprising the sequence QVQLVQSGAEVKKPGSSVKVSCKAS (SEQ ID NO:278), a FW-2 comprising the sequence AISWVRQAPGQGLEWMGGI (SEQ ID NO:279), a FW-3 comprising the sequence ANYAQKFQGRVTITADESTSTAYMELSSLRSEDTAVYYCAR (SEQ ID NO:280), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233 and a VL domain comprising a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236. In some embodiments, the VH domain further comprises a FW-1 comprising the sequence QVQLVQSGAEVKKPGSSVKVSCKAS (SEQ ID NO:278), a FW-2 comprising the sequence AISWVRQAPGQGLEWMGGI (SEQ ID NO:279), a FW-3 comprising the sequence ANYAQKFQGRVTITADESTSTAYMELSSLRSEDTAVYYCAR (SEQ ID NO:280), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233 and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:228. In some embodiments, the VH domain further comprises a FW-1 comprising the sequence QVQLVQSGAEVKKPGSSVKVSCKAS (SEQ ID NO:278), a FW-2 comprising the sequence AISWVRQAPGQGLEWMGGI (SEQ ID NO:279), a FW-3 comprising the sequence ANYAQKFQGRVTITADESTSTAYMELSSLRSEDTAVYYCAR (SEQ ID NO:280), and/or a FW-4 comprising the sequence WGQGTLVTVSS (SEQ ID NO:277). In some embodiments, the VL domain further comprises a FW-1 comprising the sequence DIQMTQSPSSLSASVGDRVTITC (SEQ ID NO:289), a FW-2 comprising the sequence WYQQKPGKAPKLLIY (SEQ ID NO:290), a FW-3 comprising the sequence GVPSRFSGSGSGTDFTLTISSLQPEDFATYYC (SEQ ID NO:291), and/or a FW-4 comprising the sequence FGGGTKVEIK (SEQ ID NO:292).

In some embodiments, an anti-CD8 antibody of the present disclosure comprises a VH domain comprising a CDR-H1 comprising the amino acid sequence of $GFTFX_1X_2Y$, wherein $X_1$ is S, D, E, Q, S, or A and $X_2$ is S, D, E, A, or Q (SEQ ID NO:271), a CDR-H2 comprising the amino acid sequence of $X_1X_2X_3GX_4X_5$, wherein $X_1$ is T, N, S, Q, E, H, R or A, $X_2$ is Y, W, F, or H, $X_3$ is A, S, Q, E, or T, $X_4$ is G or E, and $X_5$ is S or I (SEQ ID NO:272), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:273) and a VL domain comprising a CDR-L1 comprising the amino acid sequence of RASQSVSSNLA (SEQ ID NO:40), a CDR-L2 comprising the amino acid sequence of GASSRAT (SEQ ID NO:41), and a CDR-L3 comprising the amino acid sequence of QQYGSSPPVT (SEQ ID NO:42). In some embodiments, the VH domain further comprises a FW-1 comprising the sequence EVQLVESGGGLVQPGGSLRLSCAAS (SEQ ID NO:286), a FW-2 comprising the sequence AMSWVRQAPGKGLEWVSDI (SEQ ID NO:287), a FW-3 comprising the sequence TAYADSVKGRFTISRDNAKNSLYLQMNSLRAEDTAVYYCAR (SEQ ID NO:288), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:240, a CDR-H2 comprising the amino acid sequence of SEQ ID NO:241, and a CDR-H3 comprising the amino acid sequence of SEQ ID NO:242 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain further comprises a FW-1 comprising the sequence EVQLVESGGGLVQPGGSLRLSCAAS (SEQ ID NO:286), a FW-2 comprising the sequence AMSWVRQAPGKGLEWVSDI (SEQ ID NO:287), a FW-3 comprising the sequence TAYADSVKGRFTISRDNAKNSLYLQMNSLRAEDTAVYYCAR (SEQ ID NO:288), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296).

In some embodiments, an anti-CD8 antibody of the present disclosure comprises a VH domain comprising a CDR-H1 comprising the amino acid sequence of SEQ ID NO:240, a CDR-H2 comprising the amino acid sequence of SEQ ID NO:244, and a CDR-H3 comprising the amino acid sequence of SEQ ID NO:242 and a VL domain comprising a CDR-L1 comprising the amino acid sequence of SEQ ID NO:40, a CDR-L2 comprising the amino acid sequence of SEQ ID NO:41, and a CDR-L3 comprising the amino acid sequence of SEQ ID NO:42. In some embodiments, the VH domain further comprises a FW-1 comprising the sequence EVQLVESGGGLVQPGGSLRLSCAAS (SEQ ID NO:286), a FW-2 comprising the sequence AMSWVRQAPGKGLEWVSDI (SEQ ID NO:287), a FW-3 comprising the sequence TAYADSVKGRFTISRDNAKNSLYLQMNSLRAEDTAVYYCAR (SEQ ID NO:288), and/or a FW-4 comprising the sequence WGQGTMVTVSS (SEQ ID NO:284) or WGQGTLVTVSS (SEQ ID NO:285). In some embodiments, the VL domain further comprises a FW-1 comprising the sequence EIVLTQSPGTLSLSPGERATLSC (SEQ ID NO:293), a FW-2 comprising the sequence WYQQKPGQAPRLLIY (SEQ ID NO:294), a FW-3 comprising the sequence GIPDRFSGSGSGTDFTLTISRLEPEDFAVYYC (SEQ ID NO:295), and/or a FW-4 comprising the sequence FGQGTKVEIK (SEQ ID NO:296). In some embodiments, the present disclosure provides an anti-CD8 antibody comprising a VH domain comprising CDR-H1, CDR-H2, and CDR-H3 sequences of a single antibody listed in Table 1 and a VL domain comprising CDR-L1, CDR-L2, and CDR-L3 sequences of the single antibody listed in Table 1. For example, the anti-CD8 antibody comprises the six CDRs of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, xhCD8v15, V9 family, or V11 family shown in Table 1. In some embodiments, the present disclosure provides an anti-CD8 antibody comprising a VH domain comprising CDR-H1, CDR-H2, and CDR-H3 sequences of a single antibody listed in Table 2 and a VL domain comprising CDR-L1, CDR-L2, and CDR-L3 sequences of the single antibody listed in Table 2. For example, the anti-CD8 antibody comprises the six CDRs of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, xhCD8v15, V9 family, or V11 family shown in Table 2. In some embodiments, the present disclosure provides a fusion protein comprising an anti-CD8 antibody comprising a VH domain comprising CDR-H1, CDR-H2, and CDR-H3 sequences of the single antibody listed in Table 1 and a VL domain comprising CDR-L1, CDR-L2, and CDR-L3 sequences of a single antibody listed in Table 1. For example, the anti-CD8 antibody of the fusion protein comprises the six CDRs of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, xhCD8v15, V9 family, or V11 family shown in Table 1. In some embodiments, the present disclosure provides a fusion protein comprising an anti-CD8 antibody comprising a VH domain comprising CDR-H1, CDR-H2, and CDR-H3 sequences of a single antibody listed in Table 2 and a VL domain comprising CDR-L1, CDR-L2, and CDR-L3 sequences of the single antibody listed in Table 2. For example, the anti-CD8 antibody of the fusion protein comprises the six CDRs of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, xhCD8v15, V9 family, or V11 family shown in Table 2. In some embodiments, the present disclosure provides an anti-CD8 antibody comprising a VH domain comprising CDR-H1, CDR-H2, and CDR-H3 sequences of a VH domain listed in Table 3 and a VL domain comprising CDR-L1, CDR-L2, and CDR-L3 sequences of a VL domain listed in Table 3 (in some embodiments, the VH and VL domains are from the same single antibody listed in Table 3). For example, the anti-CD8 antibody comprises the VH and VL of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, or xhCD8v15 shown in Table 3. In some embodiments, the present disclosure provides a fusion protein comprising an anti-CD8 antibody comprising a VH domain comprising CDR-H1, CDR-H2, and CDR-H3 sequences of a VH domain listed in Table 3 and a VL domain comprising CDR-L1, CDR-L2, and CDR-L3 sequences of a VL domain listed in Table 3 (in some embodiments, the VH and VL domains are from the same single antibody listed in Table 3). In some embodiments, the present disclosure provides an anti-CD8 antibody comprising a VH domain sequence and a VL domain sequence for a single antibody as listed in Table 3. In some embodiments, the present disclosure provides a fusion protein comprising an anti-CD8 antibody comprising a VH domain sequence and a VL domain sequence for a single antibody as listed in Table 3. For example, the anti-CD8 antibody of the fusion protein comprises the VH and VL of antibody xhCD8v1, xhCD8v1.1, xhCD8v2, xhCD8v3, xhCD8v4, xhCD8v5, xhCD8v6, xhCD8v7, xhCD8v8, xhCD8v9, xhCD8v10, xhCD8v11, xhCD8v12, xhCD8v13, xhCD8v14, or xhCD8v15 shown in Table 3.

TABLE 1

Anti-CD8 antibody CDRs (Kabat)

| Name | CDR-H1 | CDR-H2 | CDR-H3 | CDR-L1 | CDR-L2 | CDR-L3 |
|---|---|---|---|---|---|---|
| xhCD8v1 | KYTMH (SEQ ID NO: 1) | HFNPNNDETKYNQKFTG (SEQ ID NO: 2) | DGLGLRLFAD (SEQ ID NO: 3) | GASENIYGALN (SEQ ID NO: 4) | GATNLAD (SEQ ID NO: 5) | QNILDTPWT (SEQ ID NO: 6) |
| xhCD8v1.1 | KYAIS (SEQ ID NO: 7) | HFNPNNDETKYNQKFQG (SEQ ID NO: 8) | DGLGLRLFAD (SEQ ID NO: 9) | RASENIYGALN (SEQ ID NO: 10) | GATNLAD (SEQ ID NO: 11) | QNILDTPWT (SEQ ID NO: 12) |
| xhCD8v2 | NFAIS (SEQ ID NO: 13) | GIIPGHAKANYAQKFQG (SEQ ID NO: 14) | DGLGIRLFAD (SEQ ID NO: 15) | RASQEIYGALN (SEQ ID NO: 16) | GATNLQS (SEQ ID NO: 17) | QDIYDAPWT (SEQ ID NO: 18) |
| xhCD8v3 | KFAIS (SEQ ID NO: 19) | GIIPGHAKANYAQKFQG (SEQ ID NO: 20) | DGLGIRLFAD (SEQ ID NO: 21) | RASQEIYGALN (SEQ ID NO: 22) | GATNLQS (SEQ ID NO: 23) | QDIYDAPWT (SEQ ID NO: 24) |
| xhCD8v4 | KYAIS (SEQ ID NO: 25) | GIIPGHAKANYAQKFQG (SEQ ID NO: 26) | DGLGIRLFAD (SEQ ID NO: 27) | RASQKIYGALN (SEQ ID NO: 28) | GATNLQS (SEQ ID NO: 29) | QNTYDTPWT (SEQ ID NO: 30) |
| xhCD8v5 | GHAIS (SEQ ID NO: 31) | GIIPGHAKANYAQKFQG (SEQ ID NO: 32) | DGLGIRLFAD (SEQ ID NO: 33) | RASQKIYGALN (SEQ ID NO: 34) | GATNLQS (SEQ ID NO: 35) | QNTYDTPWT (SEQ ID NO: 36) |
| xhCD8v6 | DYGMS (SEQ ID NO: 37) | DINWSGEITAYADSVKG (SEQ ID NO: 38) | SNSYRWDDALDI (SEQ ID NO: 39) | RASQSVSSNLA (SEQ ID NO: 40) | GASSRAT (SEQ ID NO: 41) | QQYGSSPPVT (SEQ ID NO: 42) |
| xhCD8v7 | DYAMH (SEQ ID NO: 43) | VISYDGSNKYYADSVKG (SEQ ID NO: 44) | DRIGWYDYDAFDI (SEQ ID NO: 45) | RASHSVGSNLA (SEQ ID NO: 46) | DASNRAT (SEQ ID NO: 47) | QQRSNWPPT (SEQ ID NO: 48) |
| xhCD8v8 | SYWMN (SEQ ID NO: 177) | QIYPGDGDTNYNGKFKG (SEQ ID NO: 178) | SGAAFSSYYAMDY (SEQ ID NO: 179) | RASENIYSNLA (SEQ ID NO: 180) | AATNLAD (SEQ ID NO: 181) | QHFWGTPWT (SEQ ID NO: 182) |
| xhCD8v9 | SYAIS (SEQ ID NO: 225) | GIIPGAATANYAQKFQG (SEQ ID NO: 226) | DAAGIRLFAD (SEQ ID NO: 227) | RASQEIYGALN (SEQ ID NO: 16) | GATNLQS (SEQ ID NO: 17) | QSTYDAPWT (SEQ ID NO: 228) |
| xhCD8v10 | SYAMS (SEQ ID NO: 229) | DITYAGGSTAYADSVKG (SEQ ID NO: 230) | SNAYAWDDALDI (SEQ ID NO: 231) | RASQSVSSNLA (SEQ ID NO: 40) | GASSRAT (SEQ ID NO: 41) | QQYGSSPPVT (SEQ ID NO: 42) |
| xhCD8v11 | SYAMS (SEQ ID NO: 229) | DITYAGGSTAYADSVKG (SEQ ID NO: 230) | SNAYAWDDALDI (SEQ ID NO: 231) | RASQSVSSNLA (SEQ ID NO: 40) | GASSRAT (SEQ ID NO: 41) | QQYGSSPPVT (SEQ ID NO: 42) |
| xhCD8v12 | SYAIS (SEQ ID NO: 225) | GIIPGYATANYAQKFQG (SEQ ID NO: 232) | DAAGIRLFAD (SEQ ID NO: 233) | RASQSIYGALN (SEQ ID NO: 234) | GASNLQS (SEQ ID NO: 235) | QSTYTAPWT (SEQ ID NO: 236) |

TABLE 1-continued

Anti-CD8 antibody CDRs (Kabat)

| Name | CDR-H1 | CDR-H2 | CDR-H3 | CDR-L1 | CDR-L2 | CDR-L3 |
|---|---|---|---|---|---|---|
| xhCD8v13 | SYAIS (SEQ ID NO: 225) | GIIPGYAT ANYAQKF QG (SEQ ID NO: 232) | DAAGIRLF AD (SEQ ID NO: 233) | RASQEIYG ALN (SEQ ID NO: 16) | GATNLQS (SEQ ID NO: 17) | QSTYDAP WT (SEQ ID NO: 228) |
| xhCD8v14 | SYAMS (SEQ ID NO: 229) | DISYAGGS TAYADSV KG (SEQ ID NO: 237) | SNAYAW DDALDI (SEQ ID NO: 231) | RASQSVSS NLA (SEQ ID NO: 40) | GASSRAT (SEQ ID NO: 41) | QQYGSSP PVT (SEQ ID NO: 42) |
| xhCD8v15 | SYAMS (SEQ ID NO: 229) | DISYAGGS TAYADSV KG (SEQ ID NO: 237) | SNAYAW DDALDI (SEQ ID NO: 231) | RASQSVSS NLA (SEQ ID NO: 40) | GASSRAT (SEQ ID NO: 41) | QQYGSSP PVT (SEQ ID NO: 42) |
| V9 family | $X_1X_2$AIS $X_1$ is S, K, G, N, R, D, T, or G $X_2$ is Y, L, H, or F (SEQ ID NO: 259) | $X_1X_2X_3$P$X_4$ $X_5X_6X_7X_8X_9$ Y$X_{10}$QKF $X_{11}$G $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, $X_{11}$ is Q or T (SEQ ID NO: 260) | $X_1X_2X_3$G$X_4$ $X_5$LF$X_6X_7$ $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, $X_7$ is D, E, A, or S (SEQ ID NO: 261) | $X_1X_2$S$X_3X_4$I $X_5$G$X_6$LN $X_1$ is R or G, $X_2$ is A or T, $X_3$ is Q or E, $X_4$ is E, N, T, S, A, K, D, G, R, or Q, $X_5$ is Y or S, $X_6$ is A or V (SEQ ID NO: 262) | G$X_1X_2X_3$L $X_4X_5$ $X_2$ is A or S, $X_2$ is T, S, E, Q, or D, $X_3$ is N, R, A, E, or H, $X_4$ is Q or A, $X_5$ is S or D (SEQ ID NO: 263) | Q$X_1X_2X_3X_4$ $X_5$PWT $X_1$ is S, N, D, Q, A, or E, $X_2$ is T, I, or S, $X_3$ is Y, L, or F, $X_4$ is D, G, T, E, Q, A, or Y, $X_5$ is A, T, R, S, K, or Y (SEQ ID NO: 264) |
| V11 family | $X_1$Y$X_2$MS $X_1$ is S, D, E, A, or Q $X_2$ is A, G, or T (SEQ ID NO: 268) | DI$X_1X_2X_3$G $X_4X_5$T$X_6$Y ADSVKG $X_1$ is T, N, S, Q, E, H, R, or A, $X_2$ is Y, W, F, or H, $X_3$ is A, S, Q, E, or T, $X_4$ is G or E, $X_5$ is S or I, $X_6$ is A or G (SEQ ID NO: 269) | $X_1X_2X_3$Y$X_4$ W$X_5X_6$A$X_7$ D$X_8$ $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, $X_8$ is I, Y, or V (SEQ ID NO: 270) | RASQSVSS NLA (SEQ ID NO: 40) | GASSRAT (SEQ ID NO: 41) | QQYGSSP PVT (SEQ ID NO: 42) |

TABLE 2

Anti-CD8 antibody CDRs (Chothia)

| Name | CDR-H1 | CDR-H2 | CDR-H3 | CDR-L1 | CDR-L2 | CDR-L3 |
|---|---|---|---|---|---|---|
| xhCD8v1 | GYTFTKY (SEQ ID NO: 49) | NPNNDE (SEQ ID NO: 50) | DGLGLRL FAD (SEQ ID NO: 3) | GASENIY GALN (SEQ ID NO: 4) | GATNLAD (SEQ ID NO: 5) | QNILDTP WT (SEQ ID NO: 6) |
| xhCD8v1.1 | GYTFTKY (SEQ ID NO: 49) | NPNNDE (SEQ ID NO: 50) | DGLGLRL FAD (SEQ ID NO: 9) | RASENIYG ALN (SEQ ID NO: 10) | GATNLAD (SEQ ID NO: 11) | QNILDTP WT (SEQ ID NO: 12) |
| xhCD8v2 | GYRFHNF (SEQ ID NO: 51) | IPGHAK (SEQ ID NO: 52) | DGLGIRLF AD (SEQ ID NO: 15) | RASQEIYG ALN (SEQ ID NO: 16) | GATNLQS (SEQ ID NO: 17) | QDIYDAP WT (SEQ ID NO: 18) |
| xhCD8v3 | GSRFYKF (SEQ ID NO: 53) | IPGHAK (SEQ ID NO: 52) | DGLGIRLF AD (SEQ ID NO: 21) | RASQEIYG ALN (SEQ ID NO: 22) | GATNLQS (SEQ ID NO: 23) | QDIYDAP WT (SEQ ID NO: 24) |
| xhCD8v4 | GYTFTKY (SEQ ID NO: 49) | IPGHAK (SEQ ID NO: 52) | DGLGIRLF AD (SEQ ID NO: 27) | RASQKIY GALN (SEQ ID NO: 28) | GATNLQS (SEQ ID NO: 29) | QNTYDTP WT (SEQ ID NO: 30) |
| xhCD8v5 | GSGFRGH (SEQ ID NO: 54) | IPGHAK (SEQ ID NO: 52) | DGLGIRLF AD (SEQ ID NO: 33) | RASQKIY GALN (SEQ ID NO: 34) | GATNLQS (SEQ ID NO: 35) | QNTYDTP WT (SEQ ID NO: 36) |
| xhCD8v6 | GFTFDDY (SEQ ID NO: 55) | NWSGEI (SEQ ID NO: 56) | SNSYRWD DALDI (SEQ ID NO: 39) | RASQSVSS NLA (SEQ ID NO: 40) | GASSRAT (SEQ ID NO: 41) | QQYGSSP PVT (SEQ ID NO: 42) |
| xhCD8v7 | GFTFDDY (SEQ ID NO: 55) | SYDGSN (SEQ ID NO: 57) | DRIGWYD YDAFDI (SEQ ID NO: 45) | RASHSVG SNLA (SEQ ID NO: 46) | DASNRAT (SEQ ID NO: 47) | QQRSNWP PT (SEQ ID NO: 48) |
| xhCD8v8 | GYAFSSY (SEQ ID NO: 183) | YPGDGD (SEQ ID NO: 184) | SGAAFSS YYAMDY (SEQ ID NO: 179) | RASENIYS NLA (SEQ ID NO: 180) | AATNLAD (SEQ ID NO: 181) | QHFWGTP WT (SEQ ID NO: 182) |
| xhCD8v9 | GGTFSSY (SEQ ID NO: 238) | IPGAAT (SEQ ID NO: 239) | DAAGIRLF AD (SEQ ID NO: 233) | RASQEIYG ALN (SEQ ID NO: 16) | GATNLQS (SEQ ID NO: 17) | QSTYDAP WT (SEQ ID NO: 228) |
| xhCD8v10 | GFTFSSY (SEQ ID NO: 240) | TYAGGS (SEQ ID NO: 241) | SNAYAW DDALDI (SEQ ID NO: 242) | RASQSVSS NLA (SEQ ID NO: 40) | GASSRAT (SEQ ID NO: 41) | QQYGSSP PVT (SEQ ID NO: 42) |
| xhCD8v11 | GFTFSSY (SEQ ID NO: 240) | TYAGGS (SEQ ID NO: 241) | SNAYAW DDALDI (SEQ ID NO: 242) | RASQSVSS NLA (SEQ ID NO: 40) | GASSRAT (SEQ ID NO: 41) | QQYGSSP PVT (SEQ ID NO: 42) |
| xhCD8v12 | GGTFSSY (SEQ ID NO: 238) | IPGYAT (SEQ ID NO: 243) | DAAGIRLF AD (SEQ ID NO: 233) | RASQSIYG ALN (SEQ ID NO: 234) | GASNLQS (SEQ ID NO: 235) | QSTYTAP WT (SEQ ID NO: 236) |
| xhCD8v13 | GGTFSSY (SEQ ID NO: 238) | IPGYAT (SEQ ID NO: 243) | DAAGIRLF AD (SEQ ID NO: 233) | RASQEIYG ALN (SEQ ID NO: 16) | GATNLQS (SEQ ID NO: 17) | QSTYDAP WT (SEQ ID NO: 228) |
| xhCD8v14 | GFTFSSY (SEQ ID NO: 240) | SYAGGS (SEQ ID NO: 244) | SNAYAW DDALDI (SEQ ID NO: 242) | RASQSVSS NLA (SEQ ID NO: 40) | GASSRAT (SEQ ID NO: 41) | QQYGSSP PVT (SEQ ID NO: 42) |

TABLE 2-continued

Anti-CD8 antibody CDRs (Chothia)

| Name | CDR-H1 | CDR-H2 | CDR-H3 | CDR-L1 | CDR-L2 | CDR-L3 |
|---|---|---|---|---|---|---|
| xhCD8v15 | GFTFSSY (SEQ ID NO: 240) | SYAGGS (SEQ ID NO: 244) | SNAYAW DDALDI (SEQ ID NO: 242) | RASQSVSS NLA (SEQ ID NO: 40) | GASSRAT (SEQ ID NO: 41) | QQYGSSP PVT (SEQ ID NO: 42) |
| V9 family | GX$_1$X$_2$FX$_3$ X$_4$X$_5$ X$_1$ is G, Y, S, or A, X$_2$ is T, S, G, R, N, or H, X$_3$ is S, T, R, H, Y, G, or P, X$_4$ is S, K, G, N, R, D, T, or G, X$_5$ is Y, L, H, or F (SEQ ID NO: 265) | X$_1$PX$_2$X$_3$X$_4$ X$_5$ X$_1$ is I, N, or M, X$_2$ is G, N, H, S, R, I, or A, X$_3$ is A, N, H, S, T, F, or Y, X$_4$ is A, D, or G, X$_5$ is T, E, K, V, Q, or A (SEQ ID NO: 266) | X$_1$X$_2$X$_3$GX$_4$ X$_5$LFX$_6$X$_7$ X$_1$ is D or A, X$_2$ is A, G, E, R, Y, K, N, Q, L, or F, X$_3$ is A, L, P, or Y, X$_4$ is I or L, X$_5$ is R, A, Q, or S, X$_6$ is A or D, X$_7$ is D, E, A, or S (SEQ ID NO: 267) | X$_1$X$_2$SX$_3$X$_4$I X$_5$GX$_6$LN X$_1$ is R or G, X$_2$ is A or T, X$_3$ is Q or E, X$_4$ is E, N, T, S, A, K, D, G, R, or Q, X$_5$ is Y or S, X$_6$ is A or V (SEQ ID NO: 262) | GX$_1$X$_2$X$_3$L X$_4$X$_5$ X$_1$ is A or S, X$_2$ is T, S, E, Q, or D, X$_3$ is N, R, A, E, or H, X$_4$ is Q or A, X$_5$ is S or D (SEQ ID NO: 263) | QX$_1$X$_2$X$_3$X$_4$ X$_5$PWT X$_1$ is S, N, D, Q, A, or E, X$_2$ is T, I, or S, X$_3$ is Y, L, or F, X$_4$ is D, G, T, E, Q, A, or Y, X$_5$ is A, T, R, S, K, or Y (SEQ ID NO: 264) |
| V11 family | GFTFX$_1$X$_2$ Y X$_1$ is S, D, E, Q, S, or A X$_2$ is S, D, E, A, or Q (SEQ ID NO: 271) | X$_1$X$_2$X$_3$GX$_4$ X$_5$ X$_1$ is T, N, S, Q, E, H, R or A, X$_2$ is Y, W, F, or H, X$_3$ is A, S, Q, E, or T, X$_4$ is G or E, X$_5$ is S or I (SEQ ID NO: 272) | X$_1$X$_2$X$_3$YX$_4$ WX$_5$X$_6$AX$_7$ DX$_8$ X$_1$ is S or A, X$_2$ is N, H, A, D, L, Q, Y, or R, X$_3$ is A, N, S, or G, X$_4$ is A, V, R, E, or S, X$_5$ is D or S, X$_6$ is D, N, Q, E, S, T, or L, X$_7$ is L, F, or M, X$_8$ is I, Y, or V (SEQ ID NO: 273) | RASQSVSS NLA (SEQ ID NO: 40) | GASSRAT (SEQ ID NO: 41) | QQYGSSP PVT (SEQ ID NO: 42) |

TABLE 3

Anti-CD8 antibody variable domain sequences

| Name | VH | VL |
|---|---|---|
| xhCD8v1 | QVHLQQSGPELVKPGASVKMSCKTS GYTFTKYTMHWVKQGHEESLEWIG HFNPNNDETKYNQKFTGKATLTVDK SSTTAYMELRSLTSDDSALYYCARD GLGLRLFADWGQGTLITVSA (SEQ ID NO: 58) | DIQMTQSPASLSASVGETVTITCGAS ENIYGALNWYQRKQGKSPQLLIFGA TNLADGVSSRFSGSGSDRQYSLKISS LHPDDVATYYCQNILDTPWTFGGGT KLEIK (SEQ ID NO: 59) |
| xhCD8v1.1 | QVQLVQSGAEVKKPGSSVKVSCKAS GYTFTKYAISWVRQAPGQGLEWMG HFNPNNDETKYNQKFQGRVTITADE STSTAYMELSSLRSEDTAVYYCARD GLGLRLFADWGQGTLVTVSS (SEQ ID NO: 60) | DIQMTQSPSSLSASVGDRVTITCRASE NIYGALNWYQQKPGKAPKLLIYGAT NLADGVPSRFSGSGSGTDFTLTISSLQ PEDFATYYCQNILDTPWTFGGGTKLE IK (SEQ ID NO: 61) |
| xhCD8v2 | QVQLVQSGAEVKKPGSSVKVSCKAS GYRFHNFAISWVRQAPGQGLEWMG GIIPGHAKANYAQKFQGRVTITADES TSTAYMELSSLRSEDTAVYYCARDG LGIRLFADWGQGTLVTVSS (SEQ ID NO: 62) | DIQMTQSPSSLSASVGDRVTITCRAS QEIYGALNWYQQKPGKAPKLLIYGA TNLQSGVPSRFSGSGSGTDFTLTISSL QPEDFATYYCQDIYDAPWTFGGGTK VEIK (SEQ ID NO: 63) |

TABLE 3-continued

Anti-CD8 antibody variable domain sequences

| Name | VH | VL |
|------|-----|-----|
| xhCD8v3 | QVQLVQSGAEVKKPGSSVKVSCKAS GSRFYKFAISWVRQAPGQGLEWMG GIIPGHAKANYAQKFQGRVTITADES TSTAYMELSSLRSEDTAVYYCARDG LGIRLFADWGQGTLVTVSS (SEQ ID NO: 64) | DIQMTQSPSSLSASVGDRVTITCRAS QEIYGALNWYQQKPGKAPKLLIYGA TNLQSGVPSRFSGSGSGTDFTLTISSL QPEDFATYYCQDIYDAPWTFGGGTK VEIK (SEQ ID NO: 65) |
| xhCD8v4 | QVQLVQSGAEVKKPGSSVKVSCKAS GYTFTKYAISWVRQAPGQGLEWMG GIIPGHAKANYAQKFQGRVTITADES TSTAYMELSSLRSEDTAVYYCARDG LGIRLFADWGQGTLVTVSS (SEQ ID NO: 66) | DIQMTQSPSSLSASVGDRVTITCRAS QKIYGALNWYQQKPGKAPKLLIYGA TNLQSGVPSRFSGSGSGTDFTLTISSL QPEDFATYYCQNTYDTPWTFGGGTK VEIK (SEQ ID NO: 67) |
| xhCD8v5 | QVQLVQSGAEVKKPGSSVKVSCKAS GSGFRGHAISWVRQAPGQGLEWMG GIIPGHAKANYAQKFQGRVTITADES TSTAYMELSSLRSEDTAVYYCARDG LGIRLFADWGQGTLVTVSS (SEQ ID NO: 68) | DIQMTQSPSSLSASVGDRVTITCRAS QKIYGALNWYQQKPGKAPKLLIYGA TNLQSGVPSRFSGSGSGTDFTLTISSL QPEDFATYYCQNTYDTPWTFGGGTK VEIK (SEQ ID NO: 69) |
| xhCD8v6 | EVQLVESGGGAVRPGGSLRLSCAAS GFTFDDYGMSWVRQAPGKGLEWVS DINWSGEITAYADSVKGRFTISRDNA KNSLYLQMNSLRAEDTAVYYCARSN SYRWDDALDIWGQGTMVTVSS (SEQ ID NO: 70) | EIVLTQSPATLSVSPGERATLSCRASQ SVSSNLAWYQQKPGQAPRLLIYGAS SRATGIPDRFSGSGSGTDFTLTISRLEP EDFAVYYCQQYGSSPPVTFGQGTKV EIK (SEQ ID NO: 71) |
| xhCD8v7 | EVQLVESGGGLVQPGRSLRLSCAAS GFTFDDYAMHWVRQAPGKGLEWV AVISYDGSNKYYADSVKGRFTISRDN SKNTLYLQMNSLRAEDTAVYYCAK DRIGWYDYDAFDIWGQGTMVTVSS (SEQ ID NO: 72) | EIVLTQSPATLSVTPGEGATLSCRASH SVGSNLAWYQQKPGQAPRLLIYDAS NRATGIPARFSGSGSGTDFTLTISSLE PEDLAVYYCQQRSNWPPTFGQGTRL EIK (SEQ ID NO: 73) |
| xhCD8v8 | QVQLQQSGAELVRPGSSVKISCKASG YAFSSYWMNWVKQRPGQGLEWIGQ IYPGDGDTNYNGKFKGKATLTADKS SSTAYMQLSSLTSEDSAVYFCARSGA AFSSYYAMDYWGQGTSVTVSS (SEQ ID NO: 185) | DIQMTQSPASLSVSVGETVTITCRASE NIIYSNLAWYQQKQGKSPQLLVYAAT NLADGVPSRFSGSGSGTQYSLKINSL QSEDFGSYYCQHFWGTPWTFGGGTK LEIK (SEQ ID NO: 186) |
| xhCD8v9 | QVQLVQSGAEVKKPGSSVKVSCKAS GGTFSSYAISWVRQAPGQGLEWMG GIIPGAATANYAQKFQGRVTITADES TSTAYMELSSLRSEDTAVYYCARDA AGIRLFADWGQGTLVTVSS (SEQ ID NO: 245) | DIQMTQSPSSLSASVGDRVTITCRAS QEIYGALNWYQQKPGKAPKLLIYGA TNLQSGVPSRFSGSGSGTDFTLTISSL QPEDFATYYCQSTYDAPWTFGGGTK VEIK (SEQ ID NO: 246) |
| xhCD8v10 | EVQLVESGGGLVQPGGSLRLSCAAS GFTFSSYAMSWVRQAPGKGLEWVS DITYAGGSTAYADSVKGRFTISRDNA KNSLYLQMNSLRAEDTAVYYCARSN AYAWDDALDIWGQGTMVTVSS (SEQ ID NO: 247) | EIVLTQSPGTLSLSPGERATLSCRASQ SVSSNLAWYQQKPGQAPRLLIYGAS SRATGIPDRFSGSGSGTDFTLTISRLEP EDFAVYYCQQYGSSPPVTFGQGTKV EIK (SEQ ID NO: 248) |
| xhCD8v11 | EVQLVESGGGLVQPGGSLRLSCAAS GFTFSSYAMSWVRQAPGKGLEWVS DITYAGGSTAYADSVKGRFTISRDNA KNSLYLQMNSLRAEDTAVYYCARSN AYAWDDALDIWGQGTLVTVSS (SEQ ID NO: 249) | EIVLTQSPGTLSLSPGERATLSCRASQ SVSSNLAWYQQKPGQAPRLLIYGAS SRATGIPDRFSGSGSGTDFTLTISRLEP EDFAVYYCQQYGSSPPVTFGQGTKV EIK (SEQ ID NO: 250) |
| xhCD8v12 | QVQLVQSGAEVKKPGSSVKVSCKAS GGTFSSYAISWVRQAPGQGLEWMG GIIPGYATANYAQKFQGRVTITADES TSTAYMELSSLRSEDTAVYYCARDA AGIRLFADWGQGTLVTVSS (SEQ ID NO: 251) | DIQMTQSPSSLSASVGDRVTITCRAS QSIYGALNWYQQKPGKAPKLLIYGA SNLQSGVPSRFSGSGSGTDFTLTISSL QPEDFATYYCQSTYTAPWTFGGGTK VEIK (SEQ ID NO: 252) |

TABLE 3-continued

Anti-CD8 antibody variable domain sequences

| Name | VH | VL |
|---|---|---|
| xhCD8v13 | QVQLVQSGAEVKKPGSSVKVSCKAS GGTFSSYAISWVRQAPGQGLEWMG GIIPGYATANYAQKFQGRVTITADES TSTAYMELSSLRSEDTAVYYCARDA AGIRLFADWGQGTLVTVSS (SEQ ID NO: 253) | DIQMTQSPSSLSASVGDRVTITCRAS QEIYGALNWYQQKPGKAPKLLIYGA TNLQSGVPSRFSGSGSGTDFTLTISSL QPEDFATYYCQSTYDAPWTFGGGTK VEIK (SEQ ID NO: 254) |
| xhCD8v14 | EVQLVESGGGLVQPGGSLRLSCAAS GFTFSSYAMSWVRQAPGKGLEWVS DISYAGGSTAYADSVKGRFTISRDNA KNSLYLQMNSLRAEDTAVYYCARSN AYAWDDALDIWGQGTMVTVSS (SEQ ID NO: 255) | EIVLTQSPGTLSLSPGERATLSCRASQ SVSSNLAWYQQKPGQAPRLLIYGAS SRATGIPDRFSGSGSGTDFTLTISRLEP EDFAVYYCQQYGSSPPVTFGQGTKV EIK (SEQ ID NO: 256) |
| xhCD8v15 | EVQLVESGGGLVQPGGSLRLSCAAS GFTFSSYAMSWVRQAPGKGLEWVS DISYAGGSTAYADSVKGRFTISRDNA KNSLYLQMNSLRAEDTAVYYCARSN AYAWDDALDIWGQGTLVTVSS (SEQ ID NO: 257) | EIVLTQSPGTLSLSPGERATLSCRASQ SVSSNLAWYQQKPGQAPRLLIYGAS SRATGIPDRFSGSGSGTDFTLTISRLEP EDFAVYYCQQYGSSPPVTFGQGTKV EIK (SEQ ID NO: 258) |

Fusion Proteins

Figure 7:
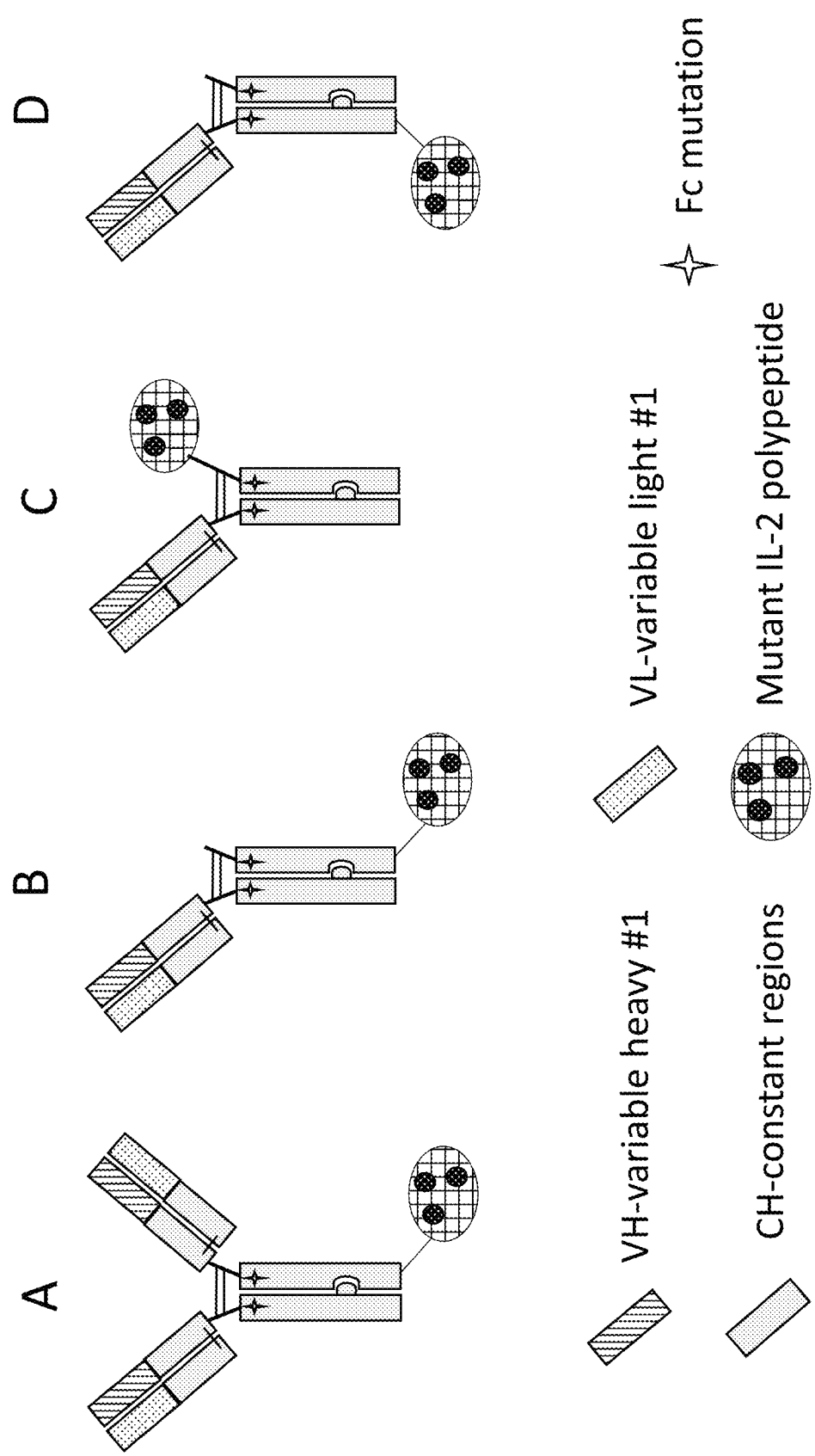
FIG. 7 depicts four different formats (formats A, B, C, and D) of fusion proteins comprising CD8ab antibodies of the present disclosure, in accordance with some embodiments.

Further provided herein are fusion proteins comprising any one of the anti-CD8 antibodies, or antigen binding domains, or antibody fragments disclosed herein. In some embodiments, a fusion protein of the present disclosure comprises a first moiety comprising a human or humanized antibody or antigen-binding fragment thereof that specifically binds CD8b and/or CD8ab (e.g., any one of the anti-CD8 antibodies described supra) and a second moiety comprising a cytokine, chemokine, or growth factor. In some embodiments, the first moiety is fused to the second moiety directly. In some embodiments, the first moiety is fused to the second moiety via a linker. Exemplary and non-limiting illustrations of fusion proteins of the present disclosure are depicted in FIG. 7.

Fusion Protein Formats

In some embodiments, the first moiety comprises an antibody (e.g., an anti-CD8 antibody of the present disclosure). In some embodiments, the first moiety comprises an antibody fragment (e.g., an anti-CD8 antibody fragment of the present disclosure). In some embodiments, the first moiety comprises a single chain antibody or single chain variable fragment (scFv). In some embodiments, the first moiety comprises a VHH antibody. In some embodiments, the first moiety comprises one or two antibody heavy chain polypeptides and one or two antibody light chain polypeptides (e.g., of an anti-CD8 antibody of the present disclosure). In some embodiments, the first moiety comprises the 3 heavy chain CDRs and/or 3 light chain CDRs of a single anti-CD8 antibody of the present disclosure, e.g., as shown in Tables 1-3. In some embodiments, the first moiety comprises the VH and/or VL domain(s) of a single anti-CD8 antibody of the present disclosure, e.g., as shown in Table 3. In some embodiments, the first moiety further comprises one or two human IgG Fc domains. In some embodiments, the one or two human IgG Fc domains are IgG1, IgG2, IgG3 or IgG4 Fc domains. In some embodiments, the one or two human IgG Fc domains do not have the C-terminus lysine residue. In some embodiments, the one or two human IgG Fc domains comprise amino acid modifications (such as substitutions, deletions, additions, etc.). In some embodiments, the Fc domain modifications promote heterodimeric formation (e.g., as shown in Table 4). In some embodiments, the one or two Fc domains comprise Fc gamma-null mutations.

In some embodiments, the first moiety comprises two antibody heavy chain polypeptides comprising a structure according to formula [I], from N-terminus to C-terminus:

VH-CH1-hinge-CH2-CH3     [I]

and two antibody light chain polypeptides comprising a structure according to formula [II], from N-terminus to C-terminus:

VL-CL     [II]

wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain. In some embodiments, the N-terminus of the second moiety is fused to the C-terminus of one of the two CH3 domains (see, e.g., format A in FIG. 7).

In some embodiments, the first moiety comprises a first antibody heavy chain polypeptide comprising a structure according to formula [I], from N-terminus to C-terminus:

VH-CH1-hinge-CH2-CH3     [I], an antibody light chain polypeptide comprising a structure according to formula [II], from N-terminus to C-terminus:

VL-CL     [II], and a second antibody heavy chain polypeptide comprising a structure according to formula [III], from N-terminus to C-terminus:

hinge-CH2-CH3     [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain. In some embodiments, the N-terminus of the second moiety is fused to the C-terminus of the CH3 domain of the second antibody heavy chain polypeptide (see, e.g., format B in FIG. 7). In some embodiments, the N-terminus of the second moiety is fused to the C-terminus of the CH3 domain of the first antibody heavy chain polypeptide (see, e.g., format D in FIG. 7).

In some embodiments, the first moiety comprises a first antibody heavy chain polypeptide comprising a structure according to formula [I], from N-terminus to C-terminus:

VH-CH1-hinge-CH2-CH3 [I], an antibody light chain polypeptide comprising a structure according to formula [II], from N-terminus to C-terminus:

VL-CL [II], and a second antibody heavy chain polypeptide comprising a structure according to formula [III], from N-terminus to C-terminus:

hinge-CH2-CH3 [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain. In some embodiments, the C-terminus of the second moiety is fused to the N-terminus of the hinge domain of the second antibody heavy chain polypeptide (see, e.g., format C in FIG. 7).

In some embodiments, an anti-CD8 antibody of the present disclosure is a multispecific (e.g., bispecific) antibody or antibody fragment. For example, in some embodiments, the multispecific antibody (e.g., bispecific antibody) comprises a first antigen binding domain that binds to CD8 (e.g., as described supra) and a second antigen binding domain that binds a target of interest. In some embodiments, a bispecific antibody can be generated via fusion of an additional binding site to either the heavy or light chain of an immunoglobulin. Examples of the additional binding site include but not limited to variable regions, scFv, Fab, VHH, and peptide.

In some embodiments, the recombinant bispecific antibodies disclosed herein can be very roughly classified in two categories, namely i) formats resulting from the combination of variable regions only and ii) formats combining variable regions with Fc domains. Representatives of the first category are tandem scFv (taFv), diabodies (db), DART, single-chain diabodies (scDbs), Fab-Fc, tandem Fab, Dual variable region Fab and tandem dAb/VHH. The two variable regions can be linked together via covalent bonds or non-covalent interaction.

Noncovalent interaction may involve the use of heterodimerization modules such as leucine zipper, dock-and-lock methods of using regulatory subunit of cAMP-dependent protein kinase (PKA) and the anchoring domains of A kinase anchor proteins (AKAPs) or knob-into-holes CH3 domain (U.S. Pat. Nos. 5,731,168; 7,695,936; Ridgway et al., Prot Eng 9, 617-621 (1996) and Carter, J Immunol Meth 248, 7-15 (2001)) to pair up the variable regions.

In some embodiments, bispecific antibodies are generated on the natural immunoglobulin architecture containing two pairs of heavy chain and light chain combination with each pair having distinct binding specificity. Homodimerization of the two heavy chains in an IgG is mediated by the CH3 interaction. To promote heterodimeric formation, genetic modifications are introduced to the two respective CH3 regions. There heterodimerization mutations often involve steric repulsion, charge steering interaction, or interchain disulfide bond formation. Exemplary and non-limiting Fc modifications to promote heterodimerization include the following:

TABLE 4

Exemplary Fc modifications to promote heterodimerization.

| Strategy | CH3 domain 1 | CH3 domain 2 | References |
| --- | --- | --- | --- |
| knobs-into-holes 1 | T366Y | Y407T | Brinkmann & Kontermann, MAbs. 2017 February-March; 9(2): 182-212; |
| knobs-into-holes 2 | T366W | T366S, L368A, Y407V | |
| knobs-into-holes 3 | S354C, T366W | Y349C, T366S, L368A, Y407V | Atwell et al, J Mol Biol 1997; 270: 26-35; Merchant et al, Nat Biotechnol 1998; 16: 677-681 |
| knobs-into-holes 4 | Y349C, T366W | S354C, T366S, L368A, Y407V | |
| HA-TF | S364H, F405A | Y349T, T394F | Moore et al, MAbs 2011; 3: 546-557 |
| ZW1 | T350V, L351Y, F405A, Y407V | T350V, T366L, K392L, T394W | Von Kreudenstein et al, MAbs 2013; 5: 646-54 |
| CH3 charge pairs (DD-KK) | K392D, K409D | E356K, D399K | Gunasekaran et al, J Biol Chem 2010; 285: 19637-46 |
| IgG1 hinge/CH3 charge pairs (EEE-RRR) | IgG1: D221E, P228E, L368E | IgG1: D221R, P228R, K409R | Strop Pet al, J Mol Biol 2012; 420: 204-19 |
| IgG2 hinge/CH3 charge pairs (EEE-RRRR) | IgG2: C223E, P228E, L368E | IgG2: C223R, E225R, P228R, K409R | |
| EW-RVT | K360E, K409W, | Q347R, D399V, F405T | Choi et al, Mol Cancer Ther 2013; 12: 2748-59 |

TABLE 4-continued

Exemplary Fc modifications to promote heterodimerization.

| Strategy | CH3 domain 1 | CH3 domain 2 | References |
|---|---|---|---|
| EW-RVT$_{S-S}$ | K360E, K409W, Y349C | Q347R, D399V, F405T, S354C | Choi et al, Mol Immunol 2015; 65: 377-83 |
| Biclonic | 366K (+351K) | 351D or E or D at 349, 368, 349, or 349 + 355 | Geuijen et al, ournal of Clinical Oncology 2014; 32: suppl: 560 |
| DuoBody (L-R) 1 | F405L | K409R | Labrijn et al, Nat Protoc 2014; 9: 2450-63; Labrijn et al, PNAS 2013; 110(13): 5145-50 |
| DuoBody (L-R) 2 | F405L-R409K | WT (R409) | |
| SEEDbody | IgG/A chimera | IgG/A chimera | Davis et al, Protein Eng Des Sel 2010; 23: 195-202 |
| BEAT | residues from TCRα interface | residues from TCRβ interface | Moretti et al, BMC Proceedings 2013; 7(Suppl 6): O9 |
| Mixed interface (MI) heterodimers | IgG—CH3 variants | igA/D/M CH3 variants or IgM CH4 variants | Skegro et al, J Biol Chem. 2017 292(23): 9745-9759. |
| XmAb | E357Q-S364K | L368D-K370S | Moore et al, Methods. 2019 154: 38-50 |
| DEKK Fc | L351D-L368E | L351K-T366K | De Nardis et al., J Biol Chem. 2017; 292(35): 14706-14717. |
| Charge pair | E356K or E357K or D399K | K370E, K409D, K439E | Igawa T, Tsunoda H. WO2006106905. 2006. |
| KKA-DDW | D356K-D399K-Y407A | K392D-K409D-T366W | Zhou et al, WO2014079000A1 |
| Charge pair | L368E-Y407E | E357K-D399K | Labrijn et al, Nat Review Drug Discovery 2019; 18, 585-608 |
| Knob-hole-electrostatic | S354C-T366W-K409A | Y349C-T366S-L368A-Y407-F405K | Wei et al., Oncotarget. 2017; 8(31): 51037-51049 |
| KA | F405K | K409A | Wei et al., Oncotarget. 2017; 8(31): 51037-51049 |
| PPV-TPP | P395K-P396K-V397K, P395K-P396K-V397C or P395R-P396R-V397R | T394D-P395D-P396D, T394C-P395D-P396D or T394E-P395E-P396E | Wenjun Zhang US10538595B2 |

In some embodiments, bispecific antibody can be generated by post-production assembly from half-antibodies, thereby solving the issues of heavy and light chain mispairing. These antibodies often contain modification to favor heterodimerization of half-antibodies. Exemplary systems include but not limited to the knob-into-hole, IgG1 (EEE-RRR), IgG2 (EEE-RRRR) (Strop et al. J Mol Biol (2012)) and DuoBody (F405L-K409R), listed in Table 5. In such case, half-antibody is individually produced in separate cell line and purified. The purified antibodies were then subjected to mild reduction to obtain half-antibodies, which were then assembled into bispecific antibodies. Heterodimeric bispecific antibody was then purified from the mixture using conventional purifications methods.

In some embodiments, strategies on bispecific antibody generation that do not rely on the preferential chain pairing can also be employed. These strategies typically involve introducing genetic modification on the antibody in such a manner that the heterodimer will have distinct biochemical or biophysical properties from the homodimers; thus the post-assembled or expressed heterodimer can be selectively purified from the homodimers. One example was to introduce H435R/Y436F in IgG1 CH3 domain to abolish the Fc binding to protein A resin and then co-express the H435R/Y436F variant with a wildtype Fc. The resulting homodimeric antibodies containing two copies of H435R/Y436F cannot bind to the Protein A column, while heterodimeric antibody comprising one copy of H435R/Y436F mutation will have a decreased affinity for protein A as compared to the strong interaction from homodimeric wildtype antibody (Tustian et al Mabs 2016). Other examples include kappa/lambda antibody (Fischer et al., Nature Communication 2015) and introduction of differential charges (E357Q, S267K or N208D/Q295E/N384D/Q418E/N421D) on the respective chains (US 2018/0142040 A1; (Strop et al. J Mol Biol (2012)).

In some embodiments, bispecific antibody can be generated via fusion of an additional binding site to either the heavy or light chain of an immunoglobulin. Examples of the additional binding site include but not limited to variable regions, scFv, Fab, VHH, and peptide.

Fusion Protein Fc Regions

In some embodiments, an antibody or fusion protein of the present disclosure comprises an Fc region. In some embodiments, the Fc region comprises one or more mutations that reduce or eliminate FcγR binding and/or effector function. In some embodiments, the Fc region (e.g., an IgG1 Fc region) comprises a substitution at one or more of the following positions: C220, C226, C229, E233, L234, L235, G237, P238, S239 D265, S267, N297, L328, P331, K322, A327 and P329. In some embodiments, the Fc region (e.g., an IgG2 Fc region) comprises a substitution at one or more of the following positions: V234, G237, D265, H268, N297, V309, A330, A331, K322. In some embodiments, the Fc region (e.g., an IgG4 Fc region) comprises a substitution at one or more of the following positions: L235, G237, D265 and E318. In some embodiments, the Fc region (e.g., an IgG1 Fc region) comprises one or more of the following mutations or groups of mutations: N297A, N297Q, N297G, D265A/N297A, D265A/N297Q, C220S/C226S/C229S/P238S, S267E/L328F, C226S/C229S/E233P/L234V/L235A, L234F/L235E/P331S, L234A/L235A, L234A/L235A/G237A, L234A/L235A/G237A/K322A, L234A/L235A/G237A/A330S/A331S, L234A/L235A/P329G, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, L234A/L235A/G237deleted. In some embodiments, the Fc region (e.g., an IgG2 Fc region) comprises one or more of the following mutations or groups of mutations: A330S/A331S, V234A/G237A, V234A/G237A/D265A, D265A/A330S/A331S, V234A/G237A/D265A/A330S/A331S, and H268Q/V309L/A330S/A331S. In some embodiments, the Fc region (e.g., an IgG4 Fc region) comprises one or more of the following mutations or groups of mutations: L235A/G237A/E318A, D265A, L235A/G237A/D265A and L235A/G237A/D265A/E318A. In some embodiments, the Fc region comprises one, two, three, or all of the following mutations: L234A, L235A, G237A, and K322A, numbering according to EU index. In some embodiments, the Fc region comprises one, two, or all of the following mutations: L234A, L235A, and G237A, numbering according to EU index.

In some embodiments, said first and second Fc domains of the fusion protein contain one or more of the following Fc mutations to decrease effector function according to EU numbering: L234A, L235A, G237A, and K322A. In some embodiments, said first and second Fc domains of the fusion protein contain the following Fc mutations to decrease effector function according to EU numbering: L234A, L235A, and G237A. In some embodiments, said first and second Fc domains of the fusion protein contain the following Fc mutations to decrease effector function according to EU numbering: L234A, L235A, G237A, and K322A. In some embodiments, said first and second Fc domains of the fusion protein contain the following amino acid substitutions to facilitate heterodimeric formation: Y349C/T366W (knob) and S354C, T366S, L368A and Y407V (hole).

In some embodiments, the heterodimeric mutations and/or mutations to modify Fc gamma receptor binding resulted in reduction of Fc stability. Therefore, additional mutation(s) was added to the Fc region to increase its stability. For example, one or more pairs of disulfide bonds such as A287C and L306C, V259C and L306C, R292C and V302C, and V323C and I332C are introduced into the Fc region. Another example is to introduce S228P to IgG4 based bispecific antibodies to stabilize the hinge disulfide. Additional example includes introducing K338I, A339K, and K340S mutations to enhance Fc stability and aggregation resistance (Gao et al, 2019 Mol Pharm. 2019; 16:3647).

Fusion Protein Cytokines

In some embodiments, the second moiety induces activation of CD8+ T cells. In some embodiments, the second moiety comprises a polypeptide that induces signaling via IL2Rβγ. For example, in some embodiments, the second moiety comprises an IL-15 polypeptide (e.g., a human IL-15 polypeptide or derivative thereof) or a neoleukin. In some embodiments, the second moiety comprises an IL-21 polypeptide (e.g., a human IL-21 polypeptide or derivative thereof).

In some embodiments, the second moiety comprises an IL-2 polypeptide (e.g., a human IL-2 polypeptide or derivative thereof).

In some embodiments, the mutant IL-2 polypeptide has a binding affinity to IL-2Rα that is reduced by 50% or more, compared to binding affinity of a wild-type IL-2 polypeptide comprising the sequence of SEQ ID: 81 for IL-2Rα. In some embodiments, the mutant IL-2 polypeptide has a binding affinity to IL-2Rβ that is reduced by 50% or more, compared to binding affinity of a wild-type IL-2 polypeptide comprising the sequence of SEQ ID: 81 for IL-2Rβ. In some embodiments, the mutant IL-2 polypeptide has a binding affinity to IL-2Rγ that is reduced by 50% or more, compared to binding affinity of a wild-type IL-2 polypeptide comprising the sequence of SEQ ID: 81 for IL-2Rγ. Differences in binding affinity of wild-type and disclosed mutant polypeptide for IL-2Rα and IL-2Rβ can be measured, e.g., in standard surface plasmon resonance (SPR) assays that measure affinity of protein-protein interactions familiar to those skilled in the art. Differences in binding affinity of wild-type and disclosed mutant polypeptide for IL-2Rγ cannot reliably be measured by SPR assays as the affinity of wild-type IL-2 polypeptide for IL-2Rγ is very low. Instead, their reduced affinity to IL-2Rγ can be deduced by performing an in vitro assay that measures pSTAT5 and compares the activity of IL-2 polypeptides with and without the IL-2Rγ affinity-reducing substitution on IL-2R-expressing cells. Exemplary sequences for IL-2Rα, IL-2Rβ, and IL-2Rγ are provided below.

IL-2Rα:

(SEQ ID NO: 82)
MDSYLLMWGLLTFIMVPGCQAELCDDDPPEIPHATFKAMAYKEGTMLNCE

CKRGFRRIKSGSLYMLCTGNSSHSSWDNQCQCTSSATRNTTKQVTPQPEE

QKERKTTEMQSPMQPVDQASLPGHCREPPPWENEATERIYHFVVGQMVYY

QCVQGYRALHRGPAESVCKMTHGKTRWTQPQLICTGEMETSQFPGEEKPQ

ASPEGRPESETSCLVTTTDFQIQTEMAATMETSIFTTEYQVAVAGCVFLL

ISVLLLSGLTWQRRQRKSRRTI

IL-2Rβ:

(SEQ ID NO: 83)
MAAPALSWRLPLLILLLPLATSWASAAVNGTSQFTCFYNSRANISCVWSQ

DGALQDTSCQVHAWPDRRRWNQTCELLPVSQASWACNLILGAPDSQKLTT

VDIVTLRVLCREGVRWRVMAIQDFKPFENLRLMAPISLQVVHVETHRCNI

-continued

```
SWEISQASHYFERHLEFEARTLSPGHTWEEAPLLTLKQKQEWICLETLTP

DTQYEFQVRVKPLQGEFTTWSPWSQPLAFRTKPAALGKDTIPWLGHLLVG

LSGAFGFIILVYLLINCRNTGPWLKKVLKCNTPDPSKFFSQLSSEHGGDV

QKWLSSPFPSSSFSPGGLAPEISPLEVLERDKVTQLLLQQDKVPEPASLS

SNHSLTSCFTNQGYFFFHLPDALEIEACQVYFTYDPYSEEDPDEGVAGAP

TGSSPQPLQPLSGEDDAYCTFPSRDDLLLFSPSLLGGPSPPSTAPGGSGA

GEERMPPSLQERVPRDWDPQPLGPPTPGVPDLVDFQPPPELVLREAGEEV

PDAGPREGVSFPWSRPPGQGEFRALNARLPLNTDAYLSLQELQGQDPTHL

V

IL-2Rγ:
                                          (SEQ ID NO: 84)
MLKPSLPFTSLLFLQLPLLGVGLNTTILTPNGNEDTTADFFLTTMPTDSL

SVSTLPLPEVQCFVFNVEYMNCTWNSSSEPQPTNLTLHYWYKNSDNDKVQ

KCSHYLFSEEITSGCQLQKKEIHLYQTFVVQLQDPREPRRQATQMLKLQN

LVIPWAPENLTLHKLSESQLELNWNNRFLNHCLEHLVQYRTDWDHSWTEQ

SVDYRHKFSLPSVDGQKRYTFRVRSRFNPLCGSAQHWSEWSHPIEWGSNT

SKENPFLFALEAVVISVGSMGLIISLLCVYFWLERTMPRIPTLKNLEDLV

TEYHGNFSAWSGVSKGLAESLQPDYSERLCLVSEIPPKGGALGEGPGASP

CNQHSPYWAPPCYTLKPET
```

In some embodiments, the IL-2 polypeptide is a mutant IL-2 polypeptide comprising one or more mutations relative to a human IL-2 polypeptide comprising the sequence of APTSSSTKKTQLQLEHLLLDLQMILNGINNYKNPKL-TRMLTFKFYMPKKATELKHLQCL EEELKPLEEVLN-LAQSKNFHLRPRDLISNINVIVLELKGSETTFMCEYA-DETATIVEFLNR WITFCQSIISTLT (SEQ ID NO:81). In some embodiments, the mutant IL-2 polypeptides of the present disclosure have one or more, two or more, or three or more affinity-reducing amino acid substitutions relative to the wild-type mature IL-2 polypeptide, e.g., having the amino acid sequence of SEQ ID NO:81. In some embodiments, one or more, two or more, or three or more substituted residues, are selected from the following group: Q11, H16, L18, L19, D20, D84, S87, Q22, R38, F42, K43, Y45, E62, P65, E68, V69, L72, D84, S87, N88, V91, I92, T123, Q126, S127, I129, and S130. Decreased affinity to IL-2Rα may be obtained by substituting one or more of the following residues in the sequence of the wild-type mature IL-2 polypeptide: R38, F42, K43, Y45, E62, P65, E68, V69, and L72. Decreased affinity to IL-2Rβ may be obtained by substituting one or more of the following residues: E15, H16, L19, D20, D84, S87, N88, V91, and 192. Decreased affinity to IL-2Rγ may be obtained by substituting one or more of the following residues in the sequence of the wild-type mature IL-2 polypeptide: Q11, L18, Q22, T123, Q126, S127, I129, and S130.

In some embodiments, the mutant IL-2 polypeptide comprises an F42A or F42K amino acid substitution relative to the wild-type mature IL-2 amino acid sequence. In some embodiments, the mutant IL-2 polypeptide comprises an F42A or F42K amino acid substitution and an R38A, R38D, R38E, E62Q, E68A, E68Q, E68K, or E68R amino acid substitution relative to the wild-type mature IL-2 amino acid sequence. For example, in some embodiments, the mutant IL-2 polypeptide comprises F42A; R38A and F42A; R38D and F42A; R38E and F42A; F42A and E62Q; F42A and E68A; F42A and E68Q; F42A and E68K; F42A and E68R; or R38A and F42K amino acid substitution(s) relative to the wild-type mature IL-2 amino acid sequence, e.g., as shown in SEQ ID NO:81. In some embodiments, the mutant IL-2 polypeptide comprises R38E and F42A amino acid substitutions relative to the wild-type IL-2 amino acid sequence. In some embodiments, the mutant IL-2 polypeptide comprises R38D and F42A amino acid substitutions relative to the wild-type IL-2 amino acid sequence. In some embodiments, the mutant IL-2 polypeptide comprises F42A and E62Q amino acid substitutions relative to the wild-type IL-2 amino acid sequence. In some embodiments, the mutant IL-2 polypeptide comprises R38A and F42K amino acid substitutions relative to the wild-type IL-2 amino acid sequence. In some embodiments, the mutant IL-2 polypeptide comprises R38D and F42A amino acid substitutions relative to the wild-type IL-2 amino acid sequence. In some embodiments, the mutant IL-2 polypeptide comprises R38A and F42K amino acid substitutions relative to the wild-type IL-2 amino acid sequence. In some embodiments, the mutant IL-2 polypeptide comprises F42A and E62Q amino acid substitutions relative to the wild-type IL-2 amino acid sequence. In some embodiments, the mutant IL-2 polypeptide comprises an H16E, H16D, D20N, M23A, M23R, M23K, D84L, D84N, D84V, D84H, D84Y, D84R, D84K, S87K, S87A, N88A, N88D, N88G, N88S, N88T, N88R, N88I, V91A, V91T, V91E, I92A, E95S, E95A, E95R, T123A, T123E, T123K, T123Q, Q126A, Q126S, Q126T, Q126E, S127A, S127E, S127K, or S127Q amino acid substitution relative to the wild-type IL-2 amino acid sequence. In some embodiments, the mutant IL-2 polypeptide comprises F42A; R38A and F42A; R38D and F42A; R38E and F42A; F42A and E62Q; F42A and E68A; F42A and E68Q; F42A and E68K; F42A and E68R; or R38A and F42K amino acid substitution(s) relative to the wild-type mature IL-2 amino acid sequence and an H16E, H16D, D20N, M23A, M23R, M23K, D84L, D84N, D84V, D84H, D84Y, D84R, D84K, S87K, S87A, N88A, N88D, N88G, N88S, N88T, N88R, N88I, V91A, V91T, V91E, I92A, E95S, E95A, E95R, T123A, T123E, T123K, T123Q, Q126A, Q126S, Q126T, Q126E, S127A, S127E, S127K, or S127Q amino acid substitution relative to the wild-type mature IL-2 amino acid sequence, e.g., as shown in SEQ ID NO:81. For example, in some embodiments, the mutant IL-2 polypeptide comprises R38E, F42A, and H16E amino acid substitutions relative to the wild-type IL-2 amino acid sequence. In some embodiments, the mutant IL-2 polypeptide comprises R38E, F42A, and H16D amino acid substitutions relative to the wild-type IL-2 amino acid sequence. In some embodiments, the mutant IL-2 polypeptide comprises R38E, F42A, and D84K amino acid substitutions relative to the wild-type IL-2 amino acid sequence. In some embodiments, the mutant IL-2 polypeptide comprises R38E, F42A, and D84R amino acid substitutions relative to the wild-type IL-2 amino acid sequence. In some embodiments, the mutant IL-2 polypeptide comprises R38E, F42A, and N88S amino acid substitutions relative to the wild-type IL-2 amino acid sequence. In some embodiments, the mutant IL-2 polypeptide comprises R38E, F42A, and N88A amino acid substitutions relative to the wild-type IL-2 amino acid sequence. In some embodiments, the mutant IL-2 polypeptide comprises R38E, F42A, and N88G amino acid substitutions relative to the wild-type IL-2 amino acid sequence. In some embodiments, the mutant IL-2 polypeptide comprises R38E, F42A, and N88R amino acid substitutions relative to the wild-type IL-2 amino acid sequence. In some embodiments, the mutant IL-2 polypeptide comprises R38E, F42A, and N88T amino acid substitutions relative to the wild-type IL-2 amino acid sequence. In some embodiments, the mutant IL-2 polypeptide comprises R38E, F42A, and N88D amino acid substitutions relative to the wild-type IL-2 amino acid sequence. In some embodiments, the mutant IL-2 polypeptide comprises R38E, F42A, and V91E amino acid substitutions relative to the wild-type IL-2 amino acid sequence. In some embodiments, the mutant IL-2 polypeptide comprises R38E, F42A, and Q126S amino acid substitutions relative to the wild-type IL-2 amino acid sequence. In some embodiments, the mutant IL-2 polypeptide comprises the amino acid sequence of SEQ ID NO:81 with one of the following sets of amino acid substitutions (relative to the sequence of SEQ ID NO:81): R38E and F42A; R38D and F42A; F42A and E62Q; R38A and F42K; R38E, F42A, and N88S; R38E, F42A, and N88A; R38E, F42A, and N88G; R38E, F42A, and N88R; R38E, F42A, and N88T; R38E, F42A, and N88D; R38E, F42A, and V91E; R38E, F42A, and D84H; R38E, F42A, and D84K; R38E, F42A, and D84R; H16D, R38E and F42A; H16E, R38E and F42A; R38E, F42A and Q126S; R38D, F42A and N88S; R38D, F42A and N88A; R38D, F42A and N88G; R38D, F42A and N88R; R38D, F42A and N88T; R38D, F42A and N88D; R38D, F42A and V91E; R38D, F42A, and D84H; R38D, F42A, and D84K; R38D, F42A, and D84R; H16D, R38D and F42A; H16E, R38D and F42A; R38D, F42A and Q126S; R38A, F42K, and N88S; R38A, F42K, and N88A; R38A, F42K, and N88G; R38A, F42K, and N88R; R38A, F42K, and N88T; R38A, F42K, and N88D; R38A, F42K, and V91E; R38A, F42K, and D84H; R38A, F42K, and D84K; R38A, F42K, and D84R; H16D, R38A, and F42K; H16E, R38A, and F42K; R38A, F42K, and Q126S; F42A, E62Q, and N88S; F42A, E62Q, and N88A; F42A, E62Q, and N88G; F42A, E62Q, and N88R; F42A, E62Q, and N88T; F42A, E62Q, and N88D; F42A, E62Q, and V91E; F42A, E62Q, and D84H; F42A, E62Q, and D84K; F42A, E62Q, and D84R; H16D, F42A, and E62Q; H16E, F42A, and E62Q; F42A, E62Q, and Q126S; R38E, F42A, and C125A; R38D, F42A, and C125A; F42A, E62Q, and C125A; R38A, F42K, and C125A; R38E, F42A, N88S, and C125A; R38E, F42A, N88A, and C125A; R38E, F42A, N88G, and C125A; R38E, F42A, N88R, and C125A; R38E, F42A, N88T, and C125A; R38E, F42A, N88D, and C125A; R38E, F42A, V91E, and C125A; R38E, F42A, D84H, and C125A; R38E, F42A, D84K, and C125A; R38E, F42A, D84R, and C125A; H16D, R38E, F42A, and C125A; H16E, R38E, F42A, and C125A; R38E, F42A, C125A and Q126S; R38D, F42A, N88S, and C125A; R38D, F42A, N88A, and C125A; R38D, F42A, N88G, and C125A; R38D, F42A, N88R, and C125A; R38D, F42A, N88T, and C125A; R38D, F42A, N88D, and C125A; R38D, F42A, V91E, and C125A; R38D, F42A, D84H, and C125A; R38D, F42A, D84K, and C125A; R38D, F42A, D84R, and C125A; H16D, R38D, F42A, and C125A; H16E, R38D, F42A, and C125A; R38D, F42A, C125A, and Q126S; R38A, F42K, N88S, and C125A; R38A, F42K, N88A, and C125A; R38A, F42K, N88G, and C125A; R38A, F42K, N88R, and C125A; R38A, F42K, N88T, and C125A; R38A, F42K, N88D, and C125A; R38A, F42K, V91E, and C125A; R38A, F42K, D84H, and C125A; R38A, F42K, D84K, and C125A; R38A, F42K, D84R, and C125A; H16D, R38A, F42K, and C125A; H16E, R38A, F42K, and C125A; R38A, F42K, C125A and Q126S; F42A, E62Q, N88S, and C125A; F42A, E62Q, N88A, and C125A; F42A, E62Q, N88G, and C125A; F42A, E62Q, N88R, and C125A; F42A, E62Q, N88T, and C125A; F42A, E62Q, N88D, and C125A; F42A, E62Q, V91E, and C125A; F42A, E62Q, and D84H, and C125A; F42A, E62Q, and D84K, and C125A; F42A, E62Q, and D84R, and C125A; H16D, F42A, and E62Q, and C125A; F42A, E62Q, C125A and Q126S; F42A, N88S, and C125A; F42A, N88A, and C125A; F42A, N88G, and C125A; F42A, N88R, and C125A; F42A, N88T, and C125A; F42A, N88D, and C125A; F42A, V91E, and C125A; F42A, D84H, and C125A; F42A, D84K, and C125A; F42A, D84R, and C125A; H16D, F42A, and C125A; H16E, F42A, and C125A; and F42A, C125A and Q126S. In some embodiments, the IL-2 polypeptide comprises the sequence of SEQ ID NO:81 with one, two, three, four, or five amino acid substitutions relative to SEQ ID NO:81, and wherein the one, two, three, four, or five substitution(s) comprise substitution(s) at positions of SEQ ID NO:81 selected from the group consisting of: Q11, H16, L18, L19, D20, Q22, R38, F42, K43, Y45, E62, P65, E68, V69, L72, D84, S87, N88, V91, I92, T123, Q126, S127, I129, and S130. In some embodiments, the IL-2 polypeptide comprises the sequence of SEQ ID NO:81 with one of the following sets of amino acid substitutions (relative to the sequence of SEQ ID NO:81): R38E and F42A; R38D and F42A; F42A and E62Q; R38A and F42K; R38E, F42A, and N88S; R38E, F42A, and N88A; R38E, F42A, and N88G; R38E, F42A, and N88R; R38E, F42A, and N88T; R38E, F42A, and N88D; R38E, F42A, and V91E; R38E, F42A, and D84H; R38E, F42A, and D84K; R38E, F42A, and D84R; H16D, R38E and F42A; H16E, R38E and F42A; R38E, F42A and Q126S; R38D, F42A and N88S; R38D, F42A and N88A; R38D, F42A and N88G; R38D, F42A and N88R; R38D, F42A and N88T; R38D, F42A and N88D; R38D, F42A and V91E; R38D, F42A, and D84H; R38D, F42A, and D84K; R38D, F42A, and D84R; H16D, R38D and F42A; H16E, R38D and F42A; R38D, F42A and Q126S; R38A, F42K, and N88S; R38A, F42K, and N88A; R38A, F42K, and N88G; R38A, F42K, and N88R; R38A, F42K, and N88T; R38A, F42K, and N88D; R38A, F42K, and V91E; R38A, F42K, and D84H; R38A, F42K, and D84K; R38A, F42K, and D84R; H16D, R38A, and F42K; H16E, R38A, and F42K; R38A, F42K, and Q126S; F42A, E62Q, and N88S; F42A, E62Q, and N88A; F42A, E62Q, and N88G; F42A, E62Q, and N88R; F42A, E62Q, and N88T; F42A, E62Q, and N88D; F42A, E62Q, and V91E; F42A, E62Q, and D84H; F42A, E62Q, and D84K; and F42A, E62Q, and D84R.

In some embodiments, the IL-2 polypeptide comprises the sequence of SEQ ID NO:81 with a further amino acid substitution relative to SEQ ID NO:81 at position C125. In some embodiments, the IL-2 polypeptide comprises the sequence of SEQ ID NO:81 with one of the following sets of amino acid substitutions (relative to the sequence of SEQ ID NO:81): R38E, F42A, and C125A; R38D, F42A, and C125A; F42A, E62Q, and C125A; R38A, F42K, and C125A; R38E, F42A, N88S, and C125A; R38E, F42A, N88A, and C125A; R38E, F42A, N88G, and C125A; R38E, F42A, N88R, and C125A; R38E, F42A, N88D, and C125A; R38E, F42A, N88T, and C125A; R38E, F42A, V91E, and C125A; R38E, F42A, D84H, and C125A; R38E, F42A, D84K, and C125A; R38E, F42A, D84R, and C125A; H16D, R38E, F42A, and C125A; H16E, R38E, F42A, and C125A; R38E, F42A, C125A and Q126S; R38D, F42A, N88S, and C125A; R38D, F42A, N88A, and C125A; R38D, F42A, N88G, and C125A; R38D, F42A, N88R, and C125A; R38D, F42A, N88T, and C125A; R38D, F42A, N88D, and C125A; R38D, F42A, V91E, and C125A; R38D, F42A, D84H, and C125A; R38D, F42A, D84K, and C125A; R38D, F42A, D84R, and C125A; H16D, R38D, F42A, and C125A; H16E, R38D, F42A, and C125A; R38D, F42A, C125A, and Q126S; R38A, F42K, N88S, and C125A; R38A, F42K, N88G, and C125A; R38A, F42K, N88R, and C125A; R38A, F42K, N88T, and C125A; R38A, F42K, N88D, and C125A; R38A, F42K, N88A, and C125A; R38A, F42K, V91E, and C125A; R38A, F42K, D84H, and C125A; R38A, F42K, D84K, and C125A; R38A, F42K, D84R, and C125A; H16D, R38A, F42K, and C125A; H16E, R38A, F42K, and C125A; R38A, F42K, C125A and Q126S; F42A, E62Q, N88S, and C125A; F42A, E62Q, N88A, and C125A; F42A, E62Q, N88G, and C125A; F42A, E62Q, N88R, and C125A; F42A, E62Q, N88T, and C125A; F42A, E62Q, N88D, and C125A; F42A, E62Q, V91E, and C125A; F42A, E62Q, and D84H, and C125A; F42A, E62Q, and D84K, and C125A; F42A, E62Q, and D84R, and C125A; H16D, F42A, and E62Q, and C125A; H16E, F42A, E62Q, and C125A; F42A, E62Q, C125A and Q126S; F42A, N88S, and C125A; F42A, N88A, and C125A; F42A, N88G, and C125A; F42A, N88R, and C125A; F42A, N88T, and C125A; F42A, N88D, and C125A; F42A, V91E, and C125A; F42A, D84H, and C125A; F42A, D84K, and C125A; F42A, D84R, and C125A; H16D, F42A, and C125A; H16E, F42A, and C125A; and F42A, C125A and Q126S.

In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISAIN-VIVLELKGSETTFMCEYADETATIVEFLNR WITFAQSIISTLT (SEQ ID NO:80). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:85). In some embodiments, the mutant IL-2 polypeptide comprises the amino acid sequence of APTSSSTKKTQLQLEHLLLDLQMILNGIN-NYKNPKLTDMLTAKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:86). In some embodiments, the mutant IL-2 polypeptide comprises the amino acid sequence of APTSSSTKKTQLQLEHLLLDLQMILNGIN-NYKNPKLTRMLTAKFYMPKKATELKHLQCL EEQLKPLEEVLNLAQSKNFHLRPRDLISNIN-VIVLELKGSETTFMCEYADETATIVEFLNR WITFCQSIISTLT (SEQ ID NO:87). In some embodiments, the mutant IL-2 polypeptide comprises the amino acid sequence of APTSSSTKKTQLQLEHLLLDLQMILNGIN-NYKNPKLTAMLTKKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:88). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISSIN-VIVLELKGSETTFMCEYADETATIVEFLNR WITFCQSIISTLT (SEQ ID NO:89). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISAIN-VIVLELKGSETTFMCEYADETATIVEFLNR WITFCQSIISTLT (SEQ ID NO:90). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISNI-NEIVLELKGSETTFMCEYADETATIVEFLNR WITFCQSIISTLT (SEQ ID NO:91). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRHLISNIN-VIVLELKGSETTFMCEYADETATIVEFLNR WITFCQSIISTLT (SEQ ID NO:92). In some embodiments, the mutant IL-2 polypeptide comprises the amino acid sequence of APTSSSTKKTQLQLEDLLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:93). In some embodiments, the mutant IL-2 polypeptide comprises the amino acid sequence of APTSSSTKKTQLQLEELLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:94). In some embodiments, the mutant IL-2 polypeptide comprises the amino acid sequence of APTSSSTKKTQLQLEHLLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFCSSIISTLT (SEQ ID NO:95). In some embodiments, the mutant IL-2 polypeptide comprises the amino acid sequence of APTSSSTKKTQLQLEHLLLDLQMILNGIN-NYKNPKLTDMLTAKFYMPKKATELKHLQCL EEELKPLEEVLNLAQSKNFHLRPRDLISSIN-VIVLELKGSETTFMCEYADETATIVEFLNR WITFCQSIISTLT (SEQ ID NO:96). In some embodiments, the mutant IL-2 polypeptide comprises the amino acid sequence of APTSSSTKKTQLQLEHLLLDLQMILNGIN-NYKNPKLTDMLTAKFYMPKKATELKHLQCL EEELKPLEEVLNLAQSKNFHLRPRDLISAIN-VIVLELKGSETTFMCEYADETATIVEFLNR WITFCQSIISTLT (SEQ ID NO:97). In some embodiments, the mutant IL-2 polypeptide comprises the amino acid sequence of APTSSSTKKTQLQLEHLLLDLQMILNGIN-NYKNPKLTDMLTAKFYMPKKATELKHLQCL EEELKPLEEVLNLAQSKNFHLRPRDLISNI-NEIVLELKGSETTFMCEYADETATIVEFLNR WITFCQSIISTLT (SEQ ID NO:98). In some embodiments, the mutant IL-2 polypeptide comprises the amino acid sequence of APTSSSTKKTQLQLEHLLLDLQMILNGIN-NYKNPKLTDMLTAKFYMPKKATELKHLQCL EEELKPLEEVLNLAQSKNFHLRPRHLISNIN-VIVLELKGSETTFMCEYADETATIVEFLNR WITFCQSIISTLT (SEQ ID NO:99). In some embodiments, the mutant IL-2 polypeptide comprises the amino acid sequence of APTSSSTKKTQLQLEDLLLDLQMILNGIN-NYKNPKLTDMLTAKFYMPKKATELKHLQCL EEELKPLEEVLNLAQSKNFHLRPRDLISNIN-VIVLELKGSETTFMCEYADETATIVEFLNR WITFCQSIISTLT (SEQ ID NO:100). In some embodiments, the mutant IL-2 polypeptide comprises the amino acid sequence of APTSSSTKKTQLQLEELLLD-LQMILNGINNYKNPKLTDMLTAKFYMPK-KATELKHLQCL EEELKPLEEVLNLAQSKNFHLR-PRDLISNINVIVLELKGSETTFMCEYADETATIVEFLNR WITFCQSIISTLT (SEQ ID NO:101). In some embodiments, the mutant IL-2 polypeptide comprises the amino acid sequence of APTSSSTKKTQLQLEHLLLD- LQMILNGINNYKNPKLTDMLTAKFYMPK-KATELKHLQCL EEELKPLEEVLNLAQSKNFHLR-PRDLISNINVIVLELKGSETTFMCEYADETATIVEFLNR WITFCSSIISTLT (SEQ ID NO:102). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLRPRD-LISSINVIVLELKGSETTFMCEYADETATIVEFLNR WITFCQSIISTLT (SEQ ID NO:103). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISAINVIVLELKGSETTFMCEYADETATIVEFLNR WITFCQSIISTLT (SEQ ID NO:104). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISNINEIVLELKGSETTFMCEYADETATIVEFLNR WITFCQSIISTLT (SEQ ID NO:105). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRHLISNINVIVLELKGSETTFMCEYADETATIVEFLNR WITFCQSIISTLT (SEQ ID NO:106). In some embodiments, the mutant IL-2 polypeptide comprises the amino acid sequence of APTSSSTKKTQLQLEDLLLD-LQMILNGINNYKNPKLTAMLTKKFYMPK-KATELKHLQCL EEELKPLEEVLNLAQSKNFHLR-PRDLISNINVIVLELKGSETTFMCEYADETATIVEFLNR WITFCQSIISTLT (SEQ ID NO:107). In some embodiments, the mutant IL-2 polypeptide comprises the amino acid sequence of APTSSSTKKTQLQLEELLLD-LQMILNGINNYKNPKLTAMLTKKFYMPK-KATELKHLQCL EEELKPLEEVLNLAQSKNFHLR-PRDLISNINVIVLELKGSETTFMCEYADETATIVEFLNR WITFCQSIISTLT (SEQ ID NO:108). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISNINVIVLELKGSETTFMCEYADETATIVEFLNR WITFCSSIISTLT (SEQ ID NO:109). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLRPRD-LISSINVIVLELKGSETTFMCEYADETATIVEFLNR WITFCQSIISTLT (SEQ ID NO:110). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISAINVIVLELKGSETTFMCEYADETATIVEFLNR WITFCQSIISTLT (SEQ ID NO:111). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISNINEIVLELKGSETTFMCEYADETATIVEFLNR WITFCQSIISTLT (SEQ ID NO: 112). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRHLISNINVIVLELKGSETTFMCEYADETATIVEFLNR WITFCQSIISTLT (SEQ ID NO: 113). In some embodiments, the mutant IL-2 polypeptide comprises the amino acid sequence of APTSSSTKKTQLQLEDLLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFCQSIISTLT (SEQ ID NO:114). In some embodiments, the mutant IL-2 polypeptide comprises the amino acid sequence of APTSSSTKKTQLQLEELLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFCQSIISTLT (SEQ ID NO: 115). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFCSSIISTLT (SEQ ID NO: 116). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO: 117). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO:118). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFAQSIISTLT (SEQ ID NO: 119). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO:120). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLRPRD-LISSINVIVLELKGSETTFMCEYADETATIVEFLNR WITFAQSIISTLT (SEQ ID NO:121). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISAINVIVLELKGSETTFMCEYADETATIVEFLNR WITFAQSIISTLT (SEQ ID NO:122). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISNINEIVLELKGSETTFMCEYADETATIVEFLNR WITFAQSIISTLT (SEQ ID NO:123). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR- PRHLISNINVIVLELKGSETTFMCEYADETATIVEFLNRWITFAQSIISTLT (SEQ ID NO:124). In some embodiments, the mutant IL-2 polypeptide comprises the amino acid sequence of APTSSSTKKTQLQLEDLLLDLQMILNGINNYKNPKLTEMLTAKFYMPKKATELKHLQCL EEELKPLEEVLNLAQSKNFHLRPRDLISNINVIVLELKGSETTFMCEYADETATIVEFLNRWITFAQSIISTLT (SEQ ID NO:125). In some embodiments, the mutant IL-2 polypeptide comprises the amino acid sequence of APTSSSTKKTQLQLEELLLDLQMILNGINNYKNPKLTEMLTAKFYMPKKATELKHLQCL EEELKPLEEVLNLAQSKNFHLRPRDLISNINVIVLELKGSETTFMCEYADETATIVEFLNRWITFAQSIISTLT (SEQ ID NO:126). In some embodiments, the mutant IL-2 polypeptide comprises the amino acid sequence of APTSSSTKKTQLQLEHLLLDLQMILNGINNYKNPKLTEMLTAKFYMPKKATELKHLQCL EEELKPLEEVLNLAQSKNFHLRPRDLISNINVIVLELKGSETTFMCEYADETATIVEFLNRWITFASSIISTLT (SEQ ID NO:127). In some embodiments, the mutant IL-2 polypeptide comprises the amino acid sequence of APTSSSTKKTQLQLEHLLLDLQMILNGINNYKNPKLTDMLTAKFYMPKKATELKHLQCL EEELKPLEEVLNLAQSKNFHLRPRDLISSINVIVLELKGSETTFMCEYADETATIVEFLNRWITFAQSIISTLT (SEQ ID NO:128). In some embodiments, the mutant IL-2 polypeptide comprises the amino acid sequence of APTSSSTKKTQLQLEHLLLDLQMILNGINNYKNPKLTDMLTAKFYMPKKATELKHLQCL EEELKPLEEVLNLAQSKNFHLRPRDLISAINVIVLELKGSETTFMCEYADETATIVEFLNRWITFAQSIISTLT (SEQ ID NO:129). In some embodiments, the mutant IL-2 polypeptide comprises the amino acid sequence of APTSSSTKKTQLQLEHLLLDLQMILNGINNYKNPKLTDMLTAKFYMPKKATELKHLQCL EEELKPLEEVLNLAQSKNFHLRPRDLISNINEIVLELKGSETTFMCEYADETATIVEFLNRWITFAQSIISTLT (SEQ ID NO:130). In some embodiments, the mutant IL-2 polypeptide comprises the amino acid sequence of APTSSSTKKTQLQLEHLLLDLQMILNGINNYKNPKLTDMLTAKFYMPKKATELKHLQCL EEELKPLEEVLNLAQSKNFHLRPRHLISNINVIVLELKGSETTFMCEYADETATIVEFLNRWITFAQSIISTLT (SEQ ID NO:131). In some embodiments, the mutant IL-2 polypeptide comprises the amino acid sequence of APTSSSTKKTQLQLEDLLLDLQMILNGINNYKNPKLTDMLTAKFYMPKKATELKHLQCL EEELKPLEEVLNLAQSKNFHLRPRDLISNINVIVLELKGSETTFMCEYADETATIVEFLNRWITFAQSIISTLT (SEQ ID NO:132). In some embodiments, the mutant IL-2 polypeptide comprises the amino acid sequence of APTSSSTKKTQLQLEELLLDLQMILNGINNYKNPKLTDMLTAKFYMPKKATELKHLQCL EEELKPLEEVLNLAQSKNFHLRPRDLISNINVIVLELKGSETTFMCEYADETATIVEFLNRWITFAQSIISTLT (SEQ ID NO:133). In some embodiments, the mutant IL-2 polypeptide comprises the amino acid sequence of APTSSSTKKTQLQLEHLLLDLQMILNGINNYKNPKLTDMLTAKFYMPKKATELKHLQCL EEELKPLEEVLNLAQSKNFHLRPRDLISNINVIVLELKGSETTFMCEYADETATIVEFLNRWITFASSIISTLT (SEQ ID NO:134). In some embodiments, the mutant IL-2 polypeptide comprises the amino acid sequence of APTSSSTKKTQLQLEHLLLDLQMILNGINNYKNPKLTAMLTKKFYMPKKATELKHLQCL EEELKPLEEVLNLAQSKNFHLRPRDLISSINVIVLELKGSETTFMCEYADETATIVEFLNRWITFAQSIISTLT (SEQ ID NO:135). In some embodiments, the mutant IL-2 polypeptide comprises the amino acid sequence of APTSSSTKKTQLQLEHLLLDLQMILNGINNYKNPKLTAMLTKKFYMPKKATELKHLQCL EEELKPLEEVLNLAQSKNFHLRPRDLISAINVIVLELKGSETTFMCEYADETATIVEFLNRWITFAQSIISTLT (SEQ ID NO:136). In some embodiments, the mutant IL-2 polypeptide comprises the amino acid sequence of APTSSSTKKTQLQLEHLLLDLQMILNGINNYKNPKLTAMLTKKFYMPKKATELKHLQCL EEELKPLEEVLNLAQSKNFHLRPRDLISNINEIVLELKGSETTFMCEYADETATIVEFLNRWITFAQSIISTLT (SEQ ID NO:137). In some embodiments, the mutant IL-2 polypeptide comprises the amino acid sequence of APTSSSTKKTQLQLEHLLLDLQMILNGINNYKNPKLTAMLTKKFYMPKKATELKHLQCL EEELKPLEEVLNLAQSKNFHLRPRHLISNINVIVLELKGSETTFMCEYADETATIVEFLNRWITFAQSIISTLT (SEQ ID NO:138). In some embodiments, the mutant IL-2 polypeptide comprises the amino acid sequence of APTSSSTKKTQLQLEDLLLDLQMILNGINNYKNPKLTAMLTKKFYMPKKATELKHLQCL EEELKPLEEVLNLAQSKNFHLRPRDLISNINVIVLELKGSETTFMCEYADETATIVEFLNRWITFAQSIISTLT (SEQ ID NO:139). In some embodiments, the mutant IL-2 polypeptide comprises the amino acid sequence of APTSSSTKKTQLQLEELLLDLQMILNGINNYKNPKLTAMLTKKFYMPKKATELKHLQCL EEELKPLEEVLNLAQSKNFHLRPRDLISNINVIVLELKGSETTFMCEYADETATIVEFLNRWITFAQSIISTLT (SEQ ID NO:140). In some embodiments, the mutant IL-2 polypeptide comprises the amino acid sequence of APTSSSTKKTQLQLEHLLLDLQMILNGINNYKNPKLTAMLTKKFYMPKKATELKHLQCL EEELKPLEEVLNLAQSKNFHLRPRDLISNINVIVLELKGSETTFMCEYADETATIVEFLNRWITFASSIISTLT (SEQ ID NO:141). In some embodiments, the mutant IL-2 polypeptide comprises the amino acid sequence of APTSSSTKKTQLQLEHLLLDLQMILNGINNYKNPKLTRMLTAKFYMPKKATELKHLQCL EEQLKPLEEVLNLAQSKNFHLRPRDLISSINVIVLELKGSETTFMCEYADETATIVEFLNRWITFAQSIISTLT (SEQ ID NO:142). In some embodiments, the mutant IL-2 polypeptide comprises the amino acid sequence of APTSSSTKKTQLQLEHLLLDLQMILNGINNYKNPKLTRMLTAKFYMPKKATELKHLQCL EEQLKPLEEVLNLAQSKNFHLRPRDLISAINVIVLELKGSETTFMCEYADETATIVEFLNRWITFAQSIISTLT (SEQ ID NO:143). In some embodiments, the mutant IL-2 polypeptide comprises the amino acid sequence of APTSSSTKKTQLQLEHLLLDLQMILNGINNYKNPKLTRMLTAKFYMPKKATELKHLQCL EEQLKPLEEVLNLAQSKNFHLRPRDLISNINEIVLELKGSETTFMCEYADETATIVEFLNRWITFAQSIISTLT (SEQ ID NO:144). In some embodiments, the mutant IL-2 polypeptide comprises the amino acid sequence of APTSSSTKKTQLQLEHLLLDLQMILNGINNYKNPKLTRMLTAKFYMPKKATELKHLQCL EEQLKPLEEVLNLAQSKNFHLRPRHLISNINVIVLELKGSETTFMCEYADETATIVEFLNRWITFAQSIISTLT (SEQ ID NO:145). In some embodiments, the mutant IL-2 polypeptide comprises the amino acid sequence of APTSSSTKKTQLQLEDLLLDLQMILNGINNYKNPKLTRMLTAKFYMPKKATELKHLQCL EEQLKPLEEVLNLAQSKNFHLRPRDLISNINVIVLELKGSETTFMCEYADETATIVEFLNRWITFAQSIISTLT (SEQ ID NO:146). In some embodiments, the mutant IL-2 polypeptide comprises the amino acid sequence of APTSSSTKKTQLQLEELLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFAQSIISTLT (SEQ ID NO:147). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISNINVIVLELKGSETTFMCEYADETATIVEFLNR WITFASSIISTLT (SEQ ID NO:148). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLRPRD-LISSINVIVLELKGSETTFMCEYADETATIVEFLNR WITFAQSIISTLT (SEQ ID NO:149). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISAINVIVLELKGSETTFMCEYADETATIVEFLNR WITFAQSIISTLT (SEQ ID NO:150). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISNINEIVLELKGSETTFMCEYADETATIVEFLNR WITFAQSIISTLT (SEQ ID NO:151). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRHLISNINVIVLELKGSETTFMCEYADETATIVEFLNR WITFAQSIISTLT (SEQ ID NO:152). In some embodiments, the mutant IL-2 polypeptide comprises the amino acid sequence of APTSSSTKKTQLQLEDLLLD-LQMILNGINNYKNPKLTRMLTAKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO:153). In some embodiments, the mutant IL-2 polypeptide comprises the amino acid sequence of APTSSSTKKTQLQLEELLLD-LQMILNGINNYKNPKLTRMLTAKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO:154). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISNINVIVLELKGSETTFMCEYADETATIVEFLNR WITFASSIISTLT (SEQ ID NO:155). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISGINVIVLELKGSETTFMCEYADETATIVEFLNR WITFCQSIISTLT (SEQ ID NO:190). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRKLISNINVIVLELKGSETTFMCEYADETATIVEFLNR WITFCQSIISTLT (SEQ ID NO:191). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRRLISNINVIVLELKGSETTFMCEYADETATIVEFLNR WITFCQSIISTLT (SEQ ID NO:192). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISGINVIVLELKGSETTFMCEYADETATIVEFLNR WITFCQSIISTLT (SEQ ID NO:193). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRKLISNINVIVLELKGSETTFMCEYADETATIVEFLNR WITFCQSIISTLT (SEQ ID NO:194). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRRLISNINVIVLELKGSETTFMCEYADETATIVEFLNR WITFCQSIISTLT (SEQ ID NO:195). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISGINVIVLELKGSETTFMCEYADETATIVEFLNR WITFCQSIISTLT (SEQ ID NO:196). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRKLISNINVIVLELKGSETTFMCEYADETATIVEFLNR WITFCQSIISTLT (SEQ ID NO:197). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRRLISNINVIVLELKGSETTFMCEYADETATIVEFLNR WITFCQSIISTLT (SEQ ID NO:198). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISGINVIVLELKGSETTFMCEYADETATIVEFLNR WITFCQSIISTLT (SEQ ID NO:199). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRKLISNINVIVLELKGSETTFMCEYADETATIVEFLNR WITFCQSIISTLT (SEQ ID NO:200). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRRLISNINVIVLELKGSETTFMCEYADETATIVEFLNR WITFCQSIISTLT (SEQ ID NO:201). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISGINVIVLELKGSETTFMCEYADETATIVEFLNR WITFAQSIISTLT (SEQ ID NO:202). In some embodiments, the mutant IL-2 polypeptide comprises the amino acid sequence of APTSSSTKKTQLQLEHLLLD- LQMILNGINNYKNPKLTEMLTAKFYMPK-KATELKHLQCL EEELKPLEEVLNLAQSKNFHLR-PRKLISNINVIVLELKGSETTFMCEYADETATIVEFLNR WITFAQSIISTLT (SEQ ID NO:203). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRRLISNINVIVLELKGSETTFMCEYADETATIVEFLNR WITFAQSIISTLT (SEQ ID NO:204). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISGINVIVLELKGSETTFMCEYADETATIVEFLNR WITFAQSIISTLT (SEQ ID NO:205). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRKLISNINVIVLELKGSETTFMCEYADETATIVEFLNR WITFAQSIISTLT (SEQ ID NO:206). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRRLISNINVIVLELKGSETTFMCEYADETATIVEFLNR WITFAQSIISTLT (SEQ ID NO:207). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISGINVIVLELKGSETTFMCEYADETATIVEFLNR WITFAQSIISTLT (SEQ ID NO:208). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRKLISNINVIVLELKGSETTFMCEYADETATIVEFLNR WITFAQSIISTLT (SEQ ID NO:209). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRRLISNINVIVLELKGSETTFMCEYADETATIVEFLNR WITFAQSIISTLT (SEQ ID NO:210). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISGINVIVLELKGSETTFMCEYADETATIVEFLNR WITFAQSIISTLT (SEQ ID NO:211). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRKLISNINVIVLELKGSETTFMCEYADETATIVEFLNR WITFAQSIISTLT (SEQ ID NO:212). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRRLISNINVIVLELKGSETTFMCEYADETATIVEFLNR WITFAQSIISTLT (SEQ ID NO:213). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISGINVIVLELKGSETTFMCEYADETATIVEFLNR WITFAQSIISTLT (SEQ ID NO:214). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRKLISNINVIVLELKGSETTFMCEYADETATIVEFLNR WITFAQSIISTLT (SEQ ID NO:215). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRRLISNINVIVLELKGSETTFMCEYADETATIVEFLNR WITFAQSIISTLT (SEQ ID NO:216). In some embodiments, the mutant IL-2 polypeptide comprises the amino acid sequence of APTSSSTKKTQLQLEELLLD-LQMILNGINNYKNPKLTEMLTAKFYMPK-KATELKHLQCL EEELKPLEEVLNLAQSKNFHLR-PRDLISNINVIVLELKGSETTFMCEYADETATIVEFLNR WITFAQSIISTLT (SEQ ID NO:297). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISDINVIVLELKGSETTFMCEYADETATIVEFLNR WITFAQSIISTLT (SEQ ID NO:354). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLRPRD-LISTINVIVLELKGSETTFMCEYADETATIVEFLNR WITFAQSIISTLT (SEQ ID NO:355). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISRINVIVLELKGSETTFMCEYADETATIVEFLNR WITFAQSIISTLT (SEQ ID NO:356). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISRINVIVLELKGSETTFMCEYADETATIVEFLNR WITFCQSIISTLT (SEQ ID NO:357). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLRPRD-LISTINVIVLELKGSETTFMCEYADETATIVEFLNR WITFCQSIISTLT (SEQ ID NO:358). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISDINVIVLELKGSETTFMCEYADETATIVEFLNR WITFCQSIISTLT (SEQ ID NO:359). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISRINVIVLELKGSETTFMCEYADETATIVEFLNR WITFCQSIISTLT (SEQ ID NO:360). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLRPRD- LISTINVIVLELKGSETTFMCEYADETATIVEFLNR WITFCQSIISTLT (SEQ ID NO:361). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISDINVIVLELKGSETTFMCEYADETATIVEFLNR WITFCQSIISTLT (SEQ ID NO:362). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISRINVIVLELKGSETTFMCEYADETATIVEFLNR WITFCQSIISTLT (SEQ ID NO:363). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLRPRD-LISTINVIVLELKGSETTFMCEYADETATIVEFLNR WITFCQSIISTLT (SEQ ID NO:364). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISDINVIVLELKGSETTFMCEYADETATIVEFLNR WITFCQSIISTLT (SEQ ID NO:365). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISRINVIVLELKGSETTFMCEYADETATIVEFLNR WITFCQSIISTLT (SEQ ID NO:366). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLRPRD-LISTINVIVLELKGSETTFMCEYADETATIVEFLNR WITFCQSIISTLT (SEQ ID NO:367). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISDINVIVLELKGSETTFMCEYADETATIVEFLNR WITFCQSIISTLT (SEQ ID NO:368). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISRINVIVLELKGSETTFMCEYADETATIVEFLNR WITFAQSIISTLT (SEQ ID NO:369). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLRPRD-LISTINVIVLELKGSETTFMCEYADETATIVEFLNR WITFAQSIISTLT (SEQ ID NO:370). In some embodiments, the mutant IL-2 polypeptide comprises the amino acid sequence of APTSSSTKKTQLQLEHLLLD-LQMILNGINNYKNPKLTEMLTAKFYMPK-KATELKHLQCL EEELKPLEEVLNLAQSKNFHLR-PRDLISDINVIVLELKGSETTFMCEYADETATIVEFLNR WITFAQSIISTLT (SEQ ID NO:371). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISRINVIVLELKGSETTFMCEYADETATIVEFLNR WITFAQSIISTLT (SEQ ID NO:372). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLRPRD-LISTINVIVLELKGSETTFMCEYADETATIVEFLNR WITFAQSIISTLT (SEQ ID NO:373). In some embodiments, the mutant IL-2 polypeptide comprises the amino acid sequence of APTSSSTKKTQLQLEHLLLD-LQMILNGINNYKNPKLTDMLTAKFYMPK-KATELKHLQCL EEELKPLEEVLNLAQSKNFHLR-PRDLISDINVIVLELKGSETTFMCEYADETATIVEFLNR WITFAQSIISTLT (SEQ ID NO:374). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISRINVIVLELKGSETTFMCEYADETATIVEFLNR WITFAQSIISTLT (SEQ ID NO:375). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLRPRD-LISTINVIVLELKGSETTFMCEYADETATIVEFLNR WITFAQSIISTLT (SEQ ID NO:376). In some embodiments, the mutant IL-2 polypeptide comprises the amino acid sequence of APTSSSTKKTQLQLEHLLLD-LQMILNGINNYKNPKLTAMLTKKFYMPK-KATELKHLQCL EEELKPLEEVLNLAQSKNFHLR-PRDLISDINVIVLELKGSETTFMCEYADETATIVEFLNR WITFAQSIISTLT (SEQ ID NO:377). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISRINVIVLELKGSETTFMCEYADETATIVEFLNR WITFAQSIISTLT (SEQ ID NO:378). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLRPRD-LISTINVIVLELKGSETTFMCEYADETATIVEFLNR WITFAQSIISTLT (SEQ ID NO:379). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEQLKPLEEVLNLAQSKNFHLR-PRDLISDINVIVLELKGSETTFMCEYADETATIVEFLNR WITFAQSIISTLT (SEQ ID NO:380). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISRINVIVLELKGSETTFMCEYADETATIVEFLNR WITFAQSIISTLT (SEQ ID NO:381). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLRPRD-LISTINVIVLELKGSETTFMCEYADETATIVEFLNR WITFAQSIISTLT (SEQ ID NO:382). In some embodiments, the mutant IL-2 polypeptide comprises the amino acid sequence of APTSSSTKKTQLQLEHLLLD-LQMILNGINNYKNPKLTRMLTAKFYMPK-KATELKHLQCL EEELKPLEEVLNLAQSKNFHLR-PRDLISDINVIVLELKGSETTFMCEYADETATIVEFLNR WITFAQSIISTLT (SEQ ID NO:383). In some embodiments, the mutant IL-2 polypeptide comprises the amino acid sequence of an IL-2 polypeptide listed in Table 7.

TABLE 7

Exemplary IL-2 polypeptide sequences

| IL-2 ID | Sequence | SEQ ID NO |
|---|---|---|
| m1 | APTSSSTKKTQLQLEHLLLDLQMILNGINNYKNPKLTEMLTAKFYMPKKATEL KHLQCLEEELKPLEEVLNLAQSKNFHLRPRDLISAINVIVLELKGSETTFMCEYA DETATIVEFLNRWITFAQSIISTLT | 80 |
| m2 | APTSSSTKKTQLQLEHLLLDLQMILNGINNYKNPKLTEMLTAKFYMPKKATEL KHLQCLEEELKPLEEVLNLAQSKNFHLRPRDLISSINVIVLELKGSETTFMCEYA DETATIVEFLNRWITFAQSIISTLT | 121 |
| m3 | APTSSSTKKTQLQLEDLLLDLQMILNGINNYKNPKLTEMLTAKFYMPKKATEL KHLQCLEEELKPLEEVLNLAQSKNFHLRPRDLISNINVIVLELKGSETTFMCEYA DETATIVEFLNRWITFAQSIISTLT | 125 |
| m4 | APTSSSTKKTQLQLEELLLDLQMILNGINNYKNPKLTEMLTAKFYMPKKATELK HLQCLEEELKPLEEVLNLAQSKNFHLRPRDLISNINVIVLELKGSETTFMCEYAD ETATIVEFLNRWITFAQSIISTLT | 297 |
| m5 | APTSSSTKKTQLQLEHLLLDLQMILNGINNYKNPKLTEMLTAKFYMPKKATEL KHLQCLEEELKPLEEVLNLAQSKNFHLRPRDLISGINVIVLELKGSETTFMCEYA DETATIVEFLNRWITFAQSIISTLT | 202 |
| m6 | APTSSSTKKTQLQLEHLLLDLQMILNGINNYKNPKLTEMLTAKFYMPKKATEL KHLQCLEEELKPLEEVLNLAQSKNFHLRPRDLISNINVIVLELKGSETTFMCEYA DETATIVEFLNRWITFAQSIISTLT | 117 |
| m7 | APTSSSTKKTQLQLEHLLLDLQMILNGINNYKNPKLTEMLTAKFYMPKKATEL KHLQCLEEELKPLEEVLNLAQSKNFHLRPRDLISNINEIVLELKGSETTFMCEYA DETATIVEFLNRWITFAQSIISTLT | 123 |
| m8 | APTSSSTKKTQLQLEHLLLDLQMILNGINNYKNPKLTEMLTAKFYMPKKATEL KHLQCLEEELKPLEEVLNLAQSKNFHLRPRHLISNINVIVLELKGSETTFMCEYA DETATIVEFLNRWITFAQSIISTLT | 124 |
| m9 | APTSSSTKKTQLQLEHLLLDLQMILNGINNYKNPKLTEMLTAKFYMPKKATEL KHLQCLEEELKPLEEVLNLAQSKNFHLRPRKLISNINVIVLELKGSETTFMCEYA DETATIVEFLNRWITFAQSIISTLT | 203 |
| m10 | APTSSSTKKTQLQLEHLLLDLQMILNGINNYKNPKLTEMLTAKFYMPKKATEL KHLQCLEEELKPLEEVLNLAQSKNFHLRPRRLISNINVIVLELKGSETTFMCEYA DETATIVEFLNRWITFAQSIISTLT | 204 |
| m11 | APTSSSTKKTQLQLEHLLLDLQMILNGINNYKNPKLTEMLTAKFYMPKKATEL KHLQCLEEELKPLEEVLNLAQSKNFHLRPRDLISDINVIVLELKGSETTFMCEYA DETATIVEFLNRWITFAQSIISTLT | 354 |
| m12 | APTSSSTKKTQLQLEHLLLDLQMILNGINNYKNPKLTEMLTAKFYMPKKATEL KHLQCLEEELKPLEEVLNLAQSKNFHLRPRDLISTINVIVLELKGSETTFMCEYA DETATIVEFLNRWITFAQSIISTLT | 355 |
| m13 | APTSSSTKKTQLQLEHLLLDLQMILNGINNYKNPKLTEMLTAKFYMPKKATEL KHLQCLEEELKPLEEVLNLAQSKNFHLRPRDLISRINVIVLELKGSETTFMCEYA DETATIVEFLNRWITFAQSIISTLT | 356 |

In some embodiments, the mutant IL-2 polypeptides of the present disclosure also contain other modifications, including but not limited to mutations and deletions, that provide additional advantages such as improved biophysical properties. Improved biophysical properties include but are not limited to improved thermostability, aggregation propensity, acid reversibility, viscosity, and production in a mammalian or bacterial or yeast cell. For example, residue C125 may be replaced with a neutral amino acid such as serine, alanine, threonine or valine; and N terminal A1 residue could be deleted, both of which were described in U.S. Pat. No. 4,518,584. Mutant IL-2 polypeptides may also include a mutation of the residue M104, such as M104A, as described in U.S. Pat. No. 5,206,344. Thus, in certain embodiments the mutant IL-2 polypeptide of the present disclosure comprises the amino acid substitution C125A. In other embodiments, one, two, or three N-terminal residues are deleted.

Fusion Protein Linkers

In some embodiments, a fusion protein of the present disclosure comprises a linker. In some embodiments, the linker is a chemical linker (for example, see disclosed in Protein Engineering, 9(3), 299-305, 1996). Synthetic chemical linkers include crosslinking agents that are routinely used to crosslink peptides, for example, N-hydroxy succinimide (NHS), disuccinimidyl suberate (DSS), bis(succinimidyl) suberate (BS3), dithiobis(succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis[2-(succinimidoxycarbonyloxy)ethyl] sulfone (sulfo-BSOCOES).

In some embodiments, the linker is an amino acid- or peptide-based linker. In some embodiments, the polypeptide linker is a peptide with a length of at least 5 amino acids, preferably with a length of 5 to 100, more preferably of 10 to 50 amino acids. In one embodiment, said peptide linker is G, S, GS, SG, SGG, GGS, and GSG (with G=glycine and S=serine). In some embodiments, the linker comprises the sequence (GGGS)xGn (SEQ ID NO:74), (GGGGS)xGn (SEQ ID NO:75), (GGGGGS)xGn (SEQ ID NO:76), S(GGGS)xGn (SEQ ID NO:386), S(GGGGS)xGn (SEQ ID NO:387), or S(GGGGGS)xGn (SEQ ID NO:388), wherein x=1, 2, 3, 4, 5, 6, 7, 8, 9, 10, 11, or 12, and wherein n=0, 1, 2 or 3. In some embodiments, the linker comprises the sequence GGGGSGGGGSGGGGS (SEQ ID NO:79) or SGGGGSGGGGSGGGGS (SEQ ID NO:389).

Fusion Protein Properties

In some embodiments, the fusion protein induces activation of cells expressing a human CD8ab heterodimer with at least 2-fold, at least 5-fold, or at least 10-fold higher potency than activation of cells expressing a human CD8aa homodimer. In some embodiments, the fusion protein induces activation of CD8+ T cells with at least 2-fold, at least 5-fold, or at least 10-fold higher potency than activation of NK cells. In some embodiments, potency of activation is measured by EC50, as assessed by cell proliferation. Exemplary assays are further described infra.

Preferential activity of the targeted IL-2 fusion proteins comprising the mutant IL-2 polypeptides on antigen-expressing cells is demonstrated in assays that contain antigen-expressing and antigen-non expressing cells that also express IL-2Rβγ or IL-2Rαβγ. One such assay is an in vitro assay that measures STAT5 (pSTAT5) phosphorylation and/or expression of the proliferation marker Ki-67 in human immune cells, such as human peripheral blood and/or tumor-infiltrating immune cells upon exposure to IL-2 polypeptides. In one format of the assay, the activity of the targeted IL-2 fusion protein is measured on antigen-expressing and non-expressing cells to demonstrate the selectivity on antigen-expressing cells. In another format of the assay, the activity of the targeted IL-2 fusion protein comprising the mutant IL-2 polypeptide on antigen-expressing cells is compared to that of the untargeted IL-2 fusion protein comprising the same mutant IL-2 polypeptide and a control antibody not recognizing any antigens on antigen-expressing cells to demonstrate the magnitude of rescue in signaling of the mutant IL-2 polypeptide when fused to an antigen binding molecule.

In some embodiments, the fusion protein of the present disclosure containing CD8b antigen binding molecules activates CD8b+ IL-2Rβ+ cells over CD8b− IL-2Rβ+ cells by at least 10-fold, at least 50-fold, or at least 100-fold. In some embodiments, said fusion protein activates CD8b+ IL-2Rβ+ cells more than 50-fold, 100 fold, or 200 fold compared to a fusion molecule comprising the said IL-2 mutant polypeptide and a control antibody not binding to any antigens expressed on said cells. Said cell activation by the IL-2 fusion protein is determined by measuring the expression of pSTAT5 or the cell proliferation marker Ki67 in said cells following the treatment with said IL-2 fusion protein.

In some embodiments, a fusion protein of the present disclosure displays one or more of the following: binds human CD8 and does not block an interaction of CD8 with MHC class I; and activates CD8+ T cells with at least 10-fold, 25-fold, 50-fold, 100-fold, 250-fold, 500-fold, or 1000-fold greater potency, e.g., as compared to activation of NK cells. In some embodiments, whether an anti-CD8 antibody or fusion protein of the present disclosure blocks the interaction of CD8 with MHC class I can be assayed, e.g., by assaying activation status of CD8+ T cells (e.g., upon antigen stimulation) in the presence or absence of the anti-CD8 antibody or fusion protein. In some embodiments, activation of CD8+ T cells and/or NK cells can be measured, e.g., by assaying one or more markers (e.g., proportion of treated cells expressing one or more markers) of proliferation (e.g., Ki67), IL-2Rβ/γ downstream signaling, and/or STAT5 downstream signaling.

Exemplary Fusion Proteins

In some embodiments, a fusion protein of the present disclosure comprises one, two, or all three polypeptides shown for a single fusion protein in Table 5. In some embodiments, a fusion protein of the present disclosure comprises two light chains, a heavy chain comprising an IL-2 fusion, and a heavy chain not comprising an IL-2 fusion for a single fusion protein in Table 5. As is known in the art, the C-terminal lysine of some antibody heavy chain species may be cleaved off in some fraction of molecules. Therefore, in some embodiments, a fusion protein of the present disclosure comprises two light chains, a heavy chain comprising an IL-2 fusion, and a heavy chain not comprising an IL-2 fusion for a single fusion protein in Table 5, wherein the heavy chain not comprising the IL-2 fusion comprises the sequence of SEQ ID Nos:158, 161, 164, 167, 170, 173, 176, 189, 300, 304, 308, 312, 326, 320, 324, 328, 332, 336, 340, 344, 348, or 352 for the respective fusion protein. In some embodiments, a fusion protein of the present disclosure comprises two light chains, a heavy chain comprising an IL-2 fusion, and a heavy chain not comprising an IL-2 fusion for a single fusion protein in Table 5, wherein the heavy chain not comprising the IL-2 fusion comprises the sequence of SEQ ID Nos:217-224, 301, 305, 309, 313, 317, 321, 325, 329, 333, 337, 341, 345, 349, or 353 for the respective fusion protein. In some embodiments, the present disclosure provides a plurality of fusion proteins of the present disclosure (e.g., in a mixture), wherein each fusion protein of the plurality comprises two light chains, a heavy chain comprising an IL-2 fusion, and a heavy chain not comprising an IL-2 fusion for a single fusion protein in Table 5, wherein the heavy chain not comprising the IL-2 fusion comprises the sequence of SEQ ID Nos:158, 161, 164, 167, 170, 173, 176, 189, 300, 304, 308, 312, 326, 320, 324, 328, 332, 336, 340, 344, 348, or 352 for the respective fusion protein, or the sequence of SEQ ID Nos:217-224, 301, 305, 309, 313, 317, 321, 325, 329, 333, 337, 341, 345, 349, or 353 for the respective fusion protein, or the plurality comprises a mixture of species representing cleaved (e.g., comprising the sequence of SEQ ID Nos:158, 161, 164, 167, 170, 173, 176, 189, 300, 304, 308, 312, 326, 320, 324, 328, 332, 336, 340, 344, 348, or 352 for the respective fusion protein) and uncleaved (e.g., comprising the sequence of SEQ ID Nos: 217-224, 301, 305, 309, 313, 317, 321, 325, 329, 333, 337, 341, 345, 349, or 353 for the respective fusion protein) species.

For example, in some embodiments, a fusion protein of the present disclosure comprises one or two light chains comprising the amino acid sequence of SEQ ID NO:156, a heavy chain comprising the amino acid sequence of SEQ ID NO:157, and a heavy chain comprising the amino acid sequence of SEQ ID NO:158. In some embodiments, a fusion protein of the present disclosure comprises one or two light chains comprising the amino acid sequence of SEQ ID NO:159, a heavy chain comprising the amino acid sequence of SEQ ID NO:160, and a heavy chain comprising the amino acid sequence of SEQ ID NO:161. In some embodiments, a fusion protein of the present disclosure comprises one or two light chains comprising the amino acid sequence of SEQ ID NO:162, a heavy chain comprising the amino acid sequence of SEQ ID NO:163, and a heavy chain comprising the amino acid sequence of SEQ ID NO:164. In some embodiments, a fusion protein of the present disclosure comprises one or two light chains comprising the amino acid sequence of SEQ ID NO:165, a heavy chain comprising the amino acid sequence of SEQ ID NO:166, and a heavy chain comprising the amino acid sequence of SEQ ID NO:167. In some embodiments, a fusion protein of the present disclosure comprises one or two light chains comprising the amino acid sequence of SEQ ID NO:168, a heavy chain comprising the amino acid sequence of SEQ ID NO:169, and a heavy chain comprising the amino acid sequence of SEQ ID NO:170. In some embodiments, a fusion protein of the present disclosure comprises one or two light chains comprising the amino acid sequence of SEQ ID NO:171, a heavy chain comprising the amino acid sequence of SEQ ID NO:172, and a heavy chain comprising the amino acid sequence of SEQ ID NO:173. In some embodiments, a fusion protein of the present disclosure comprises one or two light chains comprising the amino acid sequence of SEQ ID NO:174, a heavy chain comprising the amino acid sequence of SEQ ID NO:175, and a heavy chain comprising the amino acid sequence of SEQ ID NO:176. In some embodiments, a fusion protein of the present disclosure comprises one or two light chains comprising the amino acid sequence of SEQ ID NO:187, a heavy chain comprising the amino acid sequence of SEQ ID NO:188, and a heavy chain comprising the amino acid sequence of SEQ ID NO:189. In some embodiments, a fusion protein of the present disclosure comprises one or two light chains comprising the amino acid sequence of SEQ ID NO:298, a heavy chain comprising the amino acid sequence of SEQ ID NO:299, and a heavy chain comprising the amino acid sequence of SEQ ID NO:300. In some embodiments, a fusion protein of the present disclosure comprises one or two light chains comprising the amino acid sequence of SEQ ID NO:302, a heavy chain comprising the amino acid sequence of SEQ ID NO:303, and a heavy chain comprising the amino acid sequence of SEQ ID NO:304. In some embodiments, a fusion protein of the present disclosure comprises one or two light chains comprising the amino acid sequence of SEQ ID NO:306, a heavy chain comprising the amino acid sequence of SEQ ID NO:307, and a heavy chain comprising the amino acid sequence of SEQ ID NO:308. In some embodiments, a fusion protein of the present disclosure comprises one or two light chains comprising the amino acid sequence of SEQ ID NO:310, a heavy chain comprising the amino acid sequence of SEQ ID NO:311, and a heavy chain comprising the amino acid sequence of SEQ ID NO:312. In some embodiments, a fusion protein of the present disclosure comprises one or two light chains comprising the amino acid sequence of SEQ ID NO:314, a heavy chain comprising the amino acid sequence of SEQ ID NO:315, and a heavy chain comprising the amino acid sequence of SEQ ID NO:316. In some embodiments, a fusion protein of the present disclosure comprises one or two light chains comprising the amino acid sequence of SEQ ID NO:318, a heavy chain comprising the amino acid sequence of SEQ ID NO:319, and a heavy chain comprising the amino acid sequence of SEQ ID NO:320. In some embodiments, a fusion protein of the present disclosure comprises one or two light chains comprising the amino acid sequence of SEQ ID NO:322, a heavy chain comprising the amino acid sequence of SEQ ID NO:323, and a heavy chain comprising the amino acid sequence of SEQ ID NO:324. In some embodiments, a fusion protein of the present disclosure comprises one or two light chains comprising the amino acid sequence of SEQ ID NO:326, a heavy chain comprising the amino acid sequence of SEQ ID NO:327, and a heavy chain comprising the amino acid sequence of SEQ ID NO:328. In some embodiments, a fusion protein of the present disclosure comprises one or two light chains comprising the amino acid sequence of SEQ ID NO:334, a heavy chain comprising the amino acid sequence of SEQ ID NO:335, and a heavy chain comprising the amino acid sequence of SEQ ID NO:336. In some embodiments, a fusion protein of the present disclosure comprises one or two light chains comprising the amino acid sequence of SEQ ID NO:338, a heavy chain comprising the amino acid sequence of SEQ ID NO:339, and a heavy chain comprising the amino acid sequence of SEQ ID NO:340. In some embodiments, a fusion protein of the present disclosure comprises one or two light chains comprising the amino acid sequence of SEQ ID NO:342, a heavy chain comprising the amino acid sequence of SEQ ID NO:343, and a heavy chain comprising the amino acid sequence of SEQ ID NO:344. In some embodiments, a fusion protein of the present disclosure comprises one or two light chains comprising the amino acid sequence of SEQ ID NO:346, a heavy chain comprising the amino acid sequence of SEQ ID NO:347, and a heavy chain comprising the amino acid sequence of SEQ ID NO:348. In some embodiments, a fusion protein of the present disclosure comprises one or two light chains comprising the amino acid sequence of SEQ ID NO:350, a heavy chain comprising the amino acid sequence of SEQ ID NO:351, and a heavy chain comprising the amino acid sequence of SEQ ID NO:352.

In some embodiments, a fusion protein of the present disclosure comprises one or two light chains comprising the amino acid sequence of SEQ ID NO:156, a heavy chain comprising the amino acid sequence of SEQ ID NO:157, and a heavy chain comprising the amino acid sequence of SEQ ID NO:217. In some embodiments, a fusion protein of the present disclosure comprises one or two light chains comprising the amino acid sequence of SEQ ID NO:159, a heavy chain comprising the amino acid sequence of SEQ ID NO:160, and a heavy chain comprising the amino acid sequence of SEQ ID NO:218. In some embodiments, a fusion protein of the present disclosure comprises one or two light chains comprising the amino acid sequence of SEQ ID NO:162, a heavy chain comprising the amino acid sequence of SEQ ID NO:163, and a heavy chain comprising the amino acid sequence of SEQ ID NO:219. In some embodiments, a fusion protein of the present disclosure comprises one or two light chains comprising the amino acid sequence of SEQ ID NO:165, a heavy chain comprising the amino acid sequence of SEQ ID NO:166, and a heavy chain comprising the amino acid sequence of SEQ ID NO:220. In some embodiments, a fusion protein of the present disclosure comprises one or two light chains comprising the amino acid sequence of SEQ ID NO:168, a heavy chain comprising the amino acid sequence of SEQ ID NO:169, and a heavy chain comprising the amino acid sequence of SEQ ID NO:221. In some embodiments, a fusion protein of the present disclosure comprises one or two light chains comprising the amino acid sequence of SEQ ID NO:171, a heavy chain comprising the amino acid sequence of SEQ ID NO:172, and a heavy chain comprising the amino acid sequence of SEQ ID NO:222. In some embodiments, a fusion protein of the present disclosure comprises one or two light chains comprising the amino acid sequence of SEQ ID NO:174, a heavy chain comprising the amino acid sequence of SEQ ID NO:175, and a heavy chain comprising the amino acid sequence of SEQ ID NO:223. In some embodiments, a fusion protein of the present disclosure comprises one or two light chains comprising the amino acid sequence of SEQ ID NO:187, a heavy chain comprising the amino acid sequence of SEQ ID NO:188, and a heavy chain comprising the amino acid sequence of SEQ ID NO:224. In some embodiments, a fusion protein of the present disclosure comprises one or two light chains comprising the amino acid sequence of SEQ ID NO:298, a heavy chain comprising the amino acid sequence of SEQ ID NO:299, and a heavy chain comprising the amino acid sequence of SEQ ID NO:301. In some embodiments, a fusion protein of the present disclosure comprises one or two light chains comprising the amino acid sequence of SEQ ID NO:302, a heavy chain comprising the amino acid sequence of SEQ ID NO:303, and a heavy chain comprising the amino acid sequence of SEQ ID NO:305. In some embodiments, a fusion protein of the present disclosure comprises one or two light chains comprising the amino acid sequence of SEQ ID NO:306, a heavy chain comprising the amino acid sequence of SEQ ID NO:307, and a heavy chain comprising the amino acid sequence of SEQ ID NO:309. In some embodiments, a fusion protein of the present disclosure comprises one or two light chains comprising the amino acid sequence of SEQ ID NO:310, a heavy chain comprising the amino acid sequence of SEQ ID NO:311, and a heavy chain comprising the amino acid sequence of SEQ ID NO:313. In some embodiments, a fusion protein of the present disclosure comprises one or two light chains comprising the amino acid sequence of SEQ ID NO:314, a heavy chain comprising the amino acid sequence of SEQ ID NO:315, and a heavy chain comprising the amino acid sequence of SEQ ID NO:317. In some embodiments, a fusion protein of the present disclosure comprises one or two light chains comprising the amino acid sequence of SEQ ID NO:318, a heavy chain comprising the amino acid sequence of SEQ ID NO:319, and a heavy chain comprising the amino acid sequence of SEQ ID NO:321. In some embodiments, a fusion protein of the present disclosure comprises one or two light chains comprising the amino acid sequence of SEQ ID NO:322, a heavy chain comprising the amino acid sequence of SEQ ID NO:323, and a heavy chain comprising the amino acid sequence of SEQ ID NO:325. In some embodiments, a fusion protein of the present disclosure comprises one or two light chains comprising the amino acid sequence of SEQ ID NO:326, a heavy chain comprising the amino acid sequence of SEQ ID NO:327, and a heavy chain comprising the amino acid sequence of SEQ ID NO:329. In some embodiments, a fusion protein of the present disclosure comprises one or two light chains comprising the amino acid sequence of SEQ ID NO:330, a heavy chain comprising the amino acid sequence of SEQ ID NO:331, and a heavy chain comprising the amino acid sequence of SEQ ID NO:333. In some embodiments, a fusion protein of the present disclosure comprises one or two light chains comprising the amino acid sequence of SEQ ID NO:334, a heavy chain comprising the amino acid sequence of SEQ ID NO:335, and a heavy chain comprising the amino acid sequence of SEQ ID NO:337. In some embodiments, a fusion protein of the present disclosure comprises one or two light chains comprising the amino acid sequence of SEQ ID NO:338, a heavy chain comprising the amino acid sequence of SEQ ID NO:339, and a heavy chain comprising the amino acid sequence of SEQ ID NO:341. In some embodiments, a fusion protein of the present disclosure comprises one or two light chains comprising the amino acid sequence of SEQ ID NO:342, a heavy chain comprising the amino acid sequence of SEQ ID NO:343, and a heavy chain comprising the amino acid sequence of SEQ ID NO:345. In some embodiments, a fusion protein of the present disclosure comprises one or two light chains comprising the amino acid sequence of SEQ ID NO:346, a heavy chain comprising the amino acid sequence of SEQ ID NO:347, and a heavy chain comprising the amino acid sequence of SEQ ID NO:349. In some embodiments, a fusion protein of the present disclosure comprises one or two light chains comprising the amino acid sequence of SEQ ID NO:350, a heavy chain comprising the amino acid sequence of SEQ ID NO:351, and a heavy chain comprising the amino acid sequence of SEQ ID NO:353.

In some embodiments, the present disclosure provides a mixture of fusion protein species, wherein each species comprises one or two light chains comprising the amino acid sequence of SEQ ID NO:156, a heavy chain comprising the amino acid sequence of SEQ ID NO:157, and a heavy chain comprising the amino acid sequence of SEQ ID NO:158 or 217. In some embodiments, the present disclosure provides a mixture of fusion protein species, wherein each species comprises one or two light chains comprising the amino acid sequence of SEQ ID NO:159, a heavy chain comprising the amino acid sequence of SEQ ID NO:160, and a heavy chain comprising the amino acid sequence of SEQ ID NO:161 or 218. In some embodiments, the present disclosure provides a mixture of fusion protein species, wherein each species comprises one or two light chains comprising the amino acid sequence of SEQ ID NO:162, a heavy chain comprising the amino acid sequence of SEQ ID NO:163, and a heavy chain comprising the amino acid sequence of SEQ ID NO:164 or 219. In some embodiments, the present disclosure provides a mixture of fusion protein species, wherein each species comprises one or two light chains comprising the amino acid sequence of SEQ ID NO:165, a heavy chain comprising the amino acid sequence of SEQ ID NO:166, and a heavy chain comprising the amino acid sequence of SEQ ID NO:167 or 220. In some embodiments, the present disclosure provides a mixture of fusion protein species, wherein each species comprises one or two light chains comprising the amino acid sequence of SEQ ID NO:168, a heavy chain comprising the amino acid sequence of SEQ ID NO:169, and a heavy chain comprising the amino acid sequence of SEQ ID NO:170 or 221. In some embodiments, the present disclosure provides a mixture of fusion protein species, wherein each species comprises one or two light chains comprising the amino acid sequence of SEQ ID NO:171, a heavy chain comprising the amino acid sequence of SEQ ID NO:172, and a heavy chain comprising the amino acid sequence of SEQ ID NO:173 or 222. In some embodiments, the present disclosure provides a mixture of fusion protein species, wherein each species comprises one or two light chains comprising the amino acid sequence of SEQ ID NO:174, a heavy chain comprising the amino acid sequence of SEQ ID NO:175, and a heavy chain comprising the amino acid sequence of SEQ ID NO:176 or 223. In some embodiments, the present disclosure provides a mixture of fusion protein species, wherein each species comprises one or two light chains comprising the amino acid sequence of SEQ ID NO:187, a heavy chain comprising the amino acid sequence of SEQ ID NO:188, and a heavy chain comprising the amino acid sequence of SEQ ID NO:189 or 224. In some embodiments, the present disclosure provides a mixture of fusion protein species, wherein each species comprises one or two light chains comprising the amino acid sequence of SEQ ID NO:298, a heavy chain comprising the amino acid sequence of SEQ ID NO:299, and a heavy chain comprising the amino acid sequence of SEQ ID NO:300 or 301. In some embodiments, the present disclosure provides a mixture of fusion protein species, wherein each species comprises one or two light chains comprising the amino acid sequence of SEQ ID NO:302, a heavy chain comprising the amino acid sequence of SEQ ID NO:303, and a heavy chain comprising the amino acid sequence of SEQ ID NO:304 or 305. In some embodiments, the present disclosure provides a mixture of fusion protein species, wherein each species comprises one or two light chains comprising the amino acid sequence of SEQ ID NO:306, a heavy chain comprising the amino acid sequence of SEQ ID NO:307, and a heavy chain comprising the amino acid sequence of SEQ ID NO:308 or 309. In some embodiments, the present disclosure provides a mixture of fusion protein species, wherein each species comprises one or two light chains comprising the amino acid sequence of SEQ ID NO:310, a heavy chain comprising the amino acid sequence of SEQ ID NO:311, and a heavy chain comprising the amino acid sequence of SEQ ID NO:312 or 313. In some embodiments, the present disclosure provides a mixture of fusion protein species, wherein each species comprises one or two light chains comprising the amino acid sequence of SEQ ID NO:314, a heavy chain comprising the amino acid sequence of SEQ ID NO:315, and a heavy chain comprising the amino acid sequence of SEQ ID NO:316 or 317. In some embodiments, the present disclosure provides a mixture of fusion protein species, wherein each species comprises one or two light chains comprising the amino acid sequence of SEQ ID NO:318, a heavy chain comprising the amino acid sequence of SEQ ID NO:319, and a heavy chain comprising the amino acid sequence of SEQ ID NO:320 or 321. In some embodiments, the present disclosure provides a mixture of fusion protein species, wherein each species comprises one or two light chains comprising the amino acid sequence of SEQ ID NO:322, a heavy chain comprising the amino acid sequence of SEQ ID NO:323, and a heavy chain comprising the amino acid sequence of SEQ ID NO:324 or 325. In some embodiments, the present disclosure provides a mixture of fusion protein species, wherein each species comprises one or two light chains comprising the amino acid sequence of SEQ ID NO:326, a heavy chain comprising the amino acid sequence of SEQ ID NO:327, and a heavy chain comprising the amino acid sequence of SEQ ID NO:328 or 329. In some embodiments, the present disclosure provides a mixture of fusion protein species, wherein each species comprises one or two light chains comprising the amino acid sequence of SEQ ID NO:330, a heavy chain comprising the amino acid sequence of SEQ ID NO:331, and a heavy chain comprising the amino acid sequence of SEQ ID NO:332 or 333. In some embodiments, the present disclosure provides a mixture of fusion protein species, wherein each species comprises one or two light chains comprising the amino acid sequence of SEQ ID NO:334, a heavy chain comprising the amino acid sequence of SEQ ID NO:335, and a heavy chain comprising the amino acid sequence of SEQ ID NO:336 or 337. In some embodiments, the present disclosure provides a mixture of fusion protein species, wherein each species comprises one or two light chains comprising the amino acid sequence of SEQ ID NO:338, a heavy chain comprising the amino acid sequence of SEQ ID NO:339, and a heavy chain comprising the amino acid sequence of SEQ ID NO:340 or 341. In some embodiments, the present disclosure provides a mixture of fusion protein species, wherein each species comprises one or two light chains comprising the amino acid sequence of SEQ ID NO:342, a heavy chain comprising the amino acid sequence of SEQ ID NO:343, and a heavy chain comprising the amino acid sequence of SEQ ID NO:344 or 345. In some embodiments, the present disclosure provides a mixture of fusion protein species, wherein each species comprises one or two light chains comprising the amino acid sequence of SEQ ID NO:346, a heavy chain comprising the amino acid sequence of SEQ ID NO:347, and a heavy chain comprising the amino acid sequence of SEQ ID NO:348 or 349. In some embodiments, the present disclosure provides a mixture of fusion protein species, wherein each species comprises one or two light chains comprising the amino acid sequence of SEQ ID NO:350, a heavy chain comprising the amino acid sequence of SEQ ID NO:351, and a heavy chain comprising the amino acid sequence of SEQ ID NO:352 or 353.

In some embodiments, the present disclosure provides a fusion protein comprising two heavy chain sequences and two light chain sequences of a single fusion protein listed in Table 5, wherein one of the heavy chain sequences has an IL2 fusion and the other heavy chain sequence is without an IL2 fusion, and wherein the two light chain sequences are identical. In some embodiments, the heavy chain sequence without an IL2 fusion comprises a lysine at the C terminus. In some embodiments, the fusion protein is of format A shown in FIG. 7. For example, in some embodiments, the fusion protein comprises four polypeptide chains, wherein (1) the first polypeptide chain comprises the amino acid sequence of SEQ ID NO:334, the second polypeptide chain comprises the amino acid sequence of SEQ ID NO:335, the third polypeptide chain comprises the amino acid sequence of SEQ ID NO:336, and the fourth polypeptide chain comprises the amino acid sequence of SEQ ID NO:334; (2) the first polypeptide chain comprises the amino acid sequence of SEQ ID NO:334, the second polypeptide chain comprises the amino acid sequence of SEQ ID NO:335, the third polypeptide chain comprises the amino acid sequence of SEQ ID NO:337, and the fourth polypeptide chain comprises the amino acid sequence of SEQ ID NO:334; (3) the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:340, and the fourth polypeptide chain comprises the amino acid sequence of SEQ ID NO:338; or (4) the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:341, and the fourth polypeptide chain comprises the amino acid sequence of SEQ ID NO:338.

TABLE 5

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| xh CD8v1- IL-2m1 | DIQMTQSPAS LSASVGETVT ITCGASENIY | QVHLQQSGPE LVKPGASVKM SCKTSGYTFT | QVHLQQSGPE LVKPGASVKM SCKTSGYTFT | QVHLQQSGPE LVKPGASVKM SCKTSGYTFT |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | GALNWYQRKQ GKSPQLLIFG ATNLADGVSS RFSGSGSDRQ YSLKISSLHP DDVATYYCQN ILDTPWTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 156) | KYTMHWVKQG HEESLEWIGH FNPNNDETKY NQKFTGKATL TVDKSSTTAY MELRSLTSDD SALYYCARDG LGLRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPCREEM TKNQVSLSCA VKGFYPSDIA VEWESNGQPE NNYKTTPPVL DSDGSFFLVS KLTVDKSRWQ QGNVFSCSVM HEALHNHYTQ KSLSLSPGSG GGGSGGGGSG GGGSAPTSSS TKKTQLQLEH LLLDLQMILN GINNYKNPKL TEMLTAKFYM PKKATELKHL QCLEEELKPL EEVLNLAQSK NFHLRPRDLI SAINVIVLEL KGSETTFMCE YADETATIVE FLNRWITFAQ SIISTLT (SEQ ID NO: 157) | KYTMHWVKQG HEESLEWIGH FNPNNDETKY NQKFTGKATL TVDKSSTTAY MELRSLTSDD SALYYCARDG LGLRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPG (SEQ ID NO: 158) | KYTMHWVKQG HEESLEWIGH FNPNNDETKY NQKFTGKATL TVDKSSTTAY MELRSLTSDD SALYYCARDG LGLRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO: 217) |
| xh CD8v2- IL-2m1 | DIQMTQSPSS LSASVGDRVT ITCRASQEIY GALNWYQQKP GKAPKLLIYG ATNLQSGVPS RFSGSGSGTD FTLTISSLQP | QVQLVQSGAE VKKPGSSVKV SCKASGYRPH NFAISWVRQA PGQGLEWMGG IIPGHAKANY AQKFQGRVTI TADESTSTAY | QVQLVQSGAE VKKPGSSVKV SCKASGYRPH NFAISWVRQA PGQGLEWMGG IIPGHAKANY AQKFQGRVTI TADESTSTAY | QVQLVQSGAE VKKPGSSVKV SCKASGYRPH NFAISWVRQA PGQGLEWMGG IIPGIIAKAN YAQKFQGRVT ITADESTSTA |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | EDFATYYCQD IYDAPWTFGG GTKVEIKRTV AAPSVFIFPP SDEQLKSGTA SVVCLLNNFY PREAKVQWKV DNALQSGNSQ FSVTFQDSKD STYSLSSTLT LSKADYEKHK VYACEVTHQG LSSPVTKSFN RGEC (SEQ ID NO: 159) | MELSSLRSED TAVYYCARDG LGIRLFADWG QGTLVTVSSA STKGPSVFPL APSSKSTSGG TAALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPEAAGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPCREEMT KNQVSLSCAV KGFYPSDIAV EWESNGQPEN NYKTTPPVLD SDGSFFLVSK LTVDKSRWQQ GNVFSCSVMH EALHNHYTQK SLSLSPGSGG GGSGGGGSG GGGSAPTSSS TKKTQLQLEH LLLDLQMILN GINNYKNPKL TEMLTAKFYM PKKATELKHL QCLEEELKPL EEVLNLAQSK NFHLRPRDLI SAINVIVLEL KGSETTFMCE YADETATIVE FLNRWITFAQ SIISTLT (SEQ ID NO: 160) | MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSNT KVDKKVEPKS CDKTHTCPPC PAPEAAGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSREEMT K NQVSLWCLVK GFYPSDIAVE WESNGQPENN YKTTPPVLDS DGSFFLYSKL TVDKSRWQQG NVFSCSVMHE ALHNHYTQKS LSLSPG (SEQ ID NO: 161) | YMELSSLRSE DTAVYYCARD GLGIRLFADW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGA PSVFLFPPPK KDTLMISRTP EVTCVVVDVS HEDPEVKFNW YVDGVEVHNA KTKPREEQYN STYRVVSVLT VLHQDWLNGK EYKCKVS NKALPAPIEK TISKAKGQPR EPQVCTLPPS REEMTKNQVS LWCLVKGFYP SDIAVEWESN GQPENNYKTT PPVLDSDGSF FLYSKLTVDK SRWQQGNVFS CSVMHEALHN HYTQKSLSLS PGK (SEQ ID NO: 218) |
| xh CD8v3-IL-2m1 | DIQMTQSPSS LSASVGDRVT ITCRASQEIY GALNWYQQKP GKAPKLLIYG ATNLQSGVPS RFSGSGSGTD FTLTISSLQP EDFATYYCQD IYDAPWTFGG GTKVEIKRTV AAPSVFIFPP SDEQLKSGTA | QVQLVQSGAE VKKPGSSVKV SCKASGSRFY KFAISWVRQA PGQGLEWMGG IIPGHAKANY AQKFQGRVTI TADESTSTAY MELSSLRSED TAVYYCARDG LGIRLFADWG QGTLVTVSSA STKGPSVFPL | QVQLVQSGAE VKKPGSSVKV SCKASGSRFY KFAISWVRQA PGQGLEWMGG IIPGHAKANY AQKFQGRVTI TADESTSTAY MELSSLRSED TAVYYCARDG LGIRLFADWG QGTLVTVSSA STKGPSVFPL | QVQLVQSGAE VKKPGSSVKV SCKASGSRFY KFAISWVRQA PGQGLEWMGG IIPGHAKANY AQKFQGRVTI TADESTSTAY MELSSLRSED TAVYYCARDG LGIRLFADWG QGTLVTVSSA STKGPSVFPL |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 162) | APSSKSTSGG TAALGCLVKD YFPEPVTVSW NSGALTSGVI ITFPAVLQSS GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPCREE MTKNQVSLSC AVKGFYPSDI AVEWESNGQP ENNYKTTPPV LDSDGSFFLV SKLTVDKSRW QQGNVFSCSV MHEALHNHYT QKSLSLSPGS GGGGSGGGGS GGGGSAPTSS STKKTQLQLE HLLLDLQMIL NGINNYKNPK LTEMLTAKFY MPKKATELKH LQCLEEELKP LEEVLNLAQS KNFHLRPRDL ISAINVIVLE LKGSETTFMC EYADETATIV EFLNRWITFA QSIISTLT (SEQ ID NO: 163) | APSSKSTSGG TAALGCLVKD YFPEPVTVSW NSGALTSGVH TFPAVLQSSG LYSLSSVVTV PSSSLGTQTY CNVNHKPSNT KVDKKVEPKS CDKTHTCPPC PAPEAAGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSREEMT KNQVSLWCLV KGFYPSDIAV EWESNGQPEN NYKTTPPVLD SDGSFFLYSK LTVDKSRWQQ GNVFSCSVMH EALHNHYTQK SLSLSPG (SEQ ID NO: 164) | APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO:219) |
| xh CD8v4- IL-2m1 | DIQMTQSPSS LSASVGDRVT ITCRASQKIY GALNWYQQKP GKAPKLLIYG ATNLQSGVPS RFSGSGSGTD FTLTISSLQP EDFATYYCQN TYDTPWTFGG GTKVEIKR TVAAPS VFIFPPS DEQLKSGTAS VVCLLNNFYP REAKVQWKVD NALQSGNSQE SVTEQDSKDS | QVQLVQSGAE VKKPGSSVKV SCKASGYTFT KYAISWVRQA PGQGLEWMGG IIPGHAKANY AQKFQGRVTI TADESTSTAY MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG | QVQLVQSGAE VKKPGSSVKV SCKASGYTFT KYAISWVRQA PGQGLEWMGG IIPGHAKANY AQKFQGRVTI TADESTSTAY MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG | QVQLVQSGAE VKKPGSSVKV SCKASGYTFT KYAISWVRQA PGQGLEWMGG IIPGHAKANY AQKFQGRVTI TADESTSTAY MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | TYSLSSTLTL SKADYEKHKV YACEVTIIQG LSSPVTKSFN RGEC (SEQ ID NO: 165) | LYSLSSVVTV PSSSLGTQTY ICNVNHKPSN TKVDKKVEPK SCDKTHTCPP CPAPEAAGAP SVFLFPPKPK DTLMISRTPE VTCVVVD VSIIEDP EVKFNWYVDG VEVHNAKTKP REEQYNSTYR VVSVLTVLHQ DWLNGKEYKC KVSNKALPAP IEKTISKAKG QPREPQVYTL PPCREEMTKN QVSLSCAVKG FYPSDIAVEW ESNGQPENNY KTTPPVLDSD GSFFLVSKLT VDKSRWQQGN VFSCSVMHEA LHNHYTQKSL SLSPGSGGGG SGGGGSGGGG SAPTSSSTKK TQLQLEHLLL DLQMILNGIN NYKNPKLTEM LTAKFYMPKK ATELKHLQCL EEELKPLEEV LNLAQSKNFH LRPRDLISAI NVIVLELKGS ETTFMCEYAD ETATIVEFLN RWITFAQSII STLT (SEQ ID NO: 166) | LYSLSSVVTV PSSSLGTQTY ICNVNIIKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPG (SEQ ID NO: 167) | LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO:220) |
| xh CD8v5- IL-2m1 | DIQMTQSPSS LSASVGDRVT ITCRASQKIY GALNWYQQKP CKAPKLLI YGATNLQ SGVPSR FSGSGSGTDF TLTISSLQPE DFATYYCQNT YDTPWTFGGG TKVEIKRTVA APSVFIFPPS DEQLKSGTAS VVCLLNNFYP REAKVQWKVD NALQSGNSQE SVTEQDSKDS TYSLSSTLTL | QVQLVQSGAE VKKPGSS VKVSCKASG SGFRGHA ISWVRQAPGQ GLEWMGGIIP GHAKANYAQK FQGRVTITAD ESTSTAYMEL SSLRSEDTAV YYCARDGLGI RLFADWGQGT LVTVSSASTK GPSVFPLAPS SKSTSGGTAA LGCLVKDYFP EPVTVSWNSG ALTSGVHTFP AVLQSSGLYS | QVQLVQSGAE VKKPGSSVKV SCKASGSGFR GHAISWVRQA PGQGLEWMGG IIPGHAKANY AQKFQGRVTI TADESTSTAY MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG LYSLSSVVTV | QVQLVQSGAE VKKPGSSVKV SCKASGSGFR GHAISWVRQA PGQGLEWMGG IIPGHAKANY AQKFQGRVTI TADESTSTAY MELSSLRSED TAVYYCARDG LGIRLFADWG QGTLVTVSSA STKGPSVFPL APSSKSTSGG TAALGCLVKD YFPEPVTVSW NSGALTSGVH TFPAVLQSSG LYSLSSVVTV |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | SKADYEKHKV YACEVTHQGL SSPVTKSFNR GEC (SEQ ID NO: 168) | LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPCREEMTKN QVSLSCAVKG FYPSDIAVEW ESNGQPENNY KTTPPVLDSD GSFFLVSKLT VDKSRWQQGN VFSCSVMHEA LHNHYTQKSL SLSPGSGGGG SGGGGSGGGG SAPTSSSTKK TQLQLEHLLL DLQMILNGIN NYKNPKLTEM LTAKFYMPKK ATELKHLQCL EEELKPLEEV LNLAQSKNFH LRPRDLISAI NVIVLELKGS ETTFMCEYAD ETATIVEFLN RWITFAQSII STLT (SEQ ID NO: 169) | PSSSLGTQTY ICNVNHKPSN TKVDKKVEPK SCDKTHTCPP CPAPEAAGAP SVFLFPPKPK DTLMISRTPE VTCVVVDVSI IEDPEVKFNW YVDGVEVHNA KTKPREEQYN STYRVVSVLT VLHQDWLNGK EYKCKVSNKA LPAPIEKTIS KAKGQPREPQ VCTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSPG (SEQ ID NO: 170) | PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO:221) |
| xh CD8v6- IL-2m1 | EIVLTQSPAT LSVSPGERAT LSCRASQSVS SNLAWYQQKP GQAP RLLIYGASSR ATGIPDRFSG SGSGTDFTLT ISRLEPEDFA VYYCQQYGSS PPVTFGQGTK VEIKRTVAAP SVFIFPPSDE QLKSGTASVV CLLNNFYPRE AKVQWKVDNA LQSGNSQESV TEQDSKDSTY SLSSTLTLSK | EVQLVESGGG AVRPGGSLRL SCAASGFTFD DYGMSWVRQA PGKGLEWVSD INWSGEI TAYADSVKGR FTISRDNAKN SLYLQMNSLR AEDTAVYYCA RSNSYRWDDA LDIWGQGTMV TVSSASTKGP SVFPLAPSSK STSGGTAALG CLVKDYFPEP VTVSWNSGAL TSGVHTFPAV LQSSGLYSLS | EVQLVESGGG AVRPGGSLRL SCAASGFTFD DYGMSWVRQA PGKGL EWVSDINWSG EITAYADSVK GRFTISRDNA KNSLYLQMNS LRAEDTAVYY CARSNSYRWD DALDIWGQGT MVTVSSASTK GPSVFPLAPS SKSTSGGTAA LGCLVKDYFP EPVTVSWNSG ALTSGVHTFP AVLQSSGLYS | EVQLVESGGG AVRPGGSLRL SCAASGFTFD DYGMSWVRQA P GKGLEWVSDI NWSGEITAYA DSVKGRFTIS RDNAKNSLYL QMNSLRAEDT AVYYCARSNS YRWDDALDIW GQGTMVTVSS ASTKGPSVFP LAPSSKSTSG GTAALGCLVK DYFPEPVTVS WNSGALTSGV HTFPAVLQSS |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | ADYEKHKVYA CEVTHQGLSS PVTKSFNRGE C (SEQ ID NO: 171) | SVVTVPSSSL GTQTYICNVN HKPSNTKVDK KVEPKSCDKT HTCPPCPAPE AAGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP CREEMTKNQV SLSCAVKGFY PSDIAVEWES NGQPENNYKT TPPVLDSDGS FFLVSKLTVD KSRWQQGNVF SCSVMHEALH NHYTQKSLSL SPGSGGGGSG GGGSGGGGSA PTSSSTKKTQ LQLEHLLLDL QMILNGINNY KNPKLTEMLT AKFYMPKKAT ELKHLQCLEE ELKPLEEVLN LAQSKNFHLR PRDLISAINV IVLELKGSET TFMCEYADET ATIVEFLNRW ITFAQSIIST LT (SEQ ID NO: 172) | LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVCTL PPSREEMTKN QVSLWCLVKG FYPSDIAVEW ESNGQPENNY KTTPPVLDSD GSFFLYSKLT VDKSRWQQGN VFSCSVMHEA LHNHYTQKSL SLSPG (SEQ ID NO: 173) | GLYSLSSVVT VPSSSLGTQT YICNVNHKPS NTKVDKKVEP KSCDKTHTCP PCPAPEAAGA PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQREPQ VCTLPPSREE MTKNQVSLWC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 222) |
| xh CD8v7-IL-2m1 | EIVLTQSPAT LSVTPGEGAT LSCRASHSVG SNLAWYQQKP GQAPRLLIYD ASNRATGIPA RFSGSGSGTD FTLTISSLEP EDLAVYYCQQ RSNWPPTFGQ GTRLEIKRTV AAPSVFIFPP SDEQLKSGTA SVVCLLNNFY PREAKVQWKV DNALQSGNSQ ESVTEQDSKD STYSLSSTLT | EVQLVESGGG LVQPGRSLRL SCAASGFTFD DYAMHWVRQA PGKGLEWVAV ISYDGSNKYY ADSVKGRFTI SRDNSKNTLY LQMNSLRAED TAVYYCAKDR IGWYDYDAFD IWGQGTMVTV SSASTKGPSV FPLAPSSKST SGGTAALGCL VKDYFPEPVT VSWNSGALTS GVHTFPAVLQ | EVQLVESGGG LVQPGRSLRL SCAASGFTFD DYAMHWVRQA PGKGLEWVAV ISYDGSNKYY ADSVKGRFTI SRDNSKNTLY LQMNSLRAED TAVYYCAKDR IGWYDYDAFD IWGQGTMVTV SSASTKGPSV FPLAPSSKST SGGTAALGCL VKDYFPEPVT VSWNSGALTS GVHTFPAVLQ | EVQLVESGGG LVQPGRSLRL SCAASGFTFD DYAMHWVRQA PGKGLEWVAV ISYDGSNKYY ADSVKGRFTI SRDNSKNTLY LQMNSLRAED TAVYYCAKDR IGWYDYDAFD IWGQGTMVTV SSASTKGPSV FPLAPSSKST SGGTAALGCL VKDYFPEPVT VSWNSGALTS GVHTFPAVLQ |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | LSKADYEKHK VYACEVTHQG LSSPVTKSFN RGEC (SEQ ID NO: 174) | SSGLYSLSSV VTVPSSSLGT QTYICNVNHK PSNTKVDKKV EPKSCDKTHT CPPCPAPEAA GAPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPCR EEMTKNQVSL SCAVKGFYPS DIAVEWESNG QPENNYKTTP PVLDSDGSFF LVSKLTVDKS RWQQGNVFSC SVMHEALHNH YTQKSLSLSP GSGGGSGGG GSGGGGSAPT SSSTKKTQLQ LEHLLLDLQM ILNGINNYKN PKLTEMLTAK FYMPKKATEL KHLQCLEEEL KPLEEVLNLA QSKNFHLRPR DLISAINVIV LELKGSETTF MCEYADETAT IVEFLNRWIT FAQSIISTLT (SEQ ID NO: 175) | SSGLYSLSSV VTVPSSSLGT QTYICNVNHK PSNTKVDKKV EPKSCDKTHT CPPCPAPEAA GAPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVCTLPPSR EEMTKNQVSL WCLVKGFYPS DIAVEWESNG QPENNYKTTP PVLDSDGSFF LYSKLTVDKS RWQQGNVFSC SVMHEALHNH YTQKSLSLSP G (SEQ ID NO: 176) | SSGLYSLSSV VTVPSSSLGT QTYICNVNHK PSNTKVDKKV EPKSCDKTHT CPPCPAPEAA GAPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVCTLPPSR EEMTKNQVSL WCLVKGFYPS DIAVEWESNG QPENNYKTTP PVLDSDGSFF LYSKLTVDKS RWQQGNVFSC SVMHEALHNH YTQKSLSLSP GK (SEQ ID NO: 223) |
| xh CD8v8-IL-2m1 | DIQMTQSPAS LSVSVGETVT ITCRASENIY SNLAWYQQKQ GKSPQLLVYA ATNLADGVPS RFSGSGSGTQ YSLKINSLQS EDFGSYYCQH FWGTPWTFGG GTKLEIKRTV AAPSVFIFPP SDEQLKSGTA SVVCLLNNFY PREAKVQWKV DNAL QSGNSQESVT EQDSKDSTYS LSSTLTLSKA | QVQLQQSGAE LVRPGSSVKI SCKASGYAFS SYWMNWVKQR PGQGLEWIGQ IYPGDGDTNY NGKFKGKATL TADKSSSTAY MQLSSLTSED SAVYFCARSG AAFSSYYAMD YWGQGTSVTV SSASTKGPSV FPLAPSSKST SGGTAALGCL VKDYFPEPVT VSWNSGALTS GVHTFPAVLQ SSGLYSLSSV | QVQLQQSGAE LVRPGSSVKI SCKASGYAFS SYWMNWVKQR PGQGLEWIGQ IYPGDGDTNY NGKFKGKATL TADKSSSTAY MQLSSLTSED SAVYFCARSG AAFSSYYAMD YWGQGTSVTV SSASTKGPSV FPLAPSSKST SGGTAALGCL VKDYFPEPVT VSW NSGALTSGVH TFPAVLQSSG | QVQLQQSGAE LVRPGSSVKI SCKASGYAFS SYWMNWVKQR PGQGLEWIGQ IYPGDGDTNY NGKFKGKATL TADKSSSTAY MQLSSLTSED SAVYFCARSG AAFSSYYAMD YWGQGTSVTV SSASTKGPSV FPLAPSSKST SGGTAA LGCLVKDYFP EPVTVSWNSG ALTSGVHTFP AVLQSSGLYS |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | DYEKHKVYAC EVTHQGLSSP VTKSFNRGEC (SEQ ID NO: 187) | VTVPSSSLGT QTYICNV NHKPSNTKVD KKVEPKSCDK THTCPPCPAP EAAGAPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PCREEMTKNQ VSLSCAVKGF YPSDIAVEWE SNGQPENNYK TTPPVLDSDG SFFLVSKLTV DKSRWQQGNV FSCSVMHEAL HNHYTQKSLS LSPGSGGGGS GGGGSGGGGS APTSSSTKKT QLQLEHLLLD LQMILNGINN YKNPKLTEML TAKFYMPKKA TELKHLQCLE EELKPLEEVL NLAQSKNFHL RPRDLISAIN VIVLELKGSE TTFMCEYADE TATIVEFLNR WITFAQSIIS TLT (SEQ ID NO: 188) | LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPG (SEQ ID NO: 189) | LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVCTL PPSREEMTKN QVSLWCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 224) |
| xh CD8v9- IL-2m1 | DIQMTQSPSS LSASVGDRVT ITCRASQEIY GALNWYQQKP GKAPKLLIYG ATNLQSGVPS RFSGSGSGTD FTLTISSLQP EDFATYYCQS TYDAPWTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN | QVQLVQSGAE VKKPGSSVKV SCKASGGTFS SYAISWVRQA PGQGLEWMGG IIPGAATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN | QVQLVQSGAE VKKPGSSVKV SCKASGGTFS SYAISWVRQA PGQGLEWMGG IIPGAATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN | QVQLVQSGAE VKKPGSSVKV SCKASGGTFS SYAISWVRQA PGQGLEWMGG IIPGAATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | RGEC (SEQ ID NO: 298) | TKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLSCAVKGFYPSDIAVEWESNGQPENNYKTTPPVLDSDGSFFLVSKLTVDKSRWQQGNVFSCSVMHEALHNHYTQKSLSLSPGSGGGGSGGGGSGGGSAPTSSSTKKTQLQLEHLLLDLQMILNGINNYKNPKLTEMLTAKFYMPKKATELKHLQCLEEELKPLEEVLNLAQSKNFHLRPRDLISAINVIVLELKGSETTFMCEYADETATIVEFLNRWITFAQSIISTLT (SEQ ID NO: 299) | TKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG (SEQ ID NO: 300) | TKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 301) |
| xhCD8v10-IL-2m1 | EIVLTQSPGTLSLSPGERATLSCRASQSVSSNLAWYQQKPGQAPRLLIYGASSRATGIPDRFSGSGSGTDETLTISRLEPEDFAVYYCQQYGSSPPVTFGQGTKVEIKRTVAAPSVFIFPPSDEQLKSGTASVVCLLNNFYPREAKVQWKVDNALQSGNSQESVTEQDSKDSTYSLSSTLTLSKADYEKH | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPPAVLQSSGLYSLSSVV | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPPAVLQSSGLYSLSSVV | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPPAVLQSSGLYSLSSVV |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | KVYACEVTHQGLSSPVTKSFNRGEC (SEQ ID NO: 302) | TVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLSCAVKGFYPSDIAVEWESNGQPENNYKTTPPVLDSDGSFFLVSKLTVDKSRWQQGNVFSCSVMHEALHNHYTQKSLSLSPGGGGGSGGGGSGGGGSAPTSSSTKKTQLQLEHLLLDLQMILNGINNYKNPKLTEMLTAKFYMPKKATELKHLQCLEEELKPLEEVLNLAQSKNFHLRPRDLISAINVIVLELKGSETTFMCEYADETATIVEFLNRWITFAQSIISTLT (SEQ ID NO: 303) | TVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG (SEQ ID NO: 304) | TVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 305) |
| xhCD8v11-IL-2m1 | EIVLTQSPGTLSLSPGERATLSCRASQSVSSNLAWYQQKPGQAPRLLIYGASSRATGIPDRFSGSGSGTDFTLTISRLEPEDFAVYYCQQYGSSPPVTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSF | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKP | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKP | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKP |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | NRGEC (SEQ ID NO: 306) | SNTKVDKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPCRE EMTKNQVSLS CAVKGFYPSD IAVEWESNGQ PENNYKTTPP VLDSDGSFFL VSKLTVDKSR WQQGNVFSCS VMHEALHNHY TQKSLSLSPG SGGGGSGGGG SGGGGSAPTS SSTKKTQLQL EHLLLDLQMI LNGINNYKNP KLTEMLTAKF YMPKKATELK HLQCLEEELK PLEEVLNLAQ SKNFHLRPRD LISAINVIVL ELKGSETTFM CEYADETATI VEFLNRWITF AQSIISTLT (SEQ ID NO: 307) | SNTKVDKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG (SEQ ID NO: 308) | SNTKVDKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG K (SEQ ID NO: 309) |
| xh CD8v1- IL-2m1 | DIQMTQSPSS LSASVGDRVT ITCRASQSIY GALNWYQQKP GKAPKLLIYG ASNLQSGVPS RFSGSGSGTD FTLTISSLQP EDFATYYCQS TYTAPWTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TEPAVLQSSG LYSLSSVVTV PSSSLGTQTY ICNVNHKPSN TKVDKKVEPK SCDKTHTCPP CPAPEAAGAP |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | NO: 310) | SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPCREEM TKNQVSLSCA VKGFYPSDIA VEWESNGQPE NNYKTTPPVL DSDGSFFLVS KLTVDKSRWQ QGNVFSCSVM HEALHNHYTQ KSLSLSPGSG GGGSGGGGSG GGGSAPTSSS TKKTQLQLEH LLLDLQMILN GINNYKNPKL TEMLTAKFYM PKKATELKHL QCLEEELKPL EEVLNLAQSK NFHLRPRDLI SAINVIVLEL KGSETTFMCE YADETATIVE FLNRWITFAQ SIISTLT (SEQ ID NO: 311) | SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPG (SEQ ID NO: 312) | SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO: 313) |
| xh CD8v13- IL-2m1 | DIQMTQSPSS LSASVGDRVT ITCRASQEIY GALNWYQQKP GKAPKLLIYG ATNLQSGVPS RFSGSGSGTD FTLTISSLQP EDFATYYCQS TYDAPWTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 314) | QVQLVQSGAE VKKPGSSVKV SCKASGGTFS SYAISWVRQA PGQGLEWMGG IIPGYATANY AQKEQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSI | QVQLVQSGAE VKKPGSSVKV SCKASGGTFS SYAISWVRQA PGQGLEWMGG 1IPGYATANYA QKFQGRVTIT ADESTSTAYM ELSSLRSEDT AVYYCARDA GIRLFADWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVHKPSNT KVDKKVEPKS CDKTHTCPPC PAPEAAGAPS VFLFPPKPKD TLMISRTPEV TCVVVDVSHE | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | IEDPEVKFNW YVDGVEVHNA KTKPREEQYN STYRVVSVLT VLHQDWLNGK EYKCKVSNKA LPAPIEKTIS KAKGQPREPQ VYTLPPCREE MTKNQVSLSC AVKGFYPSDI AVEWESNGQP ENNYKTTPPV LDSDGSFFLV SKLTVDKSRW QQGNVFSCSV MHEALHNHYT QKSLSLSPGS GGGGSGGGGS GGGGSAPTSS STKKTQLQLE HLLLDLQMIL NGINNYKNPK LTEMLTAKFY MPKKATELKH LQCLEEELKP LEEVLNLAQS KNFHLRPRDL ISAINVIVLE LKGSETTFMC EYADETATIV EFLNRWITFA QSIISTLT (SEQ ID NO: 315) | DPEVKFNWYV DGVEVHNAKT KPREEQYNST YRVVSVLTVL HQDWLNGKEY KCKVSNKALP APIEKTISKA KGQPREPQVC TLPPSREEMT KNQVSLWCLV KGFYPSDIAV EWESNGQPEN NYKTTPPVLD SDGSFFLYSK LTVDKSRWQQ GNVFSCSVMH EALHNHYTQK SLSLSPG (SEQ ID NO: 316) | EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO: 317) |
| xh CD8v14- IL-2m1 | EIVLTQSPGT LSLSPGERAT LSCRASQSVS SNLAWYQQKP GQAPRLLIYG ASSRATGIPD RFSGSGSGTD FTLTISRLEP EDFAVYYCQQ YGSSPPVTFG QGTKVEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC (SEQ ID NO: 18) | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTMVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTMVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTMVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | NSTYRVVSVL TVLHQDWLNG KEYKCKVSNK ALPAPIEKTI SKAKGQPREP QVYTLPPCRE EMTKNQVSLS CAVKGFYPSD IAVEWESNGQ PENNYKTTPP VLDSDGSFFL VSKLTVDKSR WQQGNVFSCS VMHEALHNHY TQKSLSLSPG SGGGGSGGGG SGGGGSAPTS SSTKKTQLQL EHLLLDLQMI LNGINNYKNP KLTEMLTAKF YMPKKATELK HLQCLEEELK PLEEVLNLAQ SKNFHLRPRD LISAINVIVL ELKGSETTFM CEYADETATI VEFLNRWITF AQSIISTLT (SEQ ID NO: 319) | NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG (SEQ ID NO: 320) | NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG K (SEQ ID NO: 321) |
| xh CD8v15- IL-2m1 | EIVLTQSPGT LSLSPGERAT LSCRASQSVS SNLAWYQQKP GQAPRLAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC (SEQ ID NO: 326) | EVQLVESGGG LVQPGGSLRL SCAASGFTFS SYAMSWVRQA PGKGLEWVSD ISYAGGSTAY KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPCRE EMTKNQVSLS CAVKGFYPSD IAVEWESNGQ PENNYKTTPP VLDSDGSFFL VSKLTVDKSR | EVQLVESGGG LVQPGGSLRL SCAASGFTFS SYAMSWVRQA PGKGLESSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPEAAGAPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVC TLPPSREEMT KNQVSLWCLV KGFYPSDIAV EWESNGQPEN NYKTTPPVLD | EVQLVESGGG LVQPGGSLRL SCAASGFTFS SYAMSWVRQA PGLFADWGQG TLVTVSSAST KGPSVFPLAP SSKSTSGGTA ALGCLVKDYF PEPVTVSWNS GALTSGVHTP PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVCT LPPSREEMTK NQVSLWCLVK GFYPSDIAVE WESNGQPENN |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | WQQGNVFSCSVMHEALHNHYTQKSLSLSPGSGGGGSGGGGSGGGGSAPTSSSTKKTQLQLEELLLDLQMILNGINNYKNPKLTEMLTAKFYMPKKATELKHLQCLEEELKPLEEVLNLAQSKNFHLRPRDLISNINVIVLELKGSETTFMCEYADETATIVEFLNRWITFAQSIISTLT (SEQ ID NO: 327) | SDGSFFLYSKLTVDKSRWQQGNVFSCSVMHEALHNHYTQKSLSLSPG (SEQ ID NO: 328) | YKTTPPVLDSDGSFFLYSKLTVDKSRWQQGNVFSCSVMHEALHNHYTQKSLSLSPGK (SEQ ID NO: 329) |
| xhCD8v10-IL-2m4 | EIVLTQSPGTLSLSPGERATLSCRASQSVSSNLAWYQQKPGQAPRLLIYGASSRATGIPDRFSGSGSGTDFTLTISRLEPEDFAVYYCQQYGSSPPVTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 330) | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLSCAVKGFYPSDIAVEWESNGQPENNYKTTPPVLDSDGSFFLVSKLTVDKSRWQQGNVFSCSVMHEALHNHYTQKSLSLSPG | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG | EVQLVESGGGLVQPGGSLRLSCAASGFTFSSYAMSWVRQAPGKGLEWVSDITYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | SGGGGSGGGG SGGGGSAPTS SSTKKTQLQL EELLLDLQMI LNGINNYKNP KLTEMLTAKF YMPKKATELK HLQCLEEELK PLEEVLNLAQ SKNFHLRPRD LISNINVIVL ELKGSETTFM CEYADETATI VEFLNRWITF AQSIISTLT (SEQ ID NO: 331) | (SEQ ID NO: 332) | K (SEQ ID NO: 333) |
| xh CD8v11- IL-2m4 | EIVLTQSPGT LSLSPGERAT LSCRASQSVS SNLAWYQQKP GQAPRLLIYG ASSRATGIPD RFSGSGSGTD FTLTISRLEP EDFAVYYCQQ YGSSPPVTFG QGTKVEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC (SEQ ID NO: 334) | EVQLVESGGG LVQPGGSLRL SCAASGFTFS SYAMSWVRQA PGKGLEWVSD ITYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPCRE EMTKNQVSLS CAVKGFYPSD IAVEWESNGQ PENNYKTTPP VLDSDGSFFL VSKLTVDKSR | EVQLVESGGG LVQPGGSLRL SCAASGFTFS SYAMSWVRQA PGKGLEWVSD ITYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR | EVQLVESGGG LVQPGGSLRL SCAASGFTFS SYAMSWVRQA PGKGLEWVSD ITYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCL VKDYFPEP VTVSWNSGAL TSGVHTFPAV LQSSGLYSLS SVVTVPSSSL GTQTYICNVN HKPSNTKVDK KVEPKSCDKT HTCPPCPAPE AAGAPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVCTLPP SREEMTKNQV SLWCLVKGFY PSDIAVEWES NGQPENNYKT TPPVLDSDGS FFLYSKLTVD |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | WQQGNVFSCS VMHEALHNHY TQKSLSLSPG SGGGGSGGGG SGGGGSAPTS SSTKKTQLQL EELLLDLQMI LNGINNYKNP KLTEMLTAKF YMPKKATELK HLQCLEEELK PLEEVLNLAQ SKNFHLRPRD LISNINVIVL ELKGSETTFM CEYADETATI VEFLNRWITF AQSIISTLT (SEQ ID NO: 335) | WQQGNVFSCS VMHEALHNHY TQKSLSLSPG (SEQ ID NO: 336) | KSRWQQGNVF SCSVMHEALH NHYTQKSLSL SPGK (SEQ ID NO: 337) |
| xh CD8v12- IL-2m4 | DIQMTQSPSS LSASVGDRVT ITCRASQSIY GALNWYQQKP GKAPKLLIYG ASNLQSGVPS RFSGSGSGTD FTLTISSLQP EDFATYYCQS TYTAPWTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 338) | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPCREEM TKNQVSLSCA VKGFYPSDIA VEWESNGQPE NNYKTTPPVL DSDGSFFLVS KLTVDKSRWQ QGNVFSCSVM HEALHNHYTQ KSLSLSPGSG | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPG | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ QGNVFSCSVM HEALHNHYTQ KSLSLSPGK |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | GGGSGGGGSG GGGSAPTSSS TKKTQLQLEE LLLDLQMILN GINNYKNPKL TEMLTAKFYM PKKATELKHL QCLEEELKPL EEVLNLAQSK NFHLRPRDLI SNINVIVLEL KGSETTFMCE YADETATIVE FLNRWITFAQ SIISTLT (SEQ ID NO: 339) | (SEQ ID NO: 340) | (SEQ ID NO: 341) |
| xh CD8v13- IL-2m4 | DIQMTQSPSS LSASVGDRVT ITCRASQEIY GALNWYQQKP GKAPKLLIYG ATNLQSGVPS RFSGSGSGTD FTLTISSLQP EDFATYYCQS TYDAPWTEGG GTKVEIKRTV AAPSVFIFPP SDEQLKSGTA SVVCLLNNFY PREAKVQWKV DNALQSGNSQ ESVTFQDSKD STYSLSSTLT LSKADYEKHK VYACEVTHQG LSSPVTKSFN RGEC (SEQ ID NO: 342) | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGEVHNAK TKPREEQYNS TYRVVSVLTV LHQDWLNGKE YKCKVSNKAL PAPIEKTISK AKGQPREPQV YTLPPCREEM TKNQVSLSCA VKGFYPSDIA VEWESNGQPE NNYKTTPPVL DSDGSFFLVS KLTVDKSRWQ | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ | QVQLVQSGAE VKKPGSSVKV SCKASGGTFS SYAISWVRQA PGQGLEWMGG IIPGYATANY AQKFQGRVTI TADESTSTAY MELSSLRSED TAVYYCARDA AGIRLFADWG QGTLVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGEVHNAK TKPREEQYNS TYRVVSVLTV LHQDWLNGKE YKCKVSNKAL PAPIEKTISK AKGQPREPQV CTLPPSREEM TKNQVSLWCL VKGFYPSDIA VEWESNGQPE NNYKTTPPVL DSDGSFFLYS KLTVDKSRWQ |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | QGNVFSCSVMHEALHNHYTQKSLSLSPGSGGGGSGGGGSGGGGSAPTSSSTKKTQLQLEELLLDLQMILNGINNYKNPKLTEMLTAKFYMPKKATELKHLQCLEEELKPLEEVLNLAQSKNFHLRPRDLISNINVIVLELKGSETTFMCEYADETATIVEFLNRWITFAQSIISTLT (SEQ ID NO: 343) | QGNVFSCSVMHEALHNHYTQKSLSLSPG (SEQ ID NO: 344) | QGNVFSCSVMHEALHNHYTQKSLSLSPGK (SEQ ID NO: 345) |
| xhCD8v14-IL-2m4 | EIVLTQSPGTLSLSPGERATLSCRASQSVSSNLAWYQQKPGQAPRLLIYGASSRATGIPDRFSGSGSGTDFTLTISRLEPEDFAVYYCQQYGSSPPVTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 346) | EVQLVESGGGLVQPGGSLRLSCAASGFTFSSYAMSWVRQAPGKGLEWVSDISYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNIIKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLSCAVKGFYPSDIAVEWESNGQPENNYKTTPPVLDSDGSFFLVSKLTVDKSRWQQGNVF | EVQLVESGGGLVQPGGSLRLSCAASGFTFSSYAMSWVRQAPGKGLEWVSDISYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVIITFPAVLQSSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLWCLVKGFYPSDIAVEWESNGQPENNYKTTPPVLDSDGSFFLYSKLTVDKSRWQQGNVFSC | EVQLVESGGGLVQPGGSLRLSCAASGFTFSSYAMSWVRQAPGKGLEWVSDISYAGGSTAYADSVKGRFTISRDNAKNSLYLQMNSLRAEDTAVYYCARSNAYAWDDALDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLCLVKGFYPSDIAVEWESNGQPENNYKTTPPVLDSDGSFFLYSKLTVDKSRWQQGNVFSCS |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | SCSVMHEALH NHYTQKSLSL SPGSGGGGSG GGGSGGGGSA PTSSSTKKTQ LQLEELLLDL QMILNGINNY KNPKLTEMLT AKFYMPKKAT ELKHLQCLEE ELKPLEEVLN LAQSKNFHLR PRDLISNINV IVLELKGSET TFMCEYADET ATIVEFLNRW ITFAQSIIST LT (SEQ ID NO: 347) | SVMHEALHNH YTQKSLSLSP G (SEQ ID NO: 348) | VMHEALHNHY TQKSLSLSPG K (SEQ ID NO: 349) |
| xh CD8v15- IL-2m4 | EIVLTQSPGT LSLSPGERAT LSCRASQSVS SNLAWYQQKP GQAPRLLIYG ASSRATGIPD RFSGSGSGTD FTLTISRLEP EDFAVYYCQQ YGSSPPVTFG QGTKVEIKRT VAAPSVFIFP PSDEQLKSGT ASVVCLLNNF YPREAKVQWK VDNALQSGNS QESVTEQDSK DSTYSLSSTL TLSKADYEKH KVYACEVTHQ GLSSPVTKSF NRGEC (SEQ ID NO: 350) | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPCRE EMTKNQVSLS CAVKGFYPSD IAVEWESNGQ PENNYKTTPP VLDSDGSFFL VSKLTVDKSR WQQGNVFSCS VMHEALHNHY TQKSLSLSPG | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG | EVQLVESGGG LVQPGGSLRL SCAASGFTFS SYAMSWVRQA PGKGLEWVSD ISYAGGSTAY ADSVKGRFTI SRDNAKNSLY LQMNSLRAED TAVYYCARSN AYAWDDALDI WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPEAAG APSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVCTLPPSRE EMTKNQVSLW CLVKGFYPSD IAVEWESNGQ PENNYKTTPP VLDSDGSFFL YSKLTVDKSR WQQGNVFSCS VMHEALHNHY TQKSLSLSPG |

TABLE 5-continued

Anti-CD8:IL2 fusion protein sequences

| Name | Light chain sequence | Heavy chain sequence (with IL2 fusion) | Heavy chain sequence (without IL2 fusion) | Heavy chain sequence (without IL2 fusion) plus C-term lysine |
|---|---|---|---|---|
| | | SGGGGSGGGG SGGGGSAPTS SSTKKTQLQL EELLLDLQMI LNGINNYKNP KLTEMLTAKF YMPKKATELK HLQCLEEELK PLEEVLNLAQ SKNFHLRPRD LISNINVIVL ELKGSETTFM CEYADETATI VEFLNRWITF AQSIISTLT (SEQ ID NO: 351) | (SEQ ID NO: 352) | K (SEQ ID NO: 353) |

Production of Antibodies and Fusion Proteins

Further provided herein are polynucleotides (e.g., isolated polynucleotides) encoding any of the antibodies, antibody fragments, and fusion proteins described herein. Further provided herein are vectors (e.g., expression vectors) encoding any of the antibodies, antibody fragments, and fusion proteins described herein.

Further provided herein are host cells (e.g., isolated host cells or host cell lines) comprising any of the polynucleotides or vectors described herein.

Further provided herein are methods of producing any of the antibodies, antibody fragments, and fusion proteins described herein. In some embodiments, the methods comprise culturing a host cell of the present disclosure under conditions suitable for production of the antibody, antibody fragment, or fusion protein. In some embodiments, the methods further comprise recovering the antibody, antibody fragment, or fusion protein.

Antibodies, antibody fragments, and fusion proteins may be produced using recombinant methods, e.g., as exemplified infra. In some embodiments, nucleic acid encoding the antibody/fusion protein can be isolated and inserted into a replicable vector for further cloning or for expression. DNA encoding the antibody/fusion protein may be readily isolated and sequenced using conventional procedures (e.g., via oligonucleotide probes capable of binding specifically to genes encoding the heavy and light chains of the antibody/fragment). Many vectors are known in the art; vector components generally include, but are not limited to, one or more of the following: a signal sequence, an origin of replication, one or more marker genes, an enhancer element, a promoter, and a transcription termination sequence. Suitable host cells for cloning or expressing the DNA in the vectors herein are the prokaryote, yeast, or higher eukaryote cells. When using recombinant techniques, the antibody/fusion protein can be produced intracellularly, in the periplasmic space, or directly secreted into the medium. If the antibody/fragment is produced intracellularly, the particulate debris, either host cells or lysed fragments, are removed, for example, by centrifugation or ultrafiltration. Where the antibody/fusion protein is secreted into the medium, supernatants from such expression systems are generally first concentrated using a commercially available protein concentration filter.

Pharmaceutical Compositions

In some embodiments, a fusion protein of the present disclosure is part of a pharmaceutical composition, e.g., including the fusion protein and one or more pharmaceutically acceptable carriers. Pharmaceutical compositions and formulations as described herein can be prepared by mixing the active ingredients (such as a fusion protein) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). In some embodiments, a fusion protein of the present disclosure is lyophilized.

Methods and Kits

Certain aspects of the present disclosure relate to methods of treating cancer or chronic infection. In some embodiments, the methods comprise administering an effective amount of a fusion protein or antibody, or a pharmaceutical composition comprising the fusion protein or antibody and a pharmaceutically acceptable carrier, to a patient. In some embodiments, the patient in need of said treatment has been diagnosed with cancer.

In some embodiments, the fusion protein or composition is administered in combination with a T cell therapy, cancer vaccine, chemotherapeutic agent, or immune checkpoint inhibitor (ICI). In some embodiments, the chemotherapeutic agent is a kinase inhibitor, antimetabolite, cytotoxin or cytostatic agent, anti-hormonal agent, platinum-based chemotherapeutic agent, methyltransferase inhibitor, antibody, or anti-cancer peptide. In some embodiments, the immune checkpoint inhibitor targets PD-L1, PD-1, CTLA-4, CEACAM, LAIR1, CD160, 2B4, CD80, CD86, CD276, VTCN1, HVEM, KIR, A2AR, MHC class I, MHC class II, GALS, adenosine, TGFR, OX40, CD137, CD40, CD47, TREM1, TREM2, HLA-G, CCR4, CCR8, CD39, CD73, IDO, CSF1R, TIM-3, BTLA, VISTA, LAG-3, TIGIT, IDO, MICA/B, LILRB4, SIGLEC-15, or arginase, including without limitation an inhibitor of PD-1 (e.g., an anti-PD-1 antibody), PD-L1 (e.g., an anti-PD-L1 antibody), or CTLA-4 (e.g., an anti-CTLA-4 antibody).

Examples of anti-PD-1 antibodies include, without limitation, pembrolizumab, nivolumab, cemiplimab, zimberelimab (Arcus), sasanlimab (Pfizer), JTX-4014, spartalizumab (PDR001; Novartis), camrelizumab (SHR1210; Jiangsu HengRui Medicine), sintilimab (IBI308; Innovent and Eli Lilly), tislelizumab (BGB-A317), toripalimab (JS 001), dostarlimab (TSR-042, WBP-285), INCMGA00012 (MGA012), AMP-224, and AMP-514 (MEDI0680). Examples of anti-PD-L1 antibodies include, without limitation, atezolizumab, avelumab, durvalumab, KN035, and CK-301 (Checkpoint Therapeutics). Examples of PD-L1 inhibitors (non-antibody based) include, without limitation, AUNP12, CA-170, and BMS-986189. Examples of anti-CTLA-4 antibodies include, without limitation, ipilimumab, tremelimumab, BMS-986218, BMS-986249, BMS-986288, HBM4003, ONC-392, KN044, ADG116, ADU-1604, AGEN1181, AGEN1884, MK-1308, and REGN4659.

Examples of T cell therapies include, without limitation, CD4+ or CD8+ T cell-based therapies, adoptive T cell therapies, chimeric antigen receptor (CAR)-based T cell therapies, tumor-infiltrating lymphocyte (TIL)-based therapies, autologous T cell therapies, allogeneic T cell therapies, and therapies with T cells bearing a transduced TCR. Exemplary cancer vaccines include, without limitation, dendritic cell vaccines, vaccines comprising one or more polynucleotides encoding one or more cancer antigens, and vaccines comprising one or more cancer antigenic peptides.

Certain aspects of the present disclosure relate to methods of expanding T cells, e.g., ex vivo. In some embodiments, the methods comprise contacting one or more T cells, e.g., ex vivo with an effective amount of the antibody or fusion protein of the present disclosure. In some embodiments, the one or more T cells are tumor infiltrating lymphocytes (TILs). In some embodiments, the methods further comprise isolating tumor infiltrating lymphocytes (TILs) from a tumor or tumor specimen.

Certain aspects of the present disclosure relate to kits or articles of manufacture comprising any of the antibodies, antibody fragments, or fusion proteins disclosed herein. In some embodiments, the article of manufacture comprises a container and a label or package insert on or associated with the container. In some embodiments, the kit or article of manufacture further comprises instructions for using the antibody or fusion protein according to any of the methods disclosed herein, e.g., for treating cancer or chronic infection or expanding T cells, e.g., ex vivo.

Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is an antibody or fusion protein as described herein. The label or package insert indicates that the composition is used for treating the particular condition. The label or package insert will further comprise instructions for administering the antibody or fusion protein composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

EXAMPLES

Example 1: Generation and Characterization of Antibodies that Bind to Human CD8ab Materials and Methods
Recombinant DNA Techniques Techniques involving recombinant DNA manipulation were previously described in Sambrook et al., Molecular cloning: A laboratory manual; Cold Spring Harbor Laboratory Press, Cold Spring Harbor, N.Y., 1989. All reagents were used according to the manufacturer's instructions. DNA sequences were determined by double strand sequencing.

Gene Synthesis

Desired gene segments were either generated by PCR using appropriate templates or synthesized at Genewiz (South Plainfield, NJ), Integrated DNA Technologies (Coralville, IA) or GeneScript (Piscataway, NJ) from synthetic oligonucleotides. The gene segments were cloned into the expression vectors using either Gibson Assembly® method or using restriction digest followed by ligation. DNA was purified from transformed bacteria and concentration was determined by UV visible spectroscopy. DNA sequencing was used to confirm the DNA sequences of the subcloned gene fragments.

Isolation of Antibodies

Antibodies binding to CD8 antigens were generated using either humanization of mouse antibodies or in vitro phage display system.

For humanization, complementarity-determining regions (CDRs) of mouse residues were grafted into selected human framework(s) which exhibit close sequence similarity to the parental mouse framework and good stability. The resulting CDR-grafted antibodies were further humanized to remove any unnecessary non-human mutations.

For in vitro display method, a non-immune human single chain Fv phage library generated from naïve B cells was panned for 5 to 6 rounds to isolate antibodies against the CD8 antigens. After the panning, individual phage clones that exhibited specific binding to target antigen over non-specific antigens in ELISA were identified. DNA fragments of heavy and light chain V-domain of the specific binders were subsequently cloned and sequenced. Parental clones of xhCD8v6 and xhCD8v7 were isolated from a human antibody phage library. xhCD8v1 was a mouse monoclonal antibody against CD8b and xhCD8v1.1 was a humanized version of xCD8v1.

In Vitro Affinity Maturation of Human Antibodies

Affinity maturation library was generated by either shuffling the light chain of the parental clone against light chain isolated from healthy donor naïve B cell or by mutating selected CDR residues. The resulting library was displayed as scFv on the surface of either phage or yeast. Three to five rounds of screening with decreasing concentration of soluble CD8 antigen were performed. The resulting selected clones were subsequently cloned and sequenced. xhCD8v6 and xhCD8v7 are the resulting clones from affinity maturation. xhCD8v2, xhCD8v3, xhCD8v4, and xhCD8v5 are affinity matured antibodies derived from xhCD8v1.1.

Cloning of Antibody Constructs

General information regarding the nucleotide sequences of human immunoglobulins light and heavy chains is given in: IMGT® (the international ImMunoGeneTics information System®) from Lefranc et al. IMGT®, the international ImMunoGeneTics information System® 25 years on. Nucleic Acids Res. 2015 January; 43. The DNA fragments of heavy and light chain V-domains were inserted in frame into the human IgG1 and CK containing mammalian expression vector.

Preparation of Antibody

DNA sequence verified constructs containing the heavy and light chain of an antibody were transfected into Expi 293 cells using polyethylenimine (PEI). After 5 days of culture, supernatant was collected and incubated with Protein A resin for >2 hr at room temperature. Next, the resin was used multiple times with PBS, and then the antibody was eluted off the resin with 20 mM sodium citrate, pH 3.6. The eluted fractions were pooled and further purified by size exclusion chromatography (Superdex 200, GE Healthcare) in PBS.

Binding Affinity Determination by Surface Plasmon Resonance (SPR) for CD8ab Antigen Recombinant human CD8ab protein was generated. Recombinant CD8ab, comprised of the extracellular domains of CD8a, fused to an acidic leucine zipper and an 8× Histidine tag, and CD8b, fused to a basic leucine zipper and a Strep-tag II, was expressed in secreted form from HEK293 cells and purified by IMAC, size exclusion, and Streptavidin affinity column chromatography. Antibody affinity to CD8 at 37° C. was determined by surface plasmon resonance using a Biacore T200 (Cytiva). Antibodies were first captured on an anti-hJgG-Fc CM5 or CM4 surface prepared using the Human Antibody Capture Kit (Cytiva). Soluble CD8ab antigen, diluted in HBS-EP+ buffer at four or more concentrations spanning 0.1× to 10× the KD, was flowed over the surface-captured anti-CD8 mAbs for 1-2 minutes. Dissociation was monitored for 5-10 minutes, and the anti-hJgG-Fc surface was regenerated with 3M MgCl2 before recapturing mAb in each subsequent cycle. Binding data were analyzed by Biacore T200 Evaluation Software version 3.2 using a 1:1 binding model.

Results

Table 1 shows the binding kinetics of isolated anti-CD8ab antibodies (xhCD8v1 to xhCD8v7) to recombinant human CD8ab protein as determined by surface plasmon resonance.

TABLE 1

| Antibody Name | Antibody Type | $k_a$ (1/MS) | $k_d$ (1/s) | $K_D$ (nM) |
|---|---|---|---|---|
| xhCD8v1 | Mouse monoclonal | 9.22E+05 | 0.0183 | 19.8 |
| xhCD8v2 | Affinity matured based on humanized xhCD8v1.1 | 4.83E+05 | 0.02005 | 41.6 |
| xhCD8v3 | Affinity matured based on humanized xhCD8v1.1 | 5.24E+05 | 0.03787 | 72.3 |
| xhCD8v4 | Affinity matured based on humanized xhCD8v1.1 | 3.60E+05 | 0.0493 | 137.0 |
| xhCD8v5 | Affinity matured based on humanized xhCD8v1.1 | 3.57E+05 | 0.04189 | 117.4 |
| xhCD8v6 | Affinity matured based on phage/yeast library clones | 1.62E+06 | 5.71E−04 | 0.35 |
| xhCD8v7 | Affinity matured based on phage/yeast library clones | 8.55E+05 | 9.22E−04 | 1.08 |

As depicted in Table 1, the isolated CD8ab antibodies had a range of affinities varying from 0.35 nM to 137 nM.

As depicted in FIGS. 1A-1C, three types of antibodies that bind to CD8ab antigen (CD8ab antibodies) could be identified: 1) antibodies binding CD8a antigen alone but not CD8b antigen (FIG. 1A), these antibodies target epitopes present on the CD8a molecule; 2) antibodies binding weakly or not binding to CD8a alone and CD8b alone antigens (FIG. 1B), these antibodies bind epitopes that are between CD8a and CD8b on the CD8ab heterodimer; 3) antibodies binding to CD8b alone but not CD8a alone antigens (FIG. 1C), these antibodies target epitopes on the CD8b molecule.

Binding specificity of the antibodies was determined by ELISA. 2 g/mL of recombinant CD8ab, CD8a (Sino biological), CD8b (Sino biological) and ovalbumin (Sigma) or Erb2 (human epidermal growth factor receptor 2) (Sino biological) in PBS were coated onto the maxisorp plate overnight at 4° C. Ovalbumin or Erb2 was used as negative control. Plate was then blocked with casein blocking solution (Thermo Scientific) for 1 hr at room temperature. After blocking, plate was washed with wash buffer (PBS/0.05% Tween-20). Next, dilution of antibody from 30 nM to 0.0009 nM in PBS/0.5% BSA/0.05% Tween-20 was added onto the plate and incubated for 1-2 hr at room temperature. After incubation, plate was washed, and incubated with anti-human IgG (Fc specific)-HRP conjugate or anti-mouse IgG (Fc specific)-HRP conjugate (Jackson Immunoresearch) in PBS/0.5% BSA/0.05% Tween-20 for 1 hr. Binding was detected by adding TMB substrate (SeraCare) to the plate, followed by stopping solution of 0.1M HCl. Binding absorbance was read using GloMax® Discover Microplate Reader (Promega).

Figure 2A:
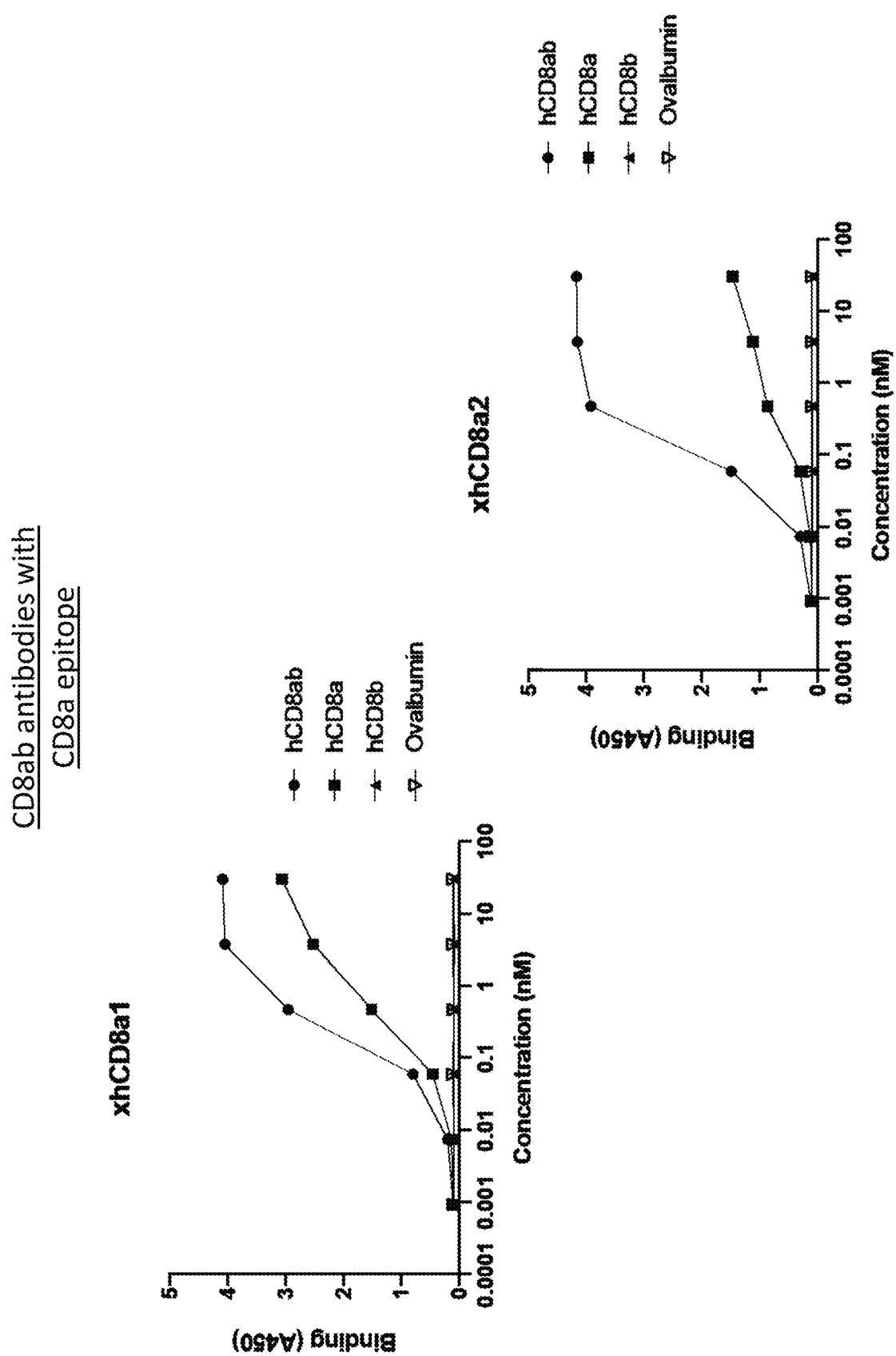
FIGS. 2A-2C show the results of an ELISA assay used to distinguish the three types of CD8ab antibodies depicted in FIGS. 1A-1C. Binding to recombinant CD8a (filled square), CD8b (filled triangle), CD8ab heterodimer (filled circle) and an irrelevant antigen, ovalbumin (open triangles) was measured. xhCD8a1 (clone OKT8) and xhCD8a2 antibodies (clone SK1) were previously described.
Figure 2B:
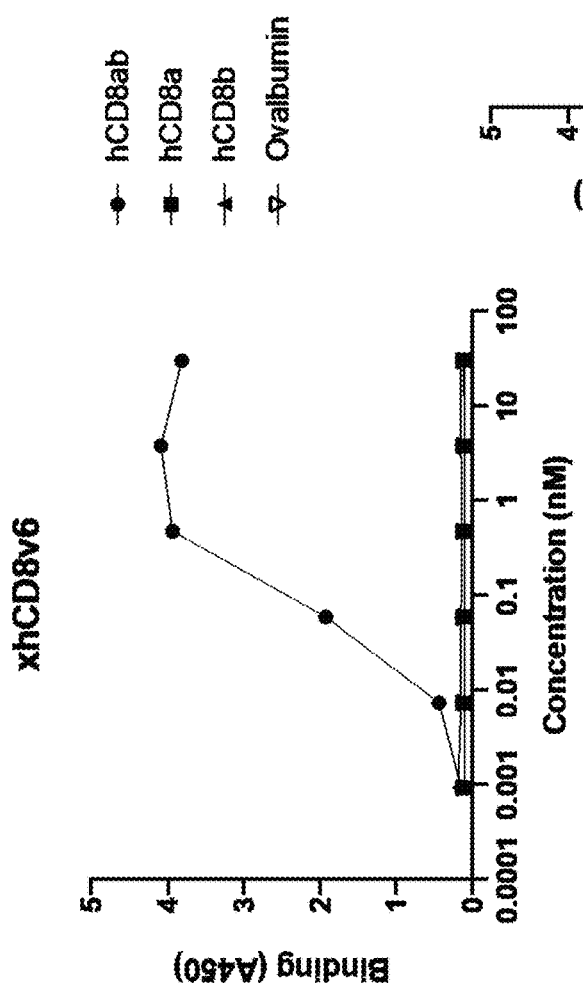
Figure 2B:
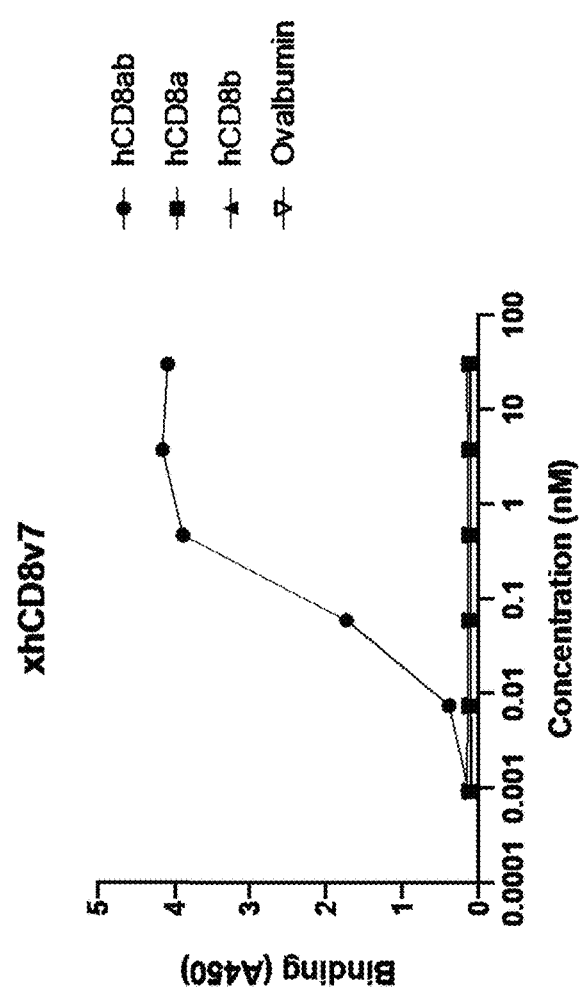
Figure 2C:
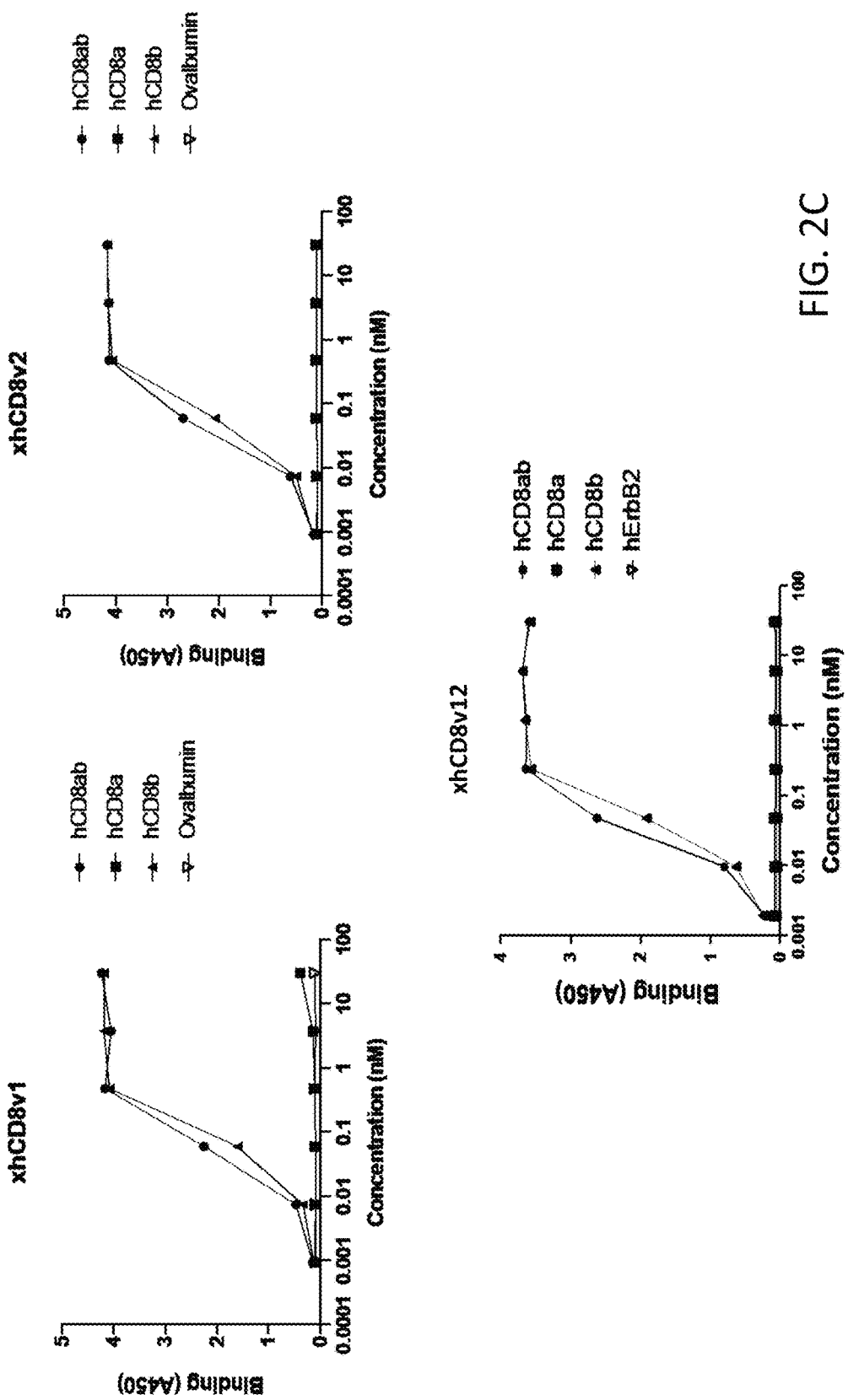

FIG. 2A shows two examples of antibodies with CD8a epitopes: xhCD8a1 (clone OKT8, Invitrogen) and xhCD8a2 (clone SK1, Biolegend), which both bind CD8a alone but not CD8b alone. Anti-CD8ab antibodies xhCD8v6 and xhCD8v7 both bind epitopes between CD8a and CD8b and do not bind to CD8a alone and CD8b alone (FIG. 2B). Mouse monoclonal antibody xhCD8v1 and its humanized variants, xhCD8v2 to xhCD8v5, xhCD8v9, xhCD8v12 and xhCD8v13 all bind to CD8b alone but not CD8 alone and therefore bind an epitope on the CD8b molecule (FIG. 2C).

Figure 3A:
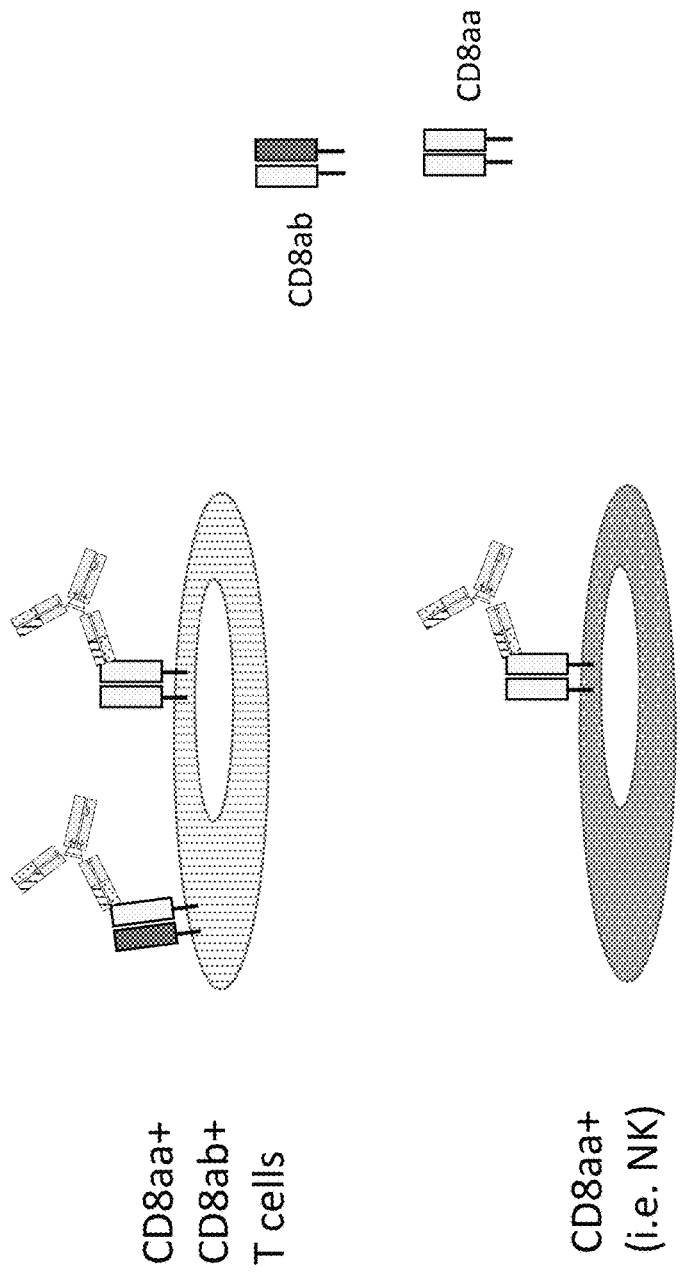
FIGS. 3A-3C depict the binding preferences on various CD8+ immune cell types by the three types of anti-CD8ab antibodies depicted in FIGS. 2A-2C. Antibodies with CD8a epitopes depicted in FIG. 1A bind to both CD8ab+ T cells and CD8aa+ NK cells as depicted in FIG. 3A. Antibodies with epitopes that span both CD8a and CD8b depicted in FIG. 1B preferentially bind to CD8ab+ T cells over CD8aa+ NK cells as depicted in FIG. 3B. Antibodies with CD8b epitopes depicted in FIG. 1C preferentially bind to CD8ab+ T cells over CD8aa+NK cells as depicted in FIG. 3C.
Figure 3B:
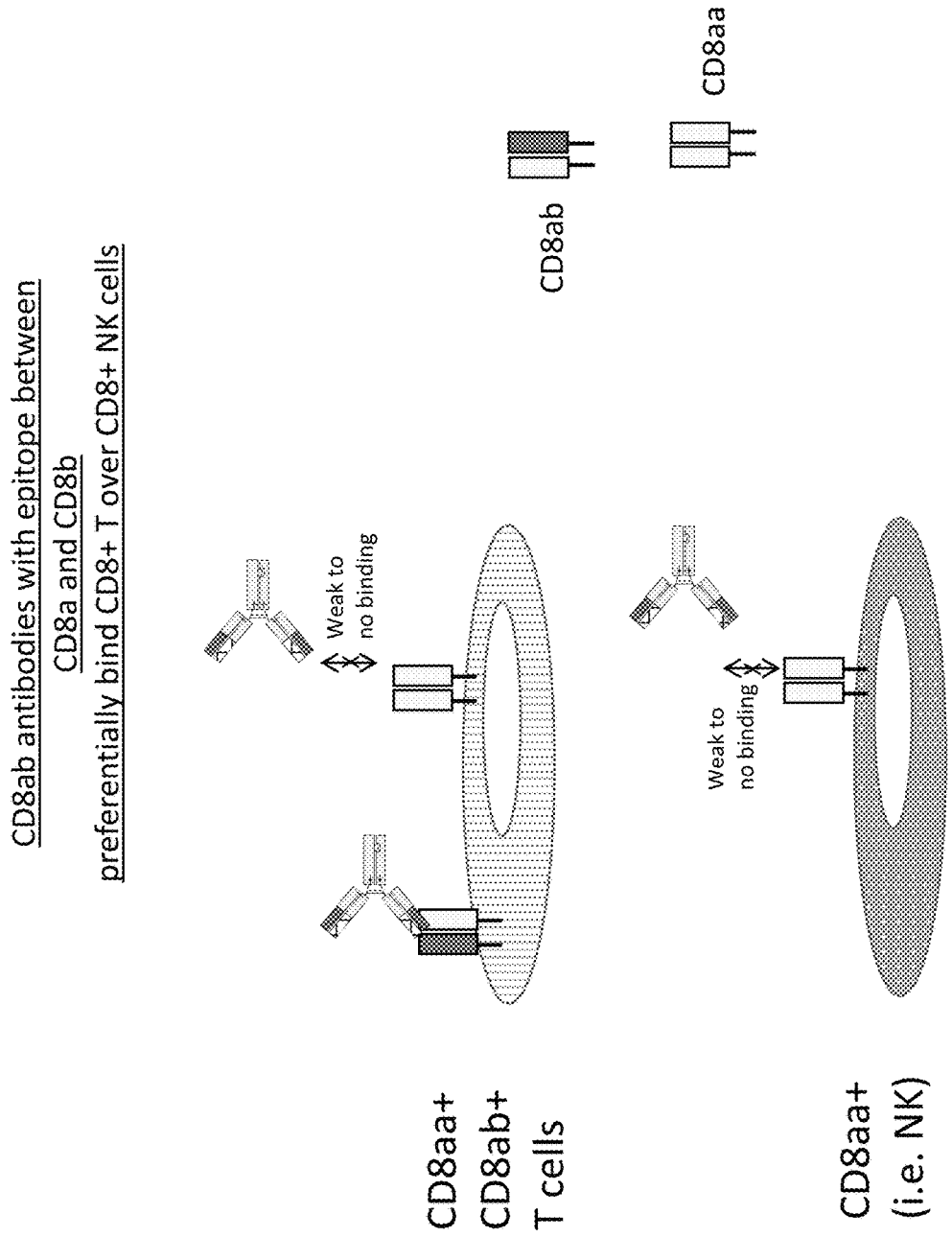
Figure 3C:
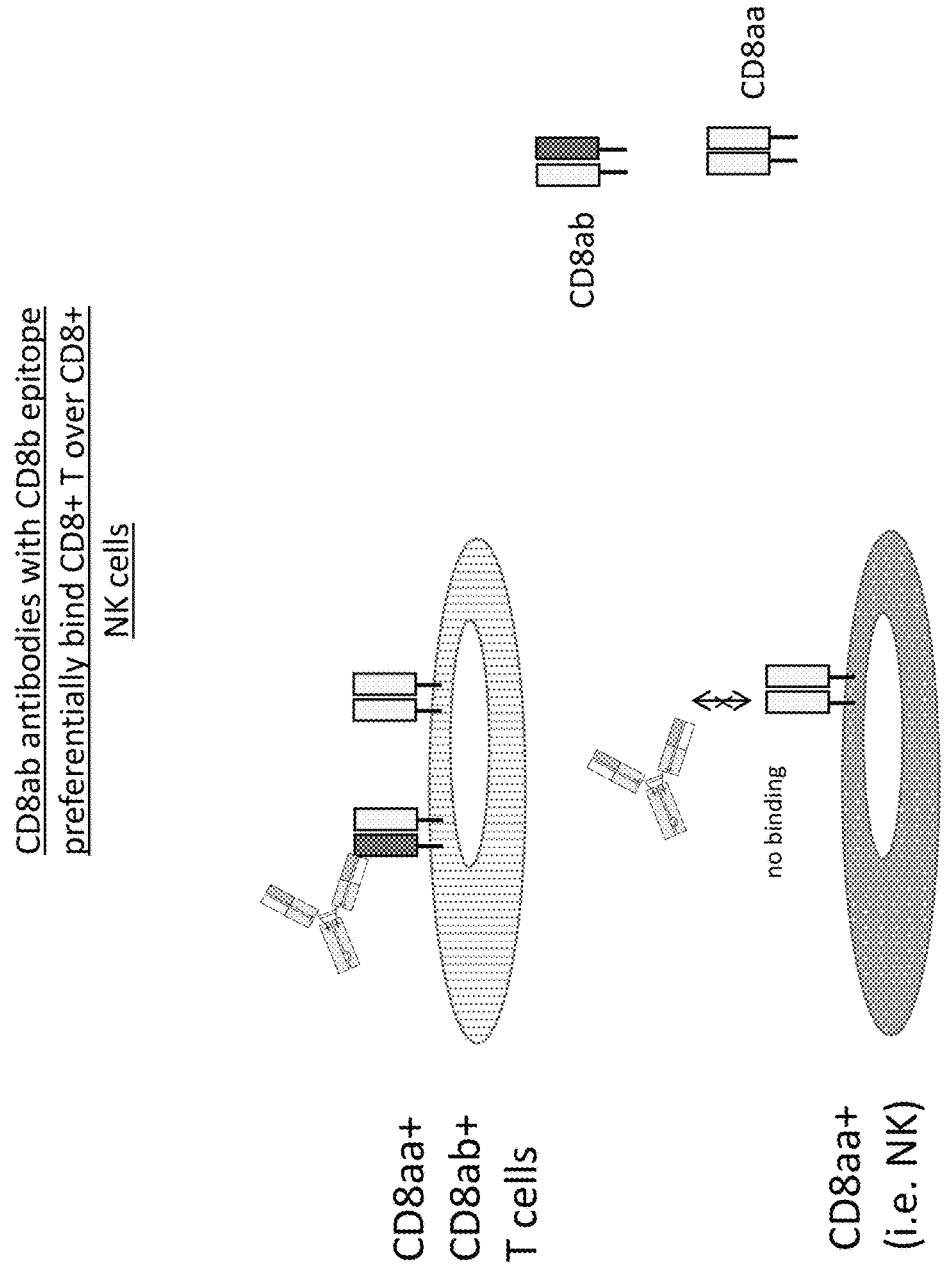

As depicted in FIGS. 3A-3C, the binding epitope for CD8ab antibodies determines their specificity for CD8+ T cells over CD8+ NK cells. Certain immune cells, such as NK cells, express only CD8aa homodimers and will be recognized by antibodies depicted in FIG. 3A. T cells typically express both CD8aa homodimers and CD8ab heterodimers and will be recognized by all three types of antibodies depicted in FIGS. 3A-3C. However, antibodies depicted in FIG. 3B and FIG. 3C will only bind to CD8+ T cells and not CD8+ NK cells and are therefore useful for distinguishing these two cell types.

The binding of CD8ab antibodies on cells was determined by flow cytometry. Freshly isolated PBMCs were incubated with CD8ab antibodies for 2 hours at 4° C. Cells were then stained with antibodies against surface markers CD3 (UCHT1), CD4 (RPA-T4), CD8a (SK1), CD56 (HCD56), and anti-human Fc antibody (HP6017). Anti-human Fc antibody was used to measure the binding of CD8ab antibodies containing hFc. Stained cells were washed and analyzed by flow cytometry and mean fluorescence intensity (MFI) of staining with anti-hFc was used to denote binding.

Figure 4:
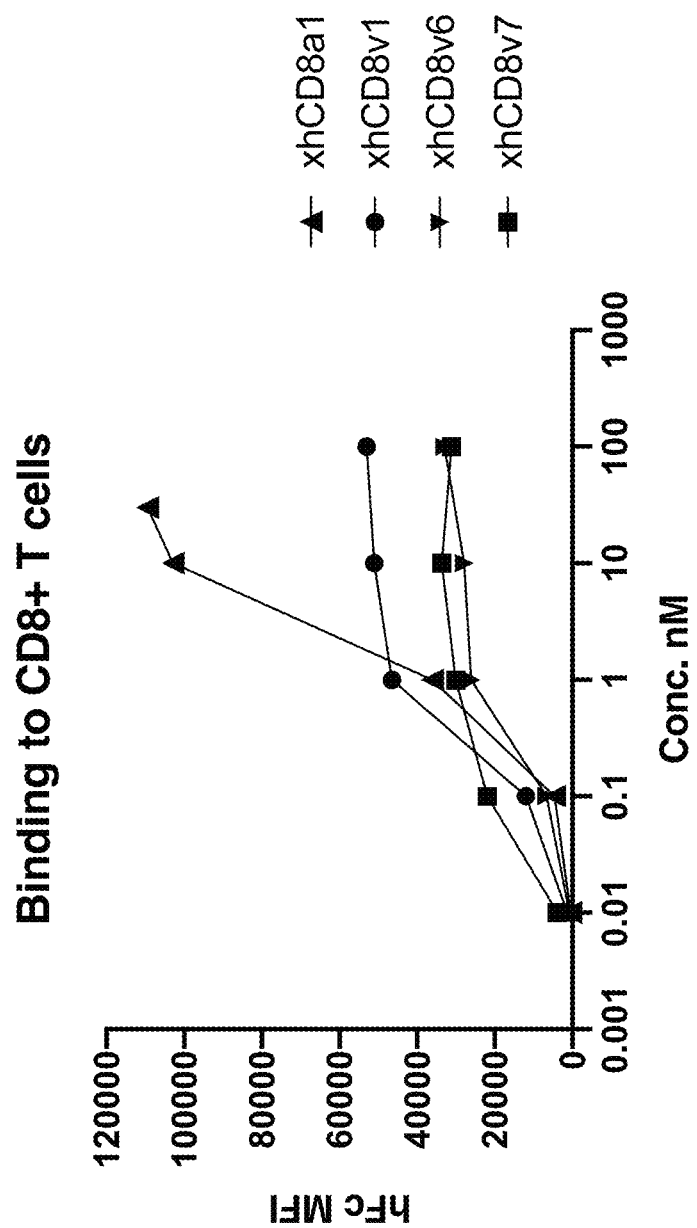
FIGS. 4 & 5 depict the results of a flow cytometry assay to detect the binding of CD8ab antibodies to human PBMCs and distinguish the three types of CD8ab antibodies depicted in FIGS. 1A-1C. Binding of CD8ab antibodies to T cells (FIG. 4) and NK cells (FIG. 5) in hPBMCs was detected by staining with anti-human Fc antibody conjugated to APC. Anti-hFc was used to measure the binding of CD8 antibodies containing hFc. Mean fluorescence intensity (MFI) of staining with anti-hFc is used to denote binding. Binding of anti-hFc was determined in CD3+CD8a+CD8b+ cells (CD8+ T cells) and CD3-CD56+CD8a+ cells (CD8+NK cells).
Figure 5:
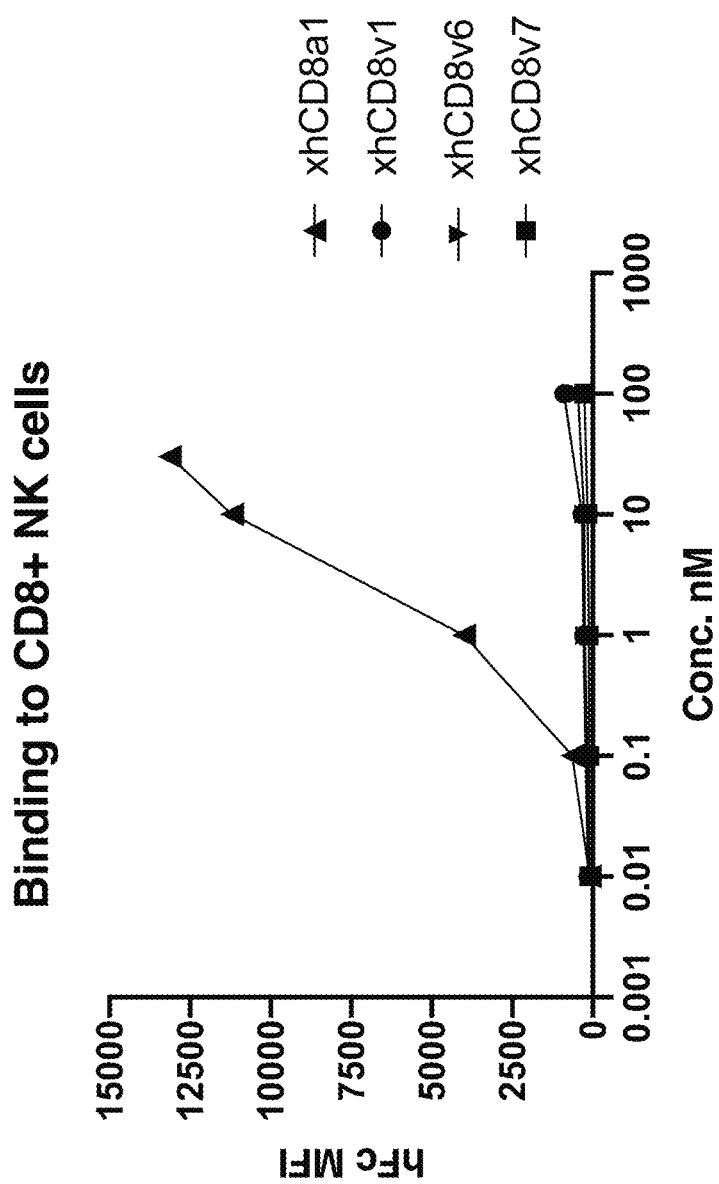

As depicted in FIGS. 4 & 5, xhCD8a1 antibody that recognizes an epitope on CD8a bound both CD8+ T cells and CD8+ NK cells. CD8ab antibodies that recognized CD8ab epitopes or CD8b epitopes selectively bound to CD8+ T cells over CD8+ NK cells.

Figure 6:
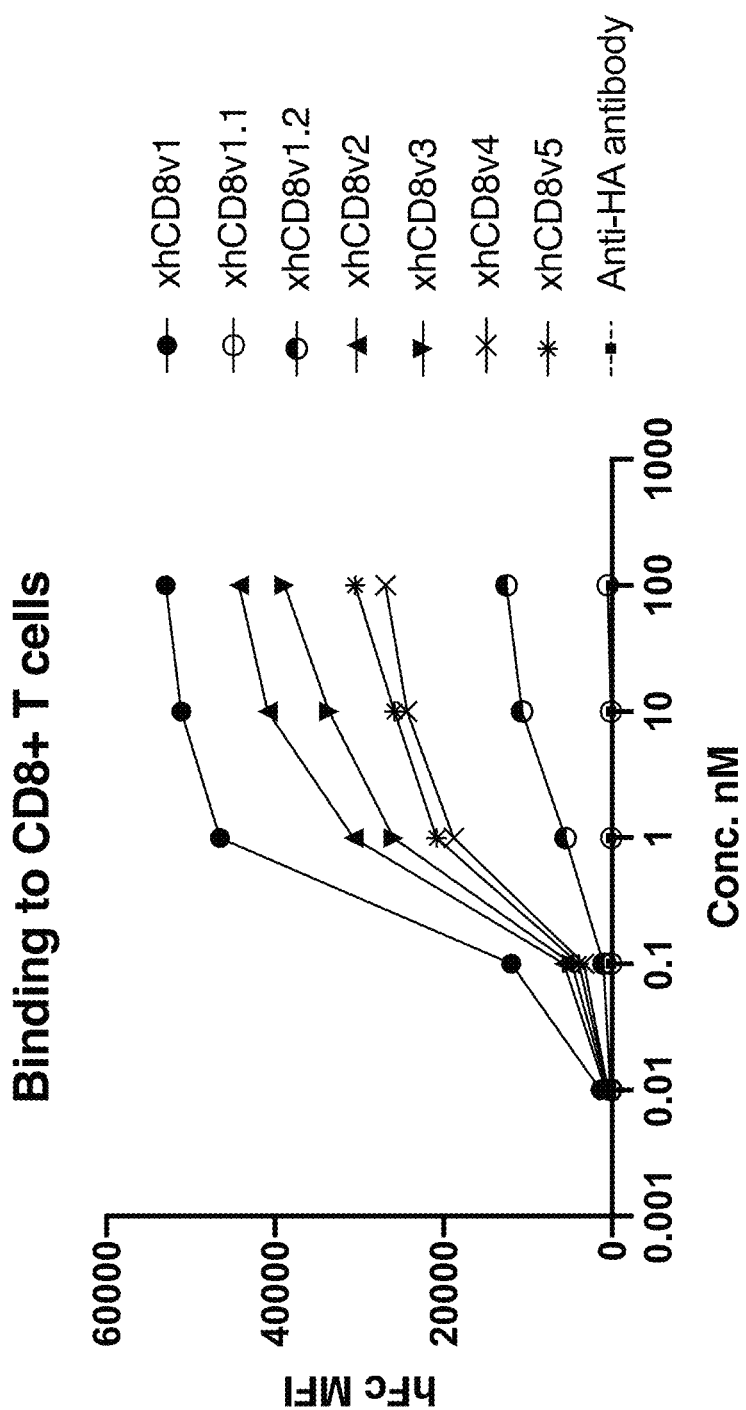
FIG. 6 depicts the results of a flow cytometry assay measuring the binding of CD8ab antibodies binding CD8b epitopes, xhCD8v1 to xhCD8v5, to CD8+ T cells. Negative control antibody, binding HA antigen, was also included.

Next, anti-CD8 antibody xhCD8v1 was humanized and affinity matured. Surprisingly, when xhCD8v1 was grafted onto human framework to generate xhCD8v1.1, the binding to CD8+ T cells was lost (FIG. 6).

Affinity maturation of xhCD8v1.1 resulted in several new variants with increased binding to CD8+ T cells, xhCD8v2, xhCD8v3, xhCD8v4, and xhCD8v5.

Example 2: Fusion Proteins Targeting CD8ab Heterodimer but not CD8aa Homodimer Selectively Activate Human CD8+ T Cells Over CD8+ NK Cells Materials and Methods
Cloning of Fusion Constructs Antibody constructs were cloned as described in Example 1. The IL-2 portions of the constructs were cloned in frame with the heavy chain using a (G4S)3 15-mer linker between the C-terminus of the IgG heavy chain and the N-terminus of IL-2. The C-terminal lysine residue of the IgG heavy chain was eliminated after fusing the IL-2 portion. To generate the construct in which a single IL-2 gene was fused to a full IgG, two heavy chain plasmids needed to be constructed and transfected for heterodimerization facilitated by a knob-into-hole modification in the IgG CH3 domains. The "hole" heavy chain connected to the IL-2 portion carried the Y349C, T366S, L368A and Y407V mutations in the CH3 domain, whereas the unfused "knob" heavy chain carried the S354C and T366W mutations in the CH3 domain (EU numbering). To abolish FcγR binding/effector function and prevent FcR co-activation, the following mutations were introduced into the CH2 domain of each of the IgG heavy chains: L234A/L235A/G237A (EU numbering). The expression of the antibody-IL-2 fusion constructs was driven by an CMV promoter and transcription terminated by a synthetic polyA signal sequence located downstream of the coding sequence.

Preparation of Fusion Proteins with IL-2 Polypeptides

Constructs encoding fusion proteins with IL-2 polypeptides as used in the examples were produced by co-transfecting exponentially growing Expi293 cells with the mammalian expression vectors using polyethylenimine (PEI). Supernatants were collected after 4-5 days of culture. IL-2 fusion constructs were first purified by affinity chromatography using a protein A matrix. The protein A column was equilibrated and washed in phosphate-buffered saline (PBS). The fusion constructs were eluted with 20 mM sodium citrate, 50 mM sodium chloride, pH 3.6. The eluted fractions were pooled and dialyzed into 10 mM MES, 25 mM sodium chloride pH 6. The proteins were further purified using ion-exchange chromatograph (Mono-S, GE Healthcare) to purify the heterodimers over the homodimers. After loading the protein, the column was washed with 10 mM MES 25 mM sodium chloride pH 6. The protein was then eluted with increasing gradient of sodium chloride from 25 mM up to 500 mM in 10 mM MES pH 6 buffer. The major eluent peak corresponding to the heterodimer was collected and concentrated. The purified protein was then polished by size exclusion chromatography (Superdex 200, GE Healthcare) in PBS.

The protein concentration of purified IL-2 fusion constructs was determined by measuring the optical density (OD) at 280 nm, using the molar extinction coefficient calculated on the basis of the amino acid sequence. Purity, integrity and monomeric state of the fusion constructs were analyzed by SDS-PAGE in the presence and absence of a reducing agent (5 mM 1,4-dithiothreitol) and stained with Coomassie blue (SimpleBlue™ SafeStain, Invitrogen). The NuPAGE® Pre-Cast gel system (Invitrogen) was used according to the manufacturer's instructions (4-20% Tris-glycine gels or 3-12% Bis-Tris). The aggregate content of immunoconjugate samples was analyzed using a Superdex 200 10/300 GL analytical size-exclusion column (GE Healthcare).

pSTAT5 and Ki-67 Assays to Measure Activation by IL-2 Fusion Proteins

Activity of IL-2 fusion proteins was determined in an assay with human PBMCs measuring the phosphorylation of STAT5. PBMCs were isolated from blood of healthy donors using Ficoll-Paque Plus (GE Healthcare) and red blood cells were lysed using ACK lysis buffer (Gibco) according to manufacturer's instructions. Typically, PBMCs were resuspended in serum-free RPMI1640 media at $20\times10^6$ cells/ml and aliquoted into 96-well U-bottom plates (50 µl per well). IL-2 fusion proteins and control proteins, such as recombinant human IL-2 and control fusion proteins, were diluted to desired concentrations and added to wells (50 µl added as 2× stimulus). Incubation was typically performed for 30 min at 37° C., after which it was stopped with 100 µl pre-warmed 8% PFA (4% final) for 10 min at room temperature. Cells were washed 3× with wash buffer (2% FBS in PBS). Cells were permeabilized in pre-chilled Phosflow Perm buffer III (BD Biosciences) according to manufacturer's protocol and stored at −20° C. overnight. The next day cells were washed 3× with wash buffer and stained for 30-45 min at 4° C. with antibodies against: CD3 (UCHT1, BD Biosciences), CD8α (SK1, Biolegend; RPA-T8, Biolegend), CD4 (RPA-T4, Biolegend), and CD25 (M-A251, Biolegend), perforin (clone 6G9, BD Biosciences), Foxp3 (clone 259D, Biolegend), pSTAT5 [pY694] (clone 47, BD Biosciences). Cells were then analyzed on a flow cytometer. Data were expressed as percent pSTAT5 positive, and in some cases as pSTAT5 mean fluorescence intensity (MFI), and imported into GraphPad Prism.

To measure cellular changes induced by IL-2 fusion proteins further downstream from pSTAT5 such as proliferation, a flow cytometry assay was used to detect the expression of the intracellular proliferation marker Ki-67. Briefly, PBMCs were isolated as described above and resuspended at $1\times10^6$ cells/ml serum-supplemented RPMI1640 (10% FBS) for 4 to 6 days or serum free AIM V media (Gibco). Cells were plated into 96-well U-bottom plates (150 µl per well) and incubated with 150 µl of IL-2 fusion proteins for five days at 37° C. On final day, cell surface staining was first performed by adding antibodies against: CD3 (UCHT1, BD Biosciences), CD8α (SK1, Biolegend), CD4 (RPA-T4, Biolegend), CD56 (HCD56, Biolegend) and CD25 (M-A251, Biolegend). Cells were washed 3× with wash buffer and intracellular staining performed using the Foxp3/Transcription Factor Staining Buffer Set (Thermo Fisher Scientific) according to manufacturer's protocol. Briefly, 1× Fix/Perm buffer was added to cells for 45 min at 4° C. in the dark. Cells were washed 3× with 1× Perm Wash buffer and stained for 45 min at 4° C. in dark with antibodies against intracellular markers Ki-67 (B56, BD Biosciences) and Foxp3 (259D, Biolegend). Cells were then washed 3× with Perm Wash buffer and analyzed on the flow cytometer.

Results

Fusion proteins comprising the CD8ab antibodies and IL-2 polypeptides of the present disclosure were made in one of four formats (formats A, B, C, and D shown in FIG. 7).

Figure 8A:
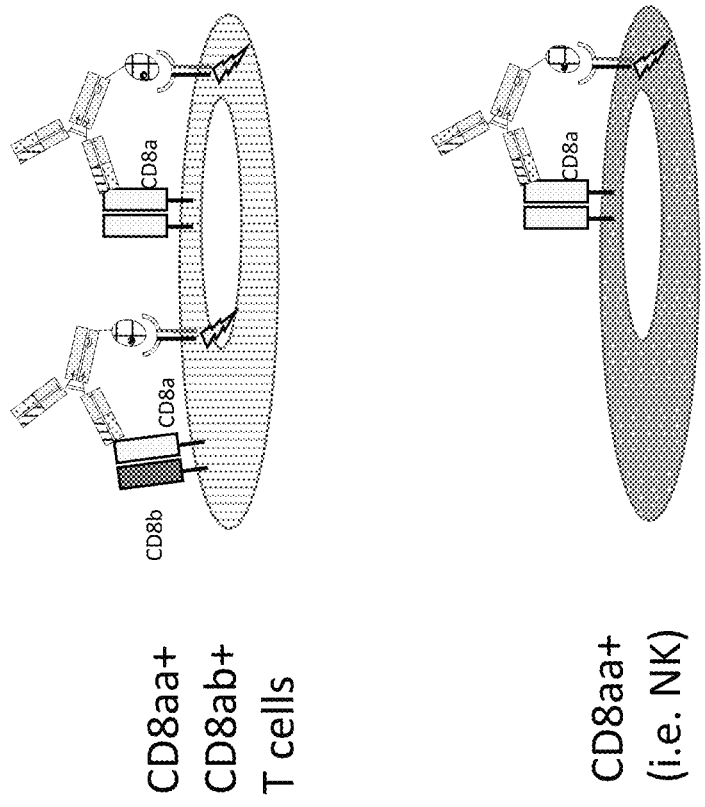
FIGS. 8A-8C depict fusion proteins comprising the three types of CD8ab antibodies depicted in FIGS. 1A-1C and FIGS. 3A-3C and an IL-2Rbg-binding polypeptide. Preferential activation of CD8ab+ T cells over CD8aa+ NK cells is shown.
Figure 8A:
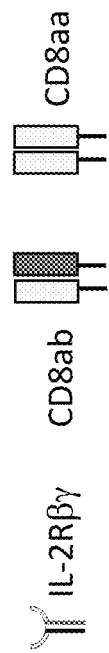
Figure 8B:
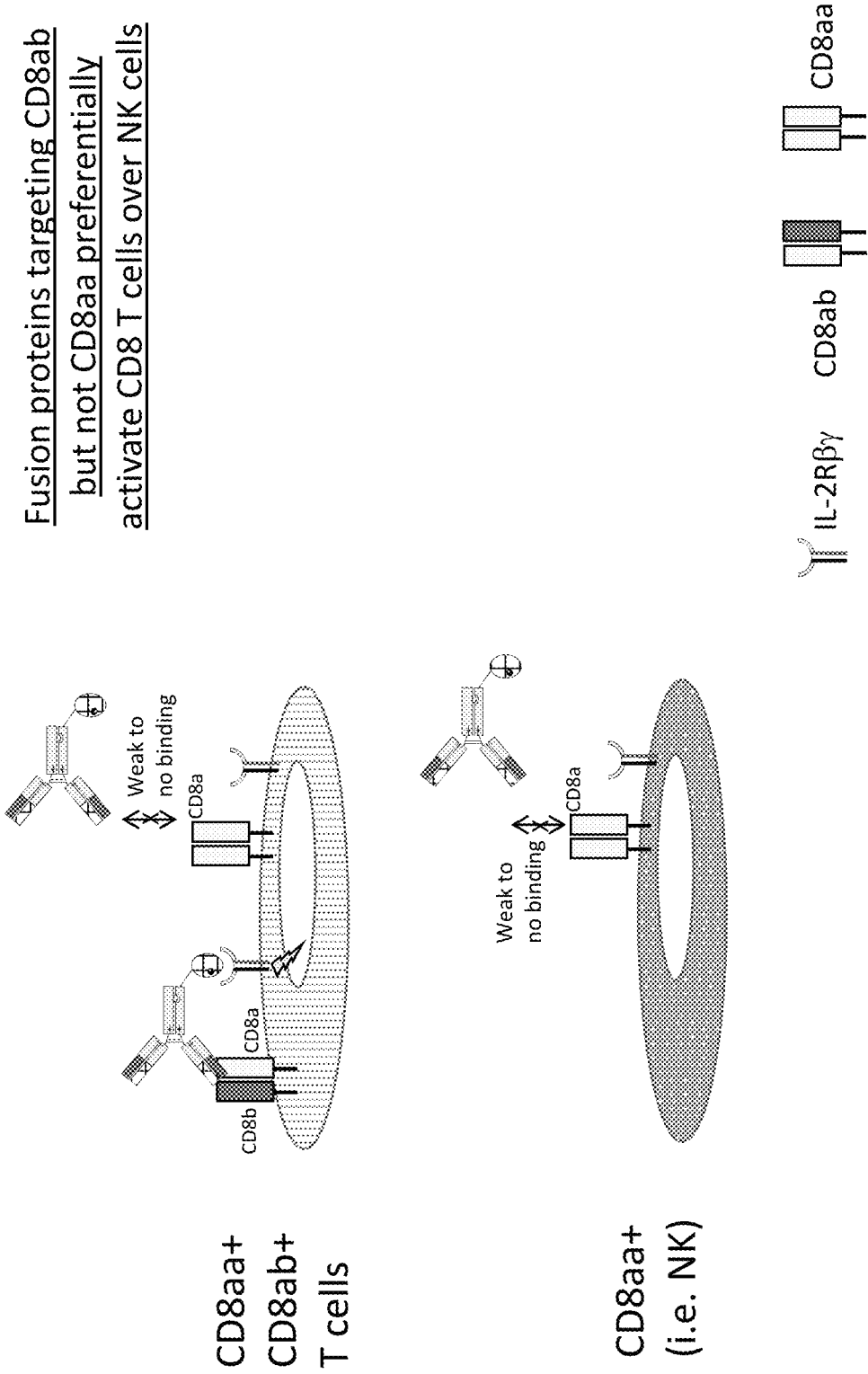
Figure 8C:
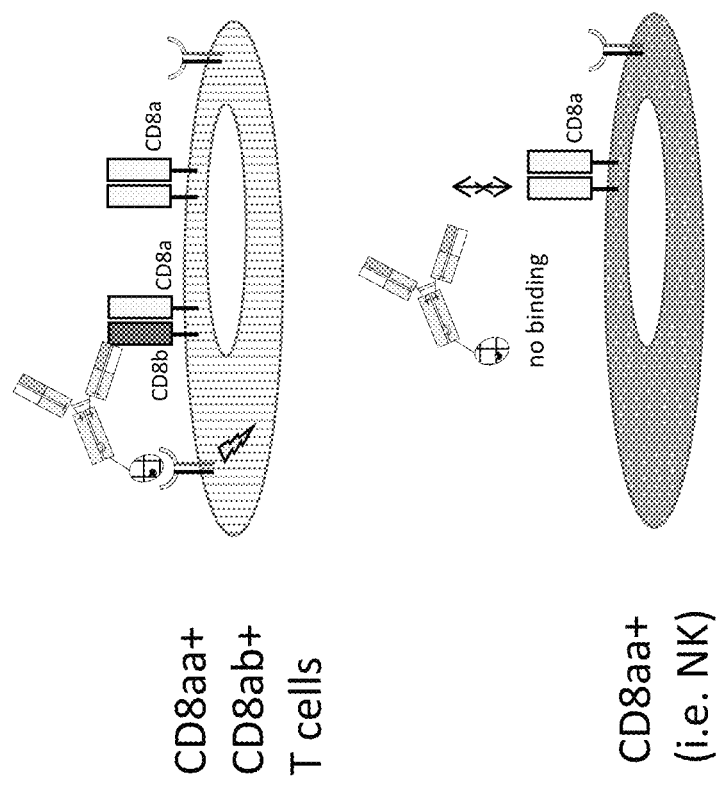
Figure 8C:
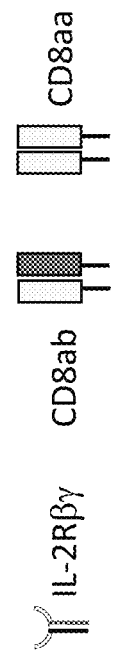

Fusion proteins comprising CD8ab antibodies targeting CD8a activate IL-2Rβγ signaling on both CD8+ T cells and CD8+ NK cells (FIG. 8A). Fusion proteins comprising CD8ab antibodies targeting epitopes between CD8a and CD8b preferentially activate IL-2Rβγ signaling on CD8+ T cells over CD8+ NK cells (FIG. 8B). Fusion proteins comprising CD8ab antibodies targeting CD8b preferentially activate IL-2Rβγ signaling on CD8+ T cells over CD8+NK cells (FIG. 8C).

Figure 9:
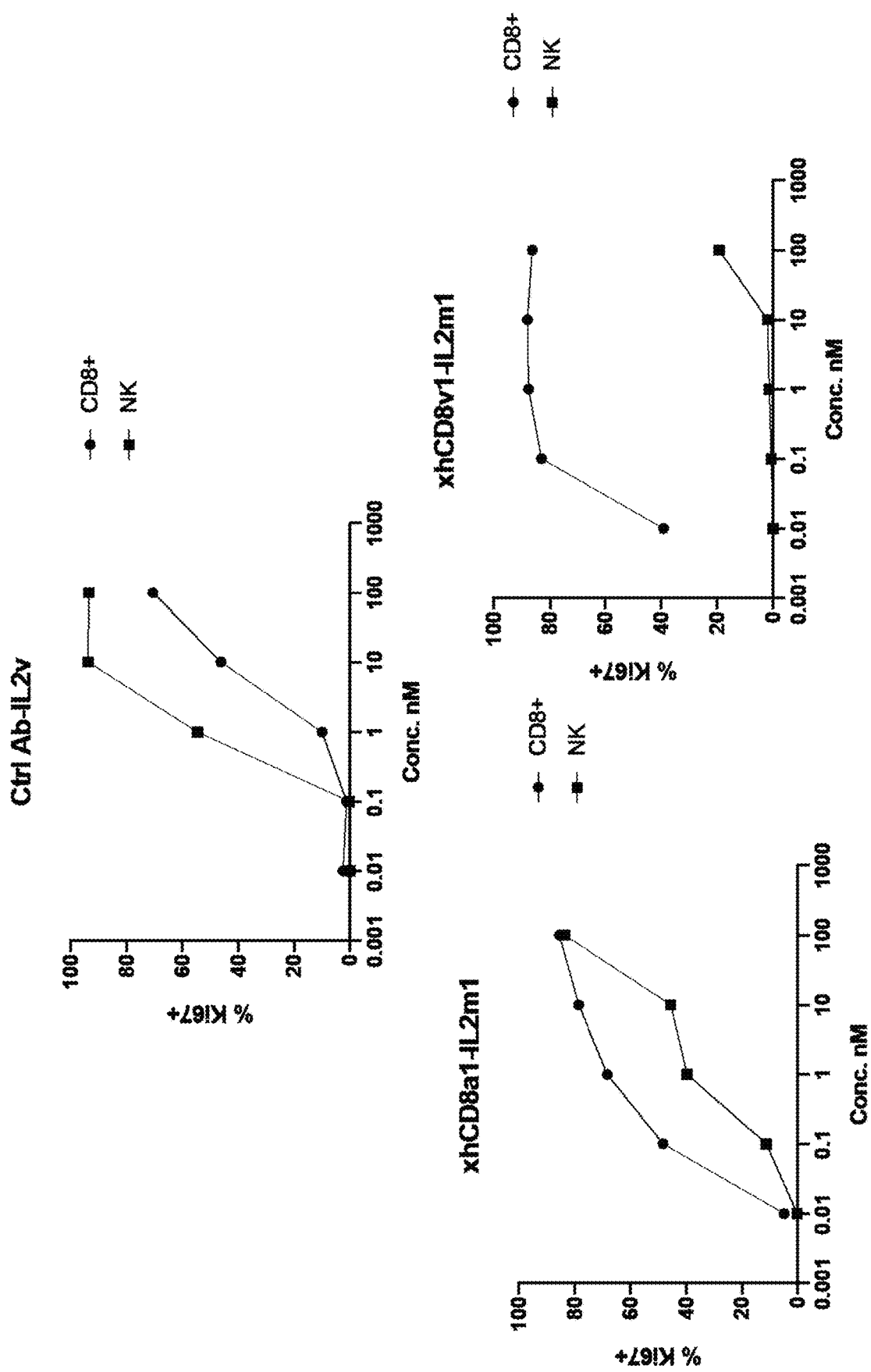
FIG. 9 shows the results of an assay to determine the selectivity of fusion proteins comprising the CD8ab antibodies and an IL-2Rbg-binding polypeptide, IL2m1. The expression of the proliferation marker Ki-67 in CD8+ T cells and NK cells from a hPBMC donor was measured by flow cytometry after five days of co-culture with the following fusion proteins: Ctrl Ab-IL2v, comprising a control antibody and a previously published IL-2 variant (Klein et al, Oncoimmunol. 2017; 6(3); e1277306) (top panel); xhCD8a1-IL-2 m1, comprising CD8 antibody, xhCD8a1, targeting CD8a epitope, and the mutant IL-2 polypeptide of the present disclosure, IL2m1 (bottom left panel); and xhCD8v1-IL2m1, comprising CD8ab antibody of the present disclosure, xhCD8v1, and IL2m1 (bottom right panel). xhCD8a1-IL-2m1 was of format C, while Ctrl Ab-IL2v and xhCD8v1-IL2m1 were of format A. Ki-67 expression was measured in CD8+T cells (filled circles) and NK cells (filled squares). NK cells were defined as CD3-CD56+. CD8 expression was measured by staining with CD8 antibody SK1.

Because large proportion of NK cells can express CD8, fusion proteins comprising CD8ab antibodies not binding to CD8a epitopes also preferentially activated CD8+ T cells over total NK cells. In FIG. 9, the selectivity of different fusion proteins for human CD8+ T cells and NK cells was determined by measuring Ki-67 expression as described in Example 1. For a fusion protein comprising the control antibody and a previously published IL-2 variant (IL2v), NK cells were preferentially activated over CD8+ T cells. For a fusion protein comprising the CD8ab antibody targeting CD8a (xhCD8a1) and IL-2 mutant polypeptide, IL2m1, CD8+ T cells were preferentially activated over NK cells however only with a preference of ~10×. Much stronger preference in activating CD8+ T cells was obtained by fusion proteins comprising CD8ab antibody targeting CD8b (xhCD8v1) and IL-2 mutant polypeptide, IL2m1 (>1000×).

Figure 10A:
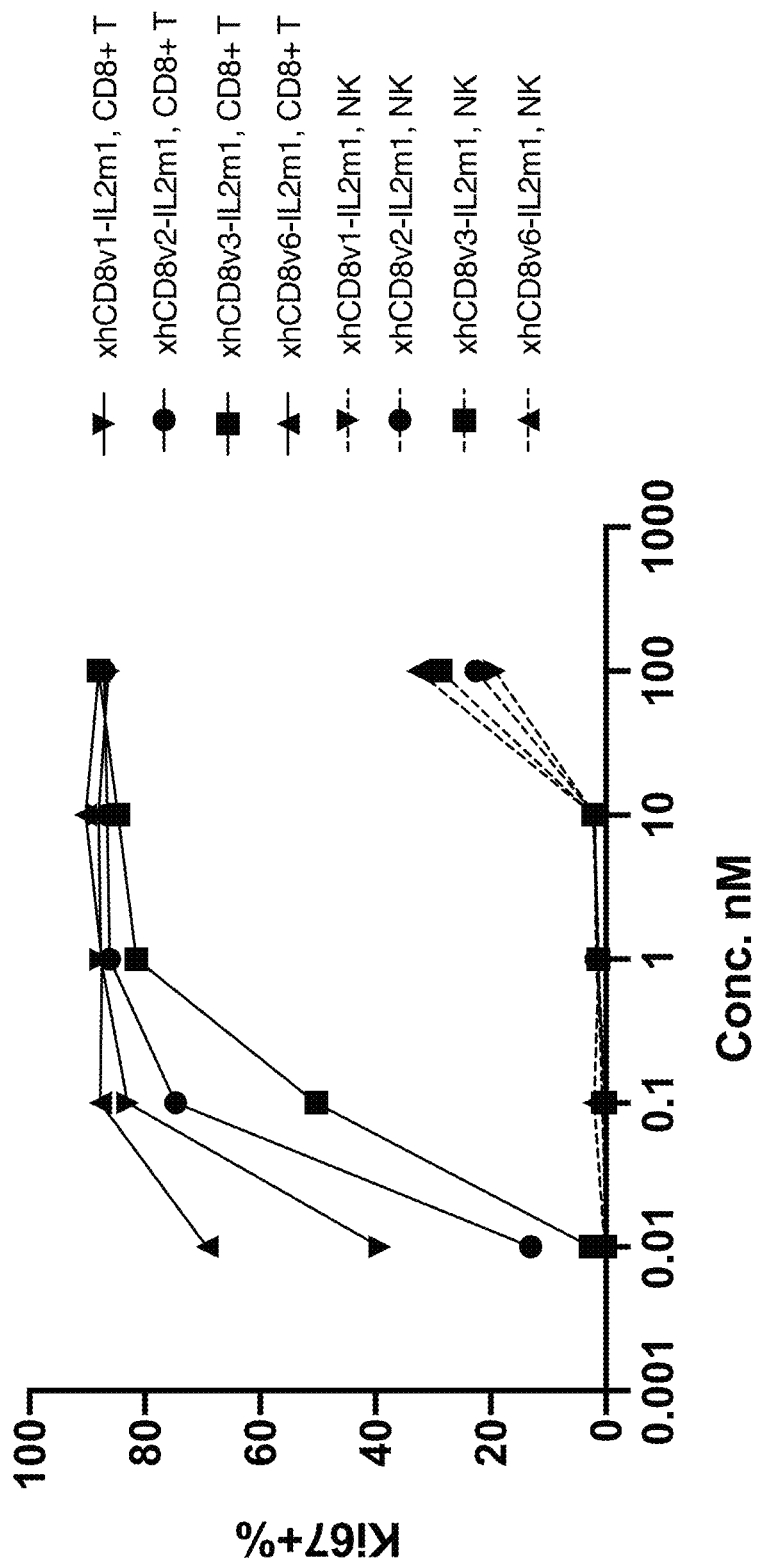
FIGS. 10A-10C depict the expression of Ki-67 proliferation marker after five day co-culture of hPBMCs from three different donors with indicated fusion proteins. All fusion proteins contained the mutant IL-2 polypeptide, IL2m1, and CD8ab antibodies of the present disclosure, xhCD8v1 to xhCD8v7 and were of format A. Ki-67 expression was measured in CD8+ T cells (solid lines) and NK cells (dashed lines).
Figure 10B:
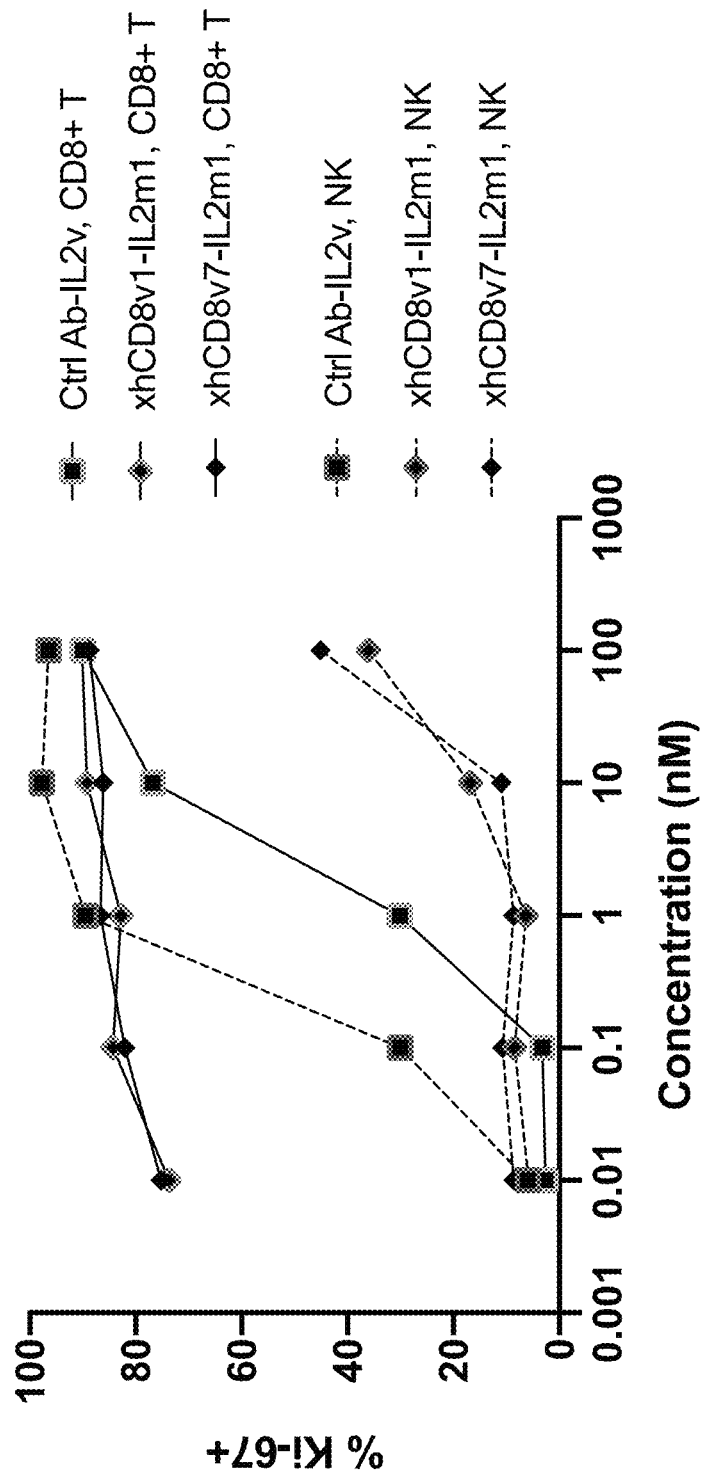
Figure 10C:
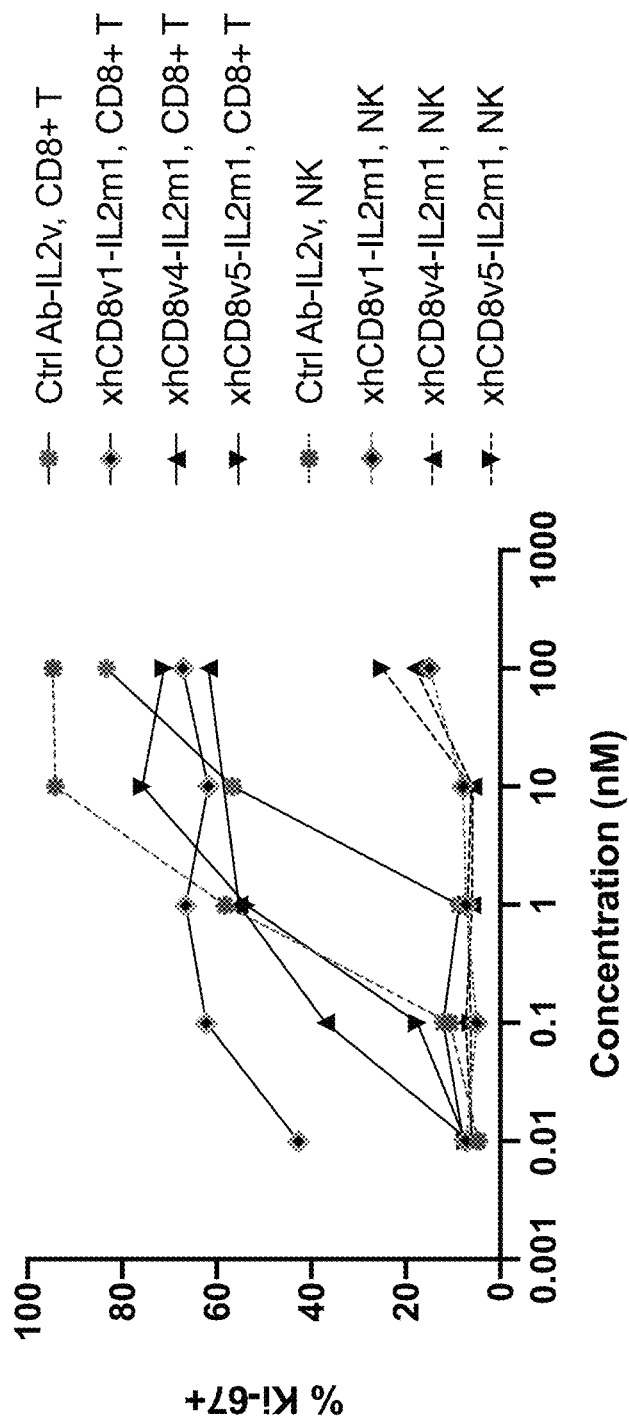
Figure 11A:
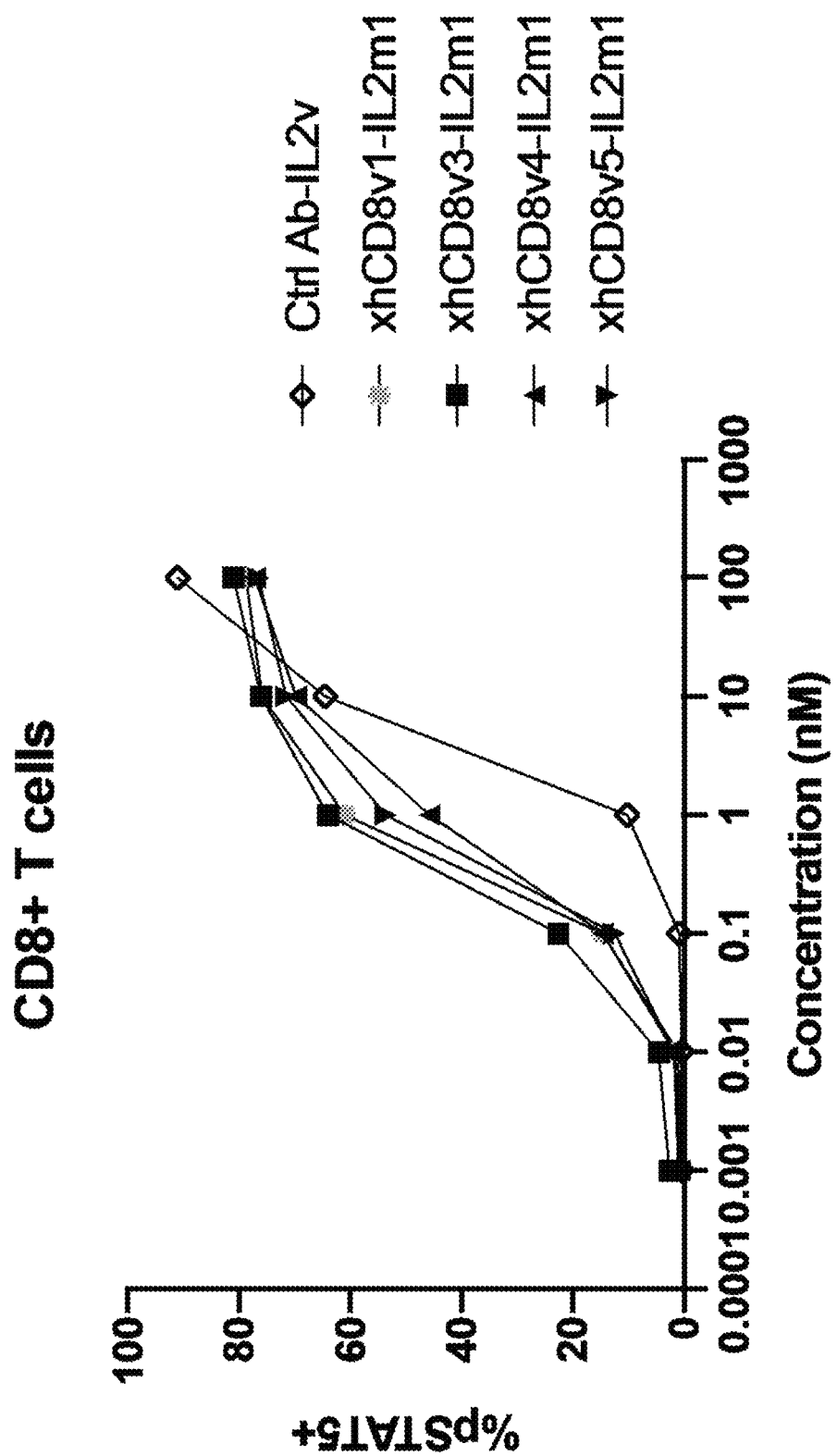
FIGS. 11A-11D show the results of the phospho-STAT5 assay with hPBMCs from one donor cultured with the indicated fusion proteins, all of format C. Percent pSTAT5-expressing cells was depicted in the following hPBMC subsets: CD8+ T cells (FIG. 11A), NK cells (FIG. 11B), Treg cells (FIG. 11C), and CD4+Foxp3- T cells (FIG. 11D). NK cells were identified as CD3-Perforin+. Treg cells were identified as CD4+Foxp3+CD25+.
Figure 11B:
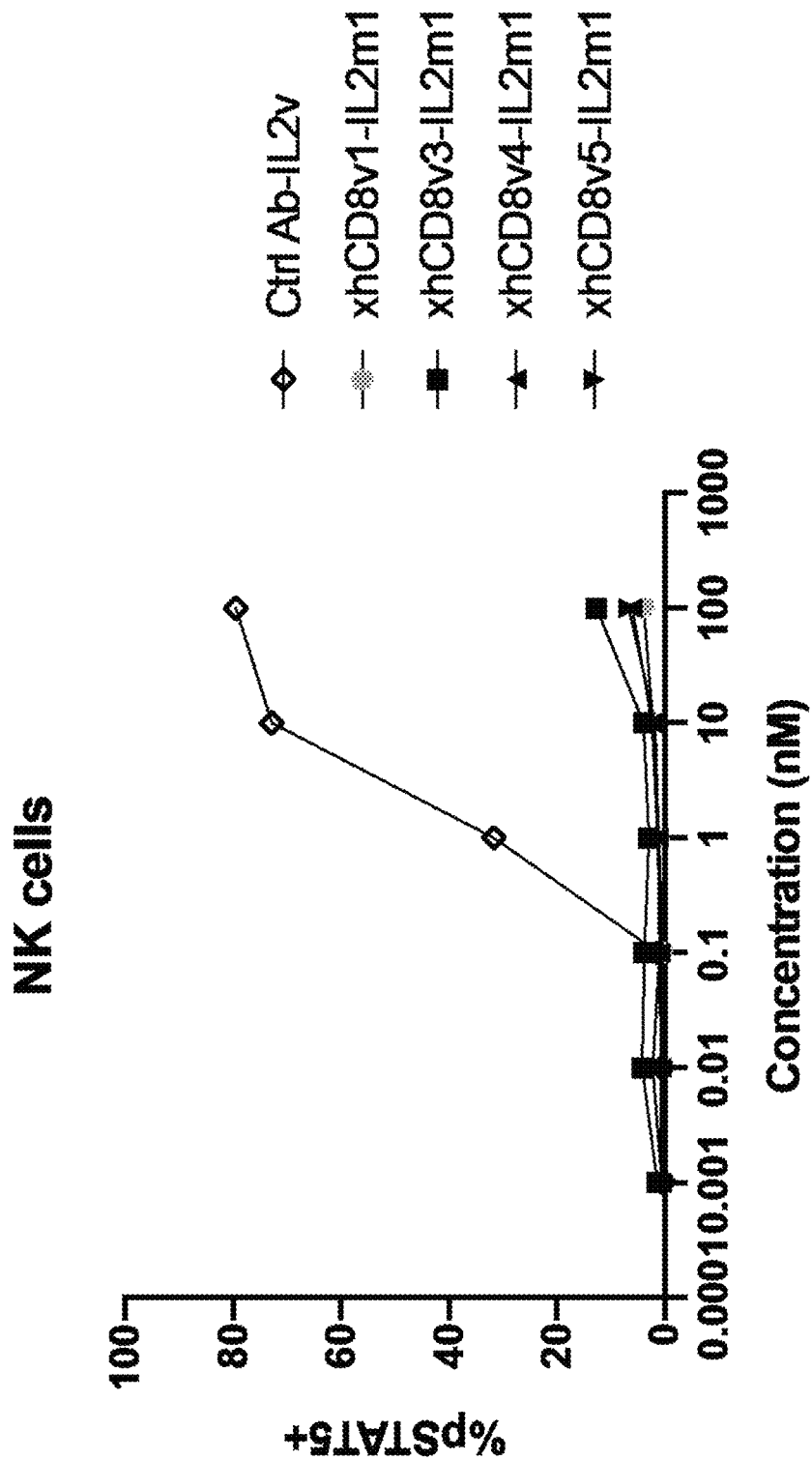
Figure 11C:
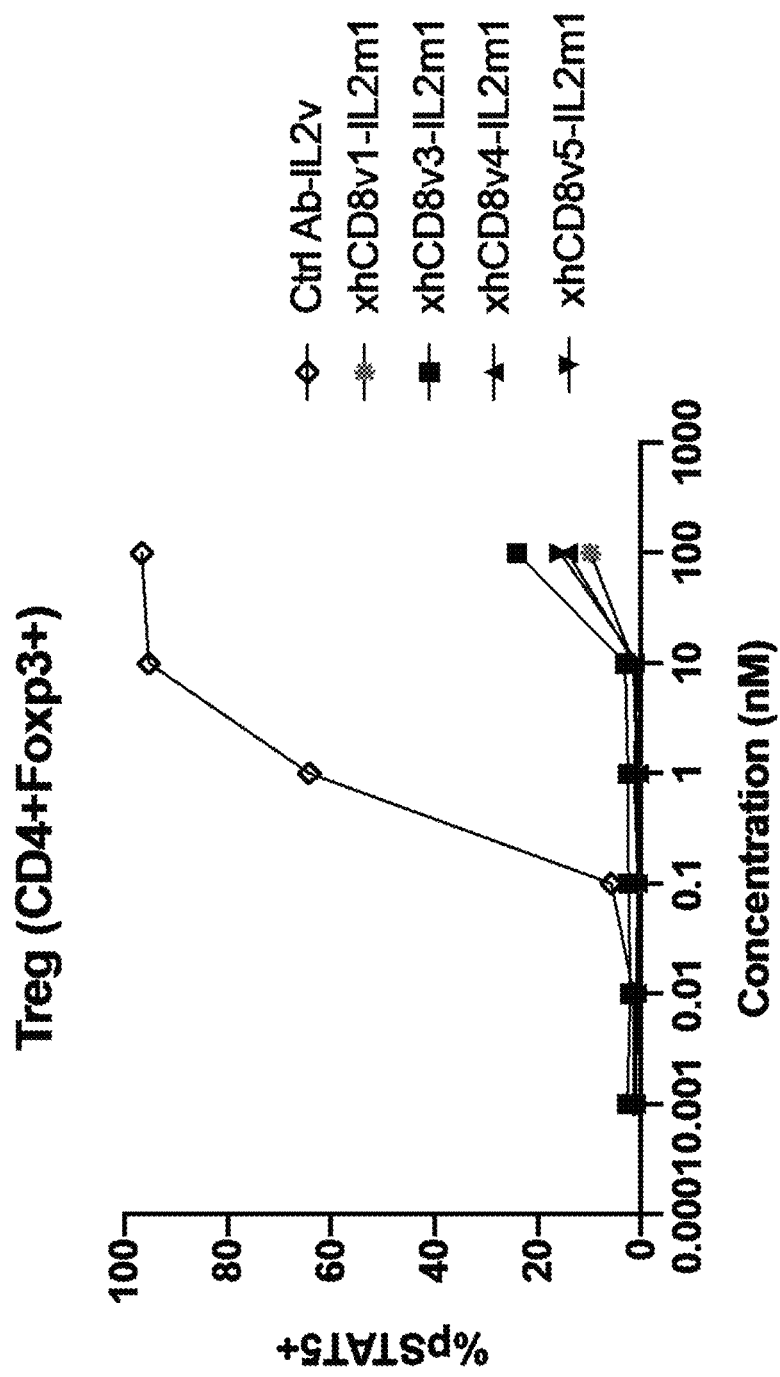
Figure 11D:
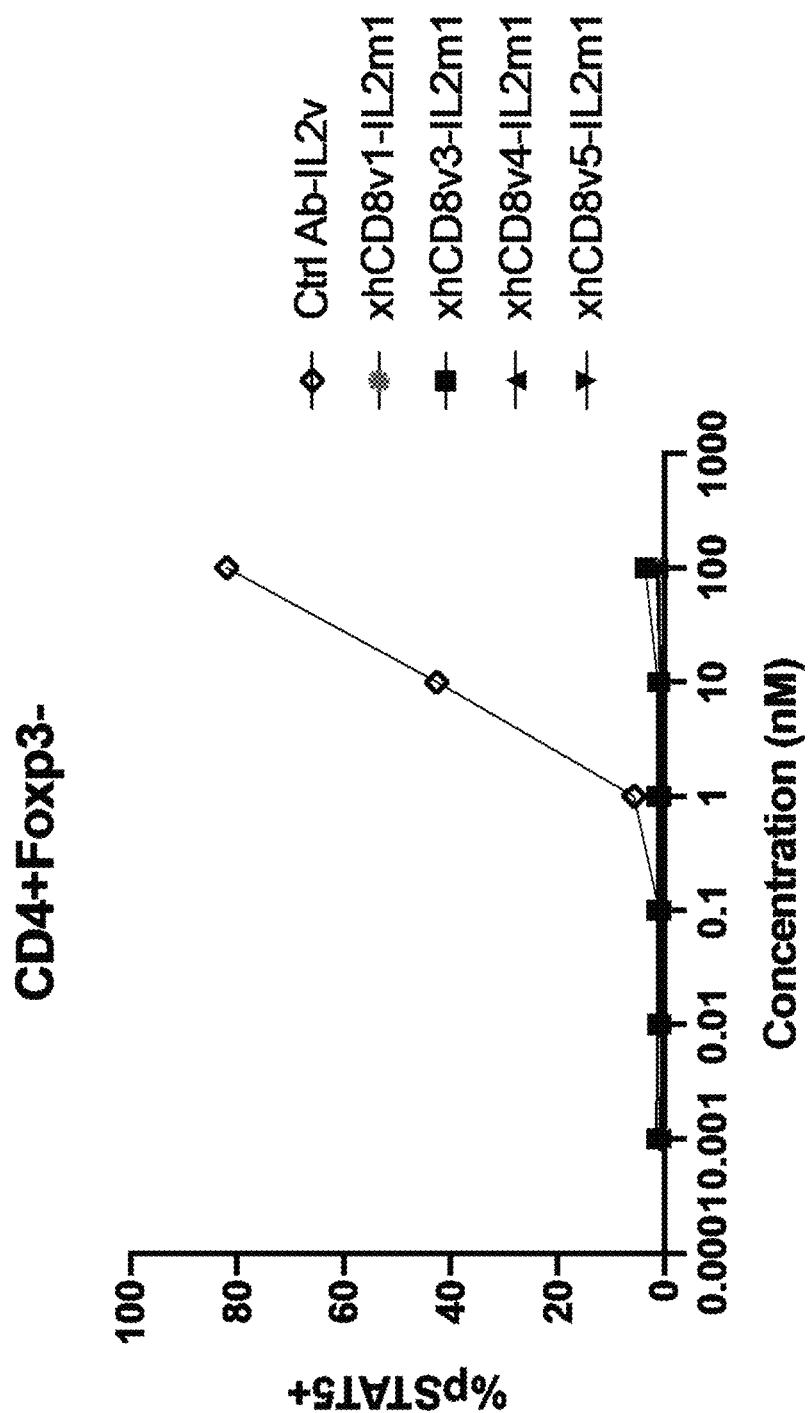

In additional examples shown in FIGS. 10A-10C, strong preference for activating Ki-67 proliferation marker on CD8+ T cells over NK cells was shown by other CD8ab antibodies targeting either epitopes between CD8a and CD8b, such as xhCD8v6 (FIG. 10A), and xhCD8v7 (FIG. 10B) or CD8b alone epitopes, such as xhCD8v2 to xhCD8v5 (FIG. 10A and FIG. 10C). For each of the tested fusion proteins comprising CD8ab antibodies, the preference for CD8 T cells over NK cells was >100× using Ki-67 assay as a readout.

Similar preference for CD8+ T cells over NK cells was also demonstrated using pSTAT5 assay as shown in FIGS. 11A-11D. STAT5 activation was measured in different lymphocyte subsets from one human PBMC donor. Fusion protein Ctrl-IL2v indiscriminately activated CD8+ T cells, NK cells, Treg cells and T effector (CD4+Foxp3−) cells while fusion proteins comprising CD8ab antibodies of the present disclosure and mutant IL-2 polypeptide selectively activated CD8+ T cells over NK cells by at least 100×.

Figure 12:
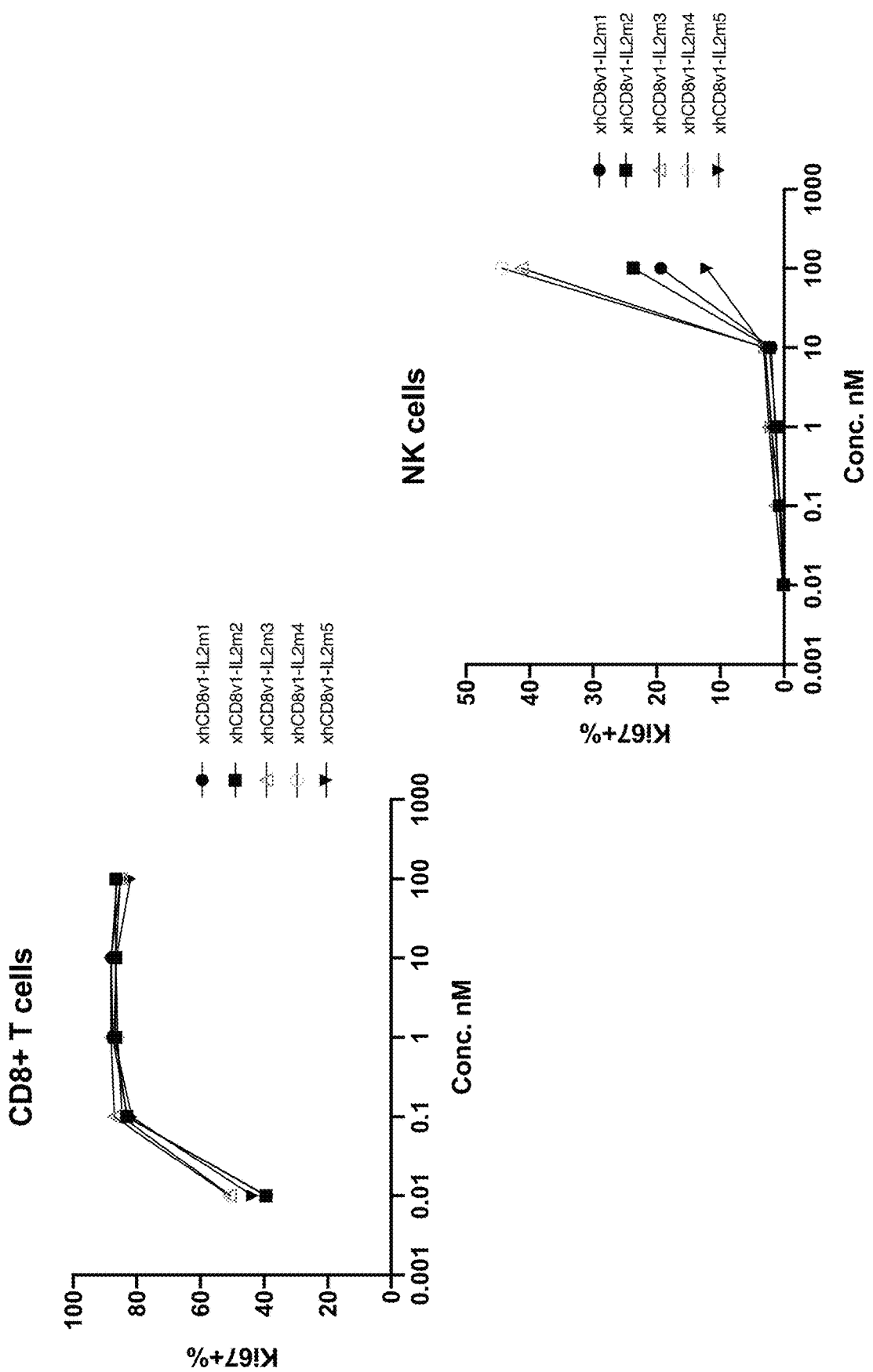
FIG. 12 shows the expression of Ki-67 proliferation marker after five day co-culture of hPBMCs from one donor with indicated fusion proteins. All fusion proteins contained the CD8ab antibody of the present disclosure, xhCD8v1, and various mutant IL-2 polypeptides of the present disclosure, IL2m1 to IL2m5, and were of format A. Ki-67 expression was measured in CD8+ T cells (left panel) and NK cells (right panel).

Ki67 activation in CD8+ T cell and NK cells was tested after incubation of hPBMCs from another donor with fusion proteins comprising the same xhCD8v1 antibody and one of the following IL-2 polypeptides: IL2m1, IL2m2, IL2m3, IL2m4 or IL2m5. IL-2 polypeptide sequences are shown in Table 7. As depicted in FIG. 12, all five fusion proteins achieved similar CD8+ T cell activation ($EC_{50}$~0.01 nM), preferentially to NK cells with the following ranking for $EC_{50}$ for NK cells: IL2m3, IL2m4<IL2m1, IL2m2<IL2m5.

Figure 13A:
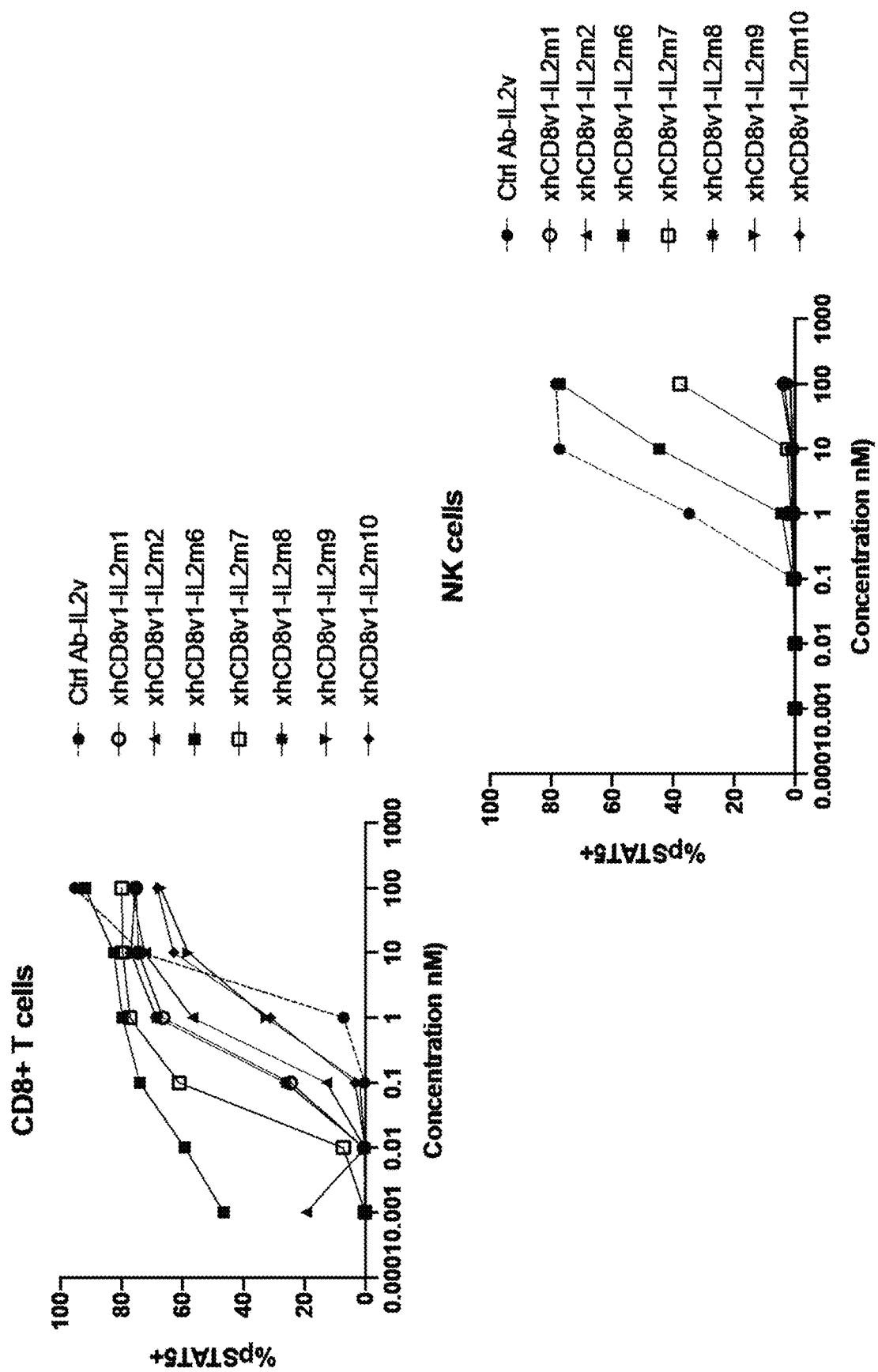
FIG. 13A and FIG. 13B show the results of the phospho-STAT5 assay with hPBMCs from one donor cultured with the indicated fusion proteins. Percent pSTAT5-expressing cells was depicted in the following hPBMC subsets: CD8+ T cells and NK cells.
Figure 13B:
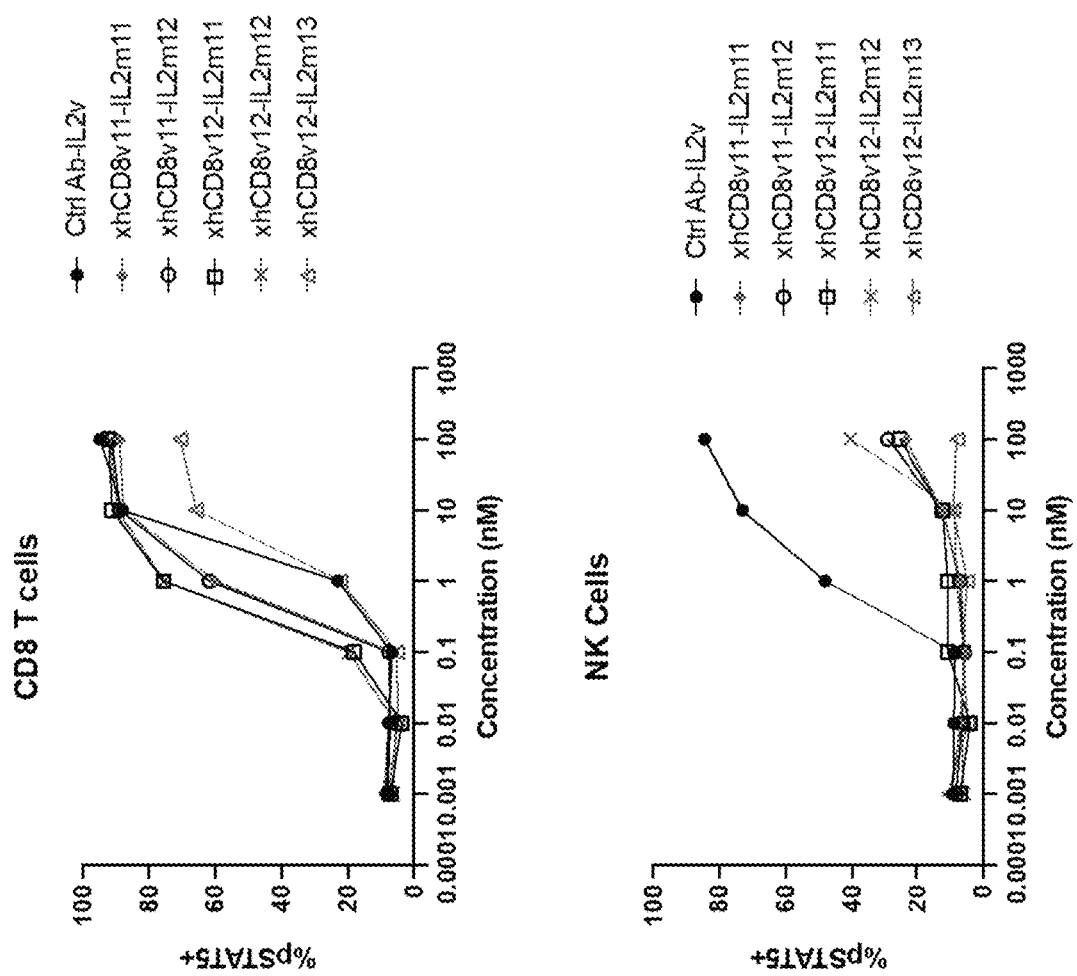

FIG. 13A shows STAT5 activation of CD8+ T cells and NK cells by fusion proteins containing the same xhCD8v1 antibody and one of the following IL-2 polypeptides: IL2m1, IL2m2, IL2m6, IL2m7, IL2m8, IL2m9 or IL2m10 (solid line) in comparison to the Ctrl Ab-IL2v (dashed line). All fusion proteins comprising xhCD8v1 activated CD8+ T cells with lower $EC_{50}$ than Ctrl Ab-IL2v and with the following ranking for $EC_{50}$: IL2m6<IL2m7<IL2m1, IL2m8<IL2m2<IL2m9, IL2m10. All fusion proteins comprising xhCD8v1 activated NK cells with higher $EC_{50}$ than Ctrl Ab-IL2v. Except for xhCD8v1-IL2m6 and xhCD8v1-IL2m7, $EC_{50}$ of STAT5 activation for NK cells was >100 nM. FIG. 13B shows the STAT5 activation of CD8+ T cells and NK cells by fusion proteins containing either xhCD8v11 or xhCD8v12 antibody and one of the following IL-2 polypeptides: IL2m11, IL2m12, or IL2m13 in comparison to the Ctrl Ab-IL2v. All fusion proteins comprising either xhCD8v11 or xhCD8v12 activated CD8+ T cells with lower EC50 than NK cells, and with the following ranking for EC50: IL2m12, IL2m11<IL2m13. All fusion proteins comprising xhCD8v11 or xhCD8v12 antibody activated NK cells with higher EC50 than Ctrl Ab-IL2v. EC50 of STAT5 activation for NK cells was >100 nM.

Example 3: Effect of Fusion Protein Format on CD8+ T Cell Activation

Figure 14A:
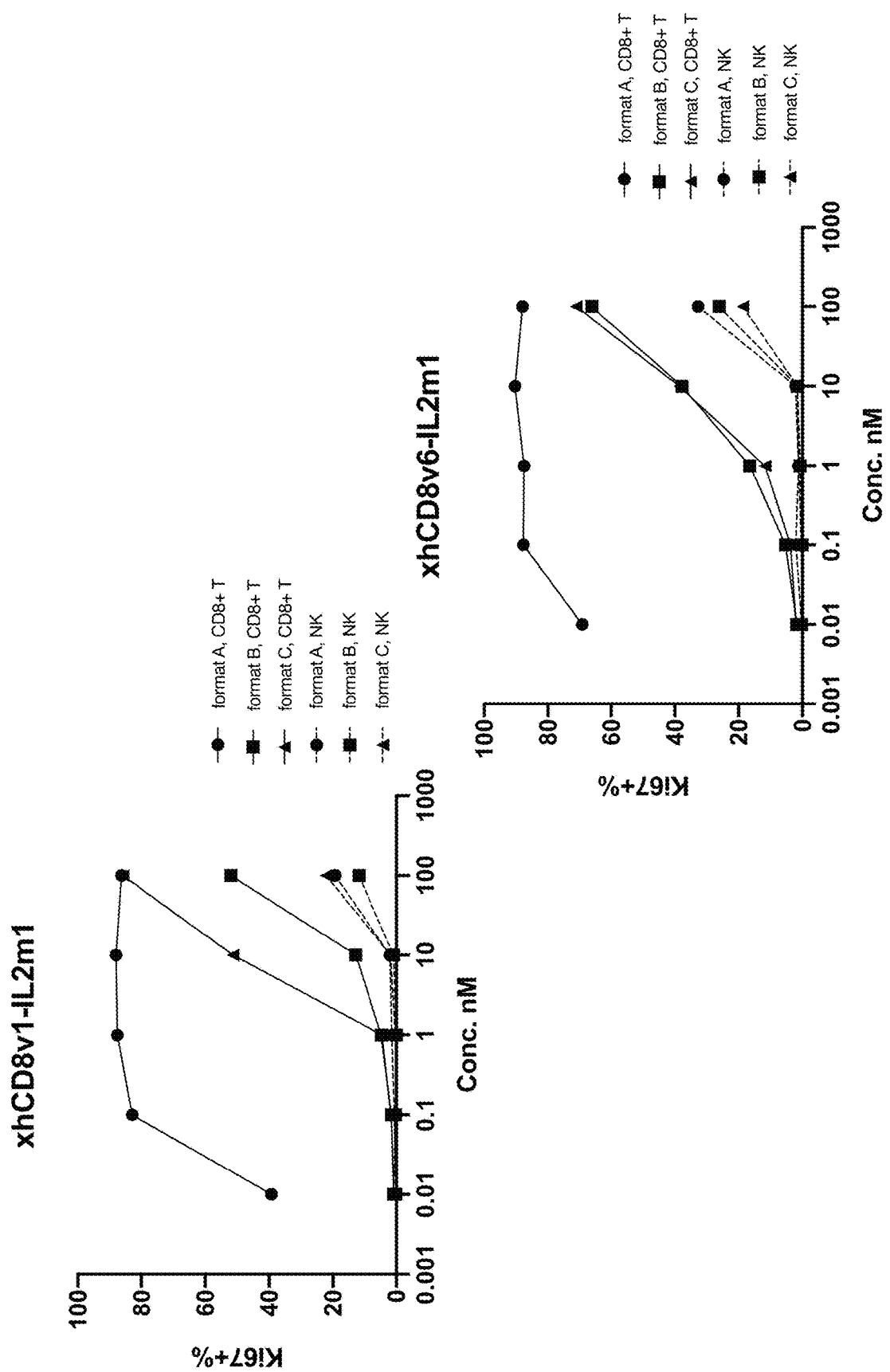
FIG. 14A shows the expression of Ki-67 proliferation marker after five day co-culture of hPBMCs from one donor with xhCD8v1-IL2m1 (left panel) and xhCD8v6-IL2m1 (right panel). Three different fusion protein formats as depicted in FIG. 7 were tested: format A, format B and format C, as indicated. Solid lines depict Ki-67 expression in CD8+ T cells and dashed lines represent Ki-67 expression in NK cells. Format A resulted in substantial increase in activity on CD8+ T cells over NK cells for both CD8ab antibodies tested suggesting this is the preferred format for fusion proteins containing CD8ab antibodies targeting epitopes between CD8a and CD8b (FIG. 8B) or CD8b epitopes (FIG. 8C).

FIG. 14A depicts the impact of fusion protein format on preferential CD8+ T cell activation. Activation of CD8+ T cells (solid lines) and NK cells (dotted lines) by xhCD8v1-IL2m1 (left panel) and xhCD8v6-IL2m1 (right panel) in 3 different formats (A, B, C, see FIG. 7) as indicated in FIG. 14A legend are shown. Although all three formats activated CD8+ T cells preferentially over NK cells, format A resulted in the largest preference compared to format B and C. This suggests that format A is optimal for fusion proteins with CD8ab antibodies targeting epitopes between CD8a and CD8b or CD8b alone.

Figure 14B:
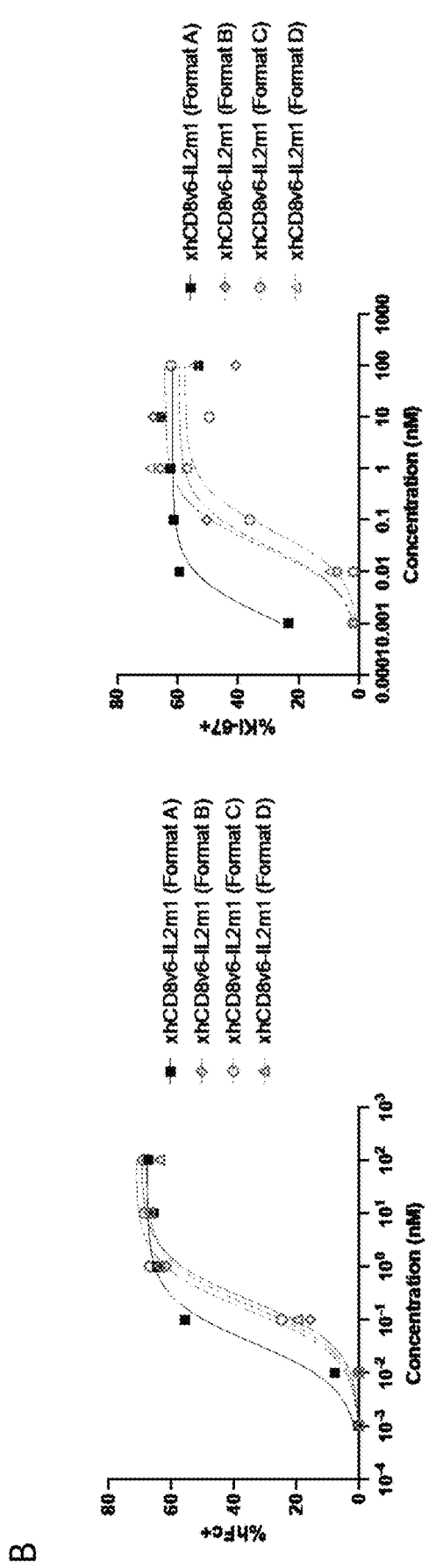
FIG. 14B depicts the binding (left panel) and induction of Ki67 (right panel) in CD8+ T cells from one donor with xhCD8v6-IL2m1. Four different fusion protein formats as depicted in FIG. 7 were tested: format A, format B, format C, and format D as indicated. While format A is approximately 5-fold stronger than other format in cell binding, format A is 20- to 40-fold more potent than other formats in inducing Ki-67.
Figure 14C:
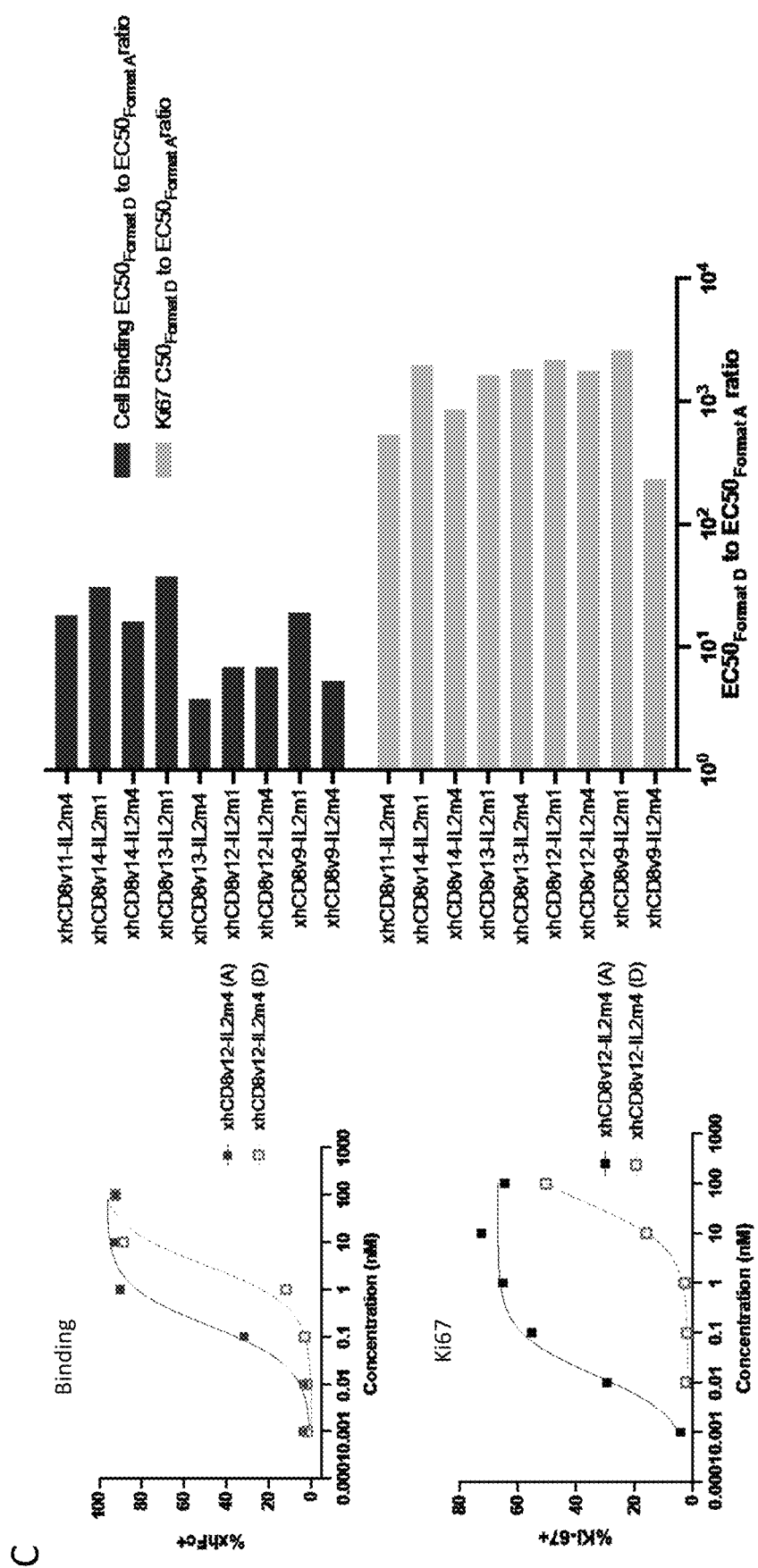
FIG. 14C depicts the results of nine fusion molecules in format A and D as assessed for binding to CD8+ T cells, and induction of Ki67 in CD8+ T cells. Examples for binding and ki-67 curves for xhCD8v12-IL2m4 were shown in the left panel. For a given binder and mutein pair, the ratio of EC50s of format D over format A is shown for binding and Ki67 in the right panel. For all the molecules tested, format A showed a potency shift over format D of approximately 10-fold in binding EC50. However, when assessed for the activation of a further downstream proliferation marker Ki67, format A exhibits approximately 1000-fold increase in potency over format D in inducing Ki-67.

FIG. 14B depicts the impact of fusion protein format on preferential CD8+ T cell activation. The binding and the ability to induce Ki67 for xhCD8v6-IL2m1 in all four formats shown in FIG. 7 (A, B, C, & D) were evaluated. Format A showed about 5-fold higher affinity in cell binding compared to other formats; this is likely due to the avidity-driven binding enhancement by format A. Surprisingly, compared to binding fold change, format A (black solid line) showed greater extent of Ki67 induction, ~20- to 40-fold, over formats B, C, and D (grey dashed lines). Results here suggested that format A can preferentially and disproportionately induce a greater level of Ki67 activation compared to other formats. FIG. 14C depicts the results of fusion molecules in format A and D as assessed for binding to CD8+ T cells, and induction of Ki67 in CD8+ T cells for a wide range of xhCD8 binders fused to IL2m1 and IL2m4. Due to the enhanced avidity mediated by bivalent binding, format A showed about 10-fold decrease in binding EC50s over format D for all fusions. Unexpectedly, format A showed a potency increase over format D of approximately 200- to over 1,000-fold in proliferation biomarker Ki-67 activation, beyond the 10-fold increase observed for binding. Therefore, results here supported that format A is more superior in inducing downstream proliferation, and hence the preferred format for fusion proteins containing CD8ab antibodies targeting epitopes between CD8a and CD8b (FIG. 8B) or CD8b epitopes (FIG. 8C).

Figure 15:
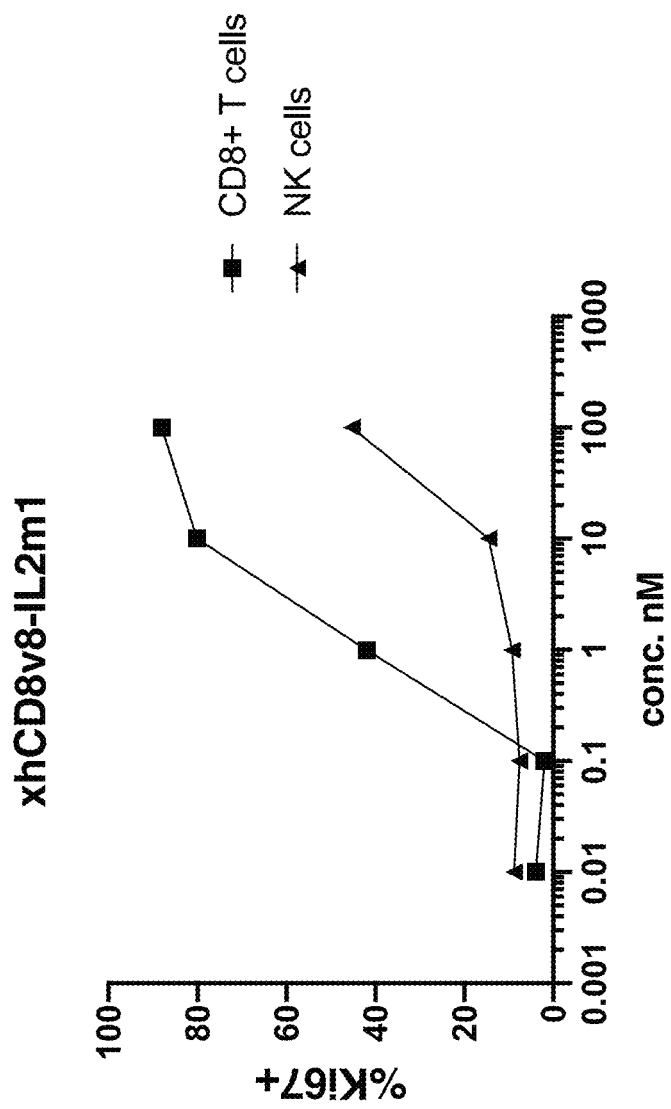
FIG. 15 shows the expression of Ki-67 proliferation marker after five day co-culture of hPBMCs with xhCD8v8-IL2m1, a fusion protein of format A containing the mutant IL-2 polypeptide, IL2m1, and CD8ab antibody of the present disclosure, xhCD8v8. Ki-67 expression was measured in CD8+ T cells (squares) and NK cells (triangles).

FIG. 15 depicts greater than 10 fold preferential Ki67 activation in CD8 T cells (filled squares) over NK cells (filled triangles) by the xCD8v8-IL2m1 fusion protein containing a CD8ab antibody xCD8v8.

Example 4: Fusion Proteins of the Present Disclosure Selectively Activate and Enrich CD8+ T Cells in TILs from Human Cancer Patients Single cell suspensions containing TILs were isolated from a tumor biopsy taken from a renal cell carcinoma patient using the Human Tumor Dissociation Kit (Miltenyi) according to manufacturer's protocol. Single cell suspensions were resuspended in complete RPMI media and plated at $1 \times 10^5$ cells/well with the indicated fusion proteins in a total of 300 µl per well. After five days the cultures were analyzed for the expression of Ki-67 in various subsets and total cell counts per well determined by flow cytometry.

Figure 16A:
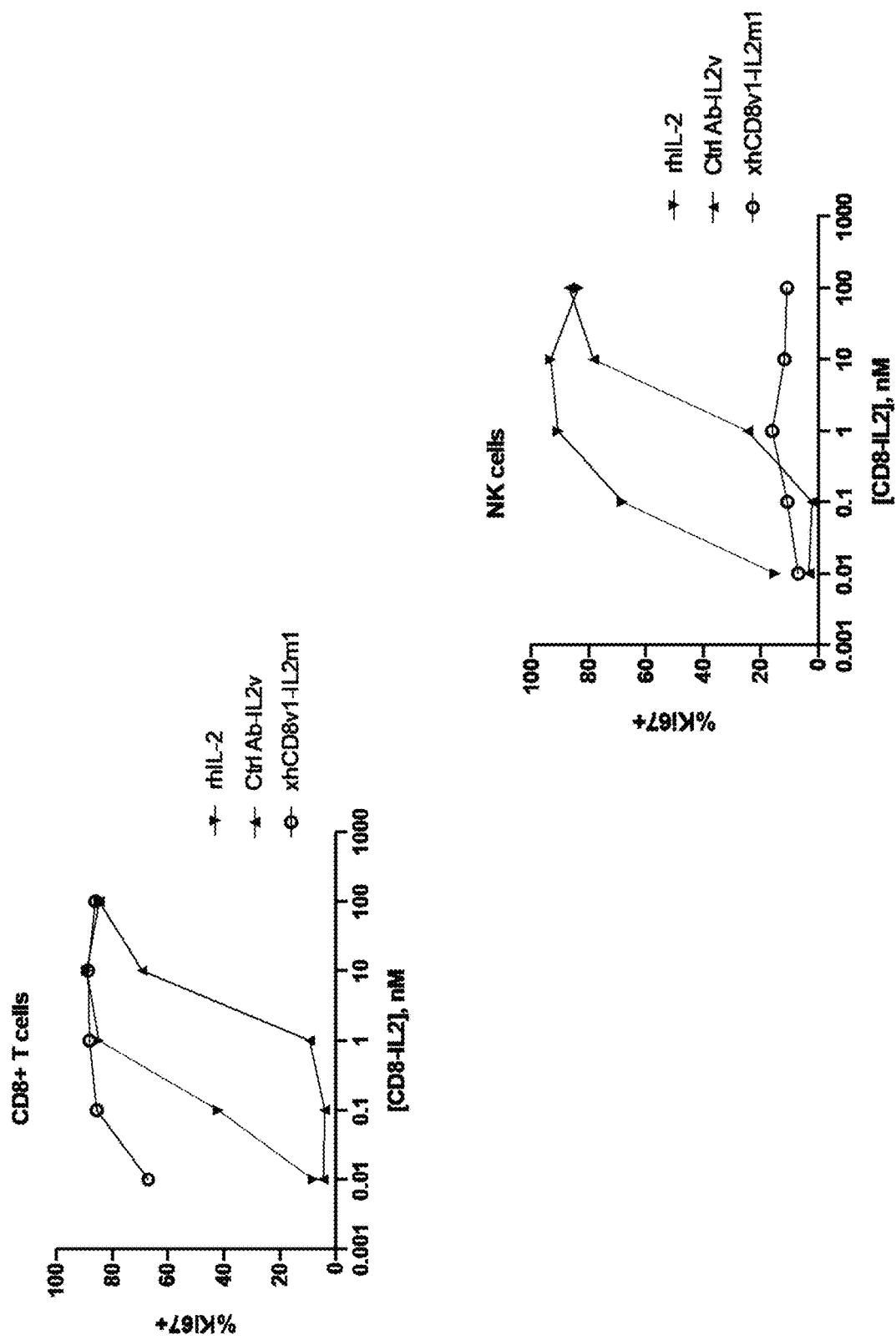
FIG. 16A depicts the expression of Ki-67 in tumor infiltrating lymphocytes (TILs) gated on CD8+ T cells (left panel) and NK cells (right panel). TILs were incubated with rhIL-2 or the indicated fusion proteins (format A) for five days before analysis.
Figure 16B:
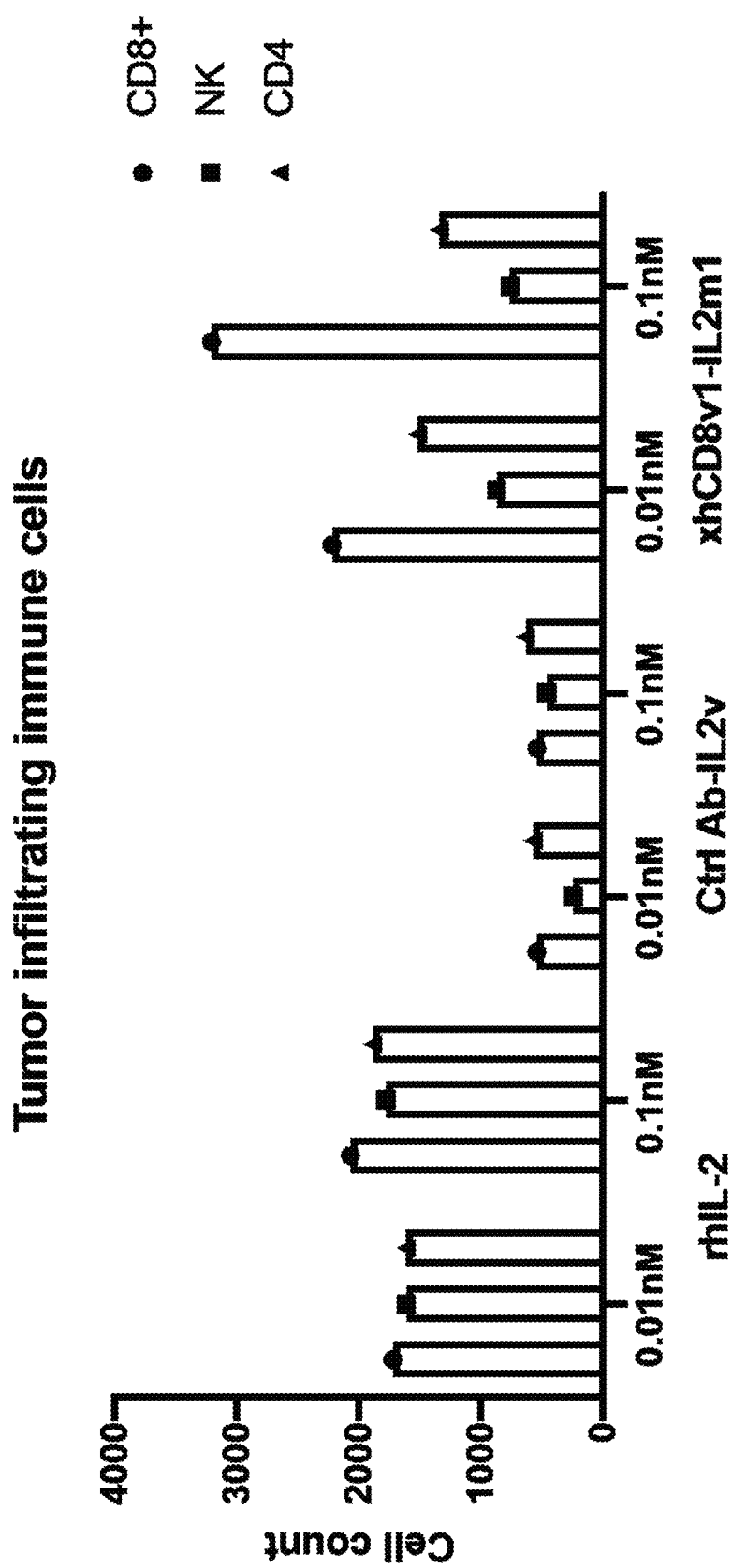
FIG. 16B depicts the number of CD8+ T cells, NK cells, and CD4+ T cells per well in each of the indicated conditions.
Figure 17A:
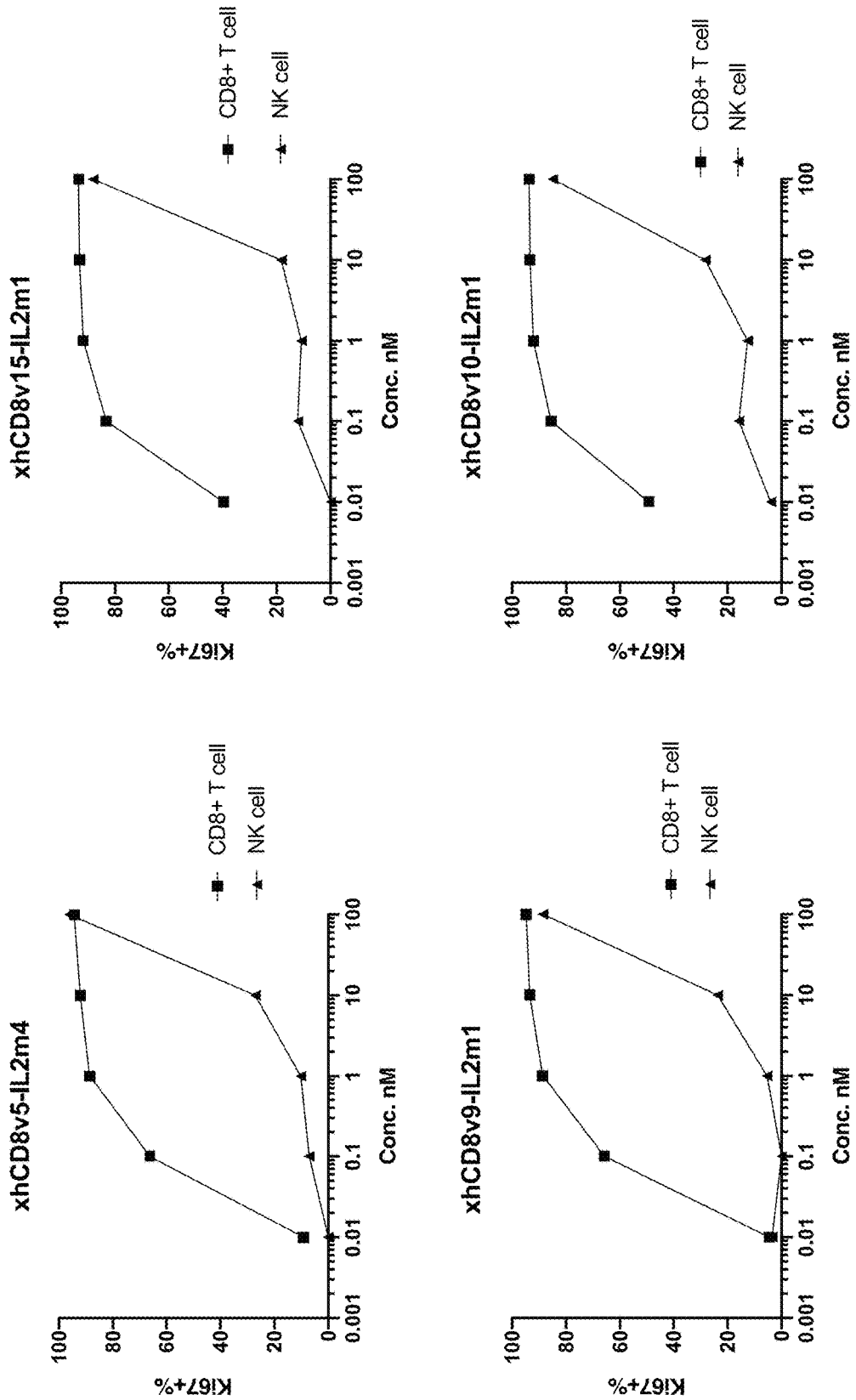
FIGS. 17A-17E show expression of Ki-67 proliferation marker after five day co-culture of hPBMCs with fusion proteins of format A containing a mutant IL-2 polypeptide (IL2m1 or IL2m4) and an CD8ab antibody of the present disclosure. CD8ab antibodies xhCD8v9-14 were tested. Ki-67 expression was measured in CD8+ T cells (squares) and NK cells (triangles).
Figure 17B:
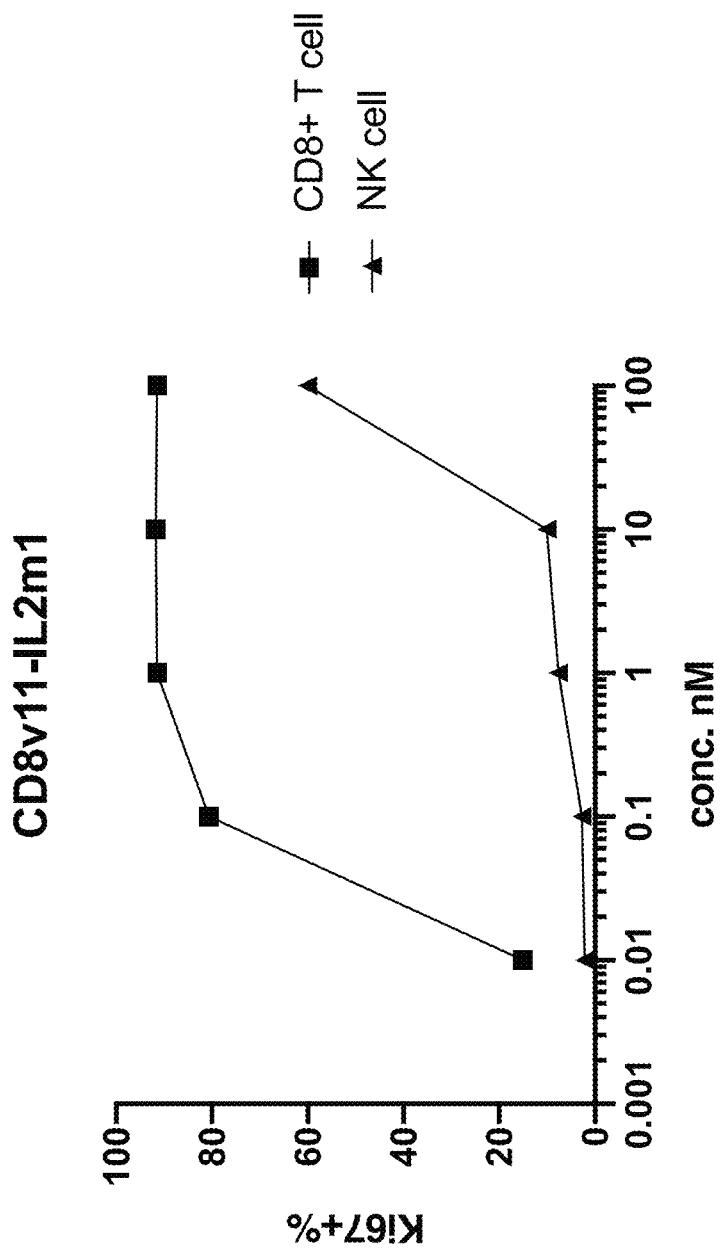
Figure 17C:
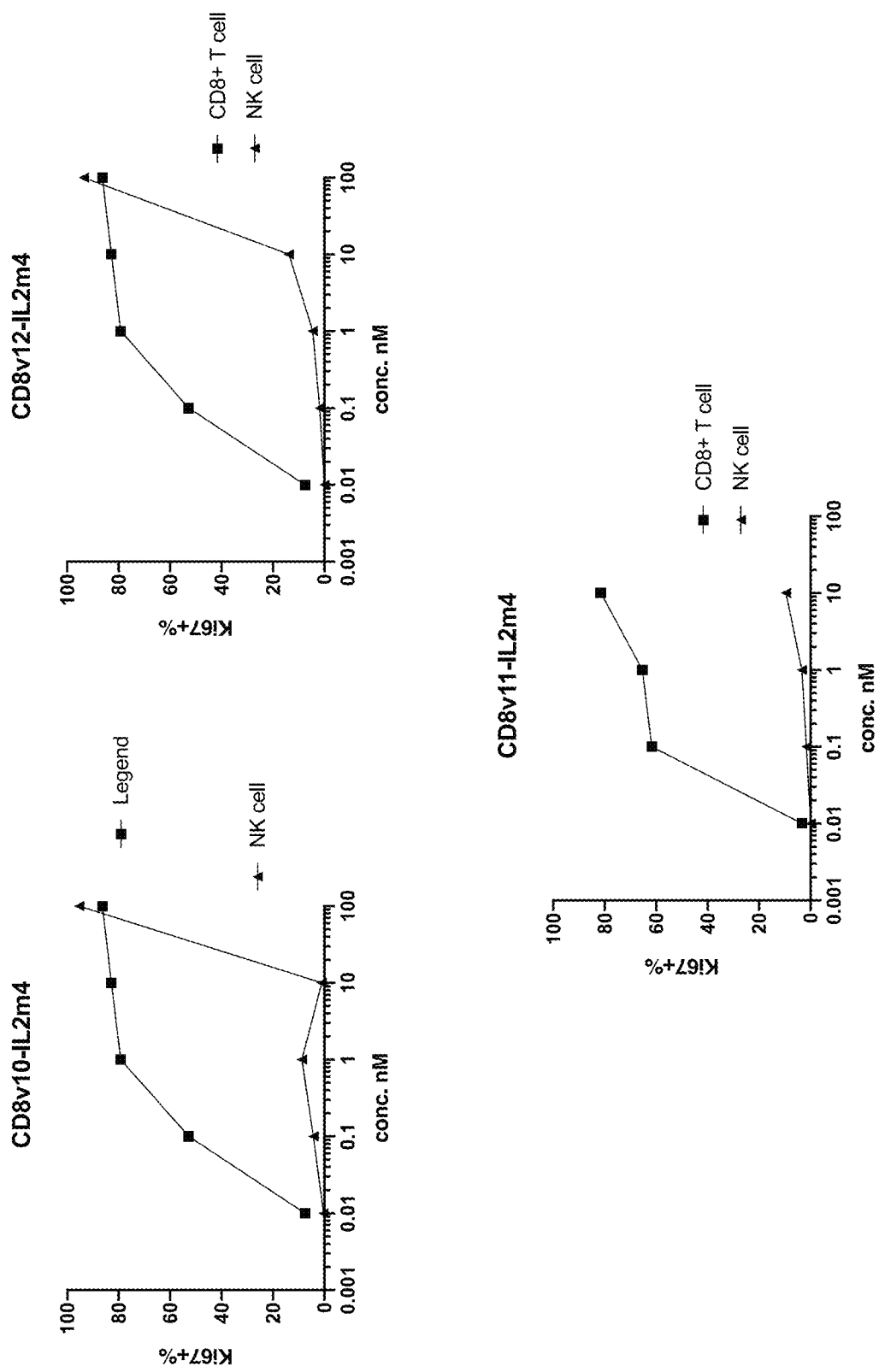
Figure 17D:
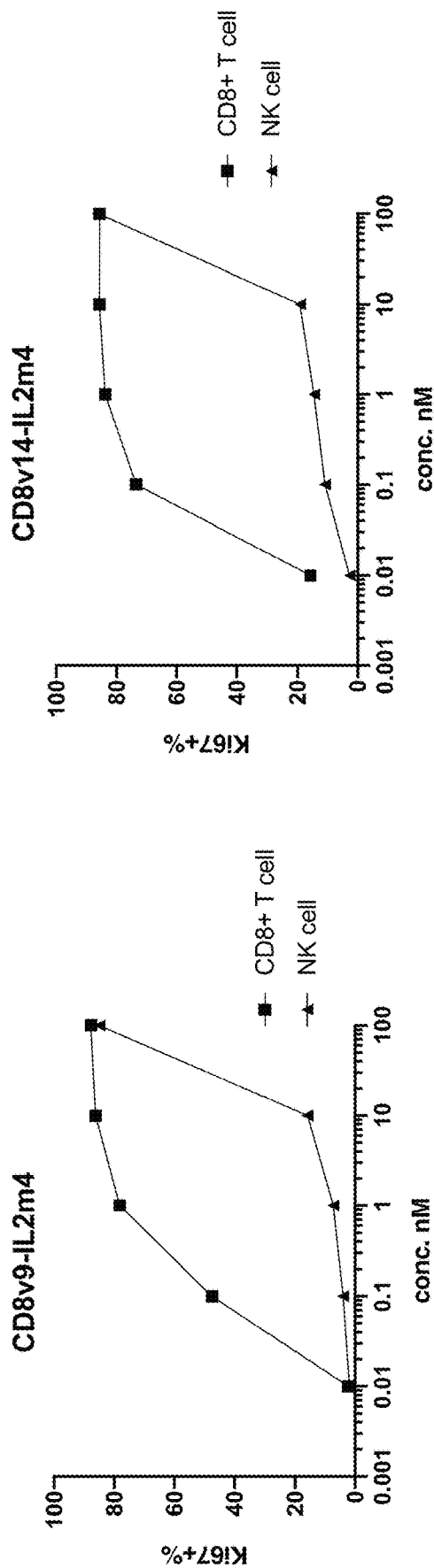
Figure 17E:
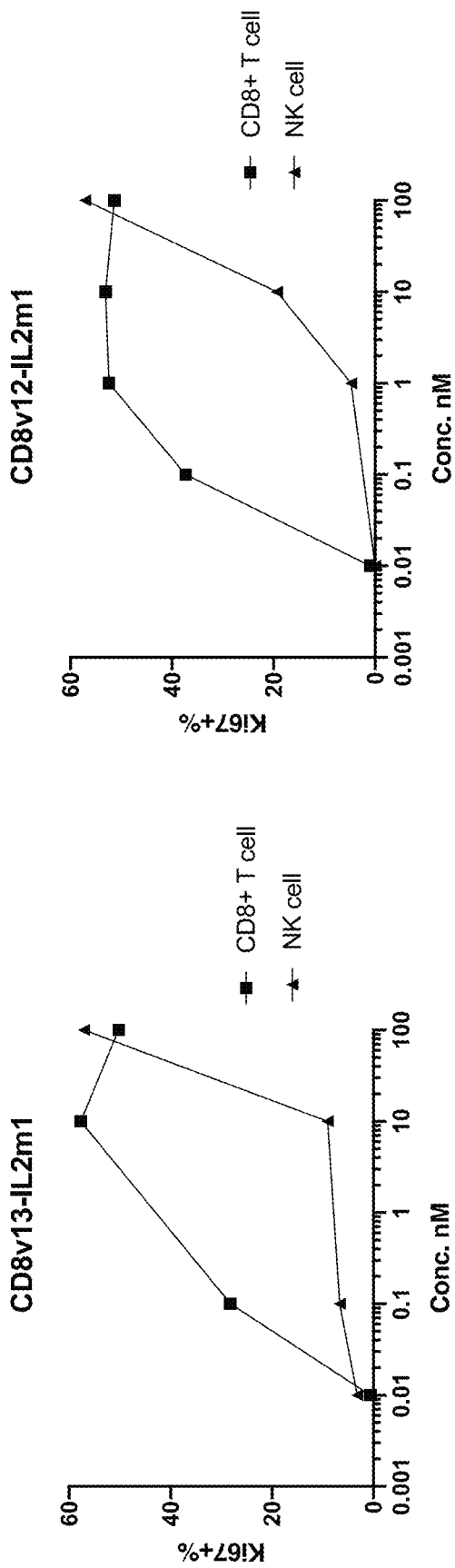

Ability of rhIL-2, Ctrl Ab-IL2v and xhCD8v1-IL2m1 to activate Ki-67 in CD8+ T cells and NK cells in isolated single cell suspensions from renal cell carcinoma was determined (FIG. 16A). Results showed that xhCD8v1-IL2m1 more potently activated Ki-67 in CD8+ T cells than rhIL-2 and Ctrl-IL2v with no activation of Ki-67 in NK cells. Furthermore, CD8+ T cell counts were preferentially increased compared to NK cell and CD4+ T cell counts (FIG. 16B).

By extension of these findings, one application of fusion proteins with CD8ab antibodies targeting is to enhance selective CD8+ T cell expansion in TILs isolated from cancer patients for the purpose of reinjecting them into patients for treatment.

Another application is to use fusion proteins with CD8ab antibodies in combination with TIL therapy or other T cell therapy, in particular TCR-T cell therapy with MHC class I-restricted T cells.

Example 5: Testing Additional CD8 Antibodies Targeting CD8ab Heterodimer for Selective Activation of Human CD8+ T Cells Over CD8+ NK Cells Additional CD8ab antibodies xhCD8v9-v15 were generated and tested for binding to recombinant CD8ab as described in Example 1. These antibodies were designed as improved versions (e.g., v9, v12, and v13 based on v2, and v10, v11, v14, and v15 based on v6) that (1) reduce the number of potential amino acid liabilities (e.g., putative N-linked glycosylation, deamination, or acid cleavage sites), potentially improving manufacturability; and (2) reduce the number of amino acid mismatches to human germline, potentially reducing immunogenicity in vivo (FIG. 18A). As noted above, when anti-CD8 antibody xhCD8v1 was grafted onto human framework to generate xhCD8v1.1 (as depicted in FIG. 18B), the binding to CD8+ T cells was surprisingly lost (FIG. 6). Further substitutions were needed in order to restore binding in the context of a humanized antibody, and yet further substitutions were introduced in order to reduce potential liabilities and/or mismatches to human germline (FIGS. 18C & 18D).

As shown in Table 6, all additional antibodies xhCD8v9-v15 showed high-affinity binding to CD8ab.

TABLE 6

Biosensor data of new CD8ab antibody binding.

| | ka (1/Ms) | kd (1/s) | $K_D$ (M) | $K_D$ (nM) |
|---|---|---|---|---|
| xhCD8v8 | — | — | 2.36E−07* | 236.0* |
| xhCD8v9 | 2.25E+05 | 2.73E−02 | 1.21E−07 | 121.0 |
| xhCD8v10 | 1.06E+05 | 3.86E−03 | 3.64E−08 | 36.4 |
| xhCD8v11 | 9.55E+04 | 3.61E−03 | 3.78E−08 | 37.8 |
| xhCD8v12 | 2.59E+05 | 2.71E−02 | 1.05E−07 | 105.0 |
| xhCD8v13 | 3.68E+05 | 3.01E−02 | 8.18E−08 | 81.8 |
| xhCD8v14 | 1.62E+05 | 8.55E−03 | 5.29E−08 | 52.9 |
| xhCD8v15 | 1.86E+05 | 1.75E−02 | 9.43E−08 | 94.3 |

*determined by steady state fit

These antibodies were also tested as fusion proteins in format A (as shown in FIG. 7) with a mutant IL-2 polypeptide (IL2m1 or IL2m4) for ability to selectively activate human CD8+ T cells over CD8+ NK cells, as described above in Example 2. As shown in FIGS. 17A-17E, these antibodies were able to promote selective activation of human CD8+ T cells over CD8+NK cells when used in the context of a fusion protein with a mutant IL-2 polypeptide.

Example 6: Thermal Stability Assessment of xhCD8v2-Related Family Clones

Material and Methods
Forced Degradation Assay

To assess molecular stability and aggregation propensity, purified antibodies at a concentration of 1 mg/mL in PBS were stressed at temperatures from 4° C. to 64° C. for 24 hours. Samples were filtered and analyzed by analytical size exclusion chromatography on a Superdex 200 5/150 GL (Cytiva). The percent monomer and monomer area were calculated using OpenLab ChemStation (Agilent Technologies). Experiments were performed in duplicate.

Thermal Stability Measurements

To determine thermal stability characteristics, intrinsic differential scanning fluorimetry (DSF) and static light scattering (SLS) were measured on a UNit instrument (Unchained labs). Purified antibodies at a concentration of 1 mg/mL in PBS were subject to a thermal ramp from 25° C.-95° C. at a rate of 1° C./min. UV spectra were recorded for DSF and SLS was recorded at 266 nm. Samples were performed in quadruplicate. Melting temperature (Tm), and aggregation temperature (Tagg) were analyzed and calculated by UNcle Analysis Software V3.2 (Unchained labs).

Results

Improved Thermal Stability of xhCD8v9, xhCD8v12 and xhCD8v13 Compared to Parental xhCD8v2

Parental antibody xhCD8v2 and its derivative xhCD8v9, xhCD8v12 and xhCD8v13 were subjected to forced degradation and thermal stability assays. Results for the forced degradation assay, depicted as the % recovery of monomer (the ratio of the monomer area at 64° C. to 4° C.) for the different antibodies, are shown in Table 7. xhCD8v9, xhCD8v12 and xhCD8v13 antibodies have greater % recovery compared to parental antibody xhCD8v2. Thermal stability measurements, shown in in Table 7, revealed that xhCD8v9, xhCD8v12 and xhCD8v13 antibodies have higher Tm and Tagg values than that of parental antibody xhCD8v2. Taken together, these results demonstrate that xhCD8v9, xhCD8v12 and xhCD8v13 molecules have improved thermal stability over the parental antibody xhCD8v2 and therefore, xhCD8v9, xhCD8v12 and xhCD8v13 are more desirable as therapeutic agents.

TABLE 7

Results of Forced Degradation and Thermostability Assays

| Construct | Forced Degradation % Recovery | Thermostability Tm (° C.) | Tagg (° C.) |
|---|---|---|---|
| xhCD8v2 | 6.3 | 67.4 ± 0.2 | 66.4 ± 0.4 |
| xhCD8v9 | 85.5 | 68.9 ± 0.1 | 74.7 ± 0.1 |
| xhCD8v12 | 78.5 | 68.8 ± 0.2 | 70.9 ± 0.8 |
| xhCD8v13 | 76.7 | 69.2 ± 0.2 | 73.7 ± 0.3 |

Example 7: Assessment of Glycan Occupancy on Parental xhCD8v6 and its Derivatives Materials and Methods Deglycosylation of Antibodies To remove both N-linked and O-linked glycosylation, 10 µg of antibody was mixed with 1 µl of 10× GlycoBuffer 2 (New England Biolabs), 1 µl Protein Deglycosylation Mix II (New England Biolabs) and brought to 10 µl with water. Reactions were incubated overnight at room temperate.

ELISA for Detection of Glycosylation of the P3F4-Related Molecule

Presence of N-linked glycosylation was determined by ELISA. Briefly, 25 µL of protein from 0.5 to 10 µg/mL was coated onto a 384-well Nunc MaxiSorp plate (Thermo Fisher Scientific) and incubated at 37° C. for 1 hour. Proteins were removed and the plate was washed with PBS+0.05% Tween-20 (PBST). Wells were filled with carbohydrate-free blocking solution (Vector Labs) and incubated at room temperature for 30 mins. The blocking solution was removed, and the wells washed with PBST. 25 µL of 5 µg/mL biotinylated wheat germ agglutinin (Vector Labs), which binds to glycoconjugates, in PBS was added and incubated at room temperature for 30 mins. It was then removed, and the plate was washed again with PBST. L of the detection reagent, VECTASTAIN Elite ABC-HRP Reagent, Peroxidase, R.T.U. (Vector Labs), was added and allowed to incubate for 30 mins at room temperature. The reagent was removed, and wells were washed with PBST. Wells were developed using 25 µL of KPL SureBlue TMB Microwell Substrate (SeraCare) for 5-7 mins and quenched with 25 µL of 0.1 M HCl. The absorbance at 450 nm was recorded on a SpectraMax iD5 plate reader (Molecular Devices). Fetuin, a glycoprotein containing sialylated N-linked and O-linked glycans, was used as a positive control. All experiments were performed with n=8.

Results

Figure 19:
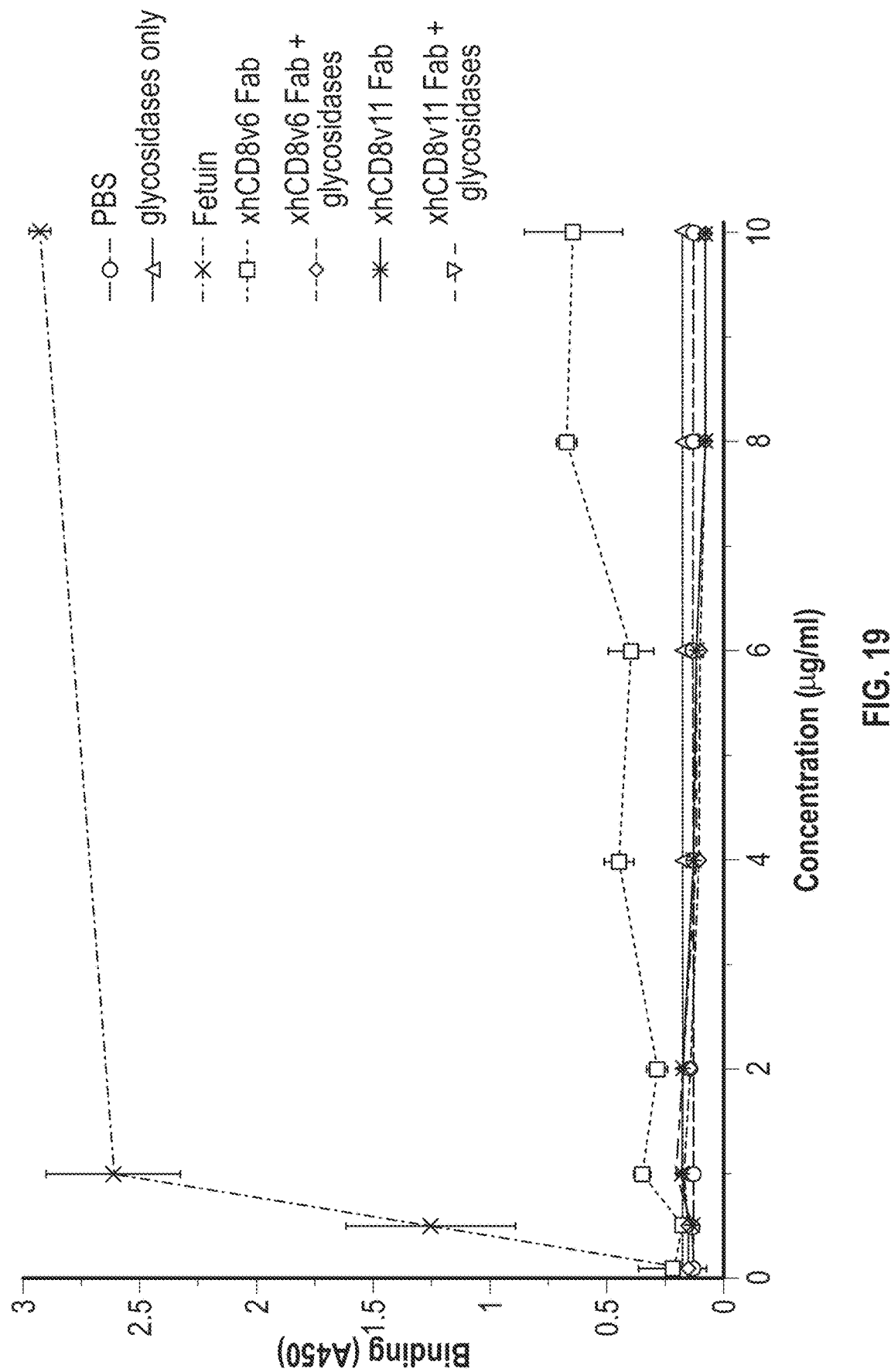
FIG. 19 shows the results of an ELISA assay used to identify glycosylation of the parental xhCD8v6 (black solid line with black squares), which is removed upon treatment with glycosidases (black dashed line with black squares). No glycosylation is detected on the xhCD8v11 (gray lines with open triangles). Fetuin is shown as a positive control.

Removal of the N-Linked Glycosylation Site on xhCD8v6 Improves Homogeneity xCD8v6 possesses a putative N-linked glycosylation motif in the CDR-H2 region. This putative N-linked glycosylation motif was removed in the derivatives of xhCD8v6, namely xhCD8v10, xhCD8v11, xhCD8v14, and xhCD8v15. Presence of variable amount of glycans in the CDR region decreases homogeneity of the final product and could affect binding capability. To probe for the presence of glycans, an ELISA using wheat germ agglutinin (WGA), which binds to N-acetylglucosamine, was performed. Fabs of parental xhCD8v6 and xhCD8v11, which served as the negative control, were assayed to examine only the variable domains. Fetuin was used as a positive control. As shown in FIG. 19, WGA binding was detected for the parental xhCD8v6, but not xhCD8v11. Upon treatment with deglycosidases, there was no binding of WGA to deglycosylated xhCD8v6, confirming the presence of glycan on xhCD8v6. Results here suggested that xhCD8v10, xhCD8v11, xhCD8v14, and xhCD8v15, which do not possess the putative N-linked glycosylation motif, are better and more homogenous therapeutics agents compared to parental xCD8v6.

What is claimed is:

1. A fusion protein, comprising:
   (a) a first moiety comprising a humanized antibody or antigen-binding fragment thereof that specifically binds CD8b, wherein the antibody or fragment comprises a heavy chain variable (VH) domain and a light chain variable (VL) domain, wherein:
   the VH domain comprises a CDR-H1 comprising the amino acid sequence of SEQ ID NO:225, a CDR-H2 comprising the amino acid sequence of SEQ ID NO:232, and a CDR-H3 comprising the amino acid sequence of SEQ ID NO:233; and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; and
   (b) a second moiety comprising an IL-2 polypeptide;
   wherein the first moiety is fused to the second moiety directly or via a linker.

2. The fusion protein of claim 1, wherein the IL-2 polypeptide induces activation of CD8+ T cells.

3. The fusion protein of claim 2, wherein the humanized antibody or antigen-binding fragment thereof of the first moiety further specifically binds CD8ab, and wherein the fusion protein induces activation of cells expressing a human CD8ab heterodimer with at least 10-fold higher potency than activation of cells expressing a human CD8aa homodimer.

4. The fusion protein of claim 2, wherein the fusion protein induces activation of CD8+ T cells with at least 10-fold higher potency than activation of NK cells.

5. The fusion protein of claim 4, wherein potency of activation is measured by EC50, as assessed by cell proliferation.

6. The fusion protein of claim 1, wherein the first moiety comprises two antibody heavy chain polypeptides comprising a structure according to formula [I], from N-terminus to C-terminus:

VH-CH1-hinge-CH2-CH3　　　　　　　　　　[I]

and two antibody light chain polypeptides comprising a structure according to formula [II], from N-terminus to C-terminus:

VL-CL            [II]

wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain; and
wherein the N-terminus of the second moiety is fused to the C-terminus of one of the two CH3 domains.

7. The fusion protein of claim 1, wherein the first moiety comprises a first antibody heavy chain polypeptide comprising a structure according to formula [I], from N-terminus to C-terminus:

VH-CH1-hinge-CH2-CH3     [I], an antibody light chain polypeptide comprising a structure according to formula [II], from N-terminus to C-terminus:

VL-CL            [II], and a second antibody heavy chain polypeptide comprising a structure according to formula [III], from N-terminus to C-terminus:

hinge-CH2-CH3    [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain; and
wherein the N-terminus of the second moiety is fused to the C-terminus of the CH3 domain of the second antibody heavy chain polypeptide.

8. The fusion protein of claim 1, wherein the first moiety comprises a first antibody heavy chain polypeptide comprising a structure according to formula [I], from N-terminus to C-terminus:

VH-CH1-hinge-CH2-CH3     [I], an antibody light chain polypeptide comprising a structure according to formula [II], from N-terminus to C-terminus:

VL-CL            [II], and a second antibody heavy chain polypeptide comprising a structure according to formula [III], from N-terminus to C-terminus:

hinge-CH2-CH3    [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain; and
wherein the C-terminus of the second moiety is fused to the N-terminus of the hinge domain of the second antibody heavy chain polypeptide.

9. The fusion protein of claim 1, wherein the first moiety comprises a first antibody heavy chain polypeptide comprising a structure according to formula [I], from N-terminus to C-terminus:

VH-CH1-hinge-CH2-CH3     [I], an antibody light chain polypeptide comprising a structure according to formula [II], from N-terminus to C-terminus:

VL-CL            [II], and a second antibody heavy chain polypeptide comprising a structure according to formula [III], from N-terminus to C-terminus:

hinge-CH2-CH3    [III], wherein VH is the VH domain, wherein CH1 is an antibody CH1 domain, wherein hinge is an antibody hinge domain, wherein CH2-CH3 is an antibody Fc domain, wherein VL is the VL domain, and wherein CL is an antibody constant light chain domain; and
wherein the N-terminus of the second moiety is fused to the C-terminus of the CH3 domain of the first antibody heavy chain polypeptide.

10. The fusion protein of claim 6, wherein:
the VH domain of both antibody heavy chain polypeptides comprises an amino acid sequence that is at least 90% identical to the sequence of SEQ ID NO:251, and wherein the VL domain of both antibody light chain polypeptides comprises an amino acid sequence that is at least 90% identical to the sequence of SEQ ID NO:252.

11. The fusion protein of claim 7, wherein:
the VH domain comprises the amino acid sequence of SEQ ID NO:251, and the VL domain comprises the amino acid sequence of SEQ ID NO:252.

12. The fusion protein of claim 6, wherein one or both of the antibody heavy chain polypeptides comprise(s) the following amino acid substitutions: L234A, L235A, and G237A, numbering according to EU index.

13. The fusion protein of claim 6, wherein a first of the antibody heavy chain polypeptides comprises amino acid substitutions Y349C and T366W, and a second of the antibody heavy chain polypeptides comprises amino acid substitutions S354C, T366S, L368A and Y407V, numbering according to EU index.

14. The fusion protein of claim 1, wherein the first moiety comprises one or two antibody heavy chain polypeptides and one or two antibody light chain polypeptides.

15. The fusion protein of claim 1, wherein the IL-2 polypeptide is a mutant IL-2 polypeptide comprising one or more mutations relative to a human IL-2 polypeptide comprising the sequence of

```
                                      (SEQ ID NO: 81)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT.
```

16. The fusion protein of claim 15, wherein the mutant IL-2 polypeptide has a binding affinity to IL-2Ra that is reduced by 50% or more, compared to binding affinity of a wild-type IL-2 polypeptide comprising the sequence of SEQ ID: 81 for IL-2Ra.

17. The fusion protein of claim 16, wherein the mutant IL-2 polypeptide has a binding affinity to IL-2R13 that is reduced by 50% or more, compared to binding affinity of a wild-type IL-2 polypeptide comprising the sequence of SEQ ID: 81 for IL-2R13; and/or
wherein the mutant IL-2 polypeptide has a binding affinity to IL-2Ry that is reduced by 50% or more, compared to binding affinity of a wild-type IL-2 polypeptide comprising the sequence of SEQ ID: 81 for IL-2Rγ.

18. The fusion protein of claim 1, wherein the IL-2 polypeptide comprises the sequence of SEQ ID NO:81 with one, two, three, four, or five amino acid substitutions relative to SEQ ID NO:81, and wherein the one, two, three, four, or five substitution(s) comprise substitution(s) at positions of SEQ ID NO:81 selected from the group consisting of: Q11, H16, L18, L19, D20, Q22, R38, F42, K43, Y45, E62, P65, E68, V69, L72, D84, S87, N88, V91, I92, T123, Q126, 5127, 1129, and 5130.

19. The fusion protein of claim 18, wherein the IL-2 polypeptide comprises the sequence of SEQ ID NO:81 with one of the following sets of amino acid substitutions: R38E and F42A; R38D and F42A; F42A and E62Q; R38A and F42K; R38E, F42A, and N88S; R38E, F42A, and N88A; R38E, F42A, and N88G; R38E, F42A, and N88R; R38E, F42A, and N88T; R38E, F42A, and N88D; R38E, F42A, and V91E; R38E, F42A, and D84H; R38E, F42A, and D84K; R38E, F42A, and D84R; H16D, R38E and F42A; H16E, R38E and F42A; R38E, F42A and Q126S; R38D, F42A and N88S; R38D, F42A and N88A; R38D, F42A and N88G; R38D, F42A and N88R; R38D, F42A and N88T; R38D, F42A and N88D; R38D, F42A and V91E; R38D, F42A, and D84H; R38D, F42A, and D84K; R38D, F42A, and D84R; H16D, R38D and F42A; H16E, R38D and F42A; R38D, F42A and Q126S; R38A, F42K, and N88S; R38A, F42K, and N88A; R38A, F42K, and N88G; R38A, F42K, and N88R; R38A, F42K, and N88T; R38A, F42K, and N88D; R38A, F42K, and V91E; R38A, F42K, and D84H; R38A, F42K, and D84K; R38A, F42K, and D84R; H16D, R38A, and F42K; H16E, R38A, and F42K; R38A, F42K, and Q126S; F42A, E62Q, and N88S; F42A, E62Q, and N88A; F42A, E62Q, and N88G; F42A, E62Q, and N88R; F42A, E62Q, and N88T; F42A, E62Q, and N88D; F42A, E62Q, and V91E; F42A, E62Q, and D84H; F42A, E62Q, and D84K; and F42A, E62Q, and D84R.

20. The fusion protein of claim 18, wherein the IL-2 polypeptide comprises the sequence of SEQ ID NO:81 with a further amino acid substitution relative to SEQ ID NO:81 at position C125.

21. The fusion protein of claim 20, wherein the IL-2 polypeptide comprises the sequence of SEQ ID NO:81 with one of the following sets of amino acid substitutions: R38E, F42A, and C125A; R38D, F42A, and C125A; F42A, E62Q, and C125A; R38A, F42K, and C125A; R38E, F42A, N88S, and C125A; R38E, F42A, N88A, and C125A; R38E, F42A, N88G, and C125A; R38E, F42A, N88R, and C125A; R38E, F42A, N88D, and C125A; R38E, F42A, N88T, and C125A; R38E, F42A, V91E, and C125A; R38E, F42A, D84H, and C125A; R38E, F42A, D84K, and C125A; R38E, F42A, D84R, and C125A; H16D, R38E, F42A, and C125A; H16E, R38E, F42A, and C125A; R38E, F42A, C125A and Q126S; R38D, F42A, N88S, and C125A; R38D, F42A, N88A, and C125A; R38D, F42A, N88G, and C125A; R38D, F42A, N88R, and C125A; R38D, F42A, N88T, and C125A; R38D, F42A, N88D, and C125A; R38D, F42A, V91E, and C125A; R38D, F42A, D84H, and C125A; R38D, F42A, D84K, and C125A; R38D, F42A, D84R, and C125A; H16D, R38D, F42A, and C125A; H16E, R38D, F42A, and C125A; R38D, F42A, C125A, and Q126S; R38A, F42K, N88S, and C125A; R38A, F42K, N88G, and C125A; R38A, F42K, N88R, and C125A; R38A, F42K, N88T, and C125A; R38A, F42K, N88D, and C125A; R38A, F42K, N88A, and C125A; R38A, F42K, V91E, and C125A; R38A, F42K, D84H, and C125A; R38A, F42K, D84K, and C125A; R38A, F42K, D84R, and C125A; H16D, R38A, F42K, and C125A; H16E, R38A, F42K, and C125A; R38A, F42K, C125A and Q126S; F42A, E62Q, N88S, and C125A; F42A, E62Q, N88A, and C125A; F42A, E62Q, N88G, and C125A; F42A, E62Q, N88R, and C125A; F42A, E62Q, N88T, and C125A; F42A, E62Q, N88D, and C125A; F42A, E62Q, V91E, and C125A; F42A, E62Q, and D84H, and C125A; F42A, E62Q, and D84K, and C125A; F42A, E62Q, and D84R, and C125A; H16D, F42A, and E62Q, and C125A; H16E, F42A, E62Q, and C125A; F42A, E62Q, C125A and Q126S; F42A, N88S, and C125A; F42A, N88A, and C125A; F42A, N88G, and C125A; F42A, N88R, and C125A; F42A, N88T, and C125A; F42A, N88D, and C125A; F42A, V91E, and C125A; F42A, D84H, and C125A; F42A, D84K, and C125A; F42A, D84R, and C125A; H16D, F42A, and C125A; H16E, F42A, and C125A; and F42A, C125A and Q126S.

22. The fusion protein of claim 1, wherein the IL-2 polypeptide comprises the sequence APTSSSTKKTQLQLEHLLLDLQMILNGIN-NYKNPKLTEMLTAKFYMPKKATELKHLQCL EEELKPLEEVLNLAQSKNFHLRPRDLISAIN-VIVLELKGSETTFMCEYADETATIVEFLNR WITFAQSIISTLT (SEQ ID NO:80) or the sequence APTSSSTKKTQLQLEELLLDLQMILNGIN-NYKNPKLTEMLTAKFYMPKKATELKHLQCL EEELKPLEEVLNLAQSKNFHLRPRDLISNIN-VIVLELKGSETTFMCEYADETATIVEFLNR WITFAQSIISTLT (SEQ ID NO:297).

23. The fusion protein of claim 1, wherein the IL-2 polypeptide comprises a sequence selected from the group consisting of SEQ ID NOs: 80, 85-155, 190-216, 297, and 354-383.

24. The fusion protein of claim 6, wherein one or both of the antibody Fc domains comprise(s) human IgG1 Fc domains with the following amino acid substitutions: L234A, L235A, and G237A, numbering according to EU index.

25. The fusion protein of claim 6, wherein a first of the two Fc domains comprises a human IgG1 Fc domain with amino acid substitutions Y349C and T366W, and a second of the two Fc domain comprises a human IgG1 Fc domain with amino acid substitutions S354C, T366S, L368A and Y407V, numbering according to EU index.

26. The fusion protein of claim 1, wherein the linker comprises the sequence (GGGS)xGn (SEQ ID NO:74), (GGGGS)xGn (SEQ ID NO:75), or (GGGGGS)xGn (SEQ ID NO:76), S(GGGS)xGn (SEQ ID NO:386), S(GGGGS)xGn (SEQ ID NO:387), or S(GGGGGS)xGn (SEQ ID NO:388), wherein x=1, 2, 3, 4, 5, 6, 7, 8, 9, 10, 11, or 12, and wherein n=0, 1, 2 or 3.

27. The fusion protein of claim 1, wherein the linker comprises the sequence GGGGSGGGGSGGGGS (SEQ ID NO:79) or SGGGGSGGGGSGGGGS (SEQ ID NO:389).

28. The fusion protein of claim 1, wherein the fusion protein comprises:
one or two light chains comprising the amino acid sequence of SEQ ID NO:310, a heavy chain comprising the amino acid sequence of SEQ ID NO:311, and a heavy chain comprising the amino acid sequence of SEQ ID NO:312;
one or two light chains comprising the amino acid sequence of SEQ ID NO:338, a heavy chain comprising the amino acid sequence of SEQ ID NO:339, and a heavy chain comprising the amino acid sequence of SEQ ID NO:340;
one or two light chains comprising the amino acid sequence of SEQ ID NO:310, a heavy chain comprising the amino acid sequence of SEQ ID NO:311, and a heavy chain comprising the amino acid sequence of SEQ ID NO:313; or one or two light chains comprising the amino acid sequence of SEQ ID NO:338, a heavy chain comprising the amino acid sequence of SEQ ID NO:339, and a heavy chain comprising the amino acid sequence of SEQ ID NO:341.

29. A fusion protein comprising a first moiety that binds to a human CD8b and a second moiety comprising an IL2 polypeptide, wherein the fusion protein comprises four polypeptide chains, wherein:

the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:340, and the fourth polypeptide chain comprises the amino acid sequence of SEQ ID NO:338; or the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:341, and the fourth polypeptide chain comprises the amino acid sequence of SEQ ID NO:338.

30. The fusion protein of claim 10, wherein the VH domain of both antibody heavy chain polypeptides comprises the amino acid sequence of SEQ ID NO:251, and the VL domain of both antibody light chain polypeptides comprises the amino acid sequence of SEQ ID NO:252.

31. The fusion protein of claim 8, wherein the VH domain comprises the amino acid sequence of SEQ ID NO:251, and the VL domain comprises the amino acid sequence of SEQ ID NO:252.

32. The fusion protein of claim 9, wherein the VH domain comprises the amino acid sequence of SEQ ID NO:251, and the VL domain comprises the amino acid sequence of SEQ ID NO:252.

33. A fusion protein comprising a first moiety that binds to a human CD8b and a second moiety comprising an IL2 polypeptide, wherein the fusion protein comprises four polypeptide chains, wherein:

the first polypeptide chain comprises the amino acid sequence of SEQ ID NO:310, the second polypeptide chain comprises the amino acid sequence of SEQ ID NO:311, the third polypeptide chain comprises the amino acid sequence of SEQ ID NO:312, and the fourth polypeptide chain comprises the amino acid sequence of SEQ ID NO:310; or the first polypeptide chain comprises the amino acid sequence of SEQ ID NO:310, the second polypeptide chain comprises the amino acid sequence of SEQ ID NO:311, the third polypeptide chain comprises the amino acid sequence of SEQ ID NO:313, and the fourth polypeptide chain comprises the amino acid sequence of SEQ ID NO:310.

34. The fusion protein of claim 29, wherein the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:340, and the fourth polypeptide chain comprises the amino acid sequence of SEQ ID NO:338.

35. The fusion protein of claim 29, wherein the first polypeptide chain comprises the amino acid sequence of SEQ ID NO:338, the second polypeptide chain comprises the amino acid sequence of SEQ ID NO:339, the third polypeptide chain comprises the amino acid sequence of SEQ ID NO:341, and the fourth polypeptide chain comprises the amino acid sequence of SEQ ID NO:338.

36. The fusion protein of claim 33, wherein the first polypeptide chain comprises the amino acid sequence of SEQ ID NO:310, the second polypeptide chain comprises the amino acid sequence of SEQ ID NO:311, the third polypeptide chain comprises the amino acid sequence of SEQ ID NO:312, and the fourth polypeptide chain comprises the amino acid sequence of SEQ ID NO:310.

37. The fusion protein of claim 33, wherein the first polypeptide chain comprises the amino acid sequence of SEQ ID NO:310, the second polypeptide chain comprises the amino acid sequence of SEQ ID NO:311, the third polypeptide chain comprises the amino acid sequence of SEQ ID NO:313, and the fourth polypeptide chain comprises the amino acid sequence of SEQ ID NO:310.

38. A fusion protein, comprising:
(a) a first moiety comprising a humanized antibody or antigen-binding fragment thereof that specifically binds CD8b and/or CD8ab, wherein the antibody or fragment comprises a heavy chain variable (VH) domain and a light chain variable (VL) domain, wherein the VH domain comprises a CDR-H1 comprising the amino acid sequence of SEQ ID NO:238, a CDR-H2 comprising the amino acid sequence of SEQ ID NO:243, and a CDR-H3 comprising the amino acid sequence of SEQ ID NO:233, and wherein the VL domain comprises a CDR-L1 comprising the amino acid sequence of SEQ ID NO:234, a CDR-L2 comprising the amino acid sequence of SEQ ID NO:235, and a CDR-L3 comprising the amino acid sequence of SEQ ID NO:236; and
(b) a second moiety comprising an IL-2 polypeptide;
wherein the first moiety is fused to the second moiety directly or via a linker.

39. The fusion protein of claim 24, wherein one or both of the antibody Fc domains do not have a C-terminal lysine.

40. The fusion protein of claim 25, wherein one or both of the antibody Fc domains do not have a C-terminal lysine.

41. A pharmaceutical composition comprising the fusion protein according to claim 1 and a pharmaceutically acceptable carrier.

42. A pharmaceutical composition comprising the fusion protein according to claim 6 and a pharmaceutically acceptable carrier.

43. A pharmaceutical composition comprising the fusion protein according to claim 30 and a pharmaceutically acceptable carrier.

44. A pharmaceutical composition comprising the fusion protein according to claim 29 and a pharmaceutically acceptable carrier.

45. A pharmaceutical composition comprising the fusion protein according to claim 33 and a pharmaceutically acceptable carrier.

46. One or more polynucleotides encoding the fusion protein according to claim 1.

47. One or more vectors comprising the one or more polynucleotides of claim 46.

48. An isolated host cell comprising the one or more polynucleotides of claim 46.

49. A method of producing a fusion protein, comprising culturing the host cell of claim 48 under conditions suitable for production of the fusion protein.

50. A method of treating cancer comprising administering to an individual with cancer an effective amount of the composition of claim 41.

51. The method of claim 50, further comprising administering to the individual a T cell therapy, cancer vaccine, chemotherapeutic agent, or immune checkpoint inhibitor (ICI).

52. The method of claim 51, wherein the ICI is an inhibitor of PD-1, PD-L1, or CTLA-4.

53. The method of claim 51, wherein the T cell therapy comprises a chimeric antigen receptor (CAR)-based T cell therapy, a tumor-infiltrating lymphocyte (TIL)-based therapy, or a therapy with T cells bearing a transduced TCR.

54. A method of expanding T cells ex vivo comprising contacting one or more T cells ex vivo with an effective amount of the composition of claim 41.

55. The method of claim 54, wherein the one or more T cells are tumor infiltrating lymphocytes (TILs).

56. One or more polynucleotides encoding the fusion protein according to claim 6.

57. One or more vectors comprising the one or more polynucleotides of claim 56.

58. An isolated host cell comprising the one or more polynucleotides of claim 56.

59. A method of producing a fusion protein, comprising culturing the host cell of claim 58 under conditions suitable for production of the fusion protein.

60. A method of treating cancer comprising administering to an individual with cancer an effective amount of the composition of claim 42.

61. The method of claim 60, further comprising administering to the individual a T cell therapy, cancer vaccine, chemotherapeutic agent, or immune checkpoint inhibitor (ICI).

62. The method of claim 61, wherein the ICI is an inhibitor of PD-1, PD-L1, or CTLA-4.

63. The method of claim 61, wherein the T cell therapy comprises a chimeric antigen receptor (CAR)-based T cell therapy, a tumor-infiltrating lymphocyte (TIL)-based therapy, or a therapy with T cells bearing a transduced TCR.

64. A method of expanding T cells ex vivo comprising contacting one or more T cells ex vivo with an effective amount of the composition of claim 42.

65. The method of claim 64, wherein the one or more T cells are tumor infiltrating lymphocytes (TILs).

66. One or more polynucleotides encoding the fusion protein according to claim 29.

67. One or more vectors comprising the one or more polynucleotides of claim 66.

68. An isolated host cell comprising the one or more polynucleotides of claim 66.

69. A method of producing a fusion protein, comprising culturing the host cell of claim 68 under conditions suitable for production of the fusion protein.

70. A method of treating cancer comprising administering to an individual with cancer an effective amount of the composition of claim 44.

71. The method of claim 70, further comprising administering to the individual a T cell therapy, cancer vaccine, chemotherapeutic agent, or immune checkpoint inhibitor (ICI).

72. The method of claim 71, wherein the ICI is an inhibitor of PD-1, PD-L1, or CTLA-4.

73. The method of claim 71, wherein the T cell therapy comprises a chimeric antigen receptor (CAR)-based T cell therapy, a tumor-infiltrating lymphocyte (TIL)-based therapy, or a therapy with T cells bearing a transduced TCR.

74. A method of expanding T cells ex vivo comprising contacting one or more T cells ex vivo with an effective amount of the composition of claim 44.

75. The method of claim 74, wherein the one or more T cells are tumor infiltrating lymphocytes (TILs).

76. One or more polynucleotides encoding the fusion protein according to claim 30.

77. One or more vectors comprising the one or more polynucleotides of claim 76.

78. An isolated host cell comprising the one or more polynucleotides of claim 76.

79. A method of producing a fusion protein, comprising culturing the host cell of claim 78 under conditions suitable for production of the fusion protein.

80. A method of treating cancer comprising administering to an individual with cancer an effective amount of the composition of claim 43.

81. The method of claim 80, further comprising administering to the individual a T cell therapy, cancer vaccine, chemotherapeutic agent, or immune checkpoint inhibitor (ICI).

82. The method of claim 81, wherein the ICI is an inhibitor of PD-1, PD-L1, or CTLA-4.

83. The method of claim 81, wherein the T cell therapy comprises a chimeric antigen receptor (CAR)-based T cell therapy, a tumor-infiltrating lymphocyte (TIL)-based therapy, or a therapy with T cells bearing a transduced TCR.

84. A method of expanding T cells ex vivo comprising contacting one or more T cells ex vivo with an effective amount of the composition of claim 43.

85. The method of claim 84, wherein the one or more T cells are tumor infiltrating lymphocytes (TILs).

86. One or more polynucleotides encoding the fusion protein according to claim 33.

87. One or more vectors comprising the one or more polynucleotides of claim 86.

88. An isolated host cell comprising the one or more polynucleotides of claim 86.

89. A method of producing a fusion protein, comprising culturing the host cell of claim 88 under conditions suitable for production of the fusion protein.

90. A method of treating cancer comprising administering to an individual with cancer an effective amount of the composition of claim 45.

91. The method of claim 90, further comprising administering to the individual a T cell therapy, cancer vaccine, chemotherapeutic agent, or immune checkpoint inhibitor (ICI).

92. The method of claim 91, wherein the ICI is an inhibitor of PD-1, PD-L1, or CTLA-4.

93. The method of claim 91, wherein the T cell therapy comprises a chimeric antigen receptor (CAR)-based T cell therapy, a tumor-infiltrating lymphocyte (TIL)-based therapy, or a therapy with T cells bearing a transduced TCR.

94. A method of expanding T cells ex vivo comprising contacting one or more T cells ex vivo with an effective amount of the composition of claim 45.

95. The method of claim 94, wherein the one or more T cells are tumor infiltrating lymphocytes (TILs).

\* \* \* \* \*